(12) United States Patent
Banner et al.

(10) Patent No.: US 7,622,492 B2
(45) Date of Patent: Nov. 24, 2009

(54) PYRAZOLONES AS INHIBITORS OF 11β-HYDROXYSTEROID DEHYDROGENASE

(75) Inventors: Bruce Lester Banner, Wayne, NJ (US); Joseph Anthony Bilotta, Astoria, NY (US); Nader Fotouhi, Basking Ridge, NJ (US); Paul Gillespie, Westfield, NJ (US); Robert Alan Goodnow, Jr., Gillette, NJ (US); Matthew Michael Hamilton, Hackettstown, NJ (US); Nancy-Ellen Haynes, Cranford, NJ (US); Agnieszka Kowalczyk, Mine Hill, NJ (US); Alexander Mayweg, Loerrach (DE); Michael Paul Myers, Ramsey, NJ (US); Sherrie Lynn Pietranico-Cole, Montclair, NJ (US); Nathan Robert Scott, Livingston, NJ (US); Kshitij Chhabilbhai Thakkar, Clifton, NJ (US); Jefferson Wright Tilley, North Caldwell, NJ (US); Kevin Richard Guertin, Verona, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 491 days.

(21) Appl. No.: 11/507,080

(22) Filed: Aug. 18, 2006

(65) Prior Publication Data
US 2007/0049632 A1    Mar. 1, 2007

Related U.S. Application Data

(60) Provisional application No. 60/817,255, filed on Jun. 29, 2006, provisional application No. 60/713,074, filed on Aug. 31, 2005.

(51) Int. Cl.
*A61K 31/416* (2006.01)
*C07D 231/54* (2006.01)
(52) U.S. Cl. .................... 514/405; 548/359.1
(58) Field of Classification Search ................. None
See application file for complete search history.

(56) References Cited

U.S. PATENT DOCUMENTS

| 3,047,461 A * | 7/1962 | Hardy, Jr. et al. ........ 514/376 |
| 2004/0122033 A1 | 6/2004 | Nargund et al. |
| 2004/0133011 A1 | 7/2004 | Waddell et al. |
| 2005/0137209 A1 | 6/2005 | Oksenberg et al. |

FOREIGN PATENT DOCUMENTS

| JP | 2005170939 | 6/2005 |
| WO | WO 0190090 | 11/2001 |
| WO | WO 0190091 | 11/2001 |
| WO | WO 0190092 | 11/2001 |
| WO | WO 0190093 | 11/2001 |
| WO | WO 0190094 | 11/2001 |
| WO | WO 02076435 A2 | 10/2002 |
| WO | WO 03043999 | 5/2003 |
| WO | WO 03044000 | 5/2003 |
| WO | WO 03044009 | 5/2003 |
| WO | WO 03059267 | 7/2003 |
| WO | WO 03065983 | 8/2003 |
| WO | WO 03075660 | 9/2003 |
| WO | WO 03104207 | 12/2003 |
| WO | WO 03104208 | 12/2003 |
| WO | WO 2004011410 | 2/2004 |
| WO | WO 2004027047 A2 | 4/2004 |
| WO | WO 2004033427 | 4/2004 |
| WO | WO 2004037251 | 5/2004 |
| WO | WO 2004041264 | 5/2004 |
| WO | WO 2004056744 | 7/2004 |
| WO | WO 2004056745 | 7/2004 |
| WO | WO 2004058741 | 7/2004 |
| WO | WO 2004065351 | 8/2004 |
| WO | WO 2004089367 | 10/2004 |
| WO | WO 2004089380 | 10/2004 |
| WO | WO 2004089415 | 10/2004 |
| WO | WO 2004089416 | 10/2004 |
| WO | WO 2004089470 | 10/2004 |
| WO | WO 2004089471 | 10/2004 |
| WO | WO 2004089896 | 10/2004 |
| WO | WO 2004097002 | 11/2004 |
| WO | WO 2004103980 | 12/2004 |
| WO | WO 2004106294 | 12/2004 |
| WO | WO 2004112779 | 12/2004 |
| WO | WO 2004112781 | 12/2004 |
| WO | WO 2004112782 | 12/2004 |

(Continued)

OTHER PUBLICATIONS

Abstract JP2005170939.

(Continued)

*Primary Examiner*—Kamal A Saeed
(74) *Attorney, Agent, or Firm*—George W. Johnston; Dennis P. Tramaloni; Samuel H. Megerditchian

(57) ABSTRACT

Provided herein are compounds of the formula (I):

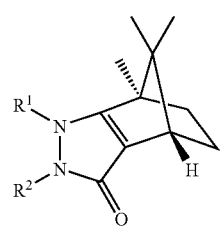

as well as pharmaceutically acceptable salts thereof, wherein the substituents are as those disclosed in the specification. These compounds, and the pharmaceutical compositions containing them, are useful for the treatment of diseases such as, for example, type II diabetes mellitus and metabolic syndrome.

22 Claims, No Drawings

FOREIGN PATENT DOCUMENTS

| WO | WO 2004112783 | 12/2004 |
|---|---|---|
| WO | WO 2004112784 | 12/2004 |
| WO | WO 2004112785 | 12/2004 |
| WO | WO 2004113310 | 12/2004 |
| WO | WO 2005016877 | 2/2005 |
| WO | WO 2005042513 | 5/2005 |
| WO | WO 2005044192 | 5/2005 |
| WO | WO 2005046685 | 5/2005 |
| WO | WO 2005047250 | 5/2005 |
| WO | WO 2005060963 | 7/2005 |

OTHER PUBLICATIONS

R. A. De Fronzo *Drugs* 1999, *58 Suppl. 1*, 29.
S. E. Inzucchi *JAMA* 2002, 287, 360.
R. C. Turner et al. *JAMA* 1999, 281, 2005.
M. Tadayyon and S. A. Smith *Expert Opin. Investig. Drugs* 2003, 12, 307.
M. Salas J. J. and Caro *Adv. Drug React. Tox. Rev.* 2002, 21, 205-217.
E. S. Ford et al. *JAMA* 2002, 287, 356.
Y. Kotolevtsev et al. *Proc. Natl. Acad. Sci. USA* 1997, 94, 14924.
N. M. Morton et al. *J. Biol. Chem.* 2001, 276, 41293.
H. Masuzaki et al. *Science*, 2001, 294, 2166.
B. R. Walker et al. *J. Clin. Endocrinol. Metab.* 1995, 80, 3155.
R. C. Andrews et al. *J. Clin. Enocrinol. Metab.* 2003, 88, 285.
T. C. Sandeep et al. *Proc. Natl. Acad. Sci USA* 2004, 101, 6734.
S. Diederich et al. *Eur. J. Endocrinol.* 2000, 142, 200.
R. A. S. Schweizer et al. *Mol. Cell. Endocrinol.* 2003, 212, 41.
H. Ansel et. al., Pharmaceutical Dosage Forms and Drug Delivery Systems (6th Ed. 1995) at pp. 196.
H. Ansel et. al., Pharmaceutical Dosage Forms and Drug Delivery Systems (6th Ed. 1995) at pp. 1456-1457.
Design of Prodrugs. Bundgaard H. ed. (Elsevier, 1985). H. Ansel et. al., Pharmaceutical Dosage Forms and Drug Delivery Systems (6th Ed. 1995) at pp. 108-109.
Krogsgaard-Larsen, et. al., Textbook of Drug Design and Development (2d Ed. 1996) at pp. 152-191.
W. W. Shumway et al. *J. Org. Chem.* 2001, 66, 5832-5839.
H. Staudinger and S. Schotz *Chem. Ber.* 1920, 53B, 1105-1124.
Chemical Abstracts 14:18286.
S. Nagai et al. *Chem. Pharm. Bull.* 1979, 27, 1764-1770.
H. Wahl, *Ber. Dtsch. Chem. Ges.* 1899, 32, 1987-1991.
A. R. Maguire et al. *Bioorg Med. Chem.* 2001, 9, 745-762.
Laboratoires Marinier FR 1.271.246 and FR 701.
G. H. Alt and J. P. Chupp *Tetrahedron Lett.* 1970, 36, 3155-3158.
P. C. Guha and N. K. Seshadriengar *Chem. Ber.* 1936, 69B, 1212-1218.
F. Ramirez and J. W. Sargent *J. Am. Chem. Soc.* 1955, 77, 6297-6306.
B. Jursic and N. Bregant *Synth. Commun.* 1989, 19, 2087-2094.
C. Dardonville et al. *New Journal of Chemistry* 1998, 22, 1421-1430.
P. Nair et al. *Tetrahedron* 1960, 11, 140-147.
M. Wolter et al. *Org. Letters* 2001, 3, 3803-3805.
A. Klapars et al. *J. Am. Chem. Soc.* 2001, 123, 7727-7729.
B. Renger *Synthesis* 1985, 856-806.
G. M. Coppola *J. Heterocycl. Chem.* 1987, 24, 1249-1251.
A. Greiner *Synthesis* 1989, 312-313.
T. Maruyama et al. *J. Chem. Soc. Perkin Trans. I* 1995, 733-734.
S.-K. Kang et al. *Synlett* 2002, 427-430.
J. H. M Lange et al. *Tetrahedron Lett.* 2002, 43, 1101-1104.
W. C Shakespeare *Tetrahedron Lett.* 1999, 40, 2035-2038.
D. M. T. Chan et al. *Tetrahedron Lett.* 1998, 39, 2933-2936.
W. W. K. R. Mederski et al. *Tetrahedron* 1999, 55, 12757-12770.
G. W. Kabalka and S. K. Guchhait *Org. Lett.* 2005, 5, 4129-4131.
O. V. Dyablo et al. *Chem. Heterocycl. Compd.* 2002, 38, 620-621.
N. J. Green et al. *Bioorg. Med. Chem.* 2003, 11, 2991-3013.
M. T. Makhija et al. *Bioorg. Med. Chem.* 2004, 12, 2317-2333.
M. van der Mey et al. *J. Med. Chem.* 2003, 46, 2008-2016.
R. West and H. F. Stewart *J. Am. Chem. Soc.* 1970, 92, 853-859.
M. Pal et al. *J. Med. Chem.* 2003, 46, 3975-3984.
E. W. Parnell *J. Chem. Soc.* 1959, 2363-2365.
L. Ondi et al. *Eur. J. Org. Chem.* 2004, 3714-3718.
N. Guillot et al. *Tetrahedron* 1990, 46, 3897-3908.
J. P. Demers and D. H. Klaubert *Tetrahedron Lett.* 1987, 28, 4933-4934.
F. D. King and D. R. M. Walton *Synthesis* 1975, 738-739.
R. C. Larock, VCH Publishers, Inc. New York, 1989, p. 313.
R. C. Larock, VCH Publishers, Inc. New York, 1989, p. 322-393.
R. C. Larock, VCH Publishers, Inc. New York, 1989, p. 353-363.
R. C. Larock, VCH Publishers, Inc. New York, 1989, 381-382.
Advanced Organic Chemistry [J. March, $3^{rd}$ Edition, John Wiley & Sons, Inc. New York, 1985], on pp. 382-384.
R. C. Larock, VCH Publishers, Inc. New York, 1989, p. 316-318.
R. C. Larock, VCH Publishers, Inc. New York, 1989, p. 345-346.
Advanced Organic Chemistry [J. March, 3Edition, John Wiley & Sons, Inc. New York, 1985], on p. 1155.
C. Glende et al. *Mutation Res.* 2002, 515, 15-38.
A. Fensome et al.; M. Gravel et al. *J. Org. Chem* 2002, 67, 3-15.
D. Florentin et al. *J. Heterocycl. Chem.* 1976, 13, 1265-1272.
M. P. Groziak et al. *J. Am. Chem. Soc.* 1994, 116, 7597-7605.
W. Li et al. *J. Org. Chem.* 2002, 67, 5394-5397.
S. L. Gilat et al. *Chem. Eur. J.* 1995, 1, 275-284.
W. J. Dale et al. *J. Org. Chem.* 1962, 27, 2598-2603.
T. E. Jacks et al. *Org. Proc. Res. Dev.* 2004, 8, 201-212.
F. C. Fischer et al. *Recl. Trav. Chim. Pays-Bas* 1974, 93, 21-24.
M. Takeshita et al. *J. Org. Chem.* 1998, 63, 6643-6649.
K. A. Jensen et al. *Acta Chem Scand.* 1968, 22, 1-50.
M.-F. Pinto et al. *Synth. Commun.* 2002, 32, 3603-3610.
N. Brosse et al. *J. Org. Chem.* 2000, 65, 4370.
H. Hilpert *Tetrahedron* 2001, 57, 7675-7683.
N. I. Ghali et al. *J. Org. Chem.* 1981, 46, 5413-5414.
A. Koziara et al. *Synth. Commun.* 1995, 25, 3805-3812.
A. R. Maguire et al. *Bioorg. Med. Chem.* 2001, 9, 745-762.
Abstract XP002401736.

\* cited by examiner

PYRAZOLONES AS INHIBITORS OF 11β-HYDROXYSTEROID DEHYDROGENASE

PRIORITY TO RELATED APPLICATIONS

This application claims the benefit of priority to U.S. Provisional Application Ser. No. 60/713,074, filed Aug. 31, 2005, and U.S. Provisional Application Ser. No. 60/817,255, filed Jun. 29, 2006, which is hereby incorporated by reference in its entirety.

FIELD OF THE INVENTION

The invention relates to inhibitors of 11β-hydroxysteroid dehydrogenase. The inhibitors include, for example, pyrazolones and derivatives thereof and are useful for the treatment of diseases such as type II diabetes mellitus and metabolic syndrome.

All documents cited or relied upon below are expressly incorporated herein by reference.

BACKGROUND OF THE INVENTION

Diabetes mellitus is a serious illness that affects an increasing number of people across the world. Its incidence is escalating parallel to the upward trend of obesity in many countries. The serious consequences of diabetes include increased risk of stroke, heart disease, kidney damage, blindness, and amputation.

Diabetes is characterized by decreased insulin secretion and/or an impaired ability of peripheral tissues to respond to insulin, resulting in increased plasma glucose levels. There are two forms of diabetes: insulin-dependent and non-insulin-dependent, with the great majority of diabetics suffering from the non-insulin-dependent form of the disease, known as type 2 diabetes or non-insulin-dependent diabetes mellitus (NIDDM). Because of the serious consequences, there is an urgent need to control diabetes.

Treatment of NIDDM generally starts with weight loss, a healthy diet and an exercise program. These factors are especially important in addressing the increased cardiovascular risks associated with diabetes, but they are generally ineffective in controlling the disease itself. There are a number of drug treatments available, including insulin, metformin, sulfonylureas, acarbose, and thiazolidinediones. However, each of these treatments has disadvantages, and there is an ongoing need for new drugs to treat diabetes.

Metformin is an effective agent that reduces fasting plasma glucose levels and enhances the insulin sensitivity of peripheral tissue. Metformin has a number of effects in vivo, including an increase in the synthesis of glycogen, the polymeric form in which glucose is stored [R. A. De Fronzo *Drugs* 1999, 58 *Suppl.* 1, 29]. Metformin also has beneficial effects on lipid profile, with favorable results on cardiovascular health. Treatment with metformin leads to reductions in the levels of LDL cholesterol and triglycerides [S. E. Inzucchi *JAMA* 2002, 287, 360]. However, over a period of years, metformin loses its effectiveness [R. C. Turner et al. *JAMA* 1999, 281, 2005] and there is consequently a need for new treatments for diabetes.

Thiazolidinediones are activators of the nuclear receptor peroxisome-proliferator activated receptor-gamma. They are effective in reducing blood glucose levels, and their efficacy has been attributed primarily to decreasing insulin resistance in skeletal muscle [M. Tadayyon and S. A. Smith *Expert Opin. Investig. Drugs* 2003, 12, 307]. One disadvantage associated with the use of thiazolidinediones is weight gain.

Sulfonylureas bind to the sulfonylurea receptor on pancreatic beta cells, stimulate insulin secretion, and consequently reduce blood glucose levels. Weight gain is also associated with the use of sulfonylureas [S. E. Inzucchi *JAMA* 2002, 287, 360] and, like metformin, they lose efficacy over time [R. C. Turner et al. *JAMA* 1999, 281, 2005]. A further problem often encountered in patients treated with sulfonylureas is hypoglycemia [M. Salas J. J. and Caro *Adv. Drug React. Tox. Rev.* 2002, 21, 205-217].

Acarbose is an inhibitor of the enzyme alpha-glucosidase, which breaks down disaccharides and complex carbohydrates in the intestine. It has lower efficacy than metformin or the sulfonylureas, and it causes intestinal discomfort and diarrhea which often lead to the discontinuation of its use [S. E. Inzucchi *JAMA* 2002, 287, 360]

Because none of these treatments is effective over the long term without serious side effects, there is a need for new drugs for the treatment of type 2 diabetes.

The metabolic syndrome is a condition where patients exhibit more than two of the following symptoms: obesity, hypertriglyceridemia, low levels of HDL-cholesterol, high blood pressure, and elevated fasting glucose levels. This syndrome is often a precursor of type 2 diabetes, and has high prevalence in the United States with an estimated prevalence of 24% (E. S. Ford et al. *JAMA* 2002, 287, 356). A therapeutic agent that ameliorates the metabolic syndrome would be useful in potentially slowing or stopping the progression to type 2 diabetes.

In the liver, glucose is produced by two different processes: gluconeogenesis, where new glucose is generated in a series of enzymatic reactions from pyruvate, and glycolysis, where glucose is generated by the breakdown of the polymer glycogen.

Two of the key enzymes in the process of gluconeogenesis are phosphoenolpyruvate carboxykinase (PEPCK) which catalyzes the conversion of oxalacetate to phosphoenolpyruvate, and glucose-6-phosphatase (G6Pase) which catalyzes the hydrolysis of glucose-6-phosphate to give free glucose. The conversion of oxalacetate to phosphoenolpyruvate, catalyzed by PEPCK, is the rate-limiting step in gluconeogenesis. On fasting, both PEPCK and G6Pase are upregulated, allowing the rate of gluconeogenesis to increase. The levels of these enzymes are controlled in part by the corticosteroid hormones (cortisol in human and corticosterone in mouse). When the corticosteroid binds to the corticosteroid receptor, a signaling cascade is triggered which results in the upregulation of these enzymes.

The corticosteroid hormones are found in the body along with their oxidized 11-dehydro counterparts (cortisone and 11-dehydrocorticosterone in human and mouse, respectively), which do not have activity at the glucocorticoid receptor. The actions of the hormone depend on the local concentration in the tissue where the corticosteroid receptors are expressed. This local concentration can differ from the circulating levels of the hormone in plasma, because of the actions of redox enzymes in the tissues. The enzymes that modify the oxidation state of the hormones are 11beta-hydroxysteroid dehydrogenases forms I and II. Form I (11β-HSD1) is responsible for the reduction of cortisone to cortisol in vivo, while form II (11β-HSD2) is responsible for the oxidation of cortisol to cortisone. The enzymes have low homology and are expressed in different tissues. 11β-HSD1 is highly expressed in a number of tissues including liver, adipose tissue, and brain, while 11β-HSD2 is highly expressed in mineralocorticoid target tissues, such as kidney and colon. 11β-HSD2 prevents the binding of cortisol to the mineralocorticoid receptor, and defects in this enzyme have been found to be associated with the syndrome of apparent mineralocorticoid excess (AME).

Since the binding of the 11β-hydroxysteroids to the corticosteroid receptor leads to upregulation of PEPCK and therefore to increased blood glucose levels, inhibition of 11β-HSD1 is a promising approach for the treatment of diabetes. In addition to the biochemical discussion above, there is evidence from transgenic mice, and also from small clinical studies in humans, that confirm the therapeutic potential of the inhibition of 11β-HSD1.

Experiments with transgenic mice indicate that modulation of the activity of 11β-HSD1 could have beneficial therapeutic effects in diabetes and in the metabolic syndrome. For example, when the 11β-HSD1 gene is knocked out in mice, fasting does not lead to the normal increase in levels of G6Pase and PEPCK, and the animals are not susceptible to stress- or obesity-related hyperglycemia. Moreover, knockout animals which are rendered obese on a high-fat diet have significantly lower fasting glucose levels than weight-matched controls (Y. Kotolevtsev et al. *Proc. Natl. Acad. Sci. USA* 1997, 94, 14924). 11β-HSD1 knockout mice have also been found to have improved lipid profile, insulin sensitivity, and glucose tolerance (N. M. Morton et al. *J. Biol. Chem.* 2001, 276, 41293). The effect of overexpressing the 11β-HSD1 gene in mice has also been studied. These transgenic mice displayed increased 11β-HSD1 activity in adipose tissue, and they also exhibit visceral obesity which is associated with the metabolic syndrome. Levels of the corticosterone were increased in adipose tissue, but not in serum, and the mice had increased levels of obesity, especially when on a high-fat diet. Mice fed on low-fat diets were hyperglycemic and hyperinsulinemic, and also showed glucose intolerance and insulin resistance (H. Masuzaki et al. *Science,* 2001, 294, 2166).

The effects of the non-selective 11β-hydroxysteroid dehydrogenase inhibitor carbenoxolone have been studied in a number of small trials in humans. In one study, carbenoxolone was found to lead to an increase in whole body insulin sensitivity, and this increase was attributed to a decrease in hepatic glucose production (B. R. Walker et al. *J. Clin. Endocrinol. Metab.* 1995, 80, 3155). In another study, decreased glucose production and glycogenolysis in response to glucagon challenge were observed in diabetic but not healthy subjects (R. C. Andrews et al. *J. Clin. Enocrinol. Metab.* 2003, 88, 285). Finally, carbenoxolone was found to improve cognitive function in healthy elderly men and also in type 2 diabetics (T. C. Sandeep et al. *Proc. Natl. Acad. Sci USA* 2004, 101, 6734).

A number of non-specific inhibitors of 11β-HSD1 and 11β-HSD2 have been identified, including glycyrrhetinic acid, abietic acid, and carbenoxolone. In addition, a number of selective inhibitors of 11β-HSD1 have been found, including chenodeoxycholic acid, flavanone and 2'-hydroxyflavanone (S. Diederich et al. *Eur. J. Endocrinol.* 2000, 142, 200 and R. A. S. Schweizer et al. *Mol. Cell. Endocrinol.* 2003, 212, 41).

WO 2004089470, WO 2004089416 and WO 2004089415 (Novo Nordisk A/S) relate to compounds as inhibitors of 11bHSD1 useful for the treatment of metabolic syndrome and related diseases and disorders.

WO 0190090, WO 0190091, WO 0190092, WO 0190093, WO 03043999 (Biovitrum AB) relate to compounds as inhibitors of 11β-HSD1. WO 2004113310, WO 2004112779, WO 2004112781, WO 2004112782, WO 2004112783 and WO 2004112784 relate to the method of use of some of these compounds for the promotion of wound healing.

WO 0190094, WO 03044000, WO 03044009, and WO 2004103980 (Biovitrum AB) relate to compounds as inhibitors of 11β-HSD1. WO 2004112785 relates to the method of use of some of these compounds for the promotion of wound healing.

WO 03065983, WO 03075660, WO 03104208, WO 03104207, US 20040133011, WO 2004058741, and WO 2004106294 (Merck & Co., Inc.) relate to compounds as inhibitors of 11β-HSD1. US 2004122033 relates to the combination of an appetite suppressant with inhibitors of 11β-HSD1 for the treatment of obesity, and obesity-related disorders.

WO 2005016877 (Merck & Co., Inc.); WO 2004065351 (Novartis); WO 2004056744 and WO 2004056745 (Janssen Pharmaceutica N. V.); WO 2004089367; WO 2004089380 and WO 2004089896 (Novo Nordisk A/S) relate to compounds as inhibitors of 11β-HSD1. Further, US 20050137209 (AGY Therapeutics, Inc.) relates to methods and compositions for the treatment of neurological disorders through inhibition of 11β-HSD1; US 20050137209 (AGY Therapeutics, Inc.) relates to methods and compositions for the treatment of neurological disorders through inhibition of 11β-HSD 1; JP 2005170939 (Takeda Chemical Industries, Ltd.) relates to inhibitors of 11β-HSD1; WO 2004097002 (The Miriam Hospital) relate to the use of inhibitors of 11β-HSD1 as a method for increasing male fertility; WO 2005060963 (Pfizer, Inc.) relates to compounds as inhibitors of 11β-HSD1; WO 2004089471 (Novo Nordisk A/S) discloses pyrazolo[1,5-a]pyrimidines as inhibitors of 11β-HSD1; WO 2005042513 (Sterix Limited) relates to phenyl carboxamide and sulfonamide derivatives as inhibitors of 11β-HSD1. WO 2004037251 (Sterix Limited) relates sulfonamides as inhibitors of 11β-HSD1; WO 2004027047A2 (Hartmut Hanauske-Abel) relates to inhibitors of 11β-HSD1; WO 2004011410, WO 2004033427, WO 2004041264, WO 2005046685, and WO 2005047250 (AstraZeneca UK Limited) relate to inhibitors of 11β-HSD1; and WO 2005044192 (Amgen SF LLC and Japan Tobacco Inc) relate to inhibitors of 11β-HSD 1.

WO 2004089415 (Novo Nordisk A/S) relates to the use of an inhibitor of 11β-HSD1 in combination with an agonist of the glucocorticoid receptor for the treatment of diseases including cancer and diseases involving inflammation. WO 2004089416 (Novo Nordisk A/S) relates to the use of an inhibitor of 11β-HSD1 in combination with an antihypertensive agent for the treatment of diseases including insulin resistance, dyslipidemia and obesity. WO 2004089470 (Novo Nordisk A/S) relates to substituted amides as inhibitors of 11β-HSD 1.

WO 02076435A2 (The University of Edinburgh) relates to the use of an agent which lowers levels of 11β-HSD1 in the manufacture of a composition for the promotion of an atheroprotective lipid profile. Agents mentioned as inhibitors of 11β-HSD 1 include carbenoxolone, 11-oxoprogesterone, 3α,17,21-trihydroxy-5β-pregnan-3-one, 21-hydroxy-pregn-4-ene-3,11,20-trione, androst-4-ene-3,11,20-trione and 3β-hydroxyandrost-5-en-17-one.

WO 03059267 (Rhode Island Hospital) relates to a method for treating a glucocorticoid-associated state by the administration of a 11β-HSD1 inhibitor such as 11-ketotestosterone, 11-keto-androsterone, 11-keto-pregnenolone, 11-keto-dehydro-epiandrostenedione, 3α,5α-reduced-11-ketoprogesterone, 3α,5α-reduced-11-ketotestosterone, 3α,5α-reduced-11-keto-androstenedione, or 3α,5α-tetrahydro-11β-dehydro-corticosterone.

A need exits in the art, however, for 11β-HSD1 inhibitors that have efficacy for the treatment of diseases such as, for example, type II diabetes mellitus and metabolic syndrome.

SUMMARY OF THE INVENTION

In one embodiment of the invention, provided is a compound of the formula (I):

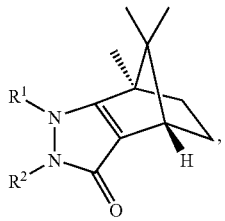

(I)

wherein:
R$^1$ is aryl, heteroaryl, aralkyl, heteroaralkyl, lower alkyl, lower-alkoxy-benzyl, lower-alkoxy-carbonyl-lower-alkyl, halo-lower-alkyl, hydroxy-lower-alkyl, lower-alkoxy-lower-alkyl, (CH$_2$)s-aryl, (CH$_2$)s-heteroaryl or (CH$_2$)s-cycloalkyl, where said aryl, heteroaryl, aralkyl, heteroaralkyl (CH$_2$)s-aryl, (CH2)s-heteroaryl or (CH$_2$)s-cycloalkyl is unsubstituted or substituted with one or more substituents selected from the group consisting of halogen, lower alkyl, lower alkoxy, cyano, lower-alkoxy-carbonyl, halo-lower-alkyl, phenyl-(oxo-lower-alkyl) and hydroxy-lower-alkyl;
p is 0 or 1;
s is 0, 1 or 2; and
R$^2$ is phenyl, which may be unsubstituted or substituted with one or more substituents selected from the group consisting of halogen, hydroxy, halo-lower-alkyl, lower alkoxy, trifluoromethoxy, aminocarbonyl, lower-alkyl,
  nitro, cyano, sulfonamido, lower-alkyl-sulfonyl, lower acyl and lower-alkoxy-carbonyl,
halo-lower-alkyl,
unsubstituted or substituted naphthyl,
biphenyl, which may be unsubstituted or substituted with one or more substituents selected from the group consisting of acetyl, halogen, lower-alkoxy and lower-alkyl,
a 5- or 6-membered monocyclic heterocycle with 1-3 atoms selected from N,
and S, which may be unsubstituted or substituted with halogen, lower-alkyl, unsubstitued or substituted phenyl, or halo-lower-alkyl, or unsubstituted or substituted benzothiophene, with the proviso that the following compounds are excluded:
1,7,8,8-Tetramethyl-2-phenyl-1,2,4,5,6,7-hexahydro-4,7-methano-indazol-3-one,
2,7,8,8-Tetramethyl-1-phenyl-1,2,4,5,6,7-hexahydro-4,7-methano-indazol-3-one,
1,7,8,8-Tetramethyl-2-naphthalen-2-yl-1,2,4,5,6,7-hexahydro-4,7-methano-indazol-3-one,
1,7,8,8-Tetramethyl-2-p-tolyl-1,2,4,5,6,7-hexahydro-4,7-methano-indazol-3-one,
2-(4-Methoxy-phenyl)-1,7,8,8-tetramethyl-1,2,4,5,6,7-hexahydro-4,7-methano-indazol-3-one and
1,7,8,8-Tetramethyl-2-o-tolyl-1,2,4,5,6,7-hexahydro-4,7-methano-indazol-3-one.

In another embodiment of the present invention, a pharmaceutical composition is provided comprising a therapeutically effective amount of a compound according to formula (I) and a pharmaceutically acceptable carrier.

In a further embodiment of the present invention, a method for the treatment of a metabolic disorder in a patient in need thereof is provided, comprising administering to said patient a therapeutically effective amount of a compound according to formula (I).

DETAILED DESCRIPTION OF THE INVENTION

The present invention pertains to inhibitors of 11β-HSD 1. In a preferred embodiment, the invention provides for pharmaceutical compositions comprising pyrazolones of the formula (I):

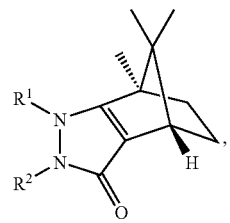

(I)

as well as pharmaceutically acceptable salts thereof, that are useful as inhibitors of 11β-HSD1.

The compounds of formula I can contain several asymmetric centers and can be present in the form of optically pure enantiomers and mixtures of enantiomers such as, for example, racemates.

The term "asymmetric carbon atom" (C*) means a carbon atom with four different substituents. According to the Cahn-Ingold-Prelog Convention the asymmetric carbon atom can be of the "R" or "S" configuration.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

In this specification the term "aryl" is used to mean a mono- or polycyclic aromatic ring system, in which the rings may be carbocyclic or may contain one or more atoms selected from O, S, and N. Examples of aryl groups are phenyl, pyridyl, benzimidazolyl, benzofuranyl, benzothiazolyl, benzothiophenyl, cinnolinyl, furyl, imidazo[4,5-c]pyridinyl, imidazolyl, indolyl, isoquinolinyl, isoxazolyl, naphthyl, [1,7] naphthyridinyl, oxadiazolyl, oxazolyl, phthalazinyl, purinyl, pyidazinyl, pyrazolyl, pyrido[2,3-d]pyrimidinyl, pyrimidinyl, pyrimido[3,2-c]pyrimidinyl, pyrrolo[2,3-d]pyrimidinyl, pyrrolyl, quinazolinyl, quinolinyl, quinoxalinyl, tetrazolyl, thiadiazolyl, thiazolyl, thiophenyl, triazolyl, and the like.

As used herein, the term "alkyl" means, for example, a branched or unbranched, cyclic (i.e., cycloalkyl) or acyclic, saturated (partially saturated if cyclic) or unsaturated hydrocarbyl radical which may be substituted or unsubstituted. Where cyclic, the alkyl group is preferably C$_3$ to C$_{12}$, more preferably C$_3$ to C$_{10}$, more preferably C$_3$ to C$_7$. Where acyclic, the alkyl group is preferably C$_1$ to C$_{10}$, more preferably C$_1$ to C$_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic or acyclic, saturated (partially saturated if cyclic) or unsaturated hydrocarbyl radical wherein said cyclic lower alkyl group is $C_3$, $C_4$, $C_5$, $C_6$ or $C_7$, and wherein said acyclic lower alkyl group is $C_1$, $C_2$, $C_3$ or $C_4$, and is preferably selected from methyl, ethyl, propyl (n-propyl or isopropyl) or butyl (n-butyl, sec-butyl, isobutyl or tertiary-butyl). It will be appreciated therefore that the term "lower alkyl" as used herein includes lower alkyl (branched or unbranched), lower alkenyl (branched or unbranched), lower alkynyl (branched or unbranched), cycloloweralkyl, cycloloweralkenyl and cycloloweralkynyl.

As used herein, the term "aralkyl", alone or in combination, signifies an alkyl or cycloalkyl group as previously defined in which one or more, preferably one hydrogen atom has been replaced by an aryl group as previously defined. Preferred are benzyl, benzyl substituted with hydroxy, alkoxy or halogen, preferably fluorine. Particularly preferred is benzyl The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as oxo, alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono-or di-alkylaminocarbonylalkyl, arylaminocarbonyl), carbamates (e.g. alkoxycarbonylamino, arloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthyridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substituents present, preferably 1 substituent.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means, for example, a fluorine, chlorine, bromine or iodine radical, preferably a fluorine, chlorine or bromine radical, and more preferably a fluorine or chlorine radical.

"Pharmaceutically acceptable salt" refers to conventional acid-addition salts or base-addition salts that retain the biological effectiveness and properties of the compounds of formula I and are formed from suitable organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a well known technique which is used in attempting to improve properties involving physical or chemical stability, e.g., hygroscopicity, flowability or solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids are those in which the hydrogen is replaced with -lower alkyl which is optionally substituted, e.g., with heterocycle, cycloalkyl, etc. Examples of substituted lower alkyl esters are those in which lower alkyl is substituted with pyrrolidine, piperidine, morpholine, N-methylpiperazine, etc. The group which is cleaved in vivo may be, for example, ethyl, morpholino ethyl, and diethylamino ethyl. In connection with the present invention, —$CONH_2$ is also considered an ester, as the —$NH_2$ may be cleaved in vivo and replaced with a hydroxy group, to form the corresponding carboxylic acid.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

General Synthesis of Compounds According to the Invention

The compounds of the present invention can be prepared by any conventional means. Suitable processes for synthesizing these compounds are provided in the examples. Generally, compounds of formula I can be prepared according to Scheme 1, or Scheme 3 (see below). The sources of the starting materials for these reactions are also described. Note that unless otherwise indicated, the structures below show relative stereochemistry, and the chemical transformations described below can be carried out on compounds derived from racemic camphor or from either of the enantiomers.

Preparation of Compounds of the Invention
According to Scheme 1

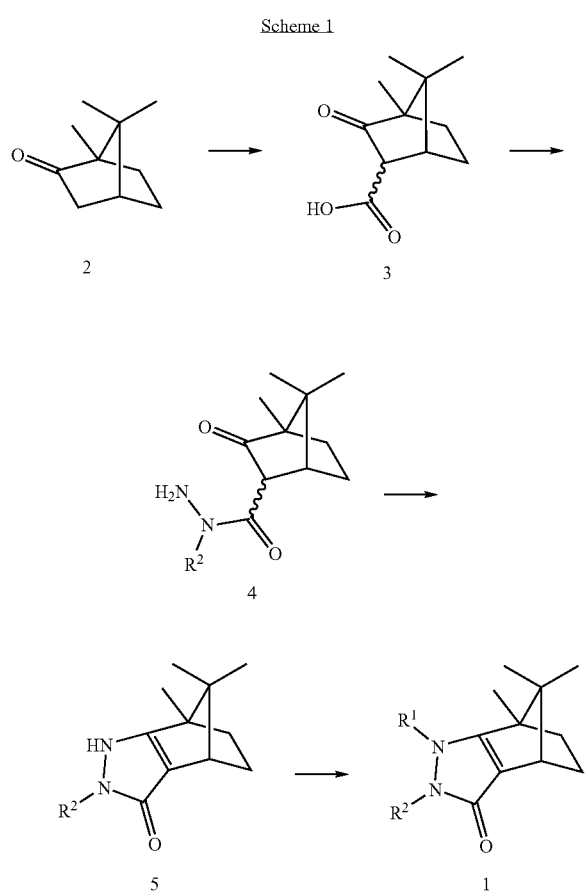

Compounds of formula 1 can be prepared from camphor which has formula 2 and which is commercially available as the racemate or as either enantiomer, for example from Aldrich Chemical Company, Milwaukee, Wis. Thus camphor is treated with a strong base such as lithium diisopropylamide or lithium hexamethyldisilazide in an inert solvent such as tetrahydrofuran at low temperature, for example about −78 degrees. The resulting solution is then added to dry ice to give a mixture of endo- and exo-camphorcarboxylic acids, or alternatively dry carbon dioxide gas is bubbled through a solution of the anion to give the same product. Conditions suitable for this reaction can be found in the literature, for example in W. W. Shumway et al. *J. Org. Chem.* 2001, 66, 5832-5839. Racemic 3-camphorcarboxylic acid is available commercially from the SALOR catalogue of Aldrich Chemical Company, Milwaukee, Wis.

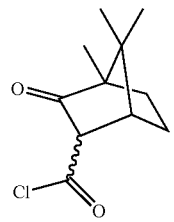

The resulting keto-acid of formula 3 can then be converted to an aryl-hydrazide of formula 4 where R2 is aryl using one of a number of procedures that are familiar to one of average skill in the art of organic synthesis. For example, the keto-acid of formula 3 can be converted to the acid chloride of formula 13 by treatment with a chlorinating agent, such as thionyl chloride, either neat or in an inert solvent such as benzene at a temperature between about −5 degrees and about 80 degrees, preferably between about −5 degrees and about room temperature. Conditions suitable for this reaction can be found in the literature, for example in H. Staudinger and S. Schotz *Chem. Ber.* 1920, 53B, 1105-1124 Chemical Abstracts 14:18286; in S. Nagai et al. *Chem. Pharm. Bull.* 1979, 27, 1764-1770; and in W. W. Shumway et al. *J. Org. Chem.* 2001, 66, 5832-5839. The acid chloride is then treated with an aryl-hydrazine of formula ArNHNH2 in an inert solvent such as an aromatic hydrocarbon such as benzene at about room temperature to give a hydrazide of formula 4. This hydrazide can then be treated with aqueous sodium hydroxide at about 100 degrees to give the pyrazolone of formula 5 where R2 is aryl. Conditions for this reaction can be found in the literature, for example in A. Esanu GB 2 157 690. Alternatively, the hydrazide can be treated with concentrated hydrochloric acid to affect the cyclization. Conditions for this reaction can be found in the literature, for example in H. Wahl, *Ber. Dtsch. Chem. Ges.* 1899, 32, 1987-1991.

Alternatively, a pyrazolone of formula 5 can be prepared from the keto-acid of formula 3 by conversion of the keto-acid to an ester followed by reaction with an aryl-hydrazine. For example, the keto-acid of formula 3 can be converted to the ethyl ester of formula 6 (see below) with sulfuric acid in ethanol at around room temperature. The resulting ethyl ester is then treated with an aryl-hydrazine in the presence of a chlorinating agent such as phosphorus trichloride or phosphorus oxychloride in an inert solvent such as toluene at about 100 degrees. Conditions suitable for this reaction can be found in the literature, for example in Laboratoires Marinier FR 1.271.246 and FR 701; and in H. Wahl *Chem. Ber.* 1899, 32, 1987-1991.

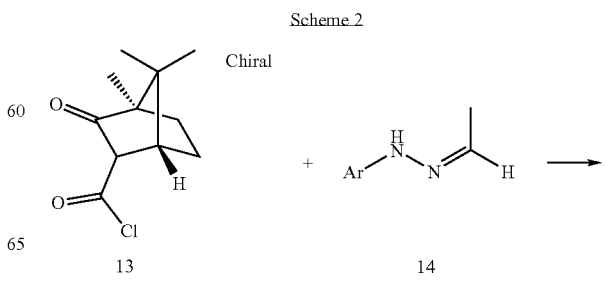

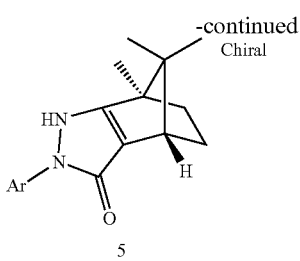

As a further alternative, the pyrazolone of formula 5 can be prepared by reaction of the acid chloride of formula 13 with the ethylidene hydrazone of formula 14. This reaction is conveniently carried out in the presence of an aromatic base such as pyridine in an inert solvent such as a chlorinated hydrocarbon (e.g., 1,2-dichloroethane) at a temperature about 50° C. The resulting hydrazide can be converted to the desired pyrazolone by treatment with acid, such as a mixture of hydrochloric acid and glacial acetic acid at a temperature about 100° C. The ethylidene hydrazone of formula 14 is prepared from an aryl-hydrazine of formula ArNHNH$_2$ using the procedure described in A. R. Maguire et al. *Bioorg. Med. Chem.* 2001, 9, 745-762.

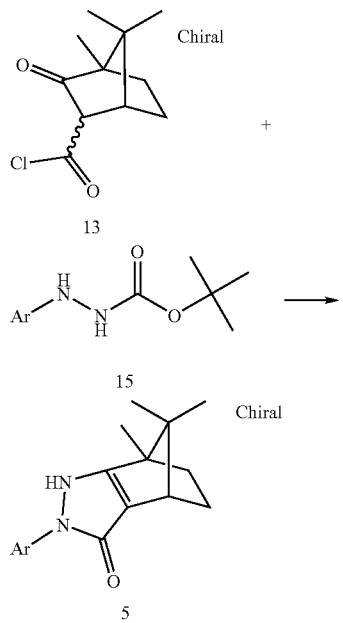

An additional approach to the synthesis of pyrazolone 5 is shown in Scheme 2b. According to this approach, the acid chloride of formula 13 can be reacted with a tert-butoxy-carbonyl-protected hydrazine of formula 15 and the intermediate can be cyclized in the presence of acid. This reaction is conveniently carried out by heating the acid chloride of formula 13 with the tert-butoxy-carbonyl-protected hydrazine of formula 15 and a base, such as triethylamine or pyridine, in the presence of an inert solvent such as 1,2-dichloroethane at a temperature about 100° C. to give the intermediate hydrazide, and then treating this with hydrochloric acid again in a solvent (such as a mixture of dioxane and acetic acid), and heating again at about 100° C.

The pyrazolone of formula 5 can be reacted with an alkyl halide or an aralkyl halide to give the compound of the invention of formula 1. The reaction can conveniently be carried out by treatment of the pyrazolone of formula 5 with an electrophile (for example, methyl sulfate, ethyl iodide, or benzyl bromide) in an inert solvent such as N,N-dimethylformamide at a temperature about 100° C. The reaction can also be carried out in the additional presence of a base (such as sodium hydroxide) again in an inert solvent, such as for example in aqueous sodium hydroxide solution in the optional additional presence of ethanol as a co-solvent. Conditions suitable for this reaction can be found in the literature, for example in Laboratoires Marinier FR 1.271.246 and FR 701; and in G. H. Alt and J. P Chupp *Tetrahedron Lett.* 1970, 36, 3155-3158. In the presence of base, the alkylation reaction typically gives a mixture of products which have been alkylated on nitrogen or oxygen. These products are typically easily separable using processes well known to one of skill in the art such as recrystallization or chromatography. Additionally, the pyrazolone of formula 5 can be converted to the compound of the invention of formula 1 by treatment with benzoyl chloride in aqueous potassium hydroxide solution at about 0° C. to give the benzoyloxypyrazole, followed by treatment with an alkyl halide or aralkyl halide at about 100° C. to give the N1-alkyl- or N1-aralkyl-3-benzoyloxypyrazole, followed by treatment with aqueous sodium hydroxide solution at about 100° C. to give the compound of formula 1. Conditions suitable for this reaction can be found in the literature, for example in H. Wahl *Chem. Ber.* 1899, 32, 1987-1991.

Preparation of Compounds of the Invention
According to Scheme 3

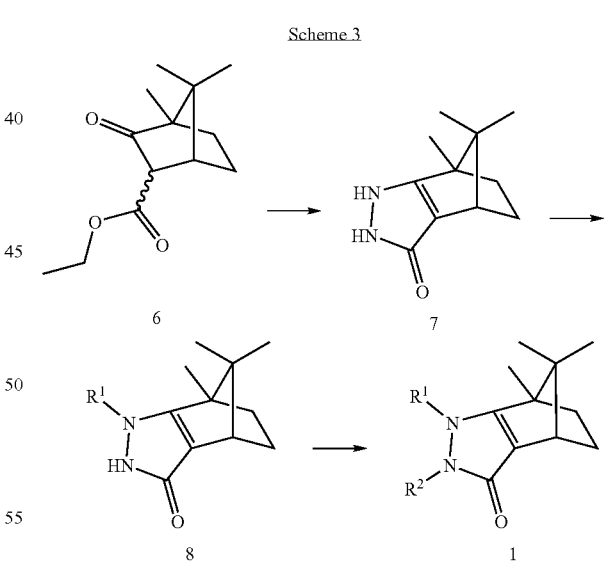

The keto-ester of formula 6, prepared as described above, can be treated with hydrazine in an inert solvent such as ethanol at reflux to give a pyrazolone of formula 7. For convenient conditions, see P. C. Guha and N. K. Seshadriengar *Chem. Ber.* 1936, 69B, 1212-1218, or F. Ramirez and J. W. Sargent *J. Am. Chem. Soc.* 1955, 77, 6297-6306. The pyrazolone of formula 7 can be converted to the substituted pyrazolone of formula 8 using reactions analogous to those described above for the conversion of a compound of formula 5 to a compound of formula 1. For an example of appropriate conditions, see B. Jursic and N. Bregant *Synth. Commun.* 1989, 19, 2087-2094. The substituted pyrazolone of formula 8 is then converted to the compound of formula 1 using one of a variety of reactions that are known in the art. For example, in the case where R2 is an aryl group, an SNAR nucleophilic aromatic substitution reaction or a copper-catalyzed arylation reaction can be used. For example, the pyrazolone of formula 8 can be treated with an electron-deficient aromatic ring bearing a leaving group (for example, 2,4-dinitro-fluorobenzene) in an inert solvent such as ethanol at the reflux temperature. See for example C. Dardonville et al. *New Journal of Chemistry* 1998, 22, 1421-1430; or P. Nair et al. *Tetrahedron* 1960, 11, 140-147. As a further example, the pyrazolone of formula 8 can be treated with a halo-aromatic compound (such as a brominated or iodinated benzene derivative or heterocycle) in the presence of a copper catalyst such as copper(I) iodide or copper(I) chloride or copper(II) oxide or copper on silica, in the presence of a base such as cesium carbonate or potassium carbonate or potassium phosphate or sodium tert-butoxide and in the optional additional presence of a ligand (for example 1,10-phenanthroline or trans-1,2-cyclohexanediamine or ethylenediamine) in an inert solvent such as dimethylformamide or dioxane or xylene or N-methylpyrrolidone at a temperature between about 80 degrees and about 150 degrees. Examples of suitable conditions can be found in the literature, for example in M. Wolter et al. *Org. Letters* 2001, 3, 3803-3805; in A. Klapars et al. *J. Am. Chem. Soc.* 2001, 123, 7727-7729; in B. Renger *Synthesis* 1985, 856-806; in G. M. Coppola *J. Heterocycl. Chem.* 1987, 24, 1249-1251; in A. Greiner *Synthesis* 1989, 312-313; in T. Maruyama et al. *J. Chem. Soc. Perkin Trans. I* 1995, 733-734; in S.-K. Kang et al. *Synlett* 2002, 427-430; and in J. H. M Lange et al. *Tetrahedron Lett.* 2002, 43, 1101-1104. It is also possible to carry out a similar reaction using palladium catalysis in place of copper catalysis (see W. C Shakespeare *Tetrahedron Lett.* 1999, 40, 2035-2038). As a third example, the pyrazolone of formula 8 can be treated with aryl-boronic acid in the presence of a copper catalyst such as copper(II) acetate in the presence of a base such as a mixture of triethylamine and pyridine in an inert solvent such as dichloromethane at about room temperature. Examples of suitable conditions can be found in the literature, for example in D. M. T. Chan et al. *Tetrahedron Lett.* 1998, 39, 2933-2936; and in W. W. K. R. Mederski et al. *Tetrahedron* 1999, 55, 12757-12770. In the case where R2 is a benzylic group or a group of formula —CH$_2$Het where Het is a heterocycle, the compound of formula 1 can be made by reaction of the pyrazolone of formula 8 with the appropriate benzyl halide or chloromethyl- or bromomethyl-heterocycle. The reaction can be conveniently carried out by treating the pyrazolone of formula 8 with the appropriate electrophile in the absence of base in an inert solvent such as N,N-dimethylformamide at a temperature around 100° C. In certain cases, for example where the R2 group contains a nucleophilic substructure such as a pyrazole, it will be appropriate to use a benzyl halide or chloromethyl- or bromomethyl-heterocycle which bears an additional protective group masking the nucleophile, for example a trityl group. An additional step will then be required to complete the synthesis of the compound of formula 1. Examples of R2 groups bearing nucleophilic substructures will be apparent to one of skill in the art of organic synthesis. One example is 1H-pyrazole, where the trityl group can be used as a convenient protective group. The trityl group is conveniently removed by treatment with trifluoroacetic acid in an inert solvent such as dichloromethane.

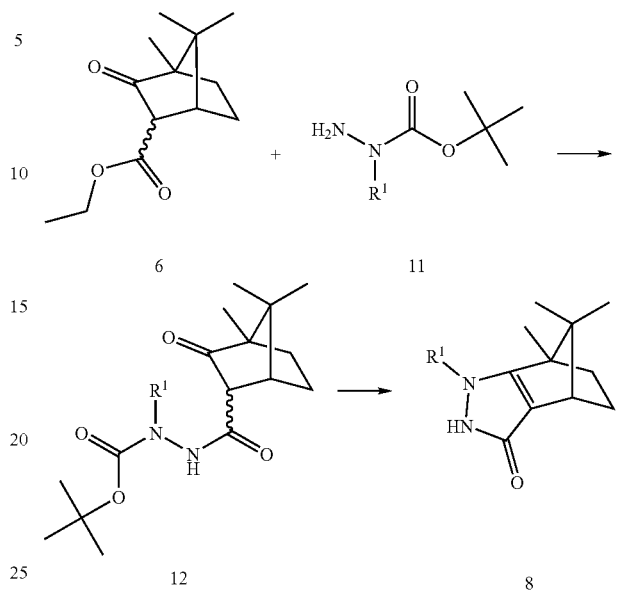

Scheme 4

An additional approach to the synthesis of pyrazolone 8 is shown in Scheme 4. According to this approach, the keto-ester of formula 6 can be reacted with a tert-butoxy-carbonyl-protected hydrazine of formula 11 to give a hydrazide of formula 12. This reaction is conveniently carried out by heating the keto-ester with the tert-butoxy-carbonyl-protected hydrazine in the absence of solvent at a temperature about 100° C. to give the intermediate hydrazide, and then treating this with concentrated hydrochloric acid, and heating again at about 100° C. It will be clear to one of average skill in the art of organic synthesis that the acid chloride derived from the keto-acid of formula 3 as described above can be used in place of the keto-ester of formula 6. In this case, the acid chloride is treated with the tert-butoxy-carbonyl-protected hydrazine of formula 11 in an inert solvent such as a chlorinated hydrocarbon (e.g., dichloromethane) or an aromatic hydrocarbon (e.g., benzene) in the presence of a base such as pyridine or diisopropylethylamine at about room temperature to give the hydrazide of formula 12.

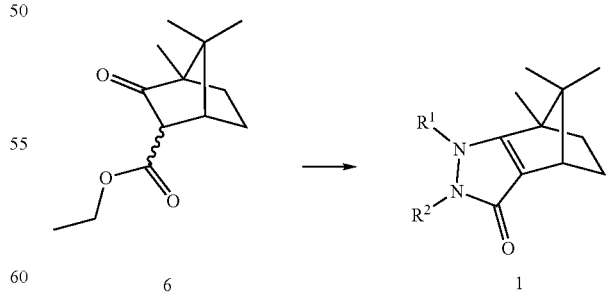

Scheme 5

As shown in Scheme 5, in cases where $R^1$=$R^2$, compounds of the invention of formula 1 can be made by treating the keto-ester of formula 6 with a hydrazine of formula R1NHNHR2 in an inert solvent such as N,N-dimethylformamide at a temperature about 100° C.

Scheme 5a

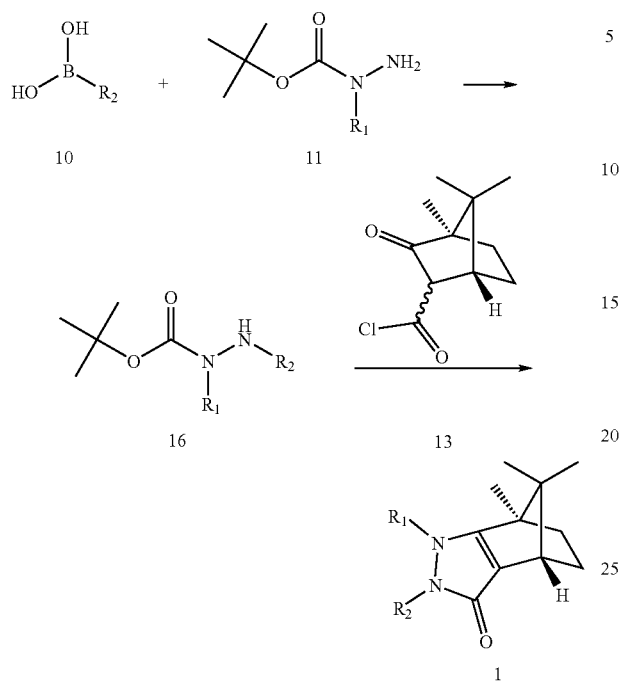

Scheme 5b

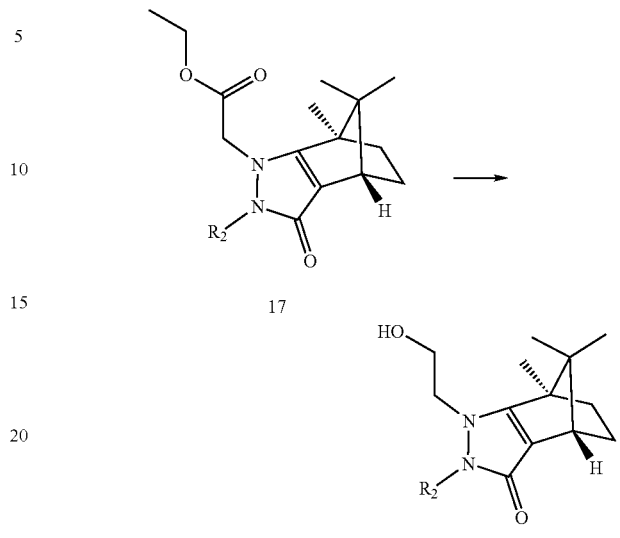

Compounds of formula 1, for example where R2 represents a carbocyclic or heterocyclic aryl group and R1 represents an optionally substituted lower-alkyl or aralkyl group, can also be prepared as shown in Scheme 5a. According to this process, a boronic acid of formula 10 reacts with a tert-butoxycarbonyl-protected aryl hydrazine of formula 11 to give an intermediate substituted hydrazine of formula 16, which reacts with the acid chloride of formula 13 to give the compound of formula 1. The reaction of the boronic acid of formula 10 with the hydrazine of formula 11 can be carried out under any conventional conditions. For example, this reaction can be conveniently carried out using a copper salt such as copper(II) acetate as a catalyst in the presence of an amine such as triethylamine in an inert solvent such as 1,2-dichloroethane at a temperature around 100° C. Slightly different reaction conditions can be found in the literature for similar or related transformations, for example in G. W. Kabalka and S. K. Guchhait *Org. Lett.* 2005, 5, 4129-4131 and in O. V. Dyablo et al. *Chem. Heterocycl. Compd.* 2002, 38, 620-621. The reaction of the substituted hydrazine derivative of formula 16 with the acid chloride of formula 13 is conveniently carried out in the presence of a base (such as triethylamine or pyridine) in an inert solvent such as 1,2-dichloroethane. The reaction can be carried out at at temperature between about 0° C. and about room temperature. This reaction results in the formation of a hydrazide intermediate which bears a tert-butoxycarbonyl protective group. Treatment of a solution of this hydrazide intermediate (for example with a solution of 4M HCl in dioxane) results in cleavage of the protective group and cyclization to the compound of formula 1. The cyclization reaction is conveniently carried out at a temperature between about 70° C. and around 100° C., preferably at around 80° C.

As will be apparent to one of skill in the art of organic synthesis, many compounds of formula 1 can be prepared from other compounds of formula 1 by functional group interconversions. Many examples of such interconversions are well known in the field of organic chemistry, and one non-limiting example is shown in Scheme 5b. According to this process, a compound of formula 17 which is a compound of formula 1 in which the R1 group bears a lower-alkoxy carbonyl substituent can be converted into a compound of formula 18 by reduction of the lower-alkoxy carbonyl group. This reaction can be carried out by any conventional means. For example, the compound of formula 17 may be treated with a reducing agent such as lithium aluminum hydride (or diisobutylaluminum hydride or the like) in an inert solvent such as tetrahydrofuran at a temperature between about 0° C. and about room temperature, conveniently at about room temperature.

Availability of Starting Materials for the Preparation of Compounds of the Invention As mentioned previously, camphor is commercially available as the racemate or as either enantiomer, for example from Aldrich Chemical Company, Milwaukee, Wis. Racemic 3-camphorcarboxylic acid of formula 3 is available commercially from the SALOR catalogue of Aldrich Chemical Company, Milwaukee, Wis. Ethyl (−)-camphorcarboxylate, one of the enantiomers of the compound of formula 6, is available from Lancaster Synthesis Ltd., Lancashire, UK.

Many examples of arylhydrazines of formula ArNHNH2 are commercially available. For example, the ACD directory of commercially available reagents lists more than 700 available arylhydrazines. In addition, many procedures are available in the literature for the preparation of additional examples. For example, a solution of an aniline in aqueous hydrochloric acid can be treated with an aqueous solution of sodium nitrite at a temperature about 0° C. to give the corresponding diazonium salt, which can be treated with an aqueous solution of tin chloride dihydrate again at a temperature about 0° C. to give the desired arylhydrazine. Conditions appropriate for this reaction can be found in the literature, for example in N. J. Green et al. *Bioorg. Med. Chem.* 2003, 11, 2991-3013; in M. T. Makhija et al. *Bioorg. Med Chem.* 2004, 12, 2317-2333; in M. van der Mey et al. *J. Med. Chem.* 2003, 46, 2008-2016; and in R. West and H. F. Stewart *J. Am. Chem. Soc.* 1970, 92, 853-859. In addition, in the case of an aromatic ring which is susceptible to nucleophilic aromatic substitution, which rings are well known to one of skill in the art of organic synthesis and which include benzene rings with a leaving group such as fluorine and an activating group such as nitro or aminosulfonyl in the ortho or para positions and which also include halo-substituted heterocycles such as 2-chloro-pyridine or 2-chloro-pyrimidine, the aryl-hydrazine can be prepared by treating the aromatic ring compound with hydrazine in an inert solvent such as acetonitrile or ethanol at a temperature about 80° C. Conditions appropriate for this reaction can be found in the literature, for example in M. Pal et al. *J. Med. Chem.* 2003, 46, 3975-3984; in E. W. Parnell *J. Chem. Soc.* 1959, 2363-2365; in L. Ondi et al. *Eur. J. Org. Chem.* 2004, 3714-3718; and in N. Guillot et al. *Tetrahedron* 1990, 46, 3897-3908. Alternatively, arylhydrazines can be prepared by the treatment of an azodicarboxylate derivative such as di-tert-butyl-azo-dicarboxylate with an organometallic reagent such as a Grignard reagent in an inert solvent such as tetrahydrofuran at a temperature about –78° C., and then removing the protective group, for example by treatment with acid such as hydrochloric acid. Conditions appropriate for this reaction can be found in the literature, for example in J. P. Demers and D. H. Klaubert *Tetrahedron Lett.* 1987, 28, 4933-4934. As a further alternative, arylhydrazines can be prepared by treatment of an aryl iodide with tris(trimethylsilyl)hydrazidocopper. Conditions suitable for this reaction can be found in F. D. King and D. R. M. Walton *Synthesis* 1975, 738-739.

A variety of alkylating and aralkylating agents can be used to introduce the $R^1$ and/or $R^2$ groups in the compounds of the invention. Examples of such groups are dimethyl sulfate, iodomethane, 2-iodoethane, 2-iodopropane, allyl bromide, unsubstituted or substituted benzyl bromide, or a bromomethyl-substituted heterocycle. Many of these compounds are commercially available from a variety of vendors, and many others are known compounds which can be prepared by methods that are well known in the field of organic synthesis. A listing of many of these methods can be found in "Comprehensive Organic Transformations: A Guide to Functional Group Preparations" [R. C. Larock, VCH Publishers, Inc. New York, 1989], for example on pages 313, 322-323, 353-363, and 381-382. Additional examples of synthetic methods appropriate for the preparation of many alkyl halides or aralkyl halides can be found in "Advanced Organic Chemistry" [J. March, $3^{rd}$ Edition, John Wiley & Sons, Inc. New York, 1985], on pages 382-384.

In compounds of the invention of formula 1 where $R^2$ represents an aryl group, this group can be derived from an electron-deficient halo-aromatic, or from an aryl-halide or aryl-boronic acid. Many of these compounds are commercially available from a variety of vendors, and many others are known compounds which can be prepared by methods that are well known in the field of organic synthesis. For example, a variety of methods useful for the preparation of aryl-halides are to be found in "Comprehensive Organic Transformations: A Guide to Functional Group Preparations" [R. C. Larock, VCH Publishers, Inc. New York, 1989], for example on pages 316-318, and 345-346. Additional examples of synthetic methods appropriate for the preparation of many aryl halides can be found in "Advanced Organic Chemistry" [J. March, $3^{rd}$ Edition, John Wiley & Sons, Inc. New York, 1985], on page 1155. According to the Available Chemicals Directory (MDL Information Systems, San Leandro, Calif.), there are 850 aryl-boronic acids available commercially. In addition, many synthetic methods suitable for the preparation of aryl-boronic acids can be found in the literature, for example in the following references: S. R. Holmes-Farley, US 2003064963; C. Glende et al. *Mutation Res.* 2002, 515, 15-38; A. Fensome et al. U.S. Pat. No. 6,355,648; M. Gravel et al. *J. Org. Chem* 2002, 67, 3-15; D. Florentin et al. *J. Heterocycl. Chem.* 1976, 13, 1265-1272; M. P. Groziak et al. *J. Am. Chem. Soc.* 1994, 116, 7597-7605; W. Li et al. *J. Org. Chem.* 2002, 67, 5394-5397; S. L. Gilat et al. *Chem. Eur. J.* 1995, 1, 275-284; W. J. Dale et al. *J. Org. Chem.* 1962, 27, 2598-2603; T. E. Jacks et al. *Org. Proc. Res. Dev.* 2004, 8, 201-212; D. Florentin et al. *J. Heterocycl. Chem.* 1976, 13, 1265-1272; A. Kuno et al. PCT Int. Appl. WO 9604241; A. D. Borthwick et al. PCT Int. Appl. WO 2003053925; F. C. Fischer et al. *Recl. Trav. Chim. Pays-Bas* 1974, 93, 21-24; M. Takeshita et al. *J. Org. Chem.* 1998, 63, 6643-6649. Further examples of methods useful for the preparation of aryl-boronic acids are given below.

Scheme 6

An aryl-boronic acid of formula 10 can conveniently be synthesized according to Scheme 6 from an aryl bromide or iodide of formula 14, by treatment with an alkyllithium (e.g., n-butyllithium) or magnesium (to form the Grignard reagent) in a suitable inert solvent such as an ether (such as tetrahydrofuran or diethyl ether) at a temperature appropriate for the reaction (for example, at approximately –78 degrees for reaction with an alkyllithium, or at approximately room temperature for reaction with magnesium), followed by treatment with a trialkyl borate to form the compound of formula 10.

Boc-protected hydrazines of formula 11 can be prepared by a variety of procedures. For example, a hydrazine of formula R1NHNH2 can be reacted with tert-butyl-S-methyl-thiocarbonate or di-tert-butyl-dicarbonate in an inert solvent at a temperature between about –5° C. and about room temperature. Suitable conditions for such reactions can be found in the literature, for example in K. A. Jensen et al. *Acta Chem Scand.* 1968, 22, 1-50, or in J.-N. Xiang et al. WO 2002070541. Alternatively, N-tert-butyloxycarbonylaminotetrachloro or N-tert-butyloxycarbonylaminophthalimide can be reacted in a Mitsunobu reaction with an alcohol of formula R1OH followed by deprotection with hydrazine to give the compound of formula 11. Again, suitable conditions for such reactions can be found in the literature, for example in M.-F. Pinto et al. *Synth. Commun.* 2002, 32, 3603-3610 or in N. Brosse et al. *J. Org. Chem.* 2000, 65, 4370.

Alkylhydrazines of formula R1NHNH2 suitable for the preparation of formula 11 are either commercially available or can be prepared using reactions that are well known in the art. For example, tert-butyl carbazate undergoes reductive alkylation by reduction of the hydrazone generated by reaction with an alkyl aldehyde or ketone. Removal of the tert-butoxycarbonyl protective group by treatment with acid (for example, sulfuric acid) gives the alkylhydrazine. Conditions suitable for this reaction can be found in the literature, for example in H. Hilpert *Tetrahedron* 2001, 57, 7675-7683; and in N. I. Ghali et al. *J. Org. Chem.* 1981, 46, 5413-5414. Alternatively, reaction of an alkyl amine with N-(diethoxy-phosphoroyl)-O-(p-nitrophenylsulfonyl)-hydroxylamine, followed by treatment of the resulting intermediate with acid (for example, p-toluenesulfonic acid monohydrate) gives the alkylhydrazine. Conditions suitable for this reaction can be found in the literature, for example in A. Koziara et al. *Synth. Commun.* 1995, 25, 3805-3812.

tert-Butoxy-carbonyl-protected aryl-hydrazines of formula 15 can be prepared by reacting an aryl-hydrazine of formula ArNHNH2 with di-tert-butyl-dicarbonate in an inert solvent such as an alcohol (e.g., methanol) or a mixture of water with an organic solvent such as ethyl acetate. The reaction is conveniently carried out at room temperature.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of from about 0.01 mg/kg to about 50 mg/kg should be appropriate, although the upper limit may be exceeded when indicated. The dosage is preferably from about 0.3 mg/kg to about 10 mg/kg per day. A preferred dosage may be from about 0.70 mg/kg to about 3.5 mg/kg per day. The daily dosage can be administered as a single dose or in divided doses, or for parenteral administration it may be given as continuous infusion.

The compounds of the present invention can be prepared by any conventional means. Suitable processes for synthesizing these compounds are provided in the examples. Generally, compounds of formula I can be prepared according to the Schemes described below. The sources of the starting materials for these reactions are also described.

EXAMPLES

Preparation of Preferred Intermediates

Intermediate 1: N-Methyl-hydrazinecarboxylic acid tert-butyl ester

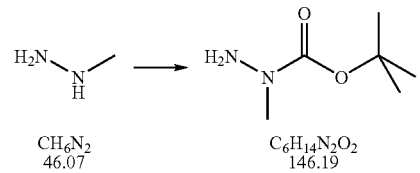

CH$_6$N$_2$
46.07

C$_6$H$_{14}$N$_2$O$_2$
146.19

Di-tert-butyl-dicarbonate (0.23.69 g, 108.5 mmol) in methanol (40 mL) was added dropwise over a period of 1.5 h to a solution of methylhydrazine (5.00 g, 106.4 mmol) in methanol (20 mL) cooled to ~5° C. When the addition was complete, tlc (10% methanol/dichloromethane) indicated that the reaction was complete. The reaction mixture was stored at −20° C. overnight, and then the solvent was evaporated to give N-methyl-hydrazinecarboxylic acid tert-butyl ester (14.34 g, 92%) as a colorless oil which was used directly in the subsequent step without further purification.

Intermediate 2: 4-Bromomethyl-3-trifluoromethyl-1-trityl-1H-pyrazole

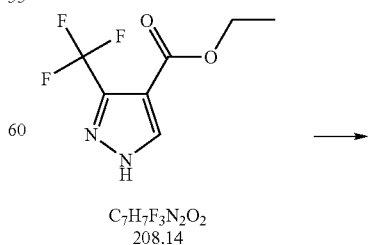

C$_7$H$_7$F$_3$N$_2$O$_2$
208.14

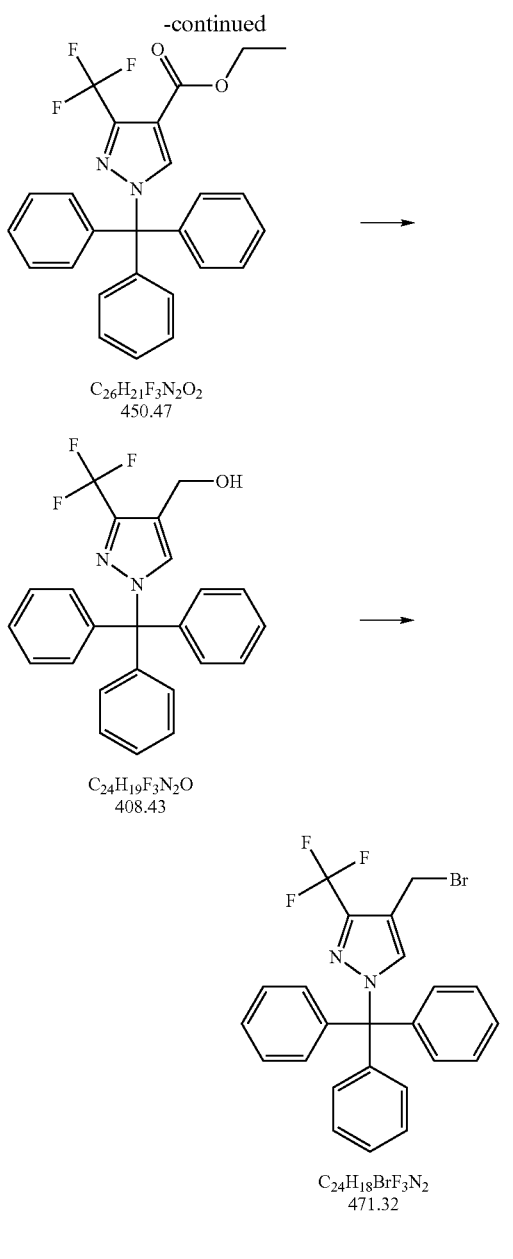

Step 1: 3-Trifluoromethyl-1-trityl-1H-pyrazole-4-carboxylic acid ethyl ester

Triphenylmethyl chloride (1.1 g, 3.6 mmol) was added to a solution of ethyl 3-(trifluoromethyl)-pyrazole-4-carboxylate (0.75 g, 3.6 mmol) and triethylamine (1 mL, 7.2 mmol) in N,N-dimethylformamide (12 mL). This mixture was stirred at room temperature overnight, then the solvent was evaporated and the residue was diluted with water (30 mL) and extracted with ethyl acetate. The organic extract was washed with water and brine, dried (magnesium sulfate), filtered, evaporated, and chromatographed (10% ethyl acetate/petroleum ether) to give 3-trifluoromethyl-1-trityl-1H-pyrazole-4-carboxylic acid ethyl ester (1.28 g, 79%).

Step 2: (3-Trifluoromethyl-1-trityl-1H-pyrazol-4-yl)-methanol

A solution of lithium aluminum hydride in THF (1.0 M; 1.6 mL, 1.6 mmol) was added to a cooled (~–15° C.) solution of 3-trifluoromethyl-1-trityl-1H-pyrazole-4-carboxylic acid ethyl ester (0.64 g, 1.4 mmol) in anhydrous tetrahydrofuran (15 mL). The solution was stirred at –10 to –15° C. for 45 min and then quenched at –10° C. with a solution of Rochelle's salt (2 mL). The mixture was stirred for 10 min and then the cooling bath was removed. Ethyl acetate (25 mL) was added and the mixture was stirred for 30 min, then it was filtered and the filter cake was washed with ethyl acetate. The filtrate was dried (magnesium sulfate), filtered, evaporated, and held under high vacuum over the weekend to give (3-trifluoromethyl-1-trityl-1H-pyrazol-4-yl)-methanol (0.62 g, quantitative) as a tacky white oil.

Step 3: 4-Bromomethyl-3-trifluoromethyl-1-trityl-1H-pyrazole

Triphenylphosphine (0.54 g, 2.1 mmol) was added to a solution of (3-trifluoromethyl-1-trityl-1H-pyrazol-4-yl)-methanol (0.6 g, 1.5 mmol) in dichloromethane (25 mL). The resulting solution was cooled to –20° C. and a solution of carbon tetrabromide (0.54 g, 1.6 mmol) in dichloromethane (5 mL) was added in four portions. The solution was stirred for 5 min at –20° C. and then at for 3 h at 0° C. Further portions of triphenylphosphine (0.17 g, 0.65 mmol) and carbon tetrabromide (0.24 g, 0.72 mmol) were added. The solution was stirred for 3 h, and further portions of triphenylphosphine (0.54 g, 2 mmol) and carbon tetrabromide were added. The solution was stirred for 30 min and then the solvent was evaporated and the residue purified by flash chromatography, eluting with 5-10% ethyl acetate/petroleum ether to give 4-bromomethyl-3-trifluoromethyl-1-trityl-1H-pyrazole (0.30 g, 43%) as a white solid.

Intermediate 3: (1R,4R)-3-Camphorcarboxylic acid

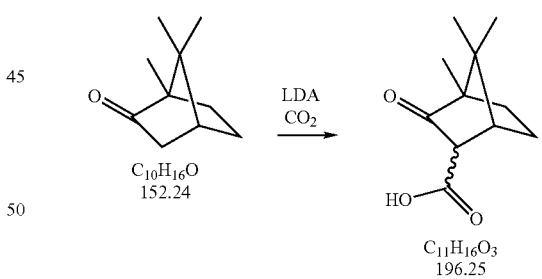

Following the procedure of W. W. Shumway et al. *J. Org. Chem.* 2001, 66, 5832-5839, D-(+)-camphor (25 g, 164 mmol) was dissolved in toluene (100 mL), cooled to –78 degrees under argon, and lithium diisopropylamide (1.8 M solution in heptane/tetrahydrofuran/ethylbenzene; 100 mL, 180 mmol, 1.1 equiv.) was added dropwise. The resulting solution was stirred at –78 degrees for 30 min, warmed to room temperature, and carefully poured over an excess of dry ice under a stream of nitrogen. The mixture was allowed to warm to room temperature with stirring and the carboxylate was taken up in water (800 mL) and washed twice with diethyl ether. The aqueous phase was acidified to pH 1 with concentrated hydrochloric acid and the resulting solid was extracted twice with diethyl ether, dried (sodium sulfate), filtered and evaporated to give (1R,4R)-3-camphorcarboxylic acid (30.4 g, 94%) as a white solid.

Intermediate 4: (1R,4R)-3-Camphorcarboxylic acid ethyl ester

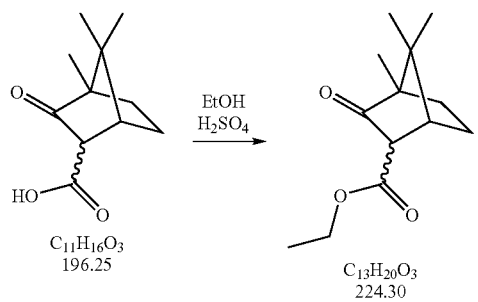

Concentrated sulfuric acid (10 m) was added dropwise to a solution of (1R,4R)-3-camphorcarboxylic acid (Intermediate 3; 30.4 g, 155 mol) in ethanol (200 mL). The solution was heated at reflux for 5 h, held at room temperature overnight, and then neutralized to pH 7 with 5 M NaOH. The solid was filtered off and discarded and the filtrate was concentrated, diluted with water (600 mL) and extracted three time with ethyl acetate. The combined organic layers were washed with concentrated sodium bicarbonate and brine, dried (sodium sulfate) and filtered. The filtrate was stirred decolorizing carbon (alkaline, Norit A), filtered through a pad of celite, and evaporated to give (1R,4R)-3-camphorcarboxylic acid ethyl ester (27.9 g, 80%) as a yellow oil. NMR indicated that this was a mixture of endo and exo epimers, Intermediate 5: (1S,4S)-3-Camphorcarboxylic acid ethyl ester

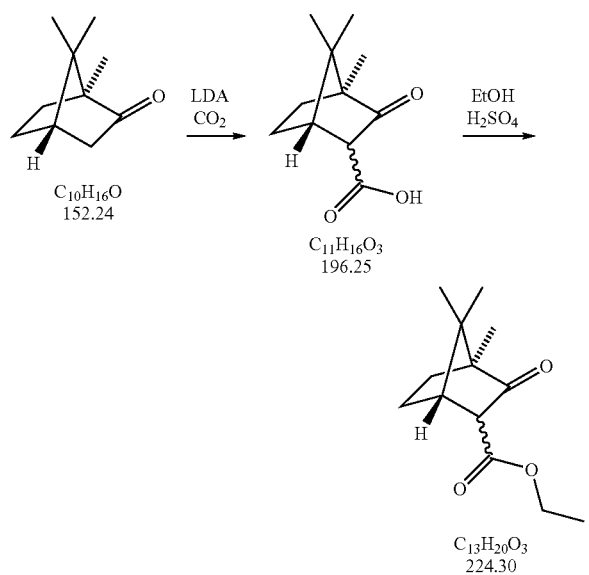

(1S,4S)-3-Camphorcarboxylic acid ethyl ester was prepared in 56% overall yield from R-(−)-camphor using the procedures described above for the preparation of (1R,4R)-3-camphorcarboxylic acid ethyl ester (Intermediate 4).

Intermediate 6: (4S,7R)-2-Phenyl-7,8,8-trimethyl-1,2,4,5,6,7-hexahydro-4,7-methano-indazol-3-one

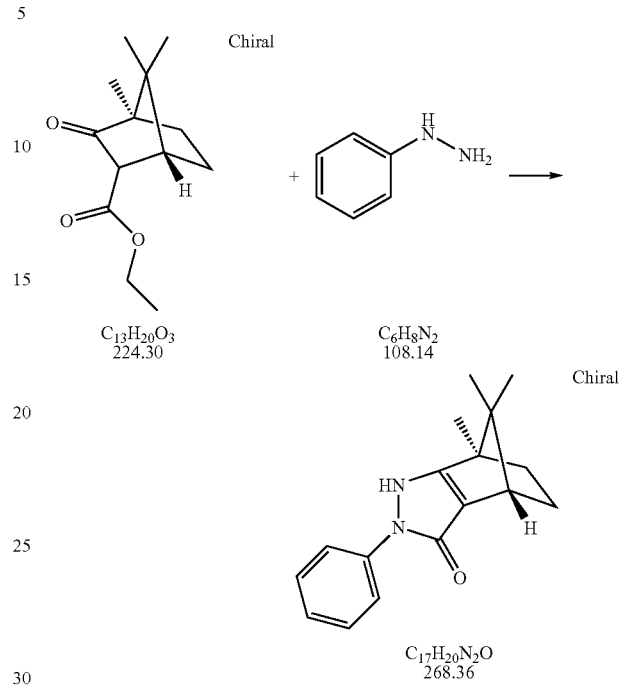

Procedure A: A solution of phosphorus oxychloride (1.1 mL, 11.7 mmol) in toluene (5 mL) was added to an ice-bath-cooled mixture of phenylhydrazine (1.75 mL, 17 mmol) and (1R,4R)-camphorcarboxylic acid ethyl ester (3.65 g, 16.3 mmol) in toluene (25 mL). The ice bath was removed and the mixture was heated at reflux for 3 h. The reaction mixture was cooled to about 10 degrees and 2.5 M NaOH solution (50 mL) was added. The reaction mixture was stirred at room temperature for 2 h, then the layers were separated and the organic layer was extracted with 2.5 M NaOH (3×50 mL). The combined aqueous layers were extracted with toluene (2×50 mL), and then the aqueous layer was acidified with glacial acetic acid and extracted with ethyl acetate. The combined organic layers were washed with water and brine, dried (magnesium sulfate), filtered, evaporated, and purified using an Analogix Intelliflash 280 system (Analogix, Inc., Burlington, Wis.) with an RS-120 column, eluting with 0-16% ethyl acetate/hexanes to give (4S,7R)-2-phenyl-7,8,8-trimethyl-1,2,4,5,6,7-hexahydro-4,7-methano-indazol-3-one (2.1 g, 48%) as a yellow solid.

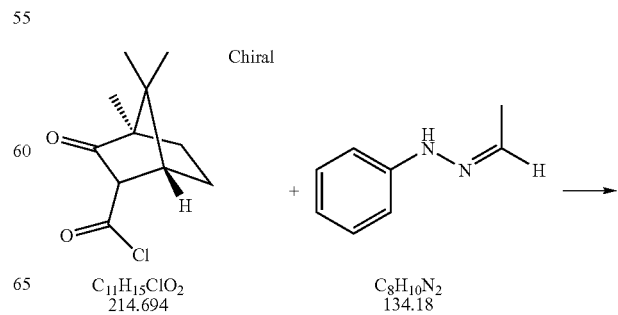

25

-continued

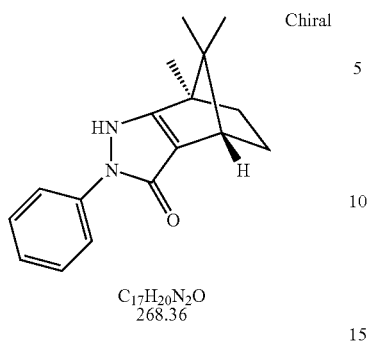

C₁₇H₂₀N₂O
268.36

Procedure B: A solution of (1R,4R)-4,7,7-trimethyl-3-oxo-bicyclo[2.2.1]heptane-2-carbonyl chloride (Intermediate 20; 4.36 g, 20.3 mmol) in 1,2-dichloroethane (40 mL) was added over a period of one minute to a cooled (~0° C.) solution of N-ethylidene-N'-phenyl-hydrazine (prepared according to A. R. Maguire et al. *Bioorg. Med. Chem.* 2001, 9, 745-762; 2.60 g, 19.4 mmol) and pyridine (2.5 mL, 30.9 mmol) in 1,2-dichloroethane (20 mL). The reaction mixture was stirred at room temperature for 15 min and then at 50° C. for 25 min. It was then cooled to room temperature and 4M HCl in dioxane (12 mL) was added. The reaction mixture was stirred for 5 min at room temperature, then glacial acetic acid (20 mL) was added and the mixture was heated in an oil bath at 100° C. for 20 min. The reaction mixture was cooled to room temperature and then evaporated. Dichloromethane (200 mL) was added, the solution was washed with 50% saturated brine (2×50 mL), and the combined aqueous layers were back-extracted with dichloromethane (2×100 mL). The combined organic layers were washed with brine (150 mL), dried (magnesium sulfate), filtered, evaporated and eluted through a plug of silica gel with 30% ethyl acetate/hexanes to give (4S,7R)-2-phenyl-7,8,8-trimethyl-1,2,4,5,6,7-hexahydro-4,7-methano-indazol-3-one (5.04 g, 97%) as an orange foam.

Intermediate 7: (4R,7S)-2-Phenyl-7,8,8-trimethyl-1,2,4,5,6,7-hexahydro-4,7-methano-indazol-3-one

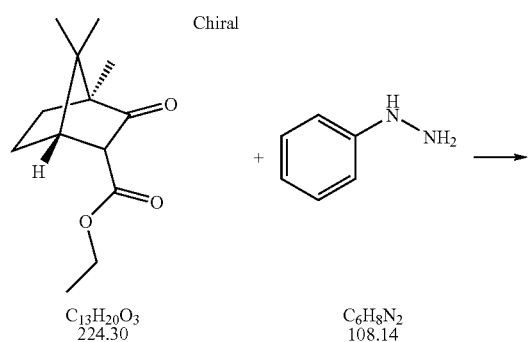

C₁₃H₂₀O₃
224.30

C₆H₈N₂
108.14

26

-continued

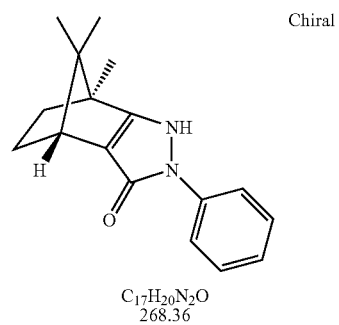

C₁₇H₂₀N₂O
268.36

Phenylhydrazine (1.17 g, 10.8 mmol) was added to a solution of (1S,4S)-camphorcarboxylic acid ethyl ester (Intermediate 5; 2.43 g, 10.8 mmol) and phosphorus trichloride (1.17 g, 8.5 mmol) in toluene (2.5 mL). The reaction mixture was stirred at room temperature under argon overnight. The mixture was heated at 120-150 degrees (oil-bath temperature) for 3 h. Toluene (150 mL) and 1 M NaOH (150 mL) were added and the mixture was shaken and the layers separated. The organic layer was extracted with 1 M NaOH (100 mL). The combined aqueous layers were washed with toluene (2×150 mL) and acidified with glacial acetic acid to pH 4.5. The resulting white solid was filtered off, washed with water, and dried in a desiccator overnight. The solid was taken up in ethyl acetate which was heated to boiling and filtered. The filtrate, which NMR showed was mainly (4R,7S)-7,8,8-trimethyl-1-phenyl-1,2,4,5,6,7-hexahydro-4,7-methano-indazol-3-one, was discarded. On cooling, a second crop of the undesired regioisomer was obtained. The filtrate was evaporated, and an unsuccessful attempt was made to recrystallize the solid from ethanol. The ethanol was evaporated to give (4R,7S)-2-phenyl-7,8,8-trimethyl-1,2,4,5,6,7-hexahydro-4,7-methano-indazol-3-one (1.33 g, 46%) as a yellow solid.

Intermediate 8: (4S,7R)-1-Phenyl-7,8,8-trimethyl-1,2,4,5,6,7-hexahydro-4,7-methano-indazol-3-one

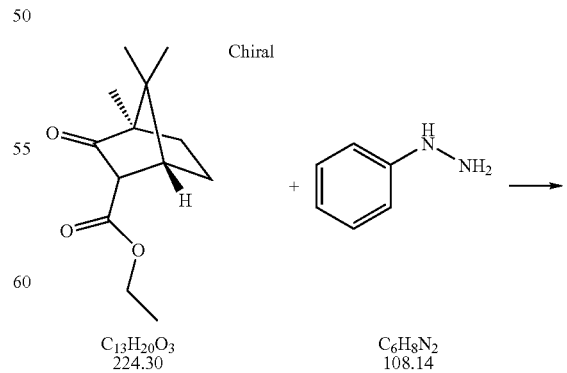

C₁₃H₂₀O₃
224.30

C₆H₈N₂
108.14

-continued

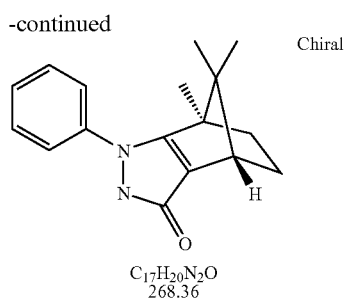

C₁₇H₂₀N₂O
268.36

A neat mixture of (1R,4R)-camphorcarboxylic acid ethyl ester (Intermediate 3; 10.0 g, 44.6 mmol) and phenylhydrazine (5 mL, 50.8 mmol) was heated at 100° C. overnight. The reaction mixture was cooled in an ice-bath and conc HCl (50 mL) was added. The reaction mixture was then heated to 100° C. for 2.5 h. A further portion of conc HCl (60 mL) was added and the reaction mixture was heated at 100° C. until LC-MS indicated only product mass. The solution was brought to pH 6 using aqueous NaOH solution and the solid was filtered off, air-dried for 1 h, and then dried in a vacuum over overnight to give (4S,7R)-1-phenyl-7,8,8-trimethyl-1,2,4,5,6,7-hexahydro-4,7-methano-indazol-3-one (10.9 g, 91%).

Intermediate 9: (4S,7R)-7,8,8-Trimethyl-2-p-tolyl-1,2,4,5,6,7-hexahydro-4,7-methano-indazol-3-one

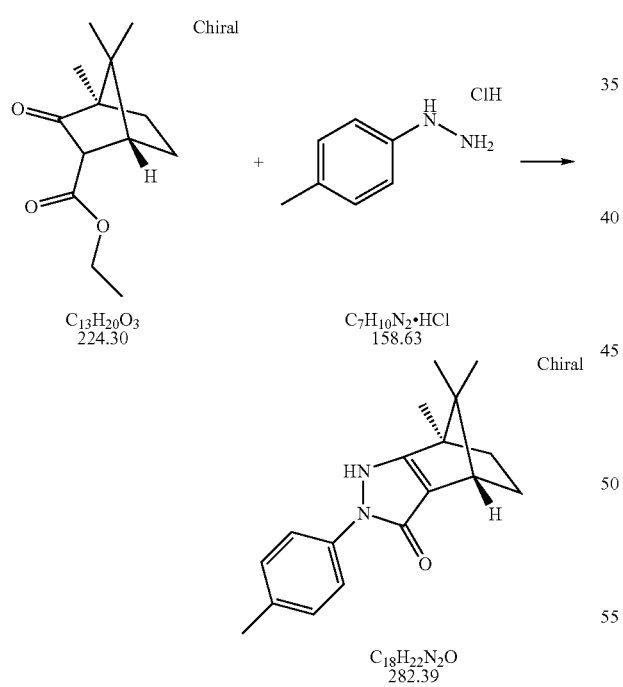

A solution of phosphorus oxychloride (0.32 mL, 3.4 mmol) in toluene (1 mL) was added to an ice-bath-cooled mixture of p-tolylhydrazine free base [prepared by treating a solution of p-tolylhydrazine hydrochloride (2.11 g, 16.4 mmol) in water with 5 M NaOH (16 mL), extracting with ethyl acetate, washing with water and brine, drying (sodium sulfate), filtering, and evaporating] and (1R,4R)-camphorcarboxylic acid ethyl ester (Intermediate 3; 3.50 g, 15.6 mmol) in toluene (19 mL).

The ice bath was removed and the mixture was heated at reflux for 3 h. 2.5 M NaOH solution (20 mL) was added and the layers were separated. The organic layer was extracted with 0.5 M NaOH (3×50 mL). The combined aqueous layers were acidified to pH 5 with glacial acetic acid and extracted with ethyl acetate (3×75 mL). The combined organic layers were washed with water and brine, dried (magnesium sulfate), filtered, and evaporated. The crude product was purified by recrystallization from ethyl acetate to give (4S,7R)-7,8,8-trimethyl-2-p-tolyl-1,2,4,5,6,7-hexahydro-4,7-methano-indazol-3-one (1.36 g, 26%) as a yellow solid.

Intermediate 10: (4S,7R)-2-(2-Chloro-phenyl)-7,8,8-trimethyl-1,2,4,5,6,7-hexahydro-4,7-methano-indazol-3-one Procedure A

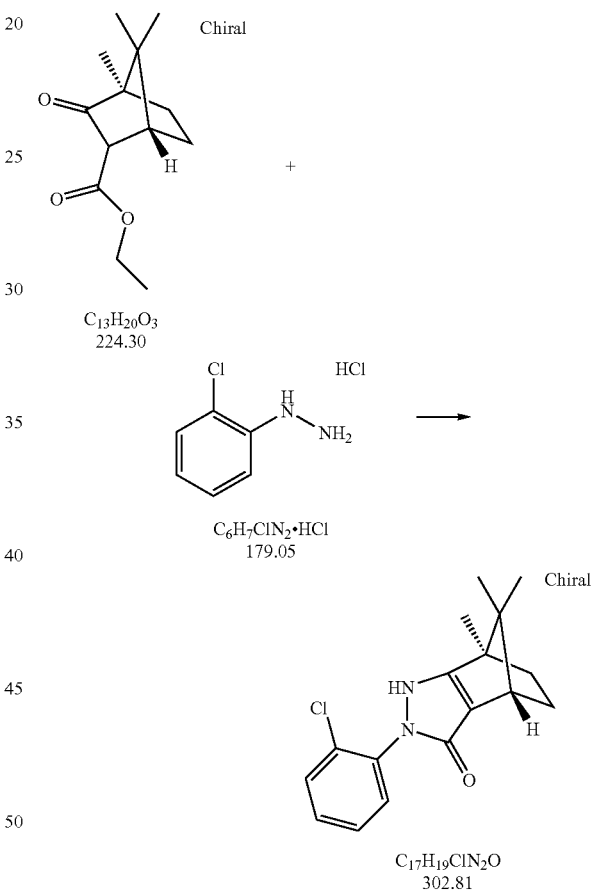

A mixture of phosphorus oxychloride (0.32 mL, 3.4 mmol), o-chloro-phenylhydrazine (0.92 g, 5.1 mmol) and (1R,4R)-camphorcarboxylic acid ethyl ester (Intermediate 3; 1.05 g, 4.7 mmol) in toluene (10 mL) was heated at reflux for 105 min and then 1 M NaOH (250 mL) was added. The mixture was extracted with ethyl acetate (3×200 mL) and the solvent was evaporated from the extract. Toluene (10 mL) and phosphorus trichloride (0.5 mL, 5.7 mmol) were added and the mixture was heated at reflux for 3 h. 1M NaOH (250 mL) was added and the mixture was washed with ethyl acetate (2×300 mL). The combined ethyl acetate layers were back-extracted with NaOH (200 mL). The combined NaOH extracts were acidified with acetic acid and extracted with ethyl acetate, and the extract was washed with brine, dried (sodium sulfate), filtered, and evaporated to give (4S,7R)-2-(2-chloro-phenyl)-7,8,8-trimethyl-1,2,4,5,6,7-hexahydro-4,7-methano-indazol-3-one (320 mg, 31%) as a yellow solid.

Procedure B

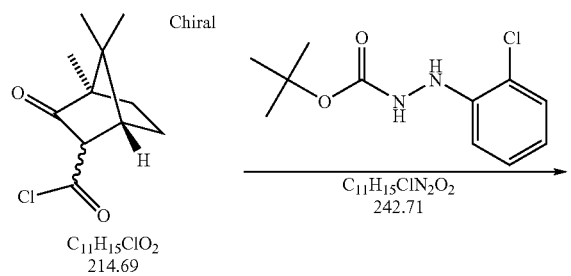

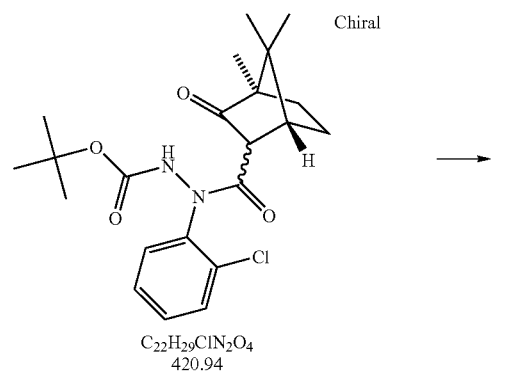

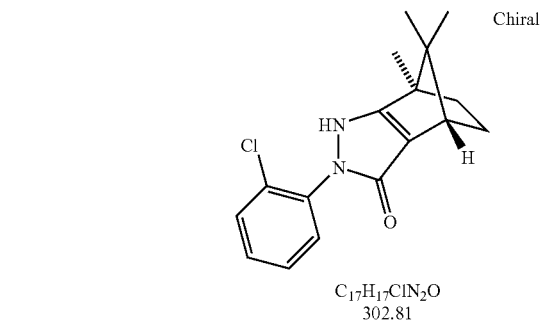

Step 1: N'-(2-Chloro-phenyl)-N'-((1R,4R)-4,7,7-trimethyl-3-oxo-bicyclo[2.2.1]heptane-2-carbonyl)-hydrazinecarboxylic acid tert-butyl ester Triethylamine (43 mL, 309 mmol) was added over 2-3 min to a cooled (0° C.) solution of (1R,4R)-4,7,7-trimethyl-3-oxo-bicyclo[2.2.1]heptane-2-carbonyl chloride (Intermediate 20; 23.2 g, 103.8 mmol) in dry dichloromethane (260 mL), yielding a heavy precipitate. Dichloromethane (25 mL) was added, followed by N'-(2-chloro-phenyl)-hydrazinecarboxylic acid tert-butyl ester (Intermediate 30; 19.36 g, 79.8 mmol) in one portion. Dichloromethane (35 mL) was added and the mixture was stirred at 0° C. for 5 min and then heated in an oil bath at 50° C. for 4 h. The mixture was poured into cold water (500 mL) and the layers were separated. The aqueous layer was extracted with dichloromethane (2×300 mL) and the combined organic layers were washed with brine (200 mL), dried (magnesium sulfate), filtered, evaporated, and purified by silica gel chromatography, eluting with 20-100% ethyl acetate/petroleum ether. Fractions homogeneous for the product were evaporated and dried under high vacuum to give N'-(2-chloro-phenyl)-N'-((1R,4R)-4,7,7-trimethyl-3-oxo-bicyclo[2.2.1]heptane-2-carbonyl)-hydrazinecarboxylic acid tert-butyl ester (23.4 g, 70%) as a pale foam.

Step 2: (4S,7R)-2-(2-Chloro-phenyl)-7,8,8-trimethyl-1,2,4,5,6,7-hexahydro-4,7-methano-indazol-3-one Trifluoroacetic acid (55 mL) was added slowly over 1-2 min to a solution of N-(2-chloro-phenyl)-N'-((1R,4R)-4,7,7-trimethyl-3-oxo-bicyclo[2.2.1]heptane-2-carbonyl)-hydrazinecarboxylic acid tert-butyl ester (23.4 g, 56 mmol) in dry dichloromethane (55 mL), and the resulting solution was stirred at room temperature for 3 h. The solvent was evaporated and dichloromethane (350 mL) was added. The solution was washed with water (3×150 mL) and brine (150 mL), dried (sodium sulfate), filtered, evaporated, and dried under high vacuum over the weekend to give (4S,7R)-2-(2-chloro-phenyl)-7,8,8-trimethyl-1,2,4,5,6,7-hexahydro-4,7-methano-indazol-3-one (16.07 g, 95%) as a pale solid.

Intermediate 11: (4S,7R)-2-(4-Chloro-phenyl)-7,8,8-trimethyl-1,2,4,5,6,7-hexahydro-4,7-methano-indazol-3-one

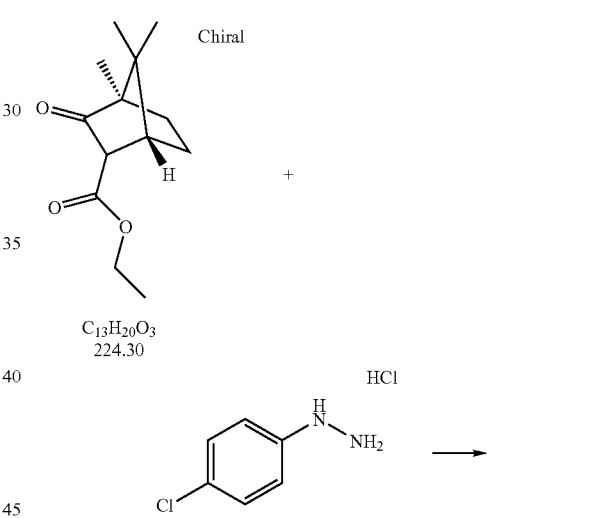

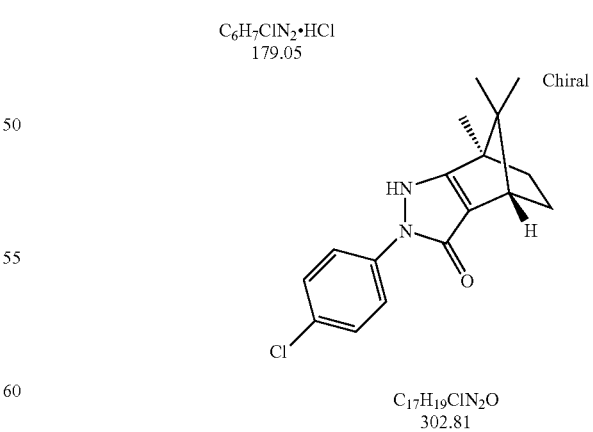

A mixture of phosphorus oxychloride (0.33 mL, 3.5 mmol), p-chloro-phenylhydrazine (700 mg, 4.9 mmol) and (1R,4R)-camphorcarboxylic acid ethyl ester (Intermediate 3; 1.1 g, 4.9 mmol) in toluene (15 mL) was heated at reflux overnight and then the toluene was decanted off to give a gum that was washed with toluene. After decanting this toluene, the gum was dissolved in 1 M NaOH solution, and this solution was extracted with toluene and then ethyl acetate. The aqueous layer was acidified with glacial acetic acid to give (4S,7R)-2-(4-chloro-phenyl)-7,8,8-trimethyl-1,2,4,5,6,7-hexahydro-4,7-methano-indazol-3-one (252 mg, 17%) as a tan solid. A further quantity of the product was obtained as follows: The ethyl acetate extract above was combined with the aqueous acetic acid solution and the mixture was stirred. The layers were separated and the aqueous layer was extracted twice with ethyl acetate. The combined ethyl acetate layers were washed with water and brine, dried (sodium sulfate), filtered and evaporated to give the product (230 mg, 16%) as a tan solid.

Intermediate 12: (4S,7R)-2-(2-Fluoro-phenyl)-7,8,8-trimethyl-1,2,4,5,6,7-hexahydro-4,7-methano-indazol-3-one

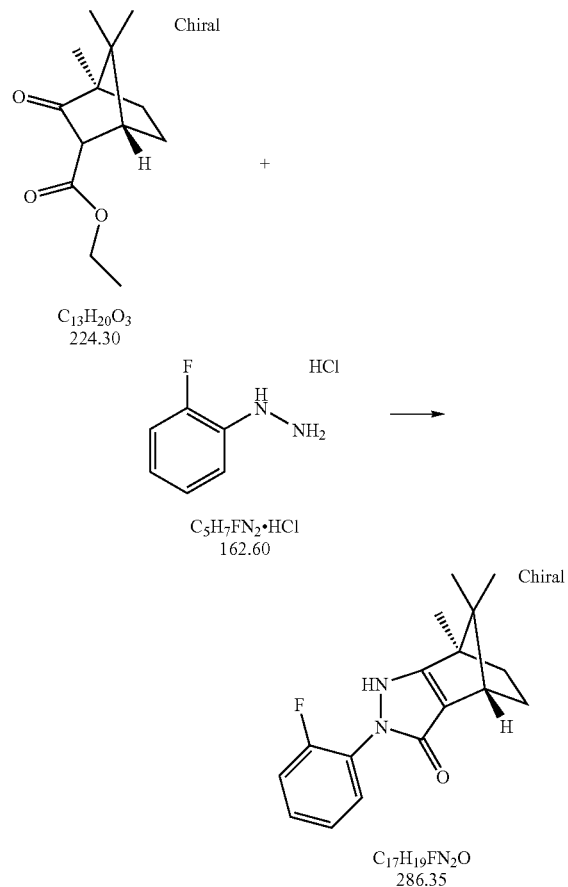

A solution of phosphorus oxychloride (1.5 mL, 16.1 mmol) in toluene (5 mL) was added to a mixture of 2-fluoro-phenylhydrazine free base [3.1 g (24.6 mmol) of material prepared by treating a solution of 2-fluoro-phenylhydrazine hydrochloride (12.6 g, 77.5 mmol) in water with 5 M NaOH, extracting with ethyl acetate, filtering, and evaporating] and (1R,4R)-camphorcarboxylic acid ethyl ester (Intermediate 3; 5.0 g, 22.3 mmol) in toluene (20 mL). The mixture was heated at reflux for 1.5 h, stored at room temperature overnight, then heated at reflux for a further 3.5 h. 1 M NaOH solution was added and the layers were separated. The aqueous layer was washed with ethyl acetate (which was discarded), then acidified to pH 5 with glacial acetic acid. The resulting solid was filtered off, washed with water and air-dried overnight to give (4S,7R)-2-(2-fluoro-phenyl)-7,8,8-trimethyl-1,2,4,5,6,7-hexahydro-4,7-methano-indazol-3-one (1.12 g, 18%) as a pale yellow solid.

Intermediate 13: (4S,7R)-2-(4-Fluoro-phenyl)-7,8,8-trimethyl-1,2,4,5,6,7-hexahydro-4,7-methano-indazol-3-one

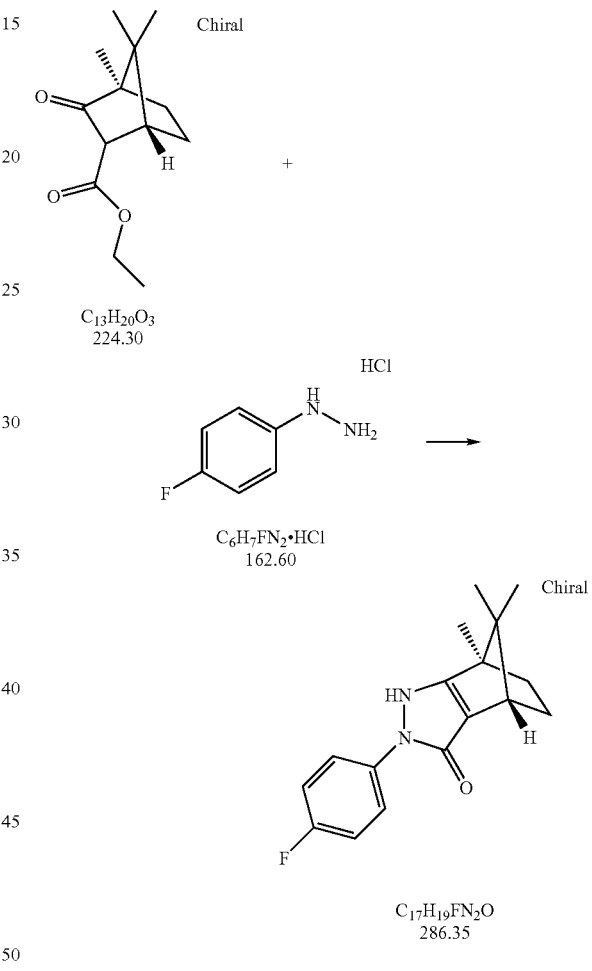

A solution of phosphorus oxychloride (1.5 mL, 16.1 mmol) in toluene (5 mL) was added to a mixture of 2-fluoro-phenylhydrazine free base [prepared by extracting a mixture of 4-fluoro-phenylhydrazine hydrochloride (9 g, 55.3 mmol), water (150 mL) and 3 M NaOH (40 mL) with ethyl acetate, filtering, and evaporating to give 3.05 g (44%) of free base] and (1R,4R)-camphorcarboxylic acid ethyl ester (Intermediate 3; 5.0 g, 22.3 mmol) in toluene (20 mL). The mixture was stirred at room temperature for 10 days, then heated at reflux for 7 h. The reaction mixture was allowed to cool, and then 1 M NaOH (400 mL) was added and the solution was washed with toluene. The toluene layer was extracted with 1 M NaOH and the combined aqueous layers were washed three times with toluene and then filtered through Celite. The filtrate was acidified with glacial acetic acid and the resulting precipitate was filtered off, dissolved in dichloromethane, and washed with 0.25 M HCl and brine. The solution was evaporated to give (4S,7R)-2-(4-fluoro-phenyl)-7,8,8-trimethyl-1,2,4,5,6,7-hexahydro-4,7-methano-indazol-3-one (1.65 g, 26%) as a pale yellow solid.

Intermediate 14: (4S,7R)-2-(2,4-Difluoro-phenyl)-7,8,8-trimethyl-1,2,4,5,6,7-hexahydro-4,7-methano-indazol-3-one Procedure A

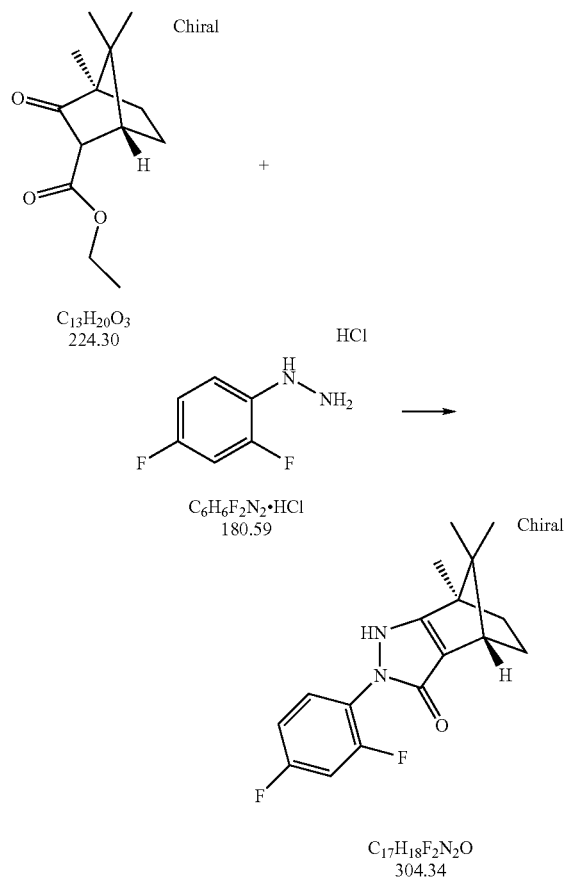

A solution of phosphorus oxychloride (1.3 mL, 14 mmol) in toluene was added to a mixture of 2,4-difluoro-phenylhydrazine free base [prepared by extracting a mixture of 2,4-difluoro-phenylhydrazine hydrochloride (5.18 g, 28.7 mmol) and 1 M NaOH (400 mL) with ethyl acetate, filtering, and evaporating to give 3.09 g (75%) of free base] and (1R,4R)-camphorcarboxylic acid ethyl ester (Intermediate 3; 4.37 g, 19.5 mmol) in toluene. The mixture was heated at reflux for 3 h, allowed to stand at room temperature over the weekend, then heated at reflux for a further 4.5 h. An additional portion of phosphorus oxychloride (0.5 mL, 5.4 mL) was added and the reaction mixture was heated at reflux for 2.5 h. 1 M NaOH was added and the solution was washed with toluene. The toluene layer was extracted with 1 M NaOH and the combined aqueous layers were washed with toluene and then filtered through Celite. The filtrate was acidified with glacial acetic acid and the resulting precipitate was filtered off, taken up in dichloromethane, filtered, and washed with 0.25 M HCl and brine. The solution was evaporated to give (4S,7R)-2-(2,4-difluoro-phenyl)-7,8,8-trimethyl-1,2,4,5,6,7-hexahydro-4,7-methano-indazol-3-one (1.65 g, 26%) as a white solid.

Procedure B

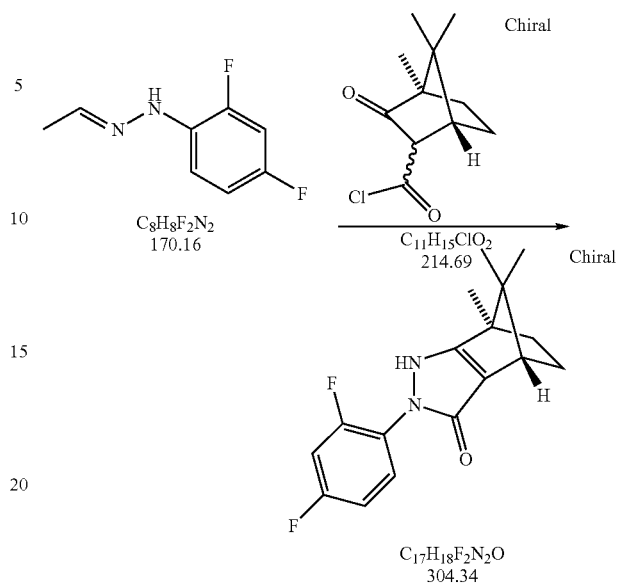

A solution of (1R,4R)-4,7,7-trimethyl-3-oxo-bicyclo[2.2.1]heptane-2-carbonyl chloride (Intermediate 20; 5.4 g, 25.15 mmol) in 1,2-dichloroethane (60 mL) was added over a period of 1 min to a cooled (0° C.) solution of N-(2,4-difluoro-phenyl)-N'-ethylidene-hydrazine (Intermediate 26; 3.92 g, 23.04 mmol) and pyridine (2.9 mL, 35.9 mmol) in 1,2-dichloroethane (30 mL). The reaction mixture was stirred at room temperature for 15 min and then at 50° C. for 40 min. The reaction mixture was cooled, and a solution of HCl in dioxane (4 M, 18 mL, 72 mmol) was added. The solution was stirred for 5 min at room temperature and then glacial acetic acid (30 mL) was added. The reaction mixture was stirred at 100° C. for 45 min. The solvent was evaporated and dichloromethane (200 mL) was added. The solution was washed with 50% saturated brine (2×50 mL), and the combined aqueous layers were back-extracted with dichloromethane (2×50 mL). The combined organic layers were washed with brine (100 mL), dried (magnesium sulfate), filtered, evaporated and eluted through a plug of silica gel with 30% ethyl acetate/hexanes to give (4S,7R)-2-(2,4-difluoro-phenyl)-7,8,8-trimethyl-1,2,4,5,6,7-hexahydro-4,7-methano-indazol-3-one (3.2 g, 45%) as an orange gummy solid.

Intermediate 15: (4S,7R)-2-(2,6-Dichloro-phenyl)-7,8,8-trimethyl-1,2,4,5,6,7-hexahydro-4,7-methano-indazol-3-one

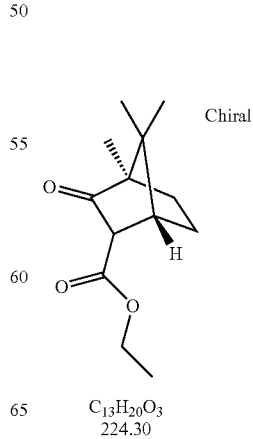

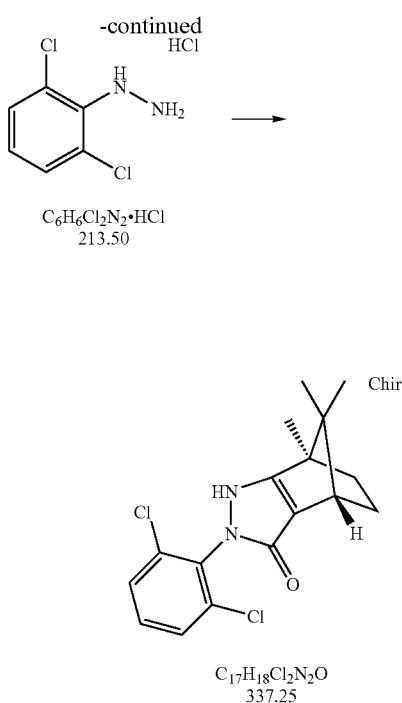

C₆H₆Cl₂N₂·HCl
213.50

C₁₇H₁₈Cl₂N₂O
337.25

Step 1: 2,6-Dichloro-phenylhydrazine

A mixture of 2,6-dichloro-phenylhydrazine hydrochloride (11.7 g, 54.8 mmol) in 1 M NaOH (55 mL), brine (200 mL) and saturated sodium bicarbonate (100 mL) was extracted with dichloromethane (3×200 mL). The organic layers were combined, dried (sodium sulfate), filtered and evaporated to give 2,6-dichloro-phenylhydrazine (9.88 g, quantitative).

Step 2: (4S,7R)-2-(2,6-Dichloro-phenyl)-7,8,8-trimethyl-1,2,4,5,6,7-hexahydro-4,7-methano-indazol-3-one A solution of phosphorus oxychloride (2 mL, 21.5 mmol) in toluene (10 mL) was added to a mixture of 2,6-dichloro-phenylhydrazine (from Step 1; 5.18 g, 29.3 mmol) and (1R, 4R)-camphorcarboxylic acid ethyl ester (Intermediate 3; 5.96 g, 26.6 mmol) in toluene (25 mL). The mixture was heated in an oil-bath at 117° C. for 7 h, and then allowed to stand at room temperature overnight. 1 M NaOH (200 mL) was added and the mixture was mechanically stirred while heating at an external temperature of 110° C. for 45 min to dissolve all of the brown precipitate. The solution was extracted with ethyl acetate (3×200 mL). The first extract was discarded, and the second and third were evaporated to give 1 g of red solid. The sodium hydroxide solution was acidified with glacial acetic acid (20 mL) to give a precipitate which was filtered off and then dissolved in ethyl acetate, washed with brine, dried (sodium sulfate) and evaporated to give 210 mg of red solid. The combined yield of (4S,7R)-2-(2,6-dichloro-phenyl)-7,8,8-trimethyl-1,2,4,5,6,7-hexahydro-4,7-methano-indazol-3-one was 1.21 g (13%).

Intermediate 16: (4S,7R)-2-(2,3-Dimethyl-phenyl)-7,8,8-trimethyl-1,2,4,5,6,7-hexahydro-4,7-methano-indazol-3-one

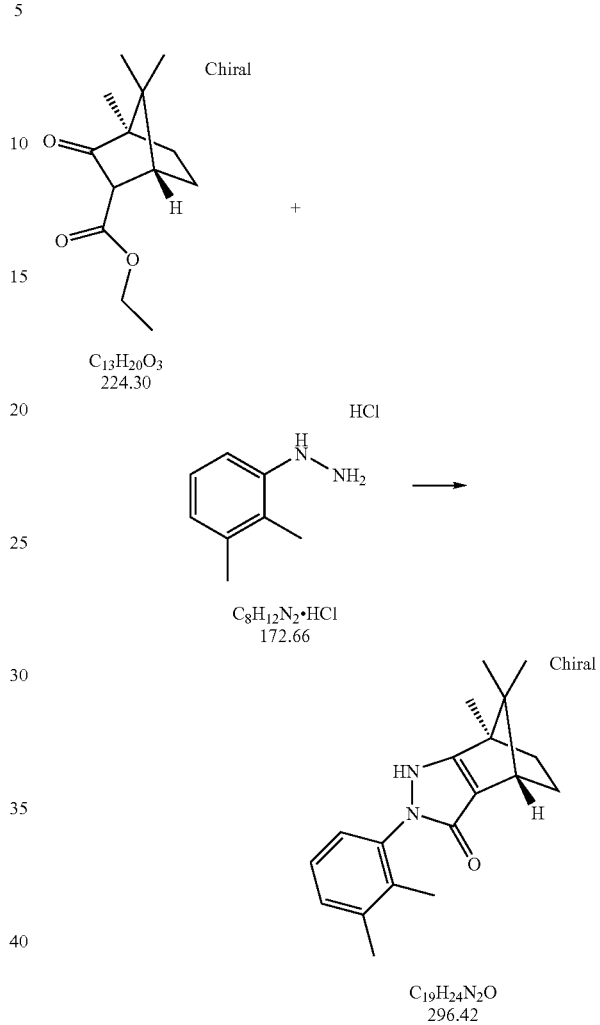

C₁₃H₂₀O₃
224.30

C₈H₁₂N₂·HCl
172.66

C₁₉H₂₄N₂O
296.42

A solution of phosphorus oxychloride (1.3 mL, 14 mmol) in toluene was added to a mixture of 2-fluoro-phenylhydrazine free base [prepared by extracting a mixture of 2,3-dimethyl-phenylhydrazine hydrochloride (5.23 g, 30.3 mmol), 1 M NaOH (200 mL), brine, and saturated sodium bicarbonate with dichloromethane, filtering, and evaporating to give 3.47 g (84%) of free base] and (1R,4R)-camphorcarboxylic acid ethyl ester (Intermediate 3; 5.20 g, 23.2 mmol) in toluene. The mixture was heated at reflux for 7 h, giving a dark red supernatant and a dark red glass. The supernatant was decanted off and evaporated. The residue was dissolved in 1M NaOH (100 mL) and washed with toluene. The dark red glass was dissolved in 1M NaOH (250 mL) with heating, and the solution was washed with toluene. The NaOH solutions were then combined and washed with ethyl acetate (2×300 mL) and then the pH was adjusted to 4.5 by the addition of glacial acetic acid. A solid precipitated. The mixture was stirred at room temperature for 15 minutes and then the solid was filtered off, washed with water, and dried under high vacuum to give (4S,7R)-2-(2,3-dimethyl-phenyl)-7,8,8-trimethyl-1,2,4,5,6,7-hexahydro-4,7-methano-indazol-3-one (4.17 g, 61%) as a cream-colored powder.

Intermediate 17: (4S,7R)-2-(3-Bromo-phenyl)-7,8,8-trimethyl-1,2,4,5,6,7-hexahydro-4,7-methano-indazol-3-one

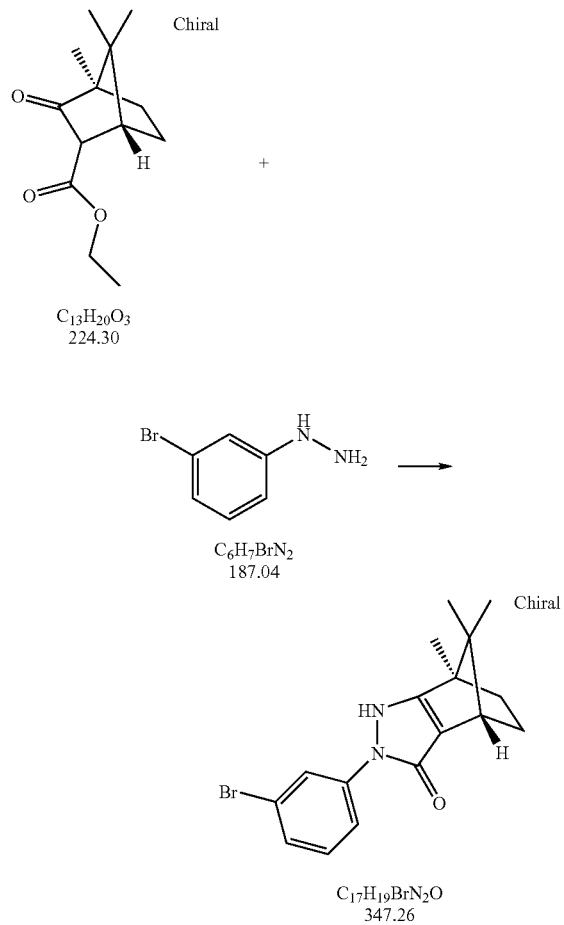

Intermediate 18: (4S,7R)-2-(3-iodo-phenyl)-7,8,8-trimethyl-1,2,4,5,6,7-hexahydro-4,7-methano-indazol-3-one

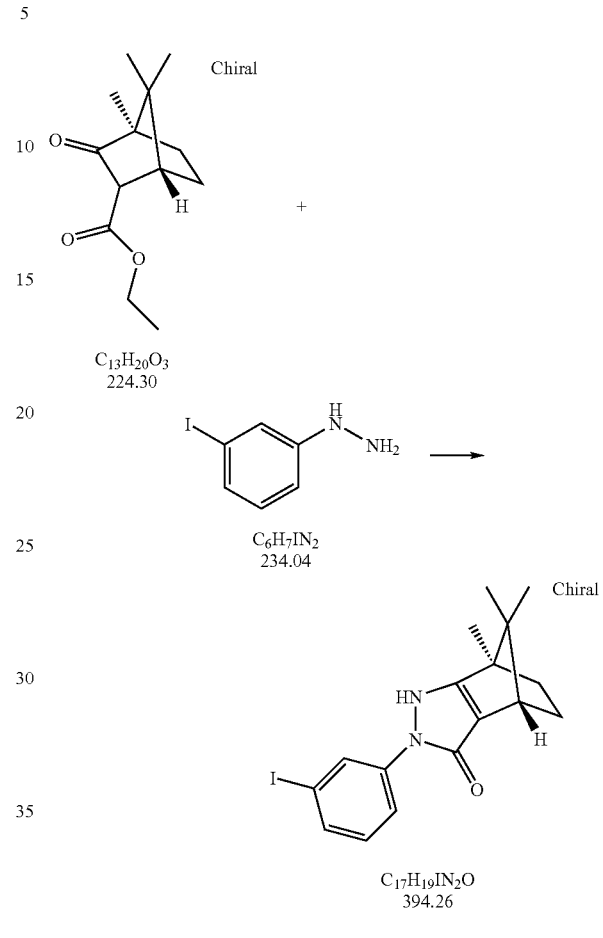

Step 1: 3-Iodo-phenylhydrazine

A solution of phosphorus oxychloride (0.8 mL, 8.6 mmol) in toluene (6 mL) was added to a mixture of 3-bromo-phenylhydrazine (2.00 g, 10.7 mmol) and (1R,4R)-camphorcarboxylic acid ethyl ester (Intermediate 3; 2.4 g, 10.7 mmol) in toluene (25 mL). A further 10 mL of toluene was added to facilitate stirring and the mixture was heated at 110-115 degrees overnight. The toluene was decanted and the residual red glassy material was washed with toluene and then dissolved in 1 M NaOH. The solution was extracted with toluene and then with ethyl acetate. TLC indicated that the toluene solution contained very little product but that there was some product in the ethyl acetate extract. The aqueous layer was acidified with acetic acid to give a tan solid which was filtered, washed with water, and dried to give (4S,7R)-2-(3-bromo-phenyl)-7,8,8-trimethyl-1,2,4,5,6,7-hexahydro-4,7-methano-indazol-3-one (525 mg, 14%). The aqueous filtrate was added to the ethyl acetate solution, the layers were separated and the aqueous layer was extracted twice with ethyl acetate and the combined extracts were washed with water, dried, filtered and evaporated to give a further batch of (4S,7R)-2-(3-bromo-phenyl)-7,8,8-trimethyl-1,2,4,5,6,7-hexahydro-4,7-methano-indazol-3-one (250 mg, 7%).

A solution of sodium nitrite (13.2 g, 186 mmol) in water (65 mL) was added over 90 minutes to a cooled (~0 degrees) mixture of 3-iodo-aniline (40.71 g, 182 mmol) in concentrated hydrochloric acid (80 mL), taking care to ensure that the temperature remained below 0 degrees). The mixture was stirred for 30 min and then filtered. To the filtrate was added dropwise a solution of tin(II) chloride dihydrate (142 g, 0.63 mol) in water, and then the mixture was stirred for 30 minutes with the temperature maintained below 0 degrees. The reaction mixture was placed in the refrigerator overnight and then filtered. The residue was washed with brine, then 1:1 petroleum ether/ether (750 mL) and then with 2:1 petroleum ether/ether (375 mL) and the washings were discarded. The remaining residue was dissolved in 5 M NaOH and ether, and the aqueous layer was extracted with ether. The combined ether layers were washed with water and brine, dried (sodium sulfate), filtered, and evaporated to give 3-iodo-phenylhydrazine (25.3 g, 53%) as a dark red viscous oil.

Step 2: (4S,7R)-2-(3-Iodo-phenyl)-7,8,8-trimethyl-1,2,4,5,6,7-hexahydro-4,7-methano-indazol-3-one A solution of phosphorus oxychloride (1.9 mL, 20 mmol) in toluene (10 mL) was added to an ice-bath-cooled mixture of 3-iodo-phenylhydrazine (from Step 1; 5.86 g, 24.5 mmol) and (1R,4R)-camphorcarboxylic acid ethyl ester (Intermediate 3; 5.00 g, 22.2 mmol) in toluene (30 mL). The ice bath was removed and the mixture was heated at reflux overnight. The reaction mixture was cooled and 2.5 M NaOH solution (50 mL) was added. The reaction mixture was stirred and solids were broken up with a spatula, then the reaction mixture was transferred to a separatory funnel and water, toluene and 2.5 M NaOH (50 mL) were added. The organic layer was extracted with 2.5 M NaOH. And the combined aqueous layers were washed with toluene (2×100 mL). The aqueous layer was acidified to pH 4.9 with glacial acetic acid and extracted with ethyl acetate (3×150 mL). The combined organic layers were washed with water and brine, dried (magnesium sulfate), filtered, evaporated, and purified using an Analogix Intelliflash 280 system (Analogix, Inc., Burlington, Wis.) with an RS-80 column, eluting with 0-20% ethyl acetate/hexanes to give (4S,7R)-2-(3-iodo-phenyl)-7,8,8-trimethyl-1,2,4,5,6,7-hexahydro-4,7-methano-indazol-3-one (1.75 g, 20%) as a yellow solid.

Intermediate 19: (4S,7R)-1,7,8,8-Tetramethyl-1,2,4,5,6,7-hexahydro-4,7-methano-indazol-3-one Procedure A

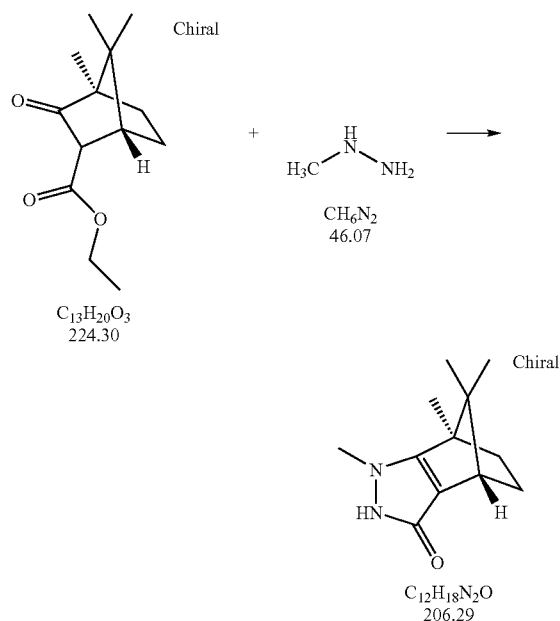

A mixture of methylhydrazine (720 μL, 13.5 mmol) and (1R,4R)-camphorcarboxylic acid ethyl ester (Intermediate 3; 5.00 g, 22.2 mmol) was heated at reflux for 2 h. The condenser was removed and the solution was heated for 2 h. A further portion of methylhydrazine (720 μL, 13.5 mmol) was added and the solution was heated at reflux for 2 h. The reaction mixture was stored at room temperature overnight and a mixture of ethanol (20 mL) and concentrated HCl (20 mL) was added. The mixture was heated at reflux for 5 h and then 5 M NaOH and toluene were added. The aqueous layer was acidified with acetic acid and extracted with ethyl acetate. Salt was added and the solution was again extracted with ethyl acetate. The combined toluene and ethyl acetate extracts were evaporated to give an oil (3 g) which was mainly unreacted keto-ester. Acetic acid (50 mL) and methylhydrazine (720 μL, 13.5 mmol) were added and the mixture was stirred at room temperature overnight and then at reflux for 1 h. The reaction mixture was filtered and evaporated. The residue was taken up in ethanol, filtered, and evaporated again. The residue was purified by flash chromatography, eluting with 10-20% methanol/dichloromethane to give (4S,7R)-1,7,8,8-tetramethyl-1,2,4,5,6,7-hexahydro-4,7-methano-indazol-3-one (270 mg, 6%) as a pale white solid.

Procedure B

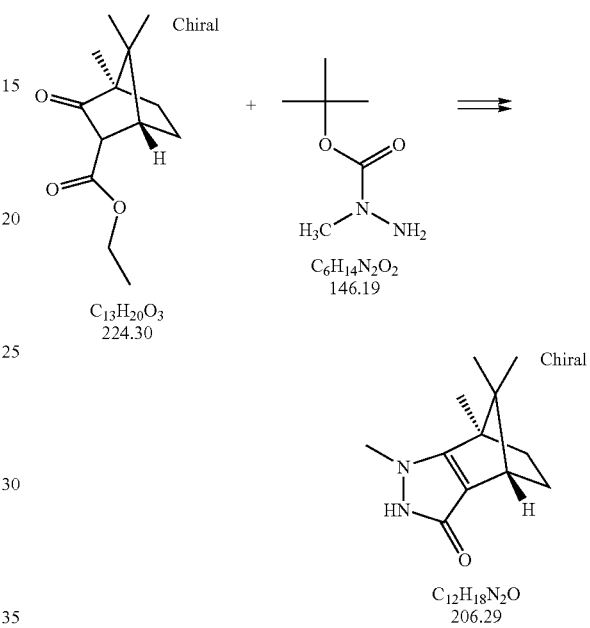

A mixture of N-methyl-hydrazinecarboxylic acid tert-butyl ester (11.5 g, 78.7 mmol) and (1R,4R)-camphorcarboxylic acid ethyl ester (Intermediate 3; 17.65 g, 78.7 mmol) was heated neat in an oil-bath at 100° C. for 3 h. Conc HCl (30 mL) was added slowly, and the reaction mixture was heated at 100° C. for 45 min. The mixture was allowed to cool to room temperature, the pH was adjusted to 6 with 1 M NaOH, and the mixture was cooled again. The solid was filtered off, washed with water and then hexane, and dried first by air-drying overnight and then under high vacuum to give (4S,7R)-1,7,8,8-tetramethyl-1,2,4,5,6,7-hexahydro-4,7-methano-indazol-3-one (8.3 g, 51%) as a white solid Intermediate 20: (1R,4R)-4,7,7-Trimethyl-3-oxo-bicyclo[2.2.1]heptane-2-carbonyl chloride

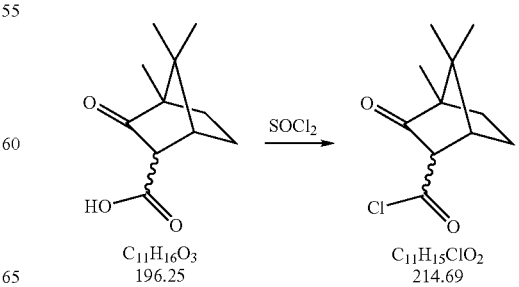

Oxalyl chloride (5.5 mL, 63.05 mmol) was added dropwise to a solution of (1R,4R)-3-camphorcarboxylic acid (Intermediate 3; 4.0 g, 20.4 mol) and N,N-dimethylformamide (3 drops) in dichloromethane (20 mL) at 0° C. The reaction mixture was stirred at 0° C. for 20 min and then at room temperature overnight. The solvent was evaporated, and the residue was co-evaporated three times with dichloromethane and then dried under high vacuum to give (1R,4R)-4,7,7-trimethyl-3-oxo-bicyclo[2.2.1]heptane-2-carbonyl chloride (4.36 g, 100%) as an orange oil.

Intermediate 21: (4S,7R)-2-(2-Chloro-4-fluoro-phenyl)-7,8,8-trimethyl-1,2,4,5,6,7-hexahydro-4,7-methano-indazol-3-one

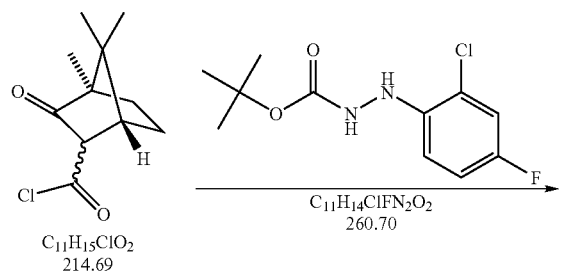

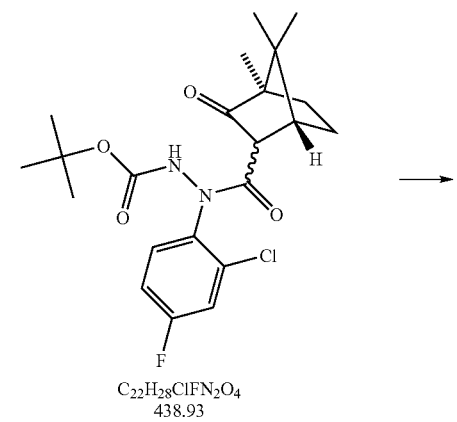

Step 1: N'-(2-Chloro-4-fluoro-phenyl)-N'-((1R,4R)-4,7,7-trimethyl-3-oxo-bicyclo[2.2.1]heptane-2-carbonyl)-hydrazinecarboxylic acid tert-butyl ester Triethylamine (21.3 mL, 153 mmol) was added in two portions to a cooled (0° C.) solution of (1R,4R)-4,7,7-trimethyl-3-oxo-bicyclo[2.2.1]heptane-2-carbonyl chloride (Intermediate 20; 10.9 g, 51 mmol) in dichloromethane (100 mL), giving a thick suspension. Dichloromethane (30 mL) was added, followed by N'-(2-chloro-4-fluoro-phenyl)-hydrazinecarboxylic acid tert-butyl ester (Intermediate 33; 9.8 g, 37.6 mmol). The reaction mixture was placed in an oil-bath at 50° C., heated at this temperature for 6 hours and then allowed to cool to room temperature and stir for 1 h. The reaction mixture was poured into water (200 mL) and two layers were separated. The organic layer was washed with water (2×200 mL) and brine (100 mL), dried (magnesium sulfate), filtered, evaporated, and then dried under high vacuum for 90 min to give N'-(2-chloro-4-fluoro-phenyl)-N'-((1R,4R)-4,7,7-trimethyl-3-oxo-bicyclo[2.2.1]heptane-2-carbonyl)-hydrazinecarboxylic acid tert-butyl ester (14.9 g, 90%) as a pale foam.

Step 2: (4S,7R)-2-(2-Chloro-4-fluoro-phenyl)-7,8,8-trimethyl-1,2,4,5,6,7-hexahydro-4,7-methano-indazol-3-one Trifluoroacetic acid (50 mL) was added in two portions to a cooled (0° C.) solution of N'-(2-chloro-4-fluoro-phenyl)-N'-((1R,4R)-4,7,7-trimethyl-3-oxo-bicyclo[2.2.1]heptane-2-carbonyl)-hydrazinecarboxylic acid tert-butyl ester (14.8 g, 33.7 mmol) in dichloromethane (50 mL). The mixture was stirred at 0° C. for 5 min and then the cooling bath was removed and the reaction mixture was allowed to warm to room temperature and stir for 4 h. Volatiles were evaporated under reduced pressure and dichloromethane (250 mL) was added. The solution was washed with water (4×125 mL), and brine (125 mL), dried (magnesium sulfate), filtered, and evaporated. The flask containing the product was covered in foil and the solid was dried overnight under high vacuum to give (4S,7R)-2-(2-chloro-4-fluoro-phenyl)-7,8,8-trimethyl-1,2,4,5,6,7-hexahydro-4,7-methano-indazol-3-one (11.4 g, 105% of the expected amount). This material was used in subsequent reactions without further purification.

Intermediate 22: (4S,7R)-2-(2-Trifluoromethyl-phenyl)-7,8,8-trimethyl-1,2,4,5,6,7-hexahydro-4,7-methano-indazol-3-one

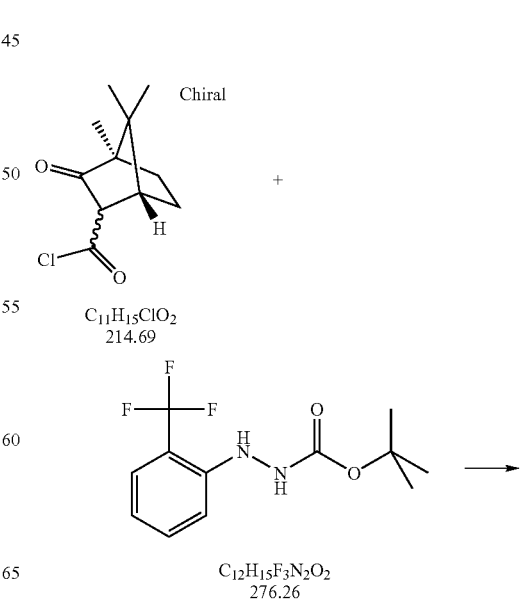

43

-continued

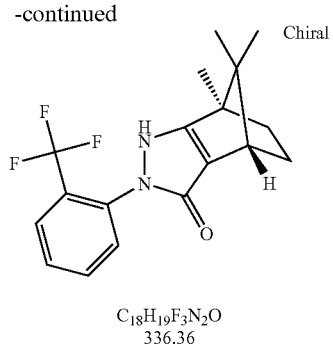

C$_{18}$H$_{19}$F$_3$N$_2$O
336.36

Step 1: N'-(2-Trifluoromethyl-phenyl)-hydrazinecarboxylic acid tert-butyl ester

A solution of di-tert-butyl-dicarbonate (2.55 g, 11.6 mmol) in methanol (20 mL) was cooled to about 2° C. and added dropwise to a solution of 2-trifluoromethyl-phenyl-hydrazine (2.00 g, 11.4 mmol) in methanol (20 mL). The solution was allowed to stir overnight at room temperature. The solvent was evaporated to give N'-(2-trifluoromethyl-phenyl)-hydrazinecarboxylic acid tert-butyl ester (3.14 g, 100%) as a yellow solid.

Step 2: (4S,7R)-2-(2-Trifluoromethyl-phenyl)-7,8,8-trimethyl-1,2,4,5,6,7-hexahydro-4,7-methano-indazol-3-one N'-(2-Trifluoromethyl-phenyl)-hydrazinecarboxylic acid tert-butyl ester (1.85 g, 6.6 mmol) was added in one portion to a ice-bath-cooled solution of (1R,4R)-4,7,7-trimethyl-3-oxo-bicyclo[2.2.1]heptane-2-carbonyl chloride (Intermediate 20; 1.09 g, 5.1 mmol) in a mixture of 1,2-dichloroethane (12 mL) and pyridine (0.6 mL, 7.6 mmol). The mixture was diluted with 1,2-dichloroethane (6 mL) to facilitate stirring. The reaction mixture was heated at 50° C. for 1 h, then cooled to room temperature. A 4 M solution of HCl in dioxane (3.6 mL) was added via the condenser and the solution was stirred for several minutes. Glacial acetic acid (7 mL) was added and the reaction mixture was heated in an oil bath at ~100° C. for 2 h. The reaction mixture was stirred overnight at room temperature and then evaporated. Dichloromethane was added and the solution was washed twice with brine. The aqueous washes were back-extracted with dichloromethane, and the combined organic layers were washed with brine, dried (magnesium sulfate), filtered, evaporated, and purified using an Analogix Intelliflash 280 system (Analogix, Inc., Burlington, Wis.) with an Analytical Sales Aspire 120 g column, eluting with 0-40% ethyl acetate/hexanes to give (4S,7R)-2-(2-trifluoromethyl-phenyl)-7,8,8-trimethyl-1,2,4,5,6,7-hexahydro-4,7-methano-indazol-3-one (0.80 g, 46%) as a light brown solid.

44

Intermediate 23: (4S,7R)-2-Benzyl-7,8,8-trimethyl-1,2,4,5,6,7-hexahydro-4,7-methano-indazol-3-one

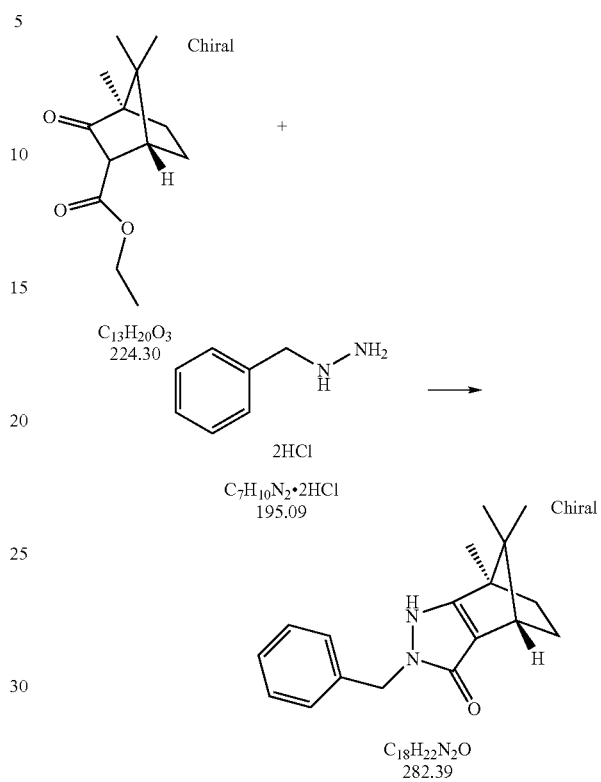

A neat mixture of (1R,4R)-camphorcarboxylic acid ethyl ester (Intermediate 3; 5 g, 22.3 mmol) and benzylhydrazine dihydrochloride (4.57 g, 23.4 mmol) was heated in a sealed tube at 100° C. for 2 days. The reaction mixture was allowed to cool, then it was diluted with ethyl acetate (300 mL) and washed with 20% saturated brine (3×120 mL), dried (magnesium sulfate), filtered, evaporated, and purified twice by chromatography. Initially, the compound was purified on an ISCO 330 g column, eluting with 20-85% ethyl acetate/hexanes, and subsequently on an ISCO 120 g column eluting with 20-70% ethyl acetate/hexanes to give (4S,7R)-2-benzyl-7,8,8-trimethyl-1,2,4,5,6,7-hexahydro-4,7-methano-indazol-3-one (545 mg, 9%) as a white foam.

Intermediate 24: (1S,4S)-4,7,7-Trimethyl-3-oxo-bicyclo[2.2.1]heptane-2-carboxylic acid

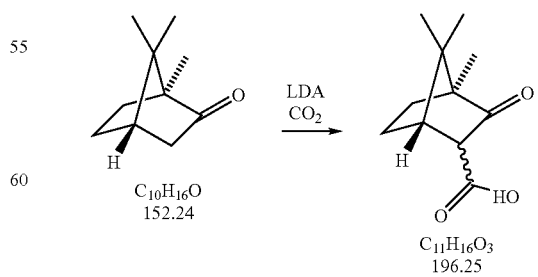

Following the procedure of W. W. Shumway et al. J. Org. Chem. 2001, 66, 5832-5839, L-(−)-camphor (15 g, 98.5 mmol) was dissolved in toluene (62 mL), cooled to −78 degrees, and lithium diisopropylamide (1.8 M solution in heptane/tetrahydrofuran/ethylbenzene; 98.5 mL, 197 mmol, 2 equiv.) was added via an addition funnel over 15 min. The resulting solution was stirred at −78 degrees for 30 min, warmed to room temperature, and carefully poured over an excess of pulverized dry ice (300 g). Toluene (30 mL) was added and the solution was allowed to warm to room temperature. Diethyl ether (100 mL) was added and the solution was extracted with water (3×150 mL). The organic layer was discarded. The aqueous layer was acidified with 2M HCl to pH 1, salted with solid sodium chloride, and extracted with ether (3×150 mL). The combined organic extracts were dried (sodium sulfate), filtered, and evaporated to give (1S,4S)-4,7,7-trimethyl-3-oxo-bicyclo[2.2.1]heptane-2-carboxylic acid (16.0 g, 83%) as a white solid.

Intermediate 25: (1S,4S)-4,7,7-Trimethyl-3-oxo-bicyclo[2.2.1]heptane-2-carbonyl chloride

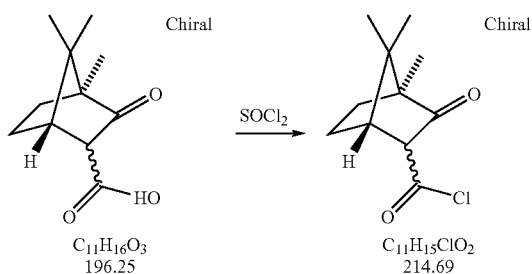

Oxalyl chloride (2.8 mL, 32.1 mmol) was added over a period of 10 min to a solution of (1S,4S)-4,7,7-trimethyl-3-oxo-bicyclo[2.2.1]heptane-2-carboxylic acid (Intermediate 24; 2.1 g, 10.7 mmol) and N,N-dimethylformamide (3 drops) in dichloromethane (15 mL) at 0° C. The reaction mixture was stirred at 0° C. for 5 min and then at room temperature for 2 h. The solvent was evaporated, and the residue was co-evaporated three times with dichloromethane and then dried under high vacuum for 20 min to give (1S,4S)-4,7,7-trimethyl-3-oxo-bicyclo[2.2.1]heptane-2-carbonyl chloride (2.2 g, 96%) as an orange oil. This was used directly in subsequent steps without further purification.

Intermediate 26: N-(2,4-Difluoro-phenyl)-N'-ethylidene-hydrazine

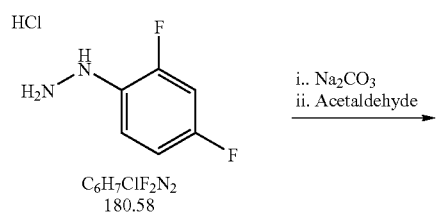

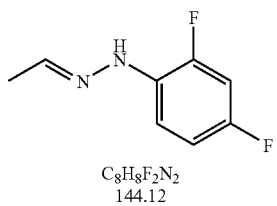

2,4-Difluorophenylhydrazine hydrochloride (Apollo; 6.00 g, 32.3 mmol) was partitioned between saturated aqueous sodium carbonate (100 mL) and ethyl acetate (150 mL). The organic layer was washed with saturated aqueous sodium carbonate (50 mL) and brine (100 mL, then 50 mL), dried (sodium sulfate), filtered, and evaporated to give 2,4-difluorophenylhydrazine (4.54 g, 98%) as a light brown solid. This was taken in dry toluene (50 mL) and the mixture was cooled to 0° C. under argon. A solution of acetaldehyde (3.0 mL, 53.4 mmol) in dry toluene (10 mL) was added dropwise over 15 min, the solution was stirred at 0° C. for 5 min and then at room temperature for 1 h. The reaction mixture was stored overnight in the freezer, then it was warmed to room temperature and filtered. The filtrate was concentrated to give a brown oil, with some water present. Toluene was added and the solution was dried (sodium sulfate), filtered and evaporated to give N-(2,4-difluoro-phenyl)-N-ethylidene-hydrazine (4.61 g, 84%) as a brown oil as a mixture of E and Z isomers (by 1H NMR).

Intermediate 27: N-Benzyl-hydrazinecarboxylic acid tert-butyl ester

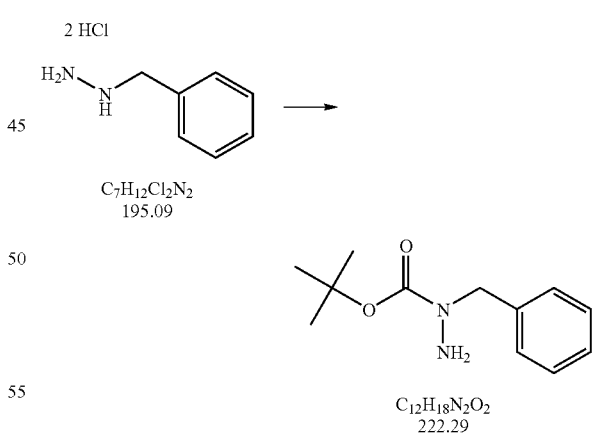

A solution of di-tert-butyl dicarbonate (11.3 g, 51.3 mmol) in tetrahydrofuran (40 mL) was added dropwise over 1 h to a cooled (0° C.) solution of benzylhydrazine (prepared by the neutralization of benzylhydrazine hydrochloride [10.00 g, 51.3 mmol] with saturated aqueous sodium carbonate [10 mL)) in methanol. The reaction mixture was stirred at 0° C. for 1 h and then the solvent was evaporated. The resulting colorless oil was purified by column chromatography, eluting with 20-40% ethyl acetate/hexanes, to give N-benzyl-hydrazinecarboxylic acid tert-butyl ester (3.60 g, 32%) as a colorless oil.

Intermediate 28:
N-Cyclopropyl-hydrazinecarboxylic acid tert-butyl ester

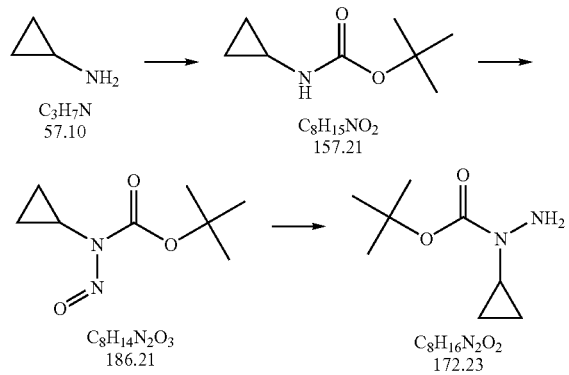

Step 1: Cyclopropyl-carbamic acid tert-butyl ester

A solution of di-tert-butyl dicarbonate (14.40 g, 66 mmol) in dichloromethane (33 mL) was added to a cooled (0° C.) solution of cyclopropylamine (5 mL, 72.1 mmol) in dichloromethane (17 mL) over 2 min, and vigorous gas evolution was observed. The cooling bath was removed and the solution was stirred at room temperature for 1 h. The solvent was evaporated to give cyclopropyl-carbamic acid tert-butyl ester (9.8 g, 95%) as a white solid which was used directly in the next step without purification.

Step 2: N-Nitroso-N-cyclopropyl-carbamic acid tert-butyl ester

A solution of cyclopropyl-carbamic acid tert-butyl ester (4.8 g, 30.5 mmol) and pyridine (5.9 mL, 73 mmol) in acetonitrile (75 mL) was cooled to approximately −25° C. in a carbon tetrachloride/dry ice bath. Nitrosonium tetrafluoroborate (4.7 g, 40.2 mmol) was added over a period of 20 min. The cooling bath was removed and the reaction mixture was stirred in an ice-bath at 0° C. for 2.5 h. Water (100 mL) and ethyl acetate (500 mL) were added and the organic layer was washed with water (100 mL), 2 M aqueous HCl (50 mL) and brine (100 mL), dried (magnesium sulfate), filtered, evaporated, and purified in two batches using an ISCO 120 g column, eluting with 10-30% ethyl acetate, to give N-nitroso-N-cyclopropyl-carbamic acid tert-butyl ester (1.5 g, 26%) as a yellow oil.

Step 3: N-Cyclopropyl-hydrazinecarboxylic acid tert-butyl ester

Water (24 mL) was added over 1 min to a mixture of N-nitroso-N-cyclopropyl-carbamic acid tert-butyl ester (2.01 g, 10.8 mmol), zinc powder (7.2 g, 110 mmol) and ammonium chloride (8.8 g, 165 mmol) in methanol (48 mL). An exotherm and gas evolution were noted. The mixture was stirred at room temperature for 2.25 h and at 50° C. for 2 h. The mixture was allowed to cool. It was filtered through Celite, and the Celite was washed well with methanol. The colvents were evaporated and dichloromethane (250 mL) was added. Salts were filtered off and the solution was dried (magnesium sulfate), filtered, and evaporated. The residue was passed through a cotton plug with a small amount of dichloromethane, the solvent was evaporated to give a clear oil. This was purified by chromatography using an ISCO 120 g column, eluting with 10-60% ethyl acetate/hexanes to give N-cyclopropyl-hydrazinecarboxylic acid tert-butyl ester (207 mg, 11%) as a pale yellow oil, along with a 36% yield of over-reduced cyclopropyl-carbamic acid tert-butyl ester.

Intermediate 29:
N'-(2-Fluoro-phenyl)-hydrazinecarboxylic acid tert-butyl ester

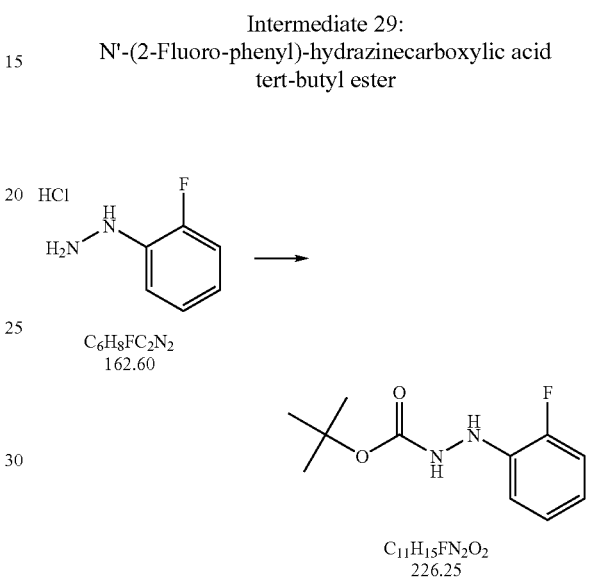

Di-tert-butyl dicarbonate (4.40 g, 20.2 mmol) was added in one portion to a cooled (0° C.) solution of triethylamine (8.3 mL, 59.6 mol) and 2-fluorophenylhydrazine hydrochloride (3.00 g, 18.5 mmol) in methanol (50 mL). The reaction mixture was stirred at 0° C. for 10 min, and at room temperature for 2 h. The solvent was evaporated and ethyl acetate (100 mL) was added. The solution was washed with water (2×25 mL) and brine (25 mL). The organic phase was dried (sodium sulfate), filtered, evaporated, and co-evaporated with hexane. A solution of 5% ethyl acetate/hexane (25 mL0 was added to the resulting gummy yellow solid and the mixture was stirred at room temperature for 20 min and then in an ice-bath at 0° C. for 1 h. The solid was filtered off, washed with hexane, and dried to give N'-(2-fluoro-phenyl)-hydrazinecarboxylic acid tert-butyl ester (2.97 g, 71%) as a pale yellow solid.

Intermediate 30:
N'-(2-Chloro-phenyl)-hydrazinecarboxylic acid tert-butyl ester

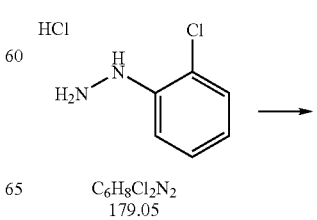

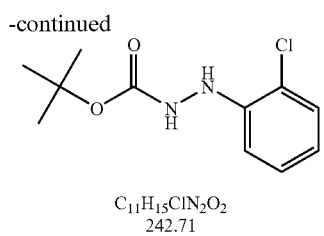

C₁₁H₁₅ClN₂O₂
242.71

A solution of di-tert-butyl dicarbonate (101.2 g, 464 mmol) in methanol (300 mL) was added dropwise over 15 min to a cooled (~0° C.) solution of triethylamine (162 mL, 1.16 mol), 2-chlorophenylhydrazine hydrochloride (69.4 g, 388 mmol) and methanol (350 mL). The reaction mixture was stirred at 0° C. for 15 min, at room temperature for 2 h, at reflux for 6 h, and then at room temperature for 14 h. A further quantity of di-tert-butyl dicarbonate (4.2 g, 19 mmol) was added and the solution was heated at reflux for 2 h. The mixture was concentrated to dryness and ethyl acetate (1 L) was added. The solution was washed with water (4×1 L), saturated aqueous sodium hydrogen carbonate (600 mL) and brine (400 mL). The organic phase was dried (sodium sulfate), filtered, and evaporated. The resulting red solid was ground and triturated several times with hexanes (total volume: 350 mL) and the resulting material was dried under high vacuum overnight to give N'-(2-chloro-phenyl)-hydrazinecarboxylic acid tert-butyl ester (77.8 g, 83%) as a light tan powder.

Intermediate 31:
N'-(4-Methoxy-phenyl)-hydrazinecarboxylic acid tert-butyl ester

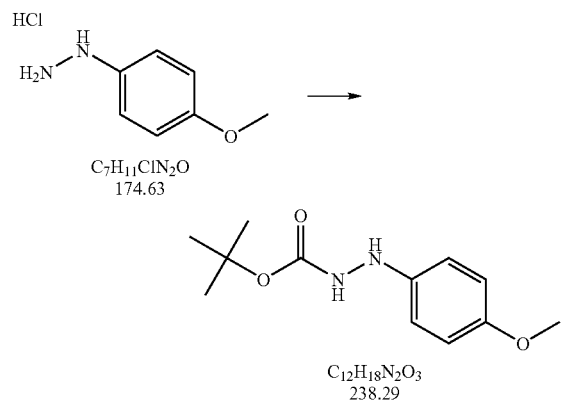

C₇H₁₁ClN₂O
174.63

C₁₂H₁₈N₂O₃
238.29

Triethylamine (60 mL, 430 mmol) was added to a cooled (0° C.) mixture of 4-methoxy-phenylhydrazine hydrochloride (25.01 g, 143.2 mmol) and methanol (275 mL). The solution was stirred for 5 min and di-tert-butyl dicarbonate (34.4 g, 157.6 mmol) was added. The reaction mixture was stirred at 0° C. for 10 minutes, at reflux for 5 h, and then at room temperature overnight. The solvent was evaporated, ethyl acetate (500 mL) was added, and the solution was washed with a mixture of water and brine (100 mL water and 250 mL brine), dried (magnesium sulfate), filtered and evaporated to give a deep red oil. Further drying under high vacuum gave a deep red solid. The solid was recrystallized from 10% ethyl acetate/hexanes (30 mL), with slow cooling to room temperature followed by cooling in the refrigerator. The crystals were crushed, filtered off, washed with hexanes and dried under high vacuum to give N'-(4-methoxy-phenyl)-hydrazinecarboxylic acid tert-butyl ester (19.85 g, 58%) as a tan solid.

Intermediate 32:
N'-(2,4-Difluoro-phenyl)-hydrazinecarboxylic acid tert-butyl ester

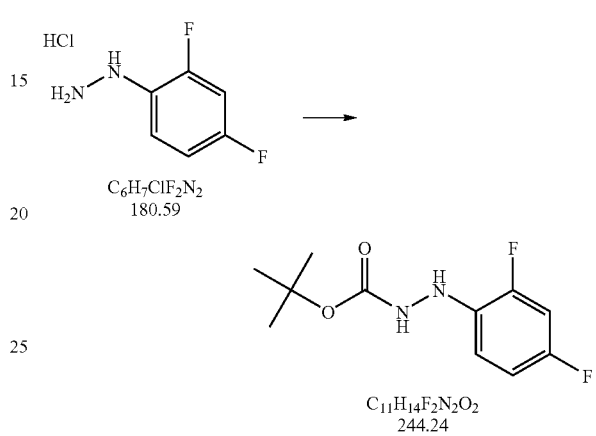

C₆H₇ClF₂N₂
180.59

C₁₁H₁₄F₂N₂O₂
244.24

Triethylamine (58 mL, 416 mmol) was added in two portions to a cooled (~0° C.) mixture of 2,4-difluoro-phenylhydrazine hydrochloride (25 g, 138 mmol) and methanol (200 mL). The solution was stirred for 5 min and di-tert-butyl dicarbonate (33.1 g, 152 mmol) was added. The reaction mixture was stirred at 0° C. for 5 min, at reflux for 11 h, and then at room temperature over a weekend. The solvent was evaporated, ethyl acetate (600 mL) was added, and the solution was washed with a mixture of water and brine, dried (magnesium sulfate), filtered and evaporated to give an orange oil. A mixture of 5% ethyl acetate/hexanes (100 mL) was added. The mixture was heated, the flask scratched with a glass rod, and the mixture placed in a freezer for 30 min. The crystals were filtered off, washed with cold hexane and dried under high vacuum to give N'-(2,4-difluoro-phenyl)-hydrazinecarboxylic acid tert-butyl ester (19.85 g, 58%) as a tan solid.

Intermediate 33: N'-(2-Chloro-4-fluoro-phenyl)-hydrazinecarboxylic acid tert-butyl ester

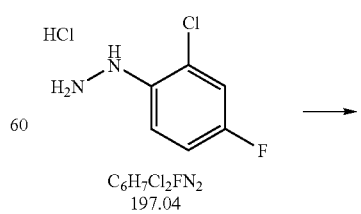

C₆H₇Cl₂FN₂
197.04

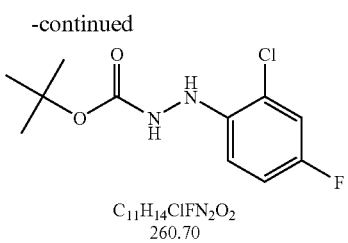

C₁₁H₁₄ClFN₂O₂
260.70

Triethylamine (21.3 mL, 153 mmol) was added in one portion to a cooled (~0° C.) mixture of 2-chloro-4-fluorophenylhydrazine hydrochloride (10 g, 50.8 mmol) and methanol (100 mL). Di-tert-butyl dicarbonate (12.2 g, 55.9 mmol) was added and the reaction mixture was stirred at 0° C. for 5 min, at 75° C. (oil-bath temperature) for 7 h, and then at room temperature overnight. The solvent was evaporated and ethyl acetate (300 mL) was added. The solution was washed with water (100 mL) and brine (100 mL), dried (magnesium sulfate), filtered, and evaporated. The residue was taken up in 5% ethyl acetate/hexanes. The glass vessel was scratched and the mixture was stored in the freezer. The solid was filtered off and washed with hexane to give N'-(2-chloro-4-fluoro-phenyl)-hydrazinecarboxylic acid tert-butyl ester (9.88 g, 75%).

Intermediate 34:
N'-(2,5-Dichloro-phenyl)-hydrazinecarboxylic acid tert-butyl ester

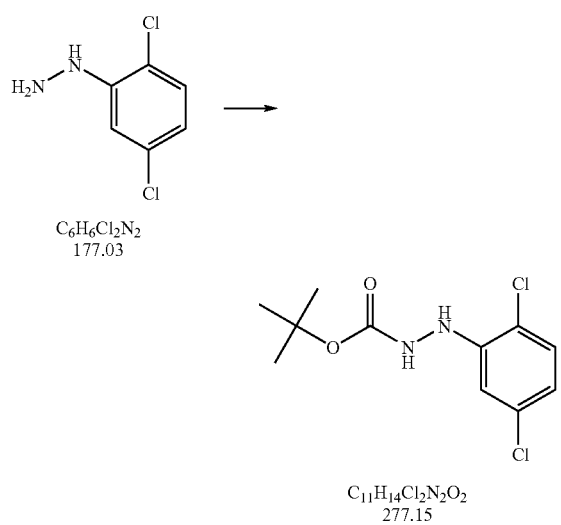

C₆H₆Cl₂N₂
177.03

C₁₁H₁₄Cl₂N₂O₂
277.15

Di-tert-butyl dicarbonate (13.56 g, 62.1 mmol) was added in one portion to a cooled (0° C.) solution of 2,5-dichlorophenylhydrazine (Aldrich; 10.00 g, 56.5 mmol) in methanol (130 mL). The reaction mixture was stirred at 0° C. for 10 min, then the cooling bath was removed and the solution was stirred at room temperature for 3 h. The solvent was evaporated, and the residue was co-evaporated with hexane. A solution of 5% ethyl acetate/hexanes was added and the glass was scratched to give a solid. The mixture was stirred in an ice-bath at 0° C. for 1 h, then the solid was filtered off, washed with hexane, and dried under high vacuum to give N'-(2,5-dichloro-phenyl)-hydrazinecarboxylic acid tert-butyl ester (8.68 g, 55%) as a tan solid.

Intermediate 35:
N'-(3,5-Dichloro-phenyl)-hydrazinecarboxylic acid tert-butyl ester

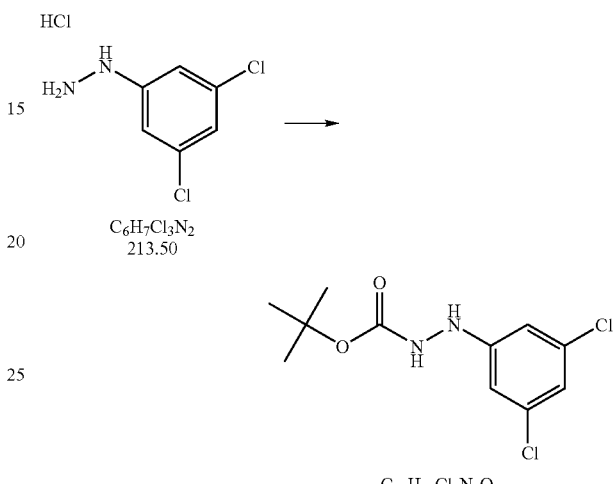

C₆H₇Cl₃N₂
213.50

C₁₁H₁₄Cl₂N₂O₂
277.15

Triethylamine (9.8 mL, 70 mmol) was added in two portions to a cooled (~0° C.) solution of 3,5-dichloro-phenylhydrazine hydrochloride (5 g, 23.4 mmol) in methanol (50 mL). Di-tert-butyl dicarbonate (33.1 g, 152 mmol) was added and the reaction mixture was stirred at 0° C. for 2-3 min, and then at 75° C. (oil-bath temperature) overnight. Further portions of di-tert-butyl dicarbonate (0.5 g, 2.3 mmol) and triethylamine (1 mL, 7.2 mmol) were added and the reaction mixture was stirred overnight at 75° C. The reaction was allowed to cool to room temperature and the solvent was evaporated. Ethyl acetate (200 mL) was added and the solution was washed with water (100 mL) and brine. The combined aqueous layers were extracted with ethyl acetate (200 mL). The combined organic extracts were dried (magnesium sulfate), filtered, evaporated, and dried under high vacuum for 3 h to give N'-(3,5-dichloro-phenyl)-hydrazinecarboxylic acid tert-butyl ester (5.5 g, 85%).

Intermediate 36: N-Methyl-N'-naphthalen-2-yl-hydrazinecarboxylic acid tert-butyl ester

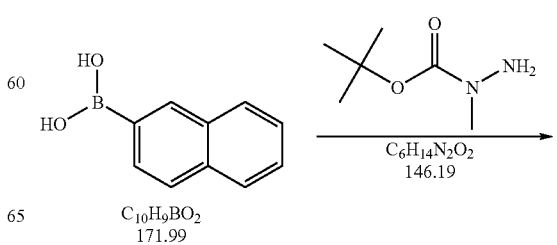

C₁₀H₉BO₂
171.99

C₆H₁₄N₂O₂
146.19

53

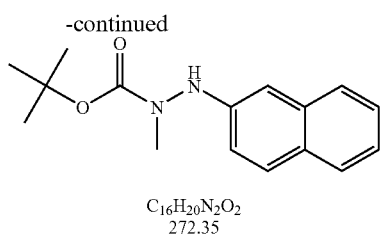

C₁₆H₂₀N₂O₂
272.35

A mixture of N-methyl-hydrazinecarboxylic acid tert-butyl ester (Intermediate 1; 1.50 g, 10.26 mmol), 2-naphthaleneboronic acid (Lancaster; 1.90 g, 11.05 mmol), copper(II) acetate (1.90 g, 10.46 mmol) and triethylamine (3.6 mL, 25.8 mmol) in 1,2-dichloroethane (40 mL) was heated in an oil bath at 50° C. for 45 min. The mixture was allowed to cool, and it was then adsorbed onto silica gel and purified by chromatography using an ISCO 120 g column, eluting with 15-20% ethyl acetate/hexanes, to give N-methyl-N'-naphthalen-2-yl-hydrazinecarboxylic acid tert-butyl ester (1.26 g, 45%) as an orange oil that partially solidified. The Boc region of the 1H NMR spectrum integrated high, but the material was used directly in subsequent steps without further purification.

Intermediate 37: N-Benzyl-N'-naphthalen-2-yl-hydrazinecarboxylic acid tert-butyl ester

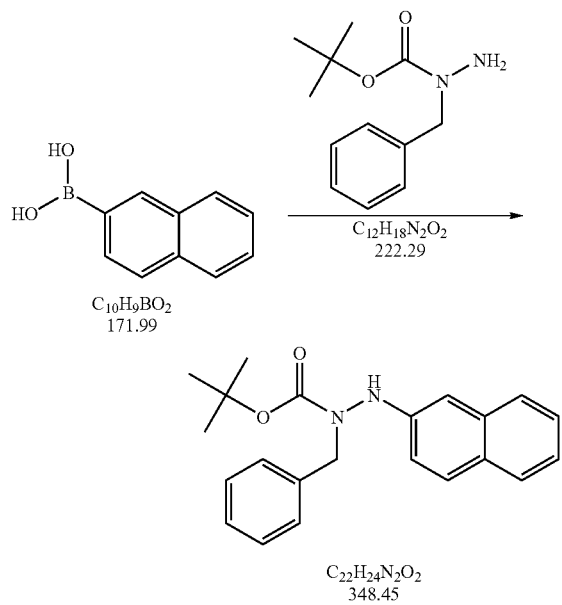

A mixture of N-benzyl-hydrazinecarboxylic acid tert-butyl ester (Intermediate 27; 1.21 g, 5.44 mmol), 2-naphthaleneboronic acid (Lancaster; 1.00 g, 5.8 mmol), copper(II) acetate (990 mg, 5.45 mmol) and triethylamine (1.9 mL, 13.6 mmol) in 1,2-dichloroethane (30 mL) was heated in an oil bath at 50° C. for 1.5 h. The mixture was allowed to cool, and it was then adsorbed onto silica gel and purified by chromatography using an ISCO 120 g column, eluting with 15-30% ethyl acetate/hexanes, to give N-benzyl-N'-naphthalen-2-yl-hydrazinecarboxylic acid tert-butyl ester (929 mg, 49%) as a yellow oil that solidified on standing.

54

Intermediate 38: (4R,7S)-2-(2-Fluoro-phenyl)-7,8,8-trimethyl-1,2,4,5,6,7-hexahydro-4,7-methano-indazol-3-one

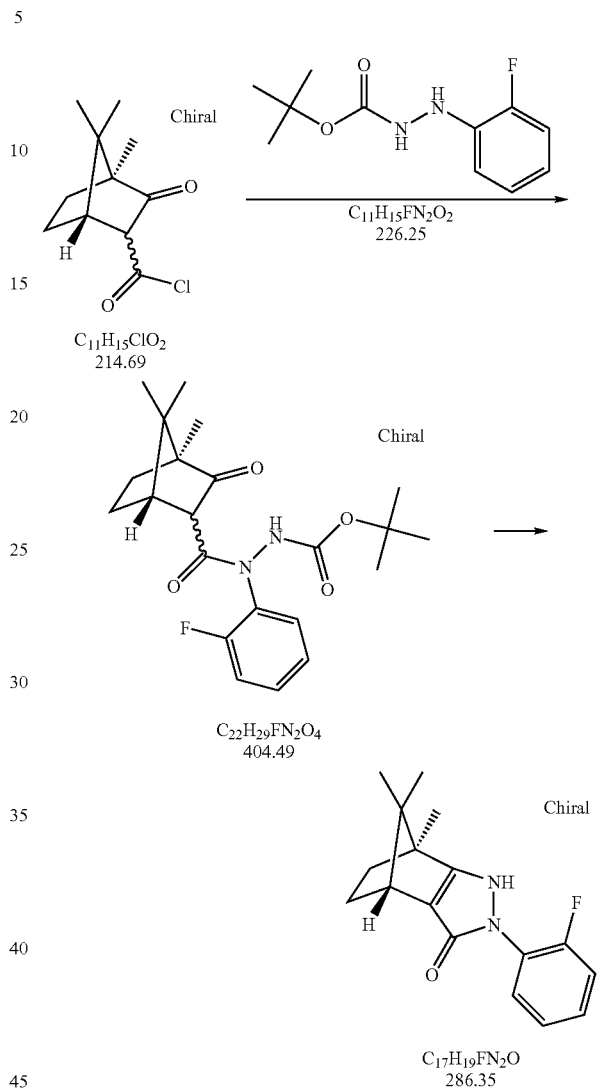

Step 1: N'-(2-Fluoro-phenyl)-N'-((1S,4S)-4,7,7-trimethyl-3-oxo-bicyclo[2.2.1]heptane-2-carbonyl)-hydrazinecarboxylic acid tert-butyl ester Triethylamine (3 mL, 21.5 mmol) was added dropwise to a cooled (0° C.) solution of (1S,4S)-4,7,7-trimethyl-3-oxo-bicyclo[2.2.1]heptane-2-carbonyl chloride (Intermediate 25; 1.50 g, 7.0 mmol) in dichloromethane (18 mL), yielding a thick suspension. This was stirred for 3 min and then N'-(2-fluoro-phenyl)-hydrazinecarboxylic acid tert-butyl ester (Intermediate 29; 1.20 g, 5.3 mmol) was added in one portion. The reaction mixture was allowed to warm to room temperature and stir for 2.5 h. The mixture was added to water (50 mL) and extracted with dichloromethane (3×40 mL). The combined organic layers were washed with brine (30 mL), dried (magnesium sulfate), filtered, evaporated, and dried under high vacuum at room temperature for 30 min to give N'-(2-fluoro-phenyl)-N'-((1S,4S)-4,7,7-trimethyl-3-oxo-bicyclo[2.2.1]heptane-2-carbonyl)-hydrazinecarboxylic acid tert-butyl ester (2.67 g, 124% of the expected amount) as an orange foam. This was used directly in the next step without further purification.

Step 2: (4R,7S)-2-(2-Fluoro-phenyl)-7,8,8-trimethyl-1,2,4,5,6,7-hexahydro-4,7-methano-indazol-3-one Trifluoroacetic acid (10 mL) was added slowly to a cooled (0° C.) solution of N'-(2-fluoro-phenyl)-N'-((1S,4S)-4,7,7-trimethyl-3-oxo-bicyclo[2.2.1]heptane-2-carbonyl)-hydrazinecarboxylic acid tert-butyl ester (~5.3 mmol) in dichloromethane (10 mL), and the resulting solution was stirred at 0° C. for 10 min and then at room temperature for 3.5 h. The solvent was evaporated and dichloromethane (80 mL) was added. The solution was washed with water (4×20 mL) and brine (20 mL), dried (magnesium sulfate), filtered, and evaporated to give an orange foam. This was triturated with 10% ethyl acetate/hexane (25 mL) and the mixture was cooled in an ice-bath at 0° C. for 1 h. The solid was filtered off and dried to give (4R,7S)-2-(2-fluoro-phenyl)-7,8,8-trimethyl-1,2,4,5,6,7-hexahydro-4,7-methano-indazol-3-one (890 mg, 58%) as a pale yellow solid.

Intermediate 39: (4R,7S)-2-(2-Chloro-phenyl)-7,8,8-trimethyl-1,2,4,5,6,7-hexahydro-4,7-methano-indazol-3-one

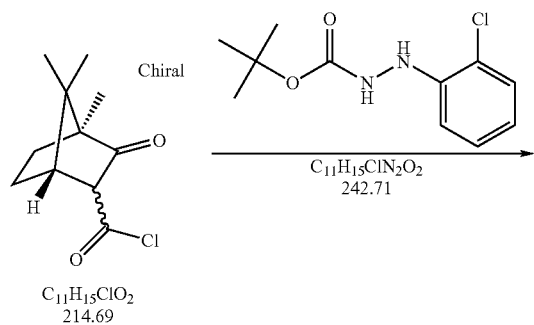

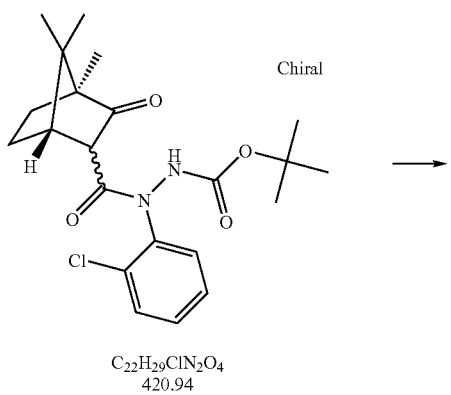

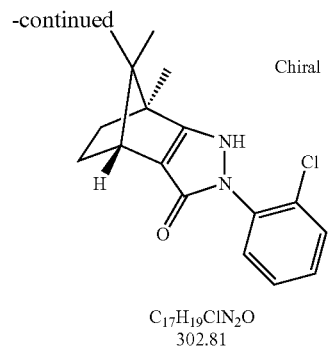

Step 1: N'-(2-Chloro-phenyl)-N'-((1S,4S)-4,7,7-trimethyl-3-oxo-bicyclo[2.2.1]heptane-2-carbonyl)-hydrazinecarboxylic acid tert-butyl ester Triethylamine (1.7 mL, 12.1 mmol) was added dropwise to a cooled (0° C.) solution of (1S,4S)-4,7,7-trimethyl-3-oxo-bicyclo[2.2.1]heptane-2-carbonyl chloride (Intermediate 25; 1.00 g, 4.66 mmol) in dichloromethane (10 mL), yielding a thick slurry. Dichloromethane (5 mL) was added to facilitate stirring. The reaction mixture was stirred at 0° C. for 5 min and then N'-(2-chloro-phenyl)-hydrazinecarboxylic acid tert-butyl ester (Intermediate 30; 936 mg, 3.85 mmol) was added in small portions over 2-3 min. The reaction mixture was allowed to warm to room temperature and stir overnight, then it was cooled again to 0° C. and triethylamine (0.5 mL, 3.6 mmol) and a solution of N'-(2-chloro-phenyl)-hydrazinecarboxylic acid tert-butyl ester (Intermediate 30; 241 mg, 1.12 mmol) in dichloromethane (1 mL) were added. The reaction mixture was stirred at 0° C. for 30 min and then at room temperature for 6 h. Again triethylamine (0.8 mL, 5.7 mmol) and a solution of N'-(2-chloro-phenyl)-hydrazinecarboxylic acid tert-butyl ester (Intermediate 30; 431 mg, 2.0 mmol) in dichloromethane (1 mL) were added at 0° C. and the reaction mixture was allowed to warm to room temperature and stir over the weekend. The solvent was evaporated and the residue was taken up in ethyl acetate and washed with water (25 mL), 1 M HCl (50 mL), and brine (2×50 mL). The organic layer was dried (sodium sulfate), filtered, evaporated, and purified using an Analogix Intelliflash 280 system (Analogix, Inc. Burlington, Wis.) with a RediSep-40 g silica gel column, eluting with 5-50% ethyl acetate/hexanes, to give N'-(2-chloro-phenyl)-N'-((1S,4S)-4,7,7-trimethyl-3-oxo-bicyclo[2.2.1]heptane-2-carbonyl)-hydrazinecarboxylic acid tert-butyl ester (1.275 g, 79%) as a pale yellow foam.

Step 2: (4R,7S)-2-(2-Chloro-phenyl)-7,8,8-trimethyl-1,2,4,5,6,7-hexahydro-4,7-methano-indazol-3-one Trifluoroacetic acid (5 mL) was added slowly to a solution of N'-(2-chloro-phenyl)-N'-((1S,4S)-4,7,7-trimethyl-3-oxo-bicyclo[2.2.1]heptane-2-carbonyl)-hydrazinecarboxylic acid tert-butyl ester (1.26 g, 3.0 mmol) in dichloromethane (5 mL), and the resulting solution was stirred at room temperature for 19 h. The solvent was evaporated and dichloromethane (100 mL) was added. The solution was washed with water (2×50 mL) and brine (50 mL), dried (sodium sulfate), filtered, and evaporated to give a light yellow solid. The solid was stored in the freezer over the weekend, and then triturated with 50% hexanes/diethyl ether (10 mL) and the mixture sonicated. The solid was collected by filtration, washed with ether, an air-dried to give (4R,7S)-2-(2-chloro-phenyl)-7,8,8-trimethyl-1,2,4,5,6,7-hexahydro-4,7-methano-indazol-3-one (790 mg, 86%) as an off-white solid.

Intermediate 40: (4S,7R)-2-(4-Methoxy-phenyl)-7,8,8-trimethyl-1,2,4,5,6,7-hexahydro-4,7-methano-indazol-3-one

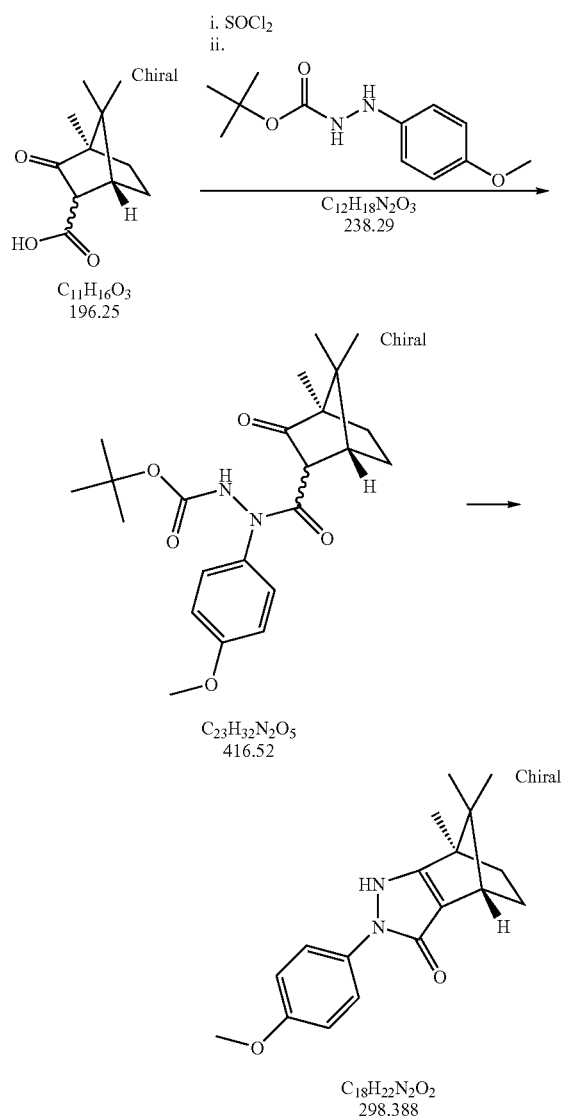

Step 1: N'-(4-Methoxy-phenyl)-N'-((1R,4R)-4,7,7-trimethyl-3-oxo-bicyclo[2.2.1]heptane-2-carbonyl)-hydrazinecarboxylic acid tert-butyl ester A solution of (1R,4R)-3-camphorcarboxylic acid (Intermediate 3; 4.81 g, 24.5 mmol) in dichloromethane (25 mL) was cooled in an ice-water bath, and oxalyl chloride (6.4 mL, 73.4 mmol) and a catalytic amount of dimethylformamide (2 drops) were added. The reaction mixture was stirred at 0° C. for 25 min and at room temperature for 2.5 h. The solvent was evaporated and ad the residue was co-evaporated three times with dichloromethane to remove residual oxalyl chloride. The residue was taken up in dichloromethane (64 mL) and the solution was cooled to ~0° C. Triethylamine (7.8 mL, 56.0 mmol) was added and the solution was stirred at 0° C. for 20 min. N'-(4-Methoxy-phenyl)-hydrazinecarboxylic acid tert-butyl ester (Intermediate 31; 4.41 g, 18.5 mmol) was added and the solution was stirred at 0° C. for 20 min, at reflux for 3 h, and then at room temperature overnight. The reaction mixture was partitioned between dichloromethane (100 mL) and water (100 mL). The aqueous layer was extracted with dichloromethane (2×100 mL) and the combined organic extracts were dried (magnesium sulfate), filtered, and evaporated to give crude N'-(4-methoxy-phenyl)-N'-((1R,4R)-4,7,7-trimethyl-3-oxo-bicyclo[2.2.1]heptane-2-carbonyl)-hydrazinecarboxylic acid tert-butyl ester (11.1 g, 144% of the expected amount) as a viscous red oil. This material was used directly in the next step without further purification.

Step 2: (4S,7R)-2-(4-Methoxy-phenyl)-7,8,8-trimethyl-1,2,4,5,6,7-hexahydro-4,7-methano-indazol-3-one Trifluoroacetic acid (15 mL) was added to a cooled (0° C.) solution of crude N'-(4-methoxy-phenyl)-N'-((1R,4R)-4,7,7-trimethyl-3-oxo-bicyclo[2.2.1]heptane-2-carbonyl)-hydrazinecarboxylic acid tert-butyl ester (~18.5 mmol) in dichloromethane (15 mL), and the solution was stirred at ~0° C. for 15 min and then at room temperature for 2.5 h. The solvent was evaporated and the residue was dissolved in dichloromethane (150 mL) and washed with water (4×250 mL) until the pH of the aqueous washing was ~5. The organic layer was washed with brine (150 mL), dried (magnesium sulfate), and then the flask was wrapped in aluminum and stored in a freezer overnight. The magnesium sulfate was filtered off, and the solvent was evaporated to give an orange/red semi-solid which was triturated with 10% dichloromethane/hexanes, filtered, and washed with hexanes. The solid was crushed, washed again with hexanes, and then dried under vacuum to give (4S,7R)-2-(4-methoxy-phenyl)-7,8,8-trimethyl-1,2,4,5,6,7-hexahydro-4,7-methano-indazol-3-one (3.95 g, 72%) as a tan solid.

Intermediate 41: (4S,7R)-2-(4-Hydroxy-phenyl)-7,8,8-trimethyl-1,2,4,5,6,7-hexahydro-4,7-methano-indazol-3-one

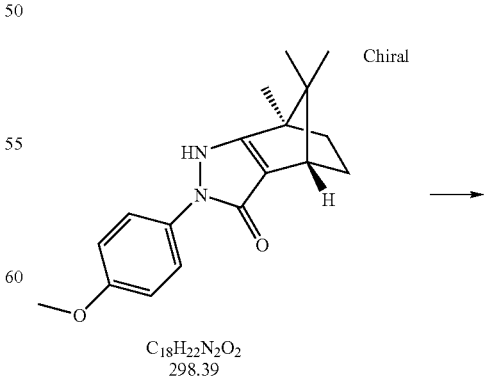

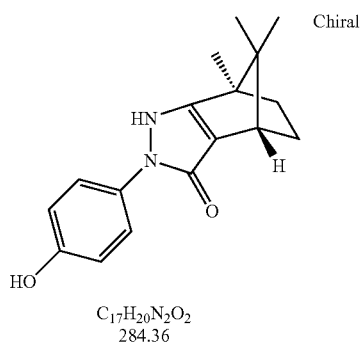

C₁₇H₂₀N₂O₂
284.36

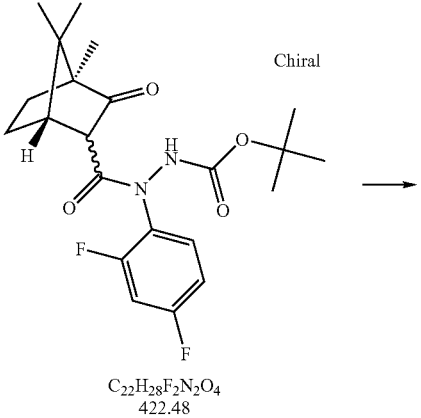

C₂₂H₂₈F₂N₂O₄
422.48

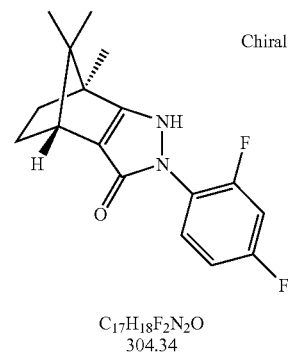

C₁₇H₁₈F₂N₂O
304.34

A solution of aluminum chloride (2.40 g, 18.0 mmol) in ethanethiol (20 mL) was cooled to 0° C. and (4S,7R)-2-(4-methoxy-phenyl)-7,8,8-trimethyl-1,2,4,5,6,7-hexahydro-4,7-methano-indazol-3-one (Intermediate 40; 2.00 g, 6.7 mmol) was added. The flask was capped and the reaction mixture was stirred at 0° C. for about 20 min and then at room temperature for 2 h. The solution was added to water (100 mL) with vigorous stirring and the resulting mixture was acidified to pH 1-2 with 1 M HCl. The resulting solid was filtered off, washed with water and then hexanes, air-dried and then dried under vacuum to give (4S,7R)-2-(4-hydroxy-phenyl)-7,8,8-trimethyl-1,2,4,5,6,7-hexahydro-4,7-methano-indazol-3-one (1.63 g, 85%) as an off-white solid.

Intermediate 42: (4R,7S)-2-(2,4-Difluoro-phenyl)-7,8,8-trimethyl-1,2,4,5,6,7-hexahydro-4,7-methano-indazol-3-one Procedure A

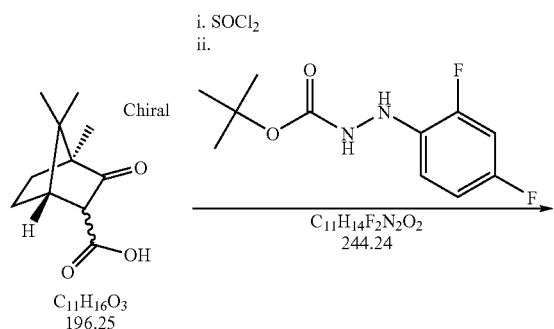

Step 1: N'-(2,4-Difluoro-phenyl)-N'-((1S,4S)-4,7,7-trimethyl-3-oxo-bicyclo[2.2.1]heptane-2-carbonyl)-hydrazinecarboxylic acid tert-butyl ester Oxalyl chloride (34 mL, 390 mmol) and N,N-dimethylformamide (4-5 drops) were added sequentially to a solution of (1S,4S)-3-camphorcarboxylic acid (Intermediate 24; 25.75 g, 131 mmol) in dichloromethane (130 mL) at 0° C. The reaction mixture was stirred at 0° C. for 20 min and then at room temperature for 2.5 h. The solvent was evaporated, and the residue was co-evaporated four times with dichloromethane and then dried under high vacuum to give crude (1S,4S)-4,7,7-trimethyl-3-oxo-bicyclo[2.2.1]heptane-2-carbonyl chloride. The crude acid chloride was dissolved in dichloromethane (340 mL) at 0° C., and triethylamine (42 mL, 301 mmol) was added. The mixture was stirred at 0° C. for 5 min, and then N'-(2,4-difluoro-phenyl)-hydrazinecarboxylic acid tert-butyl ester (Intermediate 32; 24.5 g, 100.4 mmol) was added. The mixture was stirred at 0° C. for 5 min, at reflux for 2.5 h, and then at room temperature for 2 days. Dichloromethane (250 mL) and water (250 mL) were added and the layers were separated. The aqueous layer was extracted with dichloromethane (2×100 mL) and the combined organic layers were dried (magnesium sulfate), filtered and evaporated to give crude N'-(2,4-difluoro-phenyl)-N'-((1S,4S)-4,7,7-trimethyl-3-oxo-bicyclo[2.2.1]heptane-2-carbonyl)-hydrazinecarboxylic acid tert-butyl ester (66.5 g, 157% of the expected amount) as a black oil which was used directly in the next step.

Step 2: (4R,7S)-2-(2,4-Difluoro-phenyl)-7,8,8-trimethyl-1,2,4,5,6,7-hexahydro-4,7-methano-indazol-3-one Trifluoroacetic acid (80 mL) was added to a solution of crude N'-(2,4-difluoro-phenyl)-N'-((1S,4S)-4,7,7-trimethyl-3-oxo-bicyclo[2.2.1]heptane-2-carbonyl)-hydrazinecarboxylic acid tert-butyl ester (~100 mmol) in dichloromethane (80 mL) at 0° C. The reaction mixture was stirred at 0° C. for 15 min, and then at room temperature for 4 h. The solvent was evaporated. The residue was taken up in dichloromethane (500 mL) and washed with water (4×600 mL) adding brine to help separate the layers when necessary. The solution was further washed with brine (250 mL), dried (magnesium sulfate), filtered, and evaporated. The solids were triturated with 10% dichlormethane/hexanes, filtered, washed with 5% dichloromethane/hexanes and then hexanes, stored over a weekend in the freezer, and then dried under high vacuum to give (4R,7S)-2-(2,4-difluoro-phenyl)-7,8,8-trimethyl-1,2,4,5,6,7-hexahydro-4,7-methano-indazol-3-one (25.71 g, 84%) as a light brown solid.

Procedure B

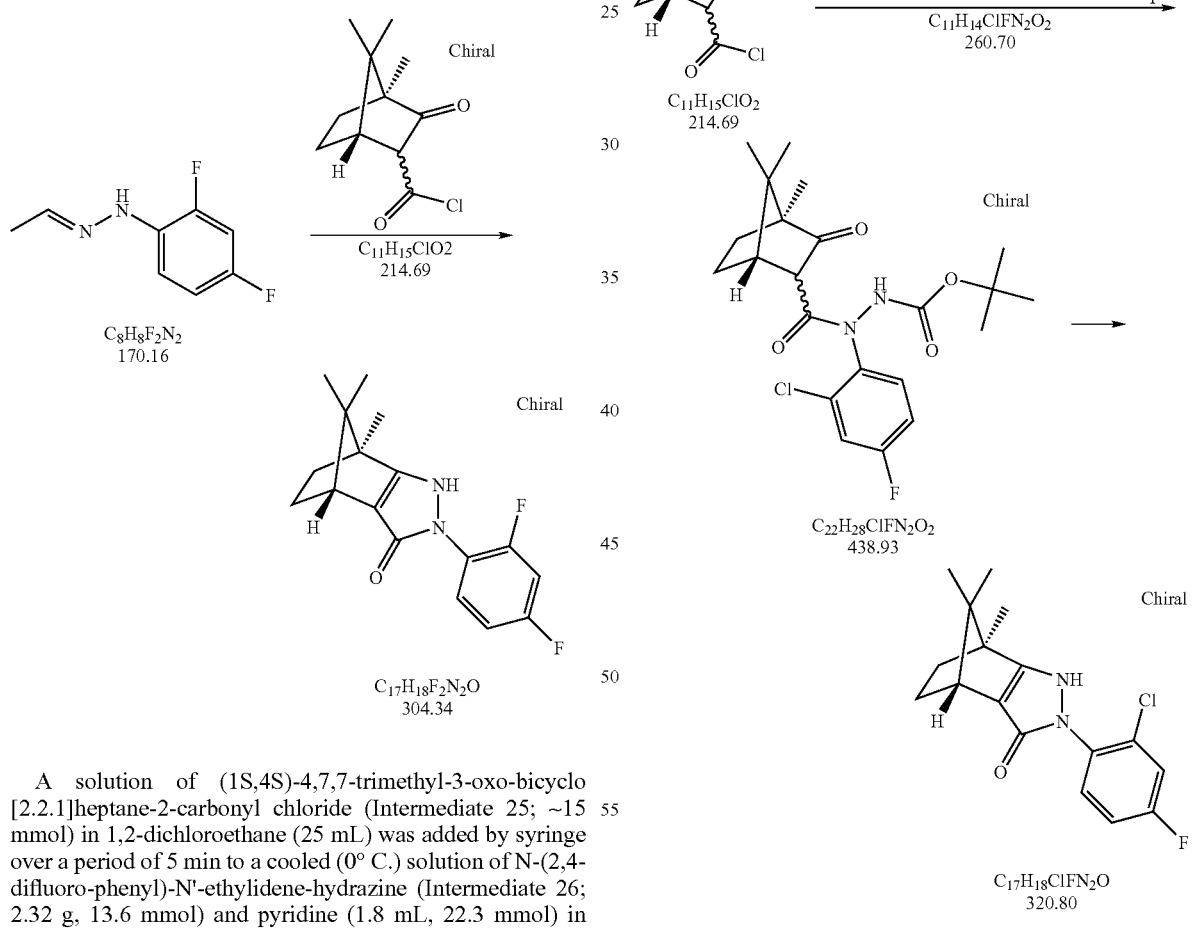

A solution of (1S,4S)-4,7,7-trimethyl-3-oxo-bicyclo[2.2.1]heptane-2-carbonyl chloride (Intermediate 25; ~15 mmol) in 1,2-dichloroethane (25 mL) was added by syringe over a period of 5 min to a cooled (0° C.) solution of N-(2,4-difluoro-phenyl)-N'-ethylidene-hydrazine (Intermediate 26; 2.32 g, 13.6 mmol) and pyridine (1.8 mL, 22.3 mmol) in 1,2-dichloroethane (15 mL). The flask containing the acid chloride was rinsed with 1,2-dichloroethane (10 mL). The reaction mixture was stirred at room temperature for 15 min and then at 50° C. for 45 min. A solution of HCl in dioxane (Aldrich; 4 M, 11 mL, 44 mmol) was added. The solution was stirred for 5 min at room temperature and then acetic acid (18 mL) was added. The reaction mixture was stirred at 100° C. under argon for 1 h. The solvent was evaporated and the residue was partitioned between ethyl acetate (150 mL) and 1:1 water/brine (75 mL). The organic layer was washed with 1:1 water/brine (50 mL), and the combined aqueous layers were extracted with ethyl acetate (50 mL). The combined ethyl acetate extracts were washed with brine (100 mL), dried (sodium sulfate), filtered, and evaporated to give a dark brown semi-solid which was stored in the freezer overnight and then triturated with diethyl ether. The solid was filtered off, washed with ether and air-dried to give (4R,7S)-2-(2,4-difluoro-phenyl)-7,8,8-trimethyl-1,2,4,5,6,7-hexahydro-4,7-methano-indazol-3-one (1.93 g, 47%) as a light brown solid which was used directly in the next step without further purification.

Intermediate 43: (4R,7S)-2-(2-Chloro-4-fluoro-phenyl)-7,8,8-trimethyl-1,2,4,5,6,7-hexahydro-4,7-methano-indazol-3-one

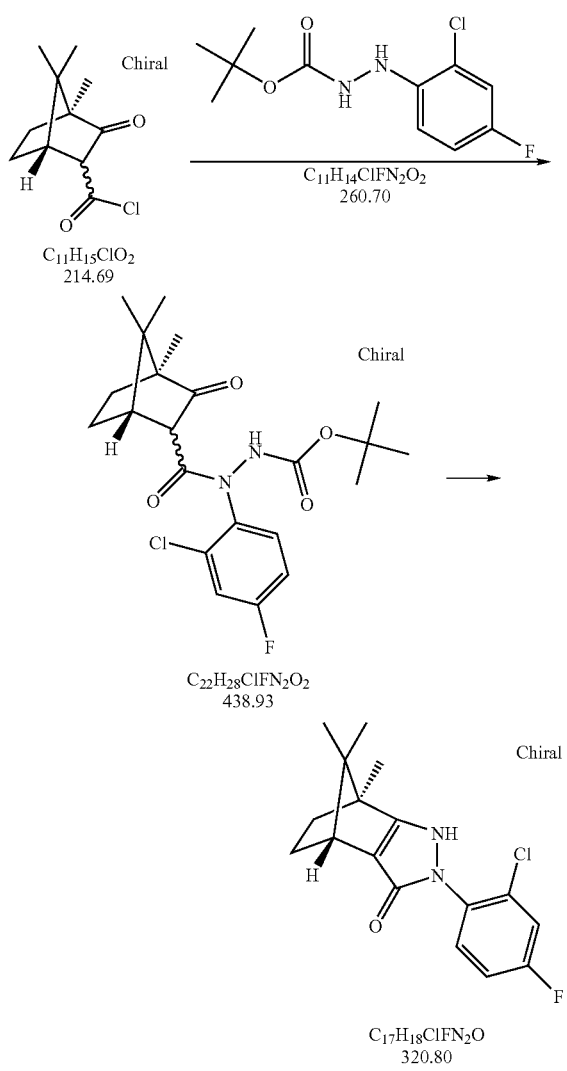

Step 1: N'-(2-Chloro-4-fluoro-phenyl)-N'-((1S,4S)-4,7,7-trimethyl-3-oxo-bicyclo[2.2.1]heptane-2-carbonyl)-hydrazinecarboxylic acid tert-butyl ester Triethylamine (3.9 mL; 28 mmol) was added over a period of 2-3 min to a cooled (0° C.) solution of (1S,4S)-4,7,7- trimethyl-3-oxo-bicyclo[2.2.1]heptane-2-carbonyl chloride (Intermediate 25; 2.2 g, 10.2 mmol) in dichloromethane (25 mL), resulting in a heavy precipitate. Dichloromethane (10 mL) was added, followed by N'-(2-chloro-4-fluoro-phenyl)-hydrazinecarboxylic acid tert-butyl ester (Intermediate 33; 1.87 g, 7.2 mmol). The reaction mixture was stirred at 0° C. for 5 min, and then at 50° C. (oil-bath temperature) over the weekend. Dichloromethane was added and the solution was washed with water (3×50 mL) and brine (50 mL), dried (magnesium sulfate, filtered, evaporated, and dried under high vacuum to give N'-(2-chloro-4-fluoro-phenyl)-N'-((1S,4S)-4,7,7-trimethyl-3-oxo-bicyclo[2.2.1]heptane-2-carbonyl)-hydrazinecarboxylic acid tert-butyl ester (3.8 g, 120% of the expected amount). This was used directly in the next step without further purification.

Step 2: (4R,7S)-2-(2-Chloro-4-fluoro-phenyl)-7,8,8-trimethyl-1,2,4,5,6,7-hexahydro-4,7-methano-indazol-3-one Trifluoroacetic acid (15 mL) was added in two portions to a cooled (0° C.) solution of N'-(2-chloro-4-fluoro-phenyl)-N'-((1S,4S)-4,7,7-trimethyl-3-oxo-bicyclo[2.2.1]heptane-2-carbonyl)-hydrazinecarboxylic acid tert-butyl ester (~7.2 mmol) in dichloromethane (15 mL). The reaction mixture was stirred at 0° C. for 5 min and then at room temperature for 2 h. The reaction mixture was evaporated (using high vacuum in the end). Dichloromethane (100 mL) was added to the residue and the solution was washed with water (4×50 mL), and brine (50 mL), dried (magnesium sulfate), filtered, and evaporated to give (4R,7S)-2-(2-chloro-4-fluoro-phenyl)-7,8,8-trimethyl-1,2,4,5,6,7-hexahydro-4,7-methano-indazol-3-one (2.6 g, 113% of the expected amount) as a tan solid. This was used directly in subsequent steps without further purification.

Intermediate 44: (4S,7R)-2-(2,5-Dichloro-phenyl)-7,8,8-trimethyl-1,2,4,5,6,7-hexahydro-4,7-methano-indazol-3-one

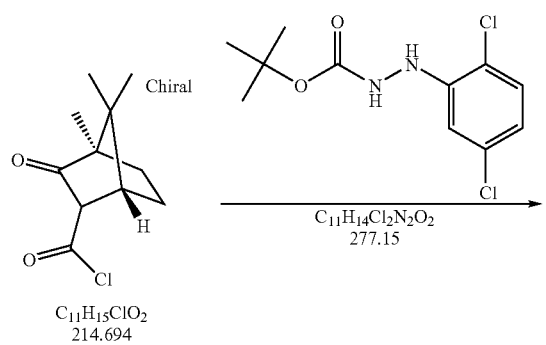

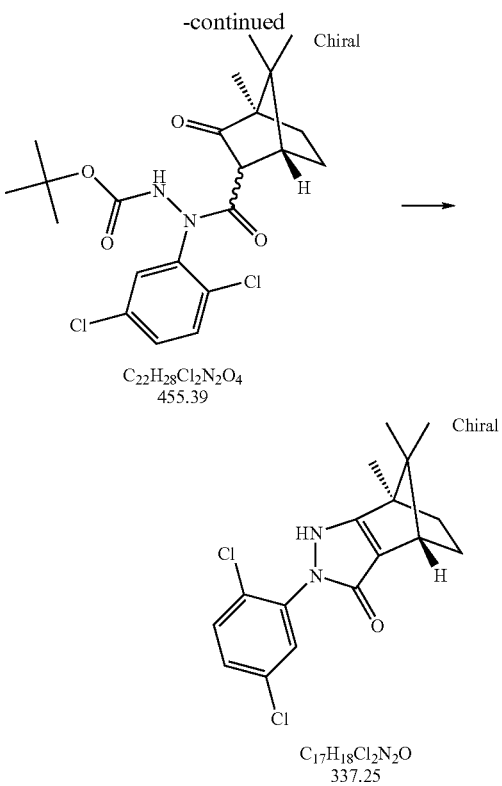

Step 1: N'-(2,5-Dichloro-phenyl)-N'-((1R,4R)-4,7,7-trimethyl-3-oxo-bicyclo[2.2.1]heptane-2-carbonyl)-hydrazinecarboxylic acid tert-butyl ester Triethylamine (26 mL, 186.5 mmol) was added dropwise to a cooled (0° C.) solution of (1R,4R)-4,7,7-trimethyl-3-oxo-bicyclo[2.2.1]heptane-2-carbonyl chloride (Intermediate 20; 13.33 g, 62.1 mmol) in dichloromethane (150 mL), yielding a thick suspension. This was stirred for 3 min and then N'-(2,5-dichloro-phenyl)-hydrazinecarboxylic acid tert-butyl ester (Intermediate 34; 13.00 g, 46.9 mmol) was added in one portion. The cooling bath was removed and the reaction mixture was stirred at room temperature for 10 min, then in an oil-bath at 50° C. for 4 h. The reaction mixture was cooled to room temperature, then added to water (200 mL) and extracted with dichloromethane (3×150 mL). The combined organic layers were washed with brine (200 mL), dried (magnesium sulfate), filtered, and evaporated to give N'-(2,5-dichloro-phenyl)-N'-((1R,4R)-4,7,7-trimethyl-3-oxo-bicyclo[2.2.1]heptane-2-carbonyl)-hydrazinecarboxylic acid tert-butyl ester (29.55 g, 138% of the expected amount) as a brown oil. This was used directly in the next step without further purification.

Step 2: (4S,7R)-2-(2,5-Dichloro-phenyl)-7,8,8-trimethyl-1,2,4,5,6,7-hexahydro-4,7-methano-indazol-3-one Trifluoroacetic acid (100 mL) was added slowly to a cooled (0° C.) solution of N'-(2,5-dichloro-phenyl)-N'-((1R,4R)-4,7,7-trimethyl-3-oxo-bicyclo[2.2.1]heptane-2-carbonyl)-hydrazinecarboxylic acid tert-butyl ester (~46.9 mmol) in dichloromethane (100 mL), and the resulting solution was stirred at 0° C. for 10 min and then at room temperature for 2 h. The solvent was evaporated and dichloromethane (200 mL) was added. The solution was washed with water (4×80 mL) and brine (80 mL), dried (magnesium sulfate), filtered, and evaporated to give a brown foam. This was triturated with 10% ethyl acetate/hexane (100 mL) and the mixture was stirred at room temperature for 20 min and then cooled in an ice-bath at 0° C. for 1 h. The solid was filtered off, washed with hexane, and dried to give (4S,7R)-2-(2,5-dichloro-phenyl)-7,8,8-trimethyl-1,2,4,5,6,7-hexahydro-4,7-methano-indazol-3-one (13.55 g, 86%) as a tan solid.

Intermediate 45: (4S,7R)-2-(3,5-Dichloro-phenyl)-7,8,8-trimethyl-1,2,4,5,6,7-hexahydro-4,7-methano-indazol-3-one

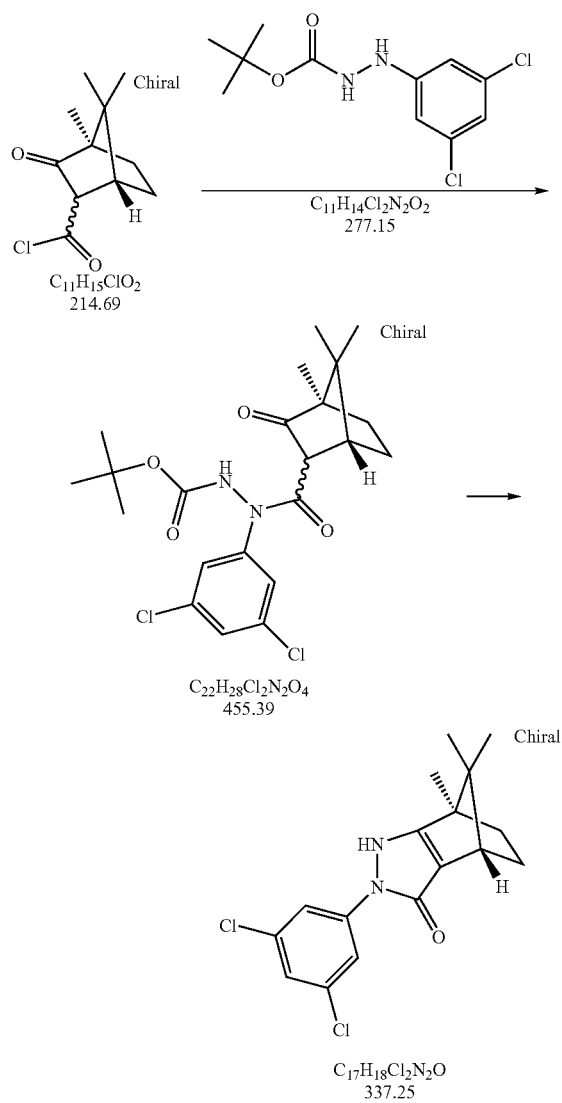

Step 1: N'-(3,5-Dichloro-phenyl)-N'-((1R,4R)-4,7,7-trimethyl-3-oxo-bicyclo[2.2.1]heptane-2-carbonyl)-hydrazinecarboxylic acid tert-butyl ester Triethylamine (10.75 mL, 77 mmol) was added in two portions to a cooled (0° C.) solution of (1R,4R)-4,7,7-trimethyl-3-oxo-bicyclo[2.2.1]heptane-2-carbonyl chloride (Intermediate 20; 5.5 g, 25.6 mmol) in dichloromethane (55 mL), giving a thick precipitate. N'-(3,5-dichloro-phenyl)-hydrazinecarboxylic acid tert-butyl ester (Intermediate 35; 5.5 g, 19.8 mmol) was added, along with dichloromethane (25-30 mL). The reaction mixture was placed in an oil-bath at 50° C., heated at this temperature overnight and then allowed to cool to room temperature and stir for 20 min. The reaction mixture was poured into water (100 mL) and two layers were separated. The organic layer was washed with water (100 mL) and brine (100 mL), dried (magnesium sulfate), filtered, evaporated, and then dried under high vacuum to give N'-(3,5-dichloro-phenyl)-N'-((1R,4R)-4,7,7-trimethyl-3-oxo-bicyclo[2.2.1]heptane-2-carbonyl)-hydrazinecarboxylic acid tert-butyl ester (10 g, 111% of the expected amount) as an orange foam, which was used directly in the next step without further purification.

Step 2: (4S,7R)-2-(3,5-Dichloro-phenyl)-7,8,8-trimethyl-1,2,4,5,6,7-hexahydro-4,7-methano-indazol-3-one Trifluoroacetic acid (15 mL) was added in one portion to a cooled (0° C.) solution of N'-(3,5-dichloro-phenyl)-N'-((1R,4R)-4,7,7-trimethyl-3-oxo-bicyclo[2.2.1]heptane-2-carbonyl)-hydrazinecarboxylic acid tert-butyl ester (~0.19 mmol) in dichloromethane (15 mL). The mixture was stirred at 0° C. for 5 min and then the cooling bath was removed and the reaction mixture was allowed to warm to room temperature and stir for 4 h. Volatiles were evaporated under reduced pressure and then under high vacuum. Dichloromethane (200 mL) was added. The solution was washed with water (4×125 mL), and brine (100 mL), dried (magnesium sulfate), filtered, evaporated, and dried overnight under high vacuum to give (4S,7R)-2-(3,5-dichloro-phenyl)-7,8,8-trimethyl-1,2,4,5,6,7-hexahydro-4,7-methano-indazol-3-one (7.2 g, 108% of the expected amount). This material was used in subsequent reactions without further purification.

Intermediate 46: (4S,7R)-7,8,8-Trimethyl-2-naphthalen-1-yl-1,2,4,5,6,7-hexahydro-4,7-methano-indazol-3-one

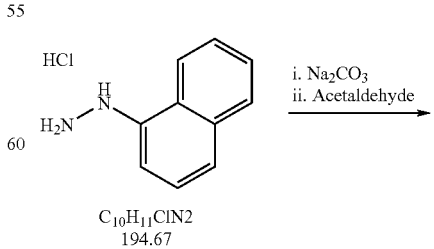

-continued

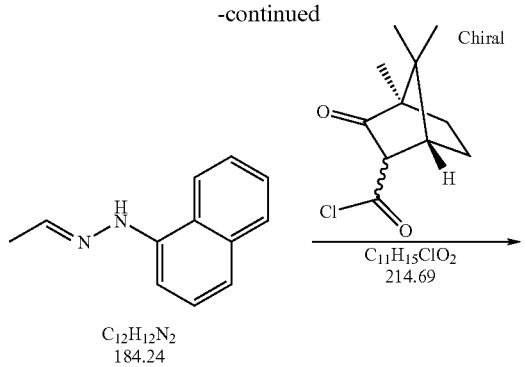

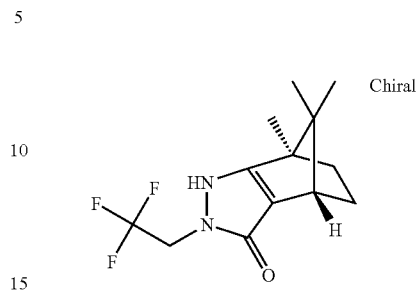

Intermediate 47: (4S,7R)-7,8,8-trimethyl-2-(2,2,2-trifluoro-ethyl)-1,2,4,5,6,7-hexahydro-4,7-methano-indazol-3-one A mixture of (1R,4R)-4,7,7-trimethyl-3-oxo-bicyclo[2.2.1]heptane-2-carboxylic acid ethyl ester (Intermediate 4; 5.00 g, 22.3 mmol) and 2,2,2-trifluoroethylhydrazine (70% in water; Aldrich; 25.00 g, 153 mmol) was heated in a sealed tube at 100° C. for 19 h. The reaction mixture was allowed to cool, and HCl in dioxane (4 M; 40 mL, 160 mmol) was added cautiously. The reaction mixture was heated again at 100° C. for 45 min, cooled to room temperature, and added to water (200 mL). The mixture was extracted with dichloromethane (3×150 mL). The combined organic layers were washed with brine (150 mL), dried (sodium sulfate), filtered, evaporated, purified by flash chromatography (20-50% ethyl acetate) to give (4S,7R)-7,8,8-trimethyl-2-(2,2,2-trifluoro-ethyl)-1,2,4,5,6,7-hexahydro-4,7-methano-indazol-3-one (1.04 g, 17%) as a light orange solid.

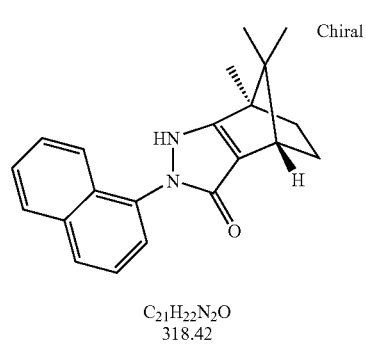

Naphthylhydrazine was prepared by treating a mixture of 1-naphthylhydrazine hydrochloride with 10% methanol/dichloromethane and saturated aqueous sodium carbonate). A solution of 1-naphthylhydrazine (501 mg, 3.2 mmol) in toluene (45 mL) was cooled to 0° C. under nitrogen, and a solution of acetaldehyde (440 µL, 7.9 mmol) in cole toluene (5 mL) was added dropwise over 15 min. The mixture was allowed to stir at 0° C. for 5 min and then at room temperature for 1 h. The solvent was decanted off and the remaining material was evaporated to give a dark oil which was dissolved in 1,2-dichloroethane (5 mL). The solution was added to a solution of (1R,4R)-4,7,7-trimethyl-3-oxo-bicyclo[2.2.1]heptane-2-carbonyl chloride (Intermediate 20; ~1 equivalent) and pyridine (~1.5 equivalents) in 1,2-dichloroethane (10 mL) at 0° C. to give an immediate precipitate. The reaction mixture was stirred at room temperature for 15 min, then at 50° C. for 40 min. The reaction mixture was cooled to room temperature and HCl in dioxane (4 M; 3 mL, 12 mmol) was added. The mixture was stirred at room temperature for 5 min, then glacial acetic acid (10 mL) was added and the mixture was stirred at 100° C. for 25 min. The reaction mixture was cooled, and solvents were evaporated. Dichloromethane (200 mL) was added and the solution was washed with 1:1 water/brine (2×50 mL). The combined aqueous layers were back-extracted with dichloromethane (2×50 mL). The combined organic layers were washed with brine (100 mL), dried (magnesium sulfate), filtered, evaporated and purified by elution through silica gel with 30% ethyl acetate/hexanes. Fractions homogeneous for the product were evaporated and dried under high vacuum for 20 min to give (4S,7R)-7,8,8-trimethyl-2-naphthalen-1-yl-1,2,4,5,6,7-hexahydro-4,7-methano-indazol-3-one (459 mg, 46%) as an orange gummy solid.

Intermediate 48: (4R,7S)-1,7,8,8-Tetramethyl-1,2,4,5,6,7-hexahydro-4,7-methano-indazol-3-one

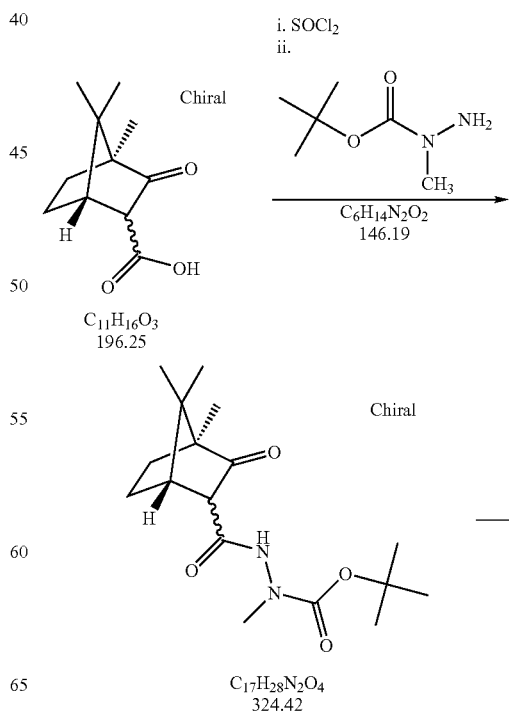

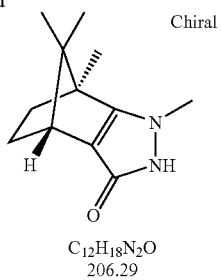

C₁₂H₁₈N₂O
206.29

Step 1: N-Methyl-N'-((1S,4S)-4,7,7-trimethyl-3-oxo-bicyclo[2.2.1]heptane-2-carbonyl)-hydrazinecarboxylic acid tert-butyl ester Oxalyl chloride (4.1 mL, 46.9 mmol) was added dropwise to a solution of (1S,4S)-3-camphorcarboxylic acid (Intermediate 24; 4.0 g, 20.4 mmol) and N,N-dimethylformamide (3 drops) in dichloromethane (20 mL) at 0° C. The reaction mixture was stirred at 0° C. for 20 min and then at room temperature for 1.5 h. The solvent was evaporated, and the residue was co-evaporated three times with dichloromethane and then dried under high vacuum to give crude (1S,4S)-4,7,7-trimethyl-3-oxo-bicyclo[2.2.1]heptane-2-carbonyl chloride as an orange-brown oil. The crude acid chloride was dissolved in dichloromethane (52 mL) at 0° C., and triethylamine (6.5 mL, 46.8 mmol) and N-methyl-hydrazinecarboxylic acid tert-butyl ester (Intermediate 1; 2.29 g, 15.7 mmol) were added. The reaction mixture was stirred at 0° C. for 15 min and then at ~50° C. for 2 h. The reaction mixture was cooled and partitioned between dichloromethane and water. The aqueous layer was extracted twice with dichloromethane and the combined organic layers were dried (sodium sulfate), filtered and evaporated to give crude N-methyl-N'-((1S,4S)-4,7,7-trimethyl-3-oxo-bicyclo[2.2.1]heptane-2-carbonyl)-hydrazinecarboxylic acid tert-butyl ester (6.15 g, 93%) which was used directly in the next step.

Step 2: (4R,7S)-1,7,8,8-Tetramethyl-1,2,4,5,6,7-hexahydro-4,7-methano-indazol-3-one Trifluoroacetic acid (15.7 mL) was added to a solution of N-methyl-N'-((1S,4S)-4,7,7-trimethyl-3-oxo-bicyclo[2.2.1]heptane-2-carbonyl)-hydrazinecarboxylic acid tert-butyl ester (6.13 g, 18.9 mmol) in dichloromethane (15.7 mL) at 0° C. The reaction mixture was stirred at 0° C. for 30 min, at room temperature for 1 h, and then heated at reflux for 6 h. Following overnight stirring at room temperature, the solvent was evaporated. The residue was taken up in dichloromethane (100 mL) and washed with water (2×100 mL) and brine (100 mL), dried (sodium sulfate), filtered, evaporated and purified using a Biotage system eluting with 2% methanol/dichloromethane to give (4R,7S)-1,7,8,8-tetramethyl-1,2,4,5,6,7-hexahydro-4,7-methano-indazol-3-one (2.46 g, 63%) as a white solid.

Intermediate 49: (4R,7S)-1-Benzyl-7,8,8-trimethyl-1,2,4,5,6,7-hexahydro-4,7-methano-indazol-3-one

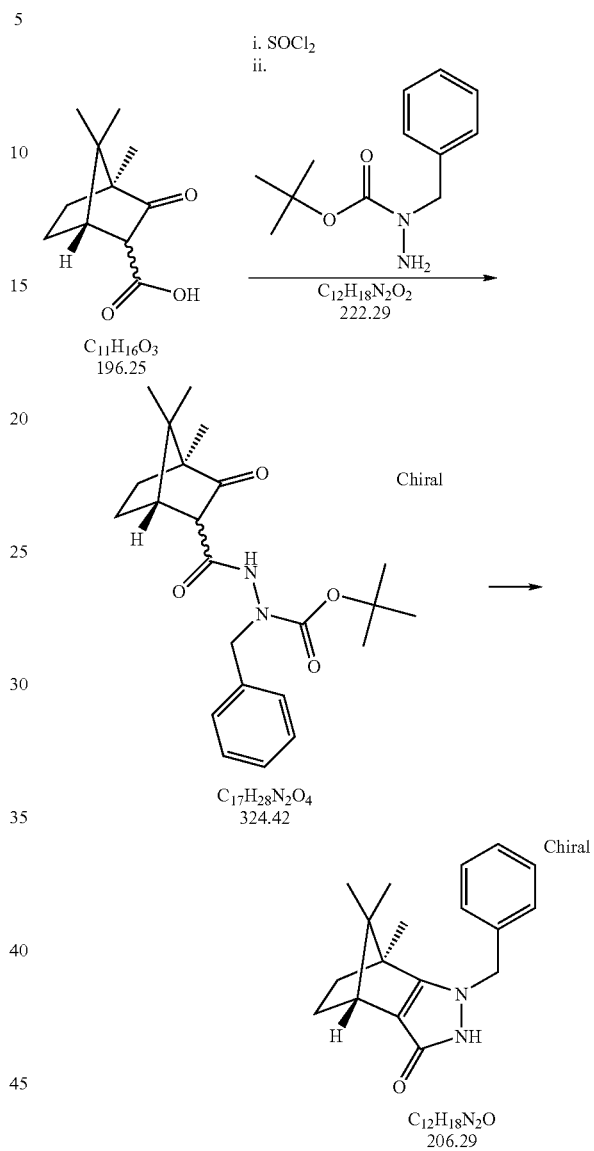

Step 1: N-Benzyl-N'-((1S,4S)-4,7,7-trimethyl-3-oxo-bicyclo[2.2.1]heptane-2-carbonyl)-hydrazinecarboxylic acid tert-butyl ester Oxalyl chloride (2 M in dichloromethane; 35.1 mL, 70.3 mmol) and dimethylformamide (a few drops) were added to a solution of (1S,4S)-3-camphorcarboxylic acid (Intermediate 24; 6.00 g, 30.6 mmol) in dichloromethane (31 mL) at 0° C. The reaction mixture was stirred at 0° C. for 30 min and then at room temperature overnight. The solvent was evaporated, and the residue was co-evaporated three times with dichloromethane and then dried under high vacuum to give crude (1S,4S)-4,7,7-trimethyl-3-oxo-bicyclo[2.2.1]heptane-2-carbonyl chloride. The crude acid chloride was dissolved a minimal amount of dichloromethane and added over a period of 20 min to a cooled (~0° C.) solution of N-benzyl-hydrazinecarboxylic acid tert-butyl ester (Intermediate 27; 7.47 g, 33.6 mmol) in a mixture of dichloromethane (93 mL) and saturated aqueous sodium hydrogen carbonate (47 mL). The reaction mixture was stirred at 0° C. for 30 min, at room temperature for 3 h, and then at about 50° C. overnight. The reaction mixture was cooled and the layers were separated. The aqueous layer was extracted with dichloromethane (2×100 mL) and the combined organic layers were dried (sodium sulfate), filtered and evaporated to give crude N-benzyl-N'-((1S,4S)-4,7,7-trimethyl-3-oxo-bicyclo[2.2.1]heptane-2-carbonyl)-hydrazinecarboxylic acid tert-butyl ester which was used directly in the next step.

Step 2: (4R,7S)-1-Benzyl-7,8,8-trimethyl-1,2,4,5,6,7-hexahydro-4,7-methano-indazol-3-one Trifluoroacetic acid (25.5 mL) was added to a solution of N-benzyl-N'-((1S,4S)-4,7,7-trimethyl-3-oxo-bicyclo[2.2.1]heptane-2-carbonyl)-hydrazinecarboxylic acid tert-butyl ester (~30 mmol) in dichloromethane (25.5 mL) at 0° C. The reaction mixture was stirred at 0° C. for 30 min, at room temperature for 2 h, heated in a flak equipped with a reflux condenser at an oil-bath temperature of 80° C. for 6 h, and then at an oil-bath temperature of 100° C. overnight in the presence of molecular sieves. The molecular sieves were filtered off and washed with dichloromethane. The filtrate was washed with water until the washings were neutral. The organic layer was dried (sodium sulfate), filtered, evaporated, and purified using a Biotage system with a 330 g column, eluting with 2-5% methanol/dichloromethane, to give (4R,7S)-1-benzyl-7,8,8-trimethyl-1,2,4,5,6,7-hexahydro-4,7-methano-indazol-3-one (610 mg, 7%) as a yellow solid.

Intermediate 50:
5-Chloromethyl-2-methoxy-pyridine

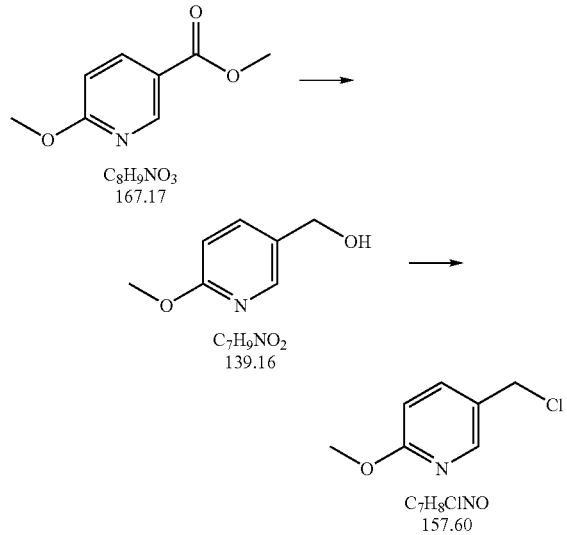

Step 1: (6-Methoxy-pyridin-3-yl)-methanol

A solution of methyl 6-methoxynicotinate (3.00 g, 17.9 mmol) in tetrahydrofuran (10 mL) was added via an addition funnel over a period of 10 min to a cooled (0° C.) mixture of lithium aluminum hydride (817 mg, 21.5 mmol) in tetrahydrofuran (18 mL). The mixture was stirred at 0° C. for 30 min and then at room temperature for 2 h. The reaction mixture was poured into a solution of potassium sodium tartrate (10% w/v; 100 mL) and the resulting mixture was stirred at room temperature for 20 min. The mixture was filtered through a pad of Celite, washing with ethyl acetate. The organic layer of the filtrate was separated and the aqueous layer was extracted with ethyl acetate (2×100 mL). The combined organic layers were dried (magnesium sulfate), filtered and eluted through a silica plug using 40% ethyl acetate/hexanes to give (6-methoxy-pyridin-3-yl)-methanol (1.8 g, 72%) as a clear oil.

Step 2: 5-Chloromethyl-2-methoxy-pyridine

Thionyl chloride (9.2 mL, 126 mmol) was added dropwise to a solution of (6-methoxy-pyridin-3-yl)-methanol (1.00 g, 7.2 mmol) in dichloromethane (38 mL). The reaction mixture was stirred at room temperature overnight. The solvent was evaporated and dichloromethane (100 mL) was added. The solution was washed with saturated aqueous sodium hydrogen carbonate (this resulted in bubbling). The organic layer was separated and the aqueous layer was extracted with dichloromethane (2×100 mL). The combined organic layers were washed with brine (150 mL), dried (sodium sulfate), filtered, and evaporated to give 5-chloromethyl-2-methoxy-pyridine (995 mg, 88%) as a clear oil.

Intermediate 51:
3-Chloromethyl-2-methoxy-pyridine

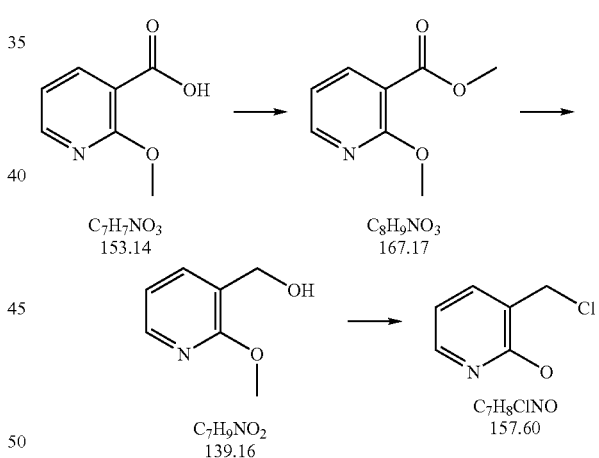

Step 1: 2-Methoxy-nicotinic acid methyl ester

A mixture of 2-methoxy-nicotinic acid (5.00 g, 32.6 mmol), thionyl chloride (50 mL) and carbon tetrachloride (50 mL) was head at reflux for 2 h. The reaction mixture was allowed to cool and volatiles were removed on a rotary evaporator. The residue was co-evaporated three times with carbon tetrachloride to remove residual oxalyl chloride. Methanol (50 mL) was added and the mixture was stirred at room temperature overnight. The solvent was evaporated and chloroform (150 mL) was added. The solution was washed with saturated aqueous sodium hydrogen carbonate (2×150 mL) and brine (150 mL), dried (magnesium sulfate), filtered, and evaporated to give 2-methoxy-nicotinic acid methyl ester (4.42 g, 81%) as a clear yellow oil.

Step 2: (2-Methoxy-pyridin-3-yl)-methanol

A solution of 2-methoxy-nicotinic acid methyl ester (4.42 g, 26.5 mmol) in tetrahydrofuran (7 mL) was added via an addition funnel over a period of 15-20 min to a cooled (0° C.) mixture of lithium aluminum hydride (1.22 g, 32.1 mmol) in tetrahydrofuran (20 mL). The mixture was stirred at 0° C. for 40 min and then at room temperature for 3 h. The reaction mixture was poured into a solution of potassium sodium tartrate (10% w/v) and the resulting mixture was stirred at room temperature for 25 min. The mixture was filtered through a pad of Celite, washing with ethyl acetate (400 mL). The organic layer of the filtrate was separated and the aqueous layer was extracted with ethyl acetate (2×100 mL). The combined organic layers were washed with brine (100 mL), dried (magnesium sulfate), filtered and purified using a Biotage 40M system, eluting with 30% ethyl acetate/hexanes, to give (2-methoxy-pyridin-3-yl)-methanol (2.97 g, 81%) as a white solid.

Step 3: 3-Chloromethyl-2-methoxy-pyridine

Thionyl chloride (9.5 mL, 130 mmol) was added portionwise to a solution of (2-methoxy-pyridin-3-yl)-methanol (1.02 g, 7.3 mmol) in dichloromethane (36 mL). The reaction mixture was stirred at room temperature overnight. The solvent was evaporated and dichloromethane (100 mL) was added. The solution was carefully treated with saturated aqueous sodium hydrogen carbonate and the mixture was stirred for 5-10 min. The organic layer was separated and the aqueous layer was extracted with dichloromethane (2×100 mL). The combined organic layers were washed with brine (100 mL), dried (sodium sulfate), filtered, and evaporated to give 3-chloromethyl-2-methoxy-pyridine (989 mg, 86%) as a light yellow oil.

Preparation of Preferred Compounds

Example 1

(4S,7R)-1,7,8,8-Tetramethyl-2-phenyl-1,2,4,5,6,7-hexahydro-4,7-methano-indazol-3-one

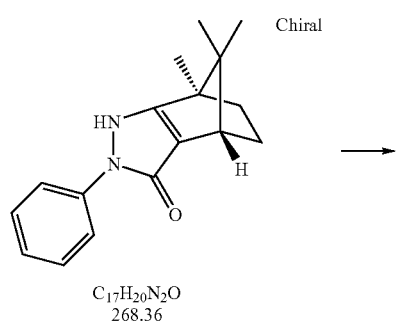

C$_{17}$H$_{20}$N$_2$O
268.36

-continued

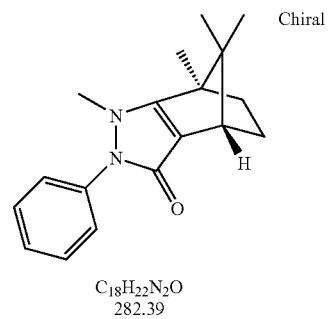

C$_{18}$H$_{22}$N$_2$O
282.39

Procedure A: A mixture of (4S,7R)-2-phenyl-7,8,8-trimethyl-1,2,4,5,6,7-hexahydro-4,7-methano-indazol-3-one (Intermediate 6; 4.77 g, 17.8 mmol) and methyl iodide (2.2 mL, 35.3 mmol) in N,N-dimethylformamide (30 mL) was purged with argon and then heated in a sealed tube at 100° C. overnight. The reaction mixture was cooled to room temperature, diluted with sodium bicarbonate and extracted three times with ethyl acetate. The combined organic extracts were washed with water and brine, dried (magnesium sulfate), filtered, evaporated and purified using an Analogix Intelliflash 280 system (Analogix, Inc., Burlington, Wis.) with an Analytical Sales 120 g column, eluting with 25-75% ethyl acetate/hexanes followed by recrystallization from ethyl acetate to give (4S,7R)-2-phenyl-1,7,8,8-tetramethyl-1,2,4,5,6,7-hexahydro-4,7-methano-indazol-3-one (2.8 g) of white crystals. The filtrate was evaporated and recrystallized from ethyl acetate to give a further 0.53 g, and the resulting filtrate was evaporated, dissolved in dichloromethane, treated with decolorizing charcoal and crystallized from dichloromethane to give a further 0.77 g of product. The total yield was 4.1 g (82%). EI(+)-MS (M+H) 283.

Procedure B: Dimethyl sulfate (0.4 mL, 4.1 mmol) was added to (4S,7R)-2-phenyl-7,8,8-trimethyl-1,2,4,5,6,7-hexahydro-4,7-methano-indazol-3-one (Intermediate 6; 1.00 g, 3.7 mmol) in 1 M NaOH (10 mL). The mixture was stirred at room temperature overnight and then diluted with water and extracted three times with ethyl acetate. The combined organic layers were washed with water and brine, dried (magnesium sulfate), filtered, evaporated, and purified using an Analogix Intelliflash 280 system (Analogix, Inc., Burlington, Wis.) with an RS-12 column, eluting with 0-16% ethyl acetate/hexanes to give (4S,7R)-1,7,8,8-tetramethyl-2-phenyl-1,2,4,5,6,7-hexahydro-4,7-methano-indazol-3-one (213 mg, 20%) as a white solid, (4S,7R)-3-methoxy-7,8,8-trimethyl-2-phenyl-4,5,6,7-tetrahydro-2H-4,7-methano-indazole (243 mg, 23%) as a yellow solid and unreacted starting material (243 mg, 24%).

Example 2

(4R,7S)-1,7,8,8-Tetramethyl-2-phenyl-1,2,4,5,6,7-hexahydro-4,7-methano-indazol-3-one

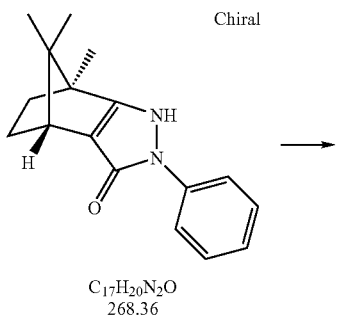

C$_{17}$H$_{20}$N$_2$O
268.36

Dimethyl sulfate (66 μL, 0.7 mmol) was added to (4R,7S)-2-phenyl-7,8,8-trimethyl-1,2,4,5,6,7-hexahydro-4,7-methano-indazol-3-one (Intermediate 7; 185 mg, 0.7 mmol) in 1 M NaOH (5 mL). The mixture was vortexed and then heated with a heat gun for 30 sec., then shaken for 10 min, and extracted twice with dichloromethane. TLC indicated that the sodium hydroxide solution still contained starting material so a further quantity of dimethyl sulfate (150 μL, 1.6 mmol) was added and the mixture was vortexed, heated with a heat gun for 30 sec and then heated for 90 min at 100 degrees. The mixture was extracted with dichloromethane and the combined dichloromethane extracts were evaporated and purified by column chromatography, eluting initially with 50% ethyl acetate/hexanes and later with 12.5% methanol/ethyl acetate to give (4R,7S)-3-methoxy-7,8,8-trimethyl-2-phenyl-4,5,6,7-tetrahydro-2H-4,7-methano-indazole (70 mg, 35%) as a yellow solid, and (4R,7S)-1,7,8,8-tetramethyl-2-phenyl-1,2,4,5,6,7-hexahydro-4,7-methano-indazol-3-one (33 mg, 17%) as a white solid. APCI-MS (M+H) 283.

Example 3

(4S,7R)-1-Ethyl-7,8,8-trimethyl-2-phenyl-1,2,4,5,6,7-hexahydro-4,7-methano-indazol-3-one

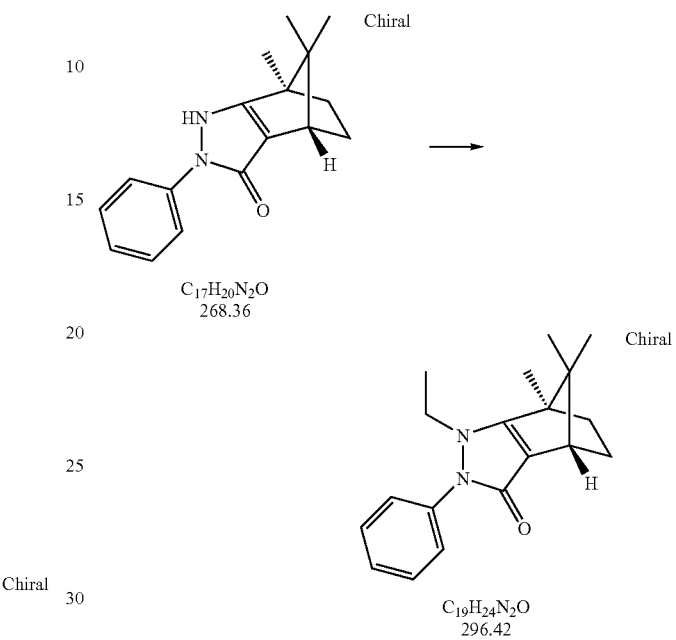

C$_{17}$H$_{20}$N$_2$O
268.36

C$_{19}$H$_{24}$N$_2$O
296.42

A mixture of bromoethane (1.05 mL, 14.1 mmol), potassium carbonate (3.58 g, 25.9 mmol), and (4S,7R)-2-phenyl-7,8,8-trimethyl-1,2,4,5,6,7-hexahydro-4,7-methano-indazol-3-one (Intermediate 6; 1.74 g, 6.5 mmol) in acetone (20 mL) and methanol (3 mL) was stirred at room temperature over the weekend then the solvent was evaporated and the residue was partitioned between water and dichloromethane. The organic layer was evaporated, and the residue was chromatographed (0-50% ethyl acetate/hexanes) and recrystallized from ethyl acetate to give (4S,7R)-1-ethyl-7,8,8-trimethyl-2-phenyl-1,2,4,5,6,7-hexahydro-4,7-methano-indazol-3-one (168 mg, 9%) as a white solid. APCI-MS (M+H) 297.

Example 4

(4S,7R)-1-Benzyl-7,8,8-trimethyl-2-phenyl-1,2,4,5,6,7-hexahydro-4,7-methano-indazol-3-one

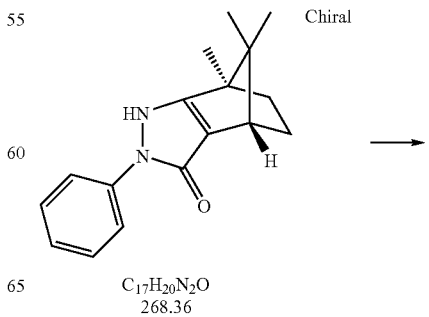

C$_{17}$H$_{20}$N$_2$O
268.36

-continued

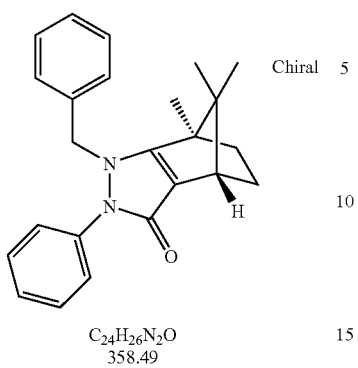

C₂₄H₂₆N₂O
358.49

Procedure A: A mixture of benzyl bromide (1.54 mL, 13.0 mmol), potassium carbonate (3.58 g, 25.9 mmol), and (4S,7R)-2-phenyl-7,8,8-trimethyl-1,2,4,5,6,7-hexahydro-4,7-methano-indazol-3-one (Intermediate 6; 1.74 g, 6.5 mmol) in acetone (20 mL) and methanol (3 mL) was heated at reflux overnight, then a further portion of benzyl bromide (0.75 mL, 6.3 mmol) was added and the reaction mixture was allowed to stir at room temperature over the weekend. The solvent was evaporated and the residue was partitioned between water and dichloromethane. The organic layer was evaporated and the residue was chromatographed (0-50% ethyl acetate/hexanes), and recrystallized from ethyl acetate/hexanes to give (4S,7R)-1-benzyl-7,8,8-trimethyl-2-phenyl-1,2,4,5,6,7-hexahydro-4,7-methano-indazol-3-one (94 mg, 3%) as a white solid. APCI-MS (M+H) 359.

Procedure B: A mixture of benzyl bromide (0.54 mL, 4.5 mmol) and (4S,7R)-2-phenyl-7,8,8-trimethyl-1,2,4,5,6,7-hexahydro-4,7-methano-indazol-3-one (Intermediate 6; 1.11 g, 4.1 mmol) in N,N-dimethylformamide was heated at 78° C. for 2.5 h. The reaction mixture was diluted with 1 M NaOH (200 mL) and extracted with ethyl acetate (200 mL). The organic layer was washed with 1 M NaOH and brine, dried (magnesium sulfate), filtered and evaporated. The residue was recrystallized from ethyl acetate/hexanes to give (4S,7R)-1-benzyl-7,8,8-trimethyl-2-phenyl-1,2,4,5,6,7-hexahydro-4,7-methano-indazol-3-one (114 mg, 8%) as a tan solid. APCI-MS (M+H) 359.

Procedure C: A mixture of benzyl bromide (3.87 mL, 31.9 mmol), (4S,7R)-2-phenyl-7,8,8-trimethyl-1,2,4,5,6,7-hexahydro-4,7-methano-indazol-3-one (Intermediate 6; 2.14 g, 8.0 mmol) and tetra-n-butylammonium iodide (2.06 g, 5.6 mmol) in N,N-dimethylformamide (50 mL) was heated in an oil-bath at 100° C. for 16 h. The solvent was evaporated and dichloromethane (100 mL) and water were added. The aqueous layer was extracted with dichloromethane (2×100 mL) and the combined organic layers were washed with water (5×100 mL). The solvent was evaporated and the residue purified on an Isco 120 g column, eluting with 33-100% ethyl acetate/hexanes to give (4S,7R)-1-benzyl-7,8,8-trimethyl-2-phenyl-1,2,4,5,6,7-hexahydro-4,7-methano-indazol-3-one (2.41 g, 84%) as an off-white/tan solid. ES(+)-MS (M+H) 359.

Example 5

(4S,7R)-1,7,8,8-Tetramethyl-2-p-tolyl-1,2,4,5,6,7-hexahydro-4,7-methano-indazol-3-one

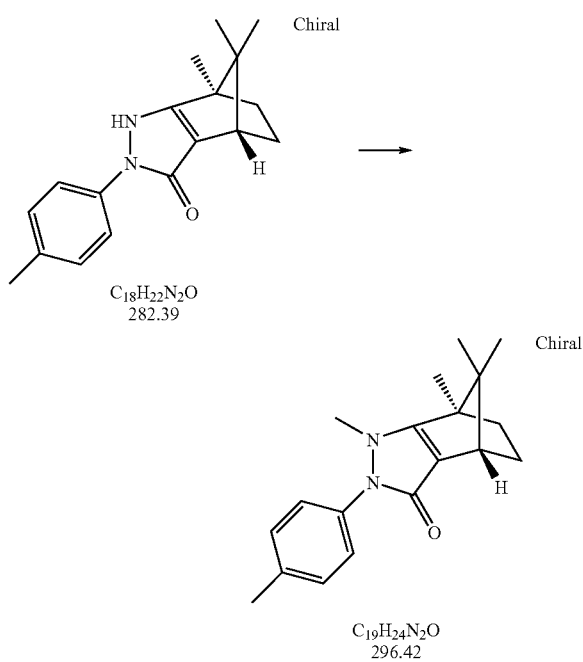

C₁₈H₂₂N₂O
282.39

C₁₉H₂₄N₂O
296.42

(4S,7R)-7,8,8-Trimethyl-2-p-tolyl-1,2,4,5,6,7-hexahydro-4,7-methano-indazol-3-one (Intermediate 9; 400 mg, 1.4 mmol) was dissolved in 1 M NaOH (5 mL) and dimethyl sulfate (0.14 mL, 1.46 mmol) was added. The mixture was stirred at room temperature overnight and then diluted with water and extracted three times with ethyl acetate. The combined organic layers were washed with water and brine, dried (magnesium sulfate), filtered, evaporated, and purified using an Analogix Intelliflash 280 system (Analogix, Inc., Burlington, Wis.) with an RS-12 column, eluting with 0-100% ethyl acetate/hexanes to give (4S,7R)-1,7,8,8-tetramethyl-2-p-tolyl-1,2,4,5,6,7-hexahydro-4,7-methano-indazol-3-one (82 mg, 20%) as an off-white solid and (4S,7R)-3-methoxy-7,8,8-trimethyl-2-p-tolyl-4,5,6,7-tetrahydro-2H-4,7-methano-indazole (134 mg, 32%) as a yellow solid. ES(+)-MS (M+H) 297.

Example 6

(4S,7R)-1-Ethyl-7,8,8-trimethyl-2-p-tolyl-1,2,4,5,6,7-hexahydro-4,7-methano-indazol-3-one

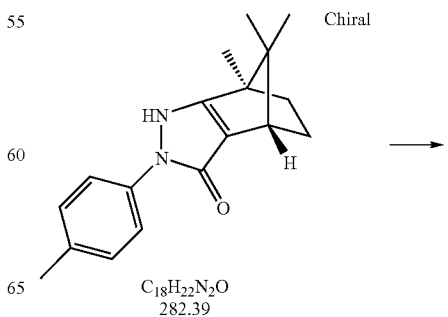

C₁₈H₂₂N₂O
282.39

-continued

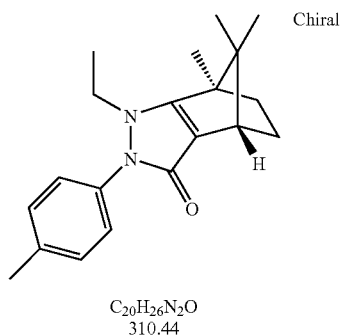

C20H26N2O
310.44

Iodoethane (0.12 mL, 1.5 mmol) was added to (4S,7R)-7,8,8-trimethyl-2-p-tolyl-1,2,4,5,6,7-hexahydro-4,7-methano-indazol-3-one (Intermediate 9; 400 mg, 1.4 mmol) and potassium carbonate (400 mg, 2.8 mmol) in dimethylformamide (5 mL). The mixture was heated at 60 degrees under argon overnight. The reaction mixture was diluted with water and extracted three times with ethyl acetate. The combined organic layers were washed with water and brine, dried (magnesium sulfate), filtered, evaporated, and purified using an Analogix Intelliflash 280 system (Analogix, Inc., Burlington, Wis.) with an RS-12 column, eluting with 0-75% ethyl acetate/hexanes to give (4S,7R)-1-ethyl-7,8,8-trimethyl-2-p-tolyl-1,2,4,5,6,7-hexahydro-4,7-methano-indazol-3-one (30 mg, 7%) as a white solid and (4S,7R)-3-ethoxy-7,8,8-trimethyl-2-p-tolyl-4,5,6,7-tetrahydro-2H-4,7-methano-indazole (266 mg, 60%) as a light yellow solid. ES(+)-MS (M+H) 311.

Example 7

(4S,7R)-1-Benzyl-7,8,8-trimethyl-2-p-tolyl-1,2,4,5,6,7-hexahydro-4,7-methano-indazol-3-one

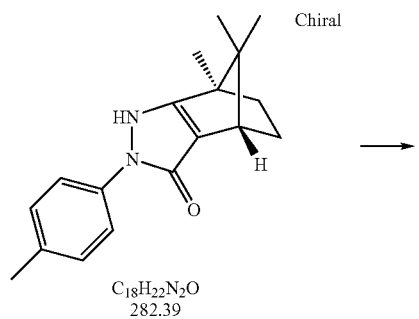

C18H22N2O
282.39

-continued

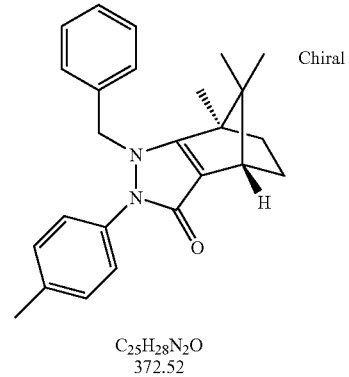

C25H28N2O
372.52

Benzyl bromide (0.18 mL, 1.5 mmol) was added to (4S,7R)-7,8,8-trimethyl-2-p-tolyl-1,2,4,5,6,7-hexahydro-4,7-methano-indazol-3-one (Intermediate 9; 400 mg, 1.4 mmol), potassium iodide (34 mg, 0.14 mmol) and potassium carbonate (400 mg, 2.8 mmol) in dimethylformamide (5 mL). The mixture was heated at 80 degrees under argon overnight. The reaction mixture was diluted with water and extracted three times with ethyl acetate. The combined organic layers were washed with water and brine, dried (magnesium sulfate), filtered, evaporated, and purified using an Analogix Intelliflash 280 system (Analogix, Inc., Burlington, Wis.) with an RS-12 column, eluting with 0-65% ethyl acetate/hexanes to give (4S,7R)-1-benzyl-7,8,8-trimethyl-2-p-tolyl-1,2,4,5,6,7-hexahydro-4,7-methano-indazol-3-one (19 mg, 3.5%) as an off-white solid and (4S,7R)-3-benzyloxy-7,8,8-trimethyl-2-p-tolyl-4,5,6,7-tetrahydro-2H-4,7-methano-indazole (279 mg, 53%) as a yellow oil. ES(+)-MS (M+H) 373.

Example 8

(4S,7R)-2-(2-Chloro-phenyl)-1,7,8,8-tetramethyl-1,2,4,5,6,7-hexahydro-4,7-methano-indazol-3-one

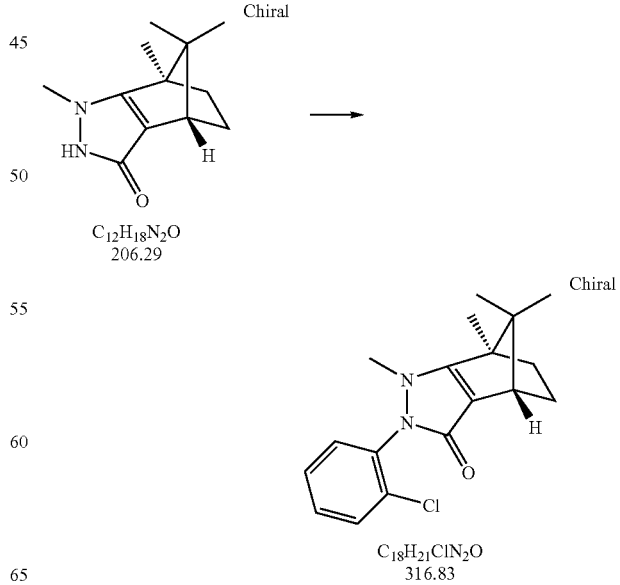

Procedure A: A mixture of (4S,7R)-1,7,8,8-tetramethyl-1,2,4,5,6,7-hexahydro-4,7-methano-indazol-3-one (Intermediate 19; 1.24 g, 6 mmol), 1-chloro-2-iodobenzene (666 µL, 5.4 mmol), copper(I) iodide (57 mg, 0.3 mmol), picolinic acid (150 mg, 1.2 mmol), and potassium bicarbonate (840 mg, 8.4 mmol) in N,N-dimethylformamide (20 mL) was irradiated in a microwave oven at 200° C. for 160 min. The reaction mixture was diluted with 0.1 M HCl (200 mL) and then extracted with ethyl acetate (200 mL). The organic layer was washed with 0.1 M HCl, 0.25 M NaOH, and brine, then dried (magnesium sulfate), filtered, evaporated and purified using an ISCO CombiFlash® Sg100c chromatography system, eluting with 5-100% ethyl acetate/dichloromethane to give a tan semi-solid which was taken up in ethyl acetate and washed with 0.1 M HCR. The solvent was evaporated and the residue was recrystallized from ethyl acetate. The mother liquor was evaporated and the residue recrystallized from ethyl acetate. The crystals were combined to give (4S,7R)-2-(2-chloro-phenyl)-1,7,8,8-tetramethyl-1,2,4,5,6,7-hexahydro-4,7-methano-indazol-3-one (80 mg, 5%) as a white solid. APCI-MS (M+H) 317.

Procedure B: A mixture of (4S,7R)-2-(2-chloro-phenyl)-7,8,8-trimethyl-1,2,4,5,6,7-hexahydro-4,7-methano-indazol-3-one (Intermediate 10; 5.11 g, 16.9 mmol) and methyl iodide (1.05 mL, 16.9 mmol) in N,N-dimethylformamide (20 mL) was heated to 80° C. for 2 h. The reaction mixture was diluted with water (50 mL) and saturated sodium bicarbonate (150 mL) and extracted with ethyl acetate (2×200 mL). The organic extracts were combined, washed with brine, dried (sodium sulfate), filtered, evaporated, and purified using an ISCO CombiFlash® Sg100c chromatography system eluting with 10-100% ethyl acetate/hexanes to give (4S,7R)-2-(2-chloro-phenyl)-1,7,8,8-tetramethyl-1,2,4,5,6,7-hexahydro-4,7-methano-indazol-3-one (233 mg, 4%). ES(+)-MS (M+H) 317.

Example 9

(4S,7R)-2-(2-Chloro-phenyl)-1-ethyl-7,8,8-trimethyl-1,2,4,5,6,7-hexahydro-4,7-methano-indazol-3-one

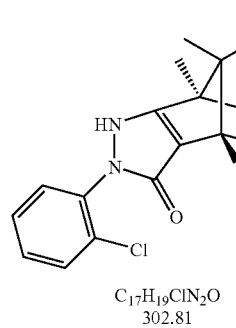

C$_{17}$H$_{19}$ClN$_2$O
302.81

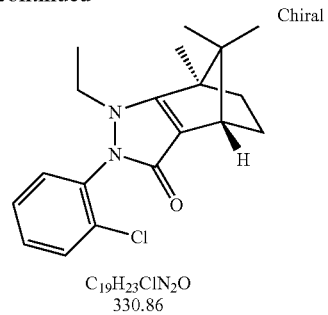

C$_{19}$H$_{23}$ClN$_2$O
330.86

Iodoethane (14 µL, 0.18 mmol) was added to (4S,7R)-2-(2-chloro-phenyl)-7,8,8-trimethyl-1,2,4,5,6,7-hexahydro-4,7-methano-indazol-3-one (Intermediate 10; 47 mg, 0.16 mmol) and potassium carbonate (43 mg, 0.31 mmol) in dimethylformamide (1 mL). The mixture was heated at 60 degrees for 4 h, and then stirred at room temperature over the weekend. The reaction mixture was diluted with ethyl acetate and washed with NaOH. The solvent was evaporated from the ethyl acetate layer and the residue was purified by flash chromatography, eluting with 0-70% ethyl acetate/hexanes, to give 2-(2-chloro-phenyl)-3-ethoxy-7,8,8-trimethyl-4,5,6,7-tetrahydro-2H-4,7-methano-indazole (12.3 mg, 16%) and (4S,7R)-2-(2-chloro-phenyl)-1-ethyl-7,8,8-trimethyl-1,2,4,5,6,7-hexahydro-4,7-methano-indazol-3-one (4.4 mg, 9%). APCI-MS (M+H) 331.

Example 10

(4S,7R)-1-Benzyl-2-(2-chloro-phenyl)-7,8,8-trimethyl-1,2,4,5,6,7-hexahydro-4,7-methano-indazol-3-one

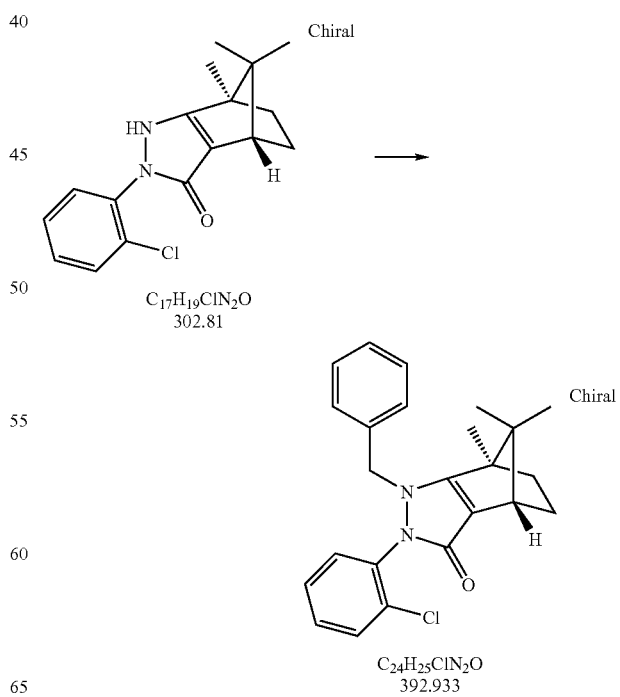

C$_{17}$H$_{19}$ClN$_2$O
302.81

C$_{24}$H$_{25}$ClN$_2$O
392.933

Benzyl-2-(2-chloro-phenyl)-7,8,8-trimethyl-1,2,4,5,6,7-hexahydro-4,7-methano-indazol-3-one was prepared from (4S,7R)-2-(2-chloro-phenyl)-7,8,8-trimethyl-1,2,4,5,6,7-hexahydro-4,7-methano-indazol-3-one (Intermediate 10) and benzyl bromide using the procedure described above for the preparation of (4S,7R)-2-(2-chloro-phenyl)-1-ethyl-7,8,8-trimethyl-1,2,4,5,6,7-hexahydro-4,7-methano-indazol-3-one (Example 9). APCI-MS (M+H) 393.

Example 11

(4S,7R)-2-(4-Chloro-phenyl)-1,7,8,8-tetramethyl-1,2,4,5,6,7-hexahydro-4,7-methano-indazol-3-one

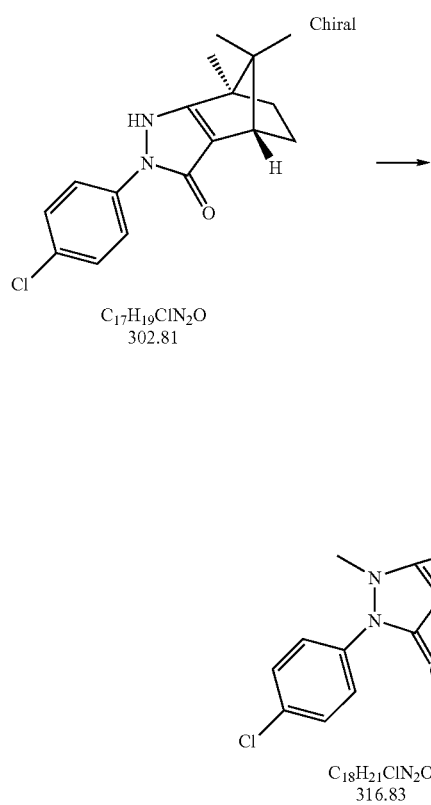

Dimethyl sulfate (84 µL, 0.92 mmol) was added to a solution of (4S,7R)-2-(4-chloro-phenyl)-7,8,8-trimethyl-1,2,4,5,6,7-hexahydro-4,7-methano-indazol-3-one (Intermediate 11; 252 mg, 0.83 mmol) in 1 M NaOH (3 mL) and the resulting solution was stirred at room temperature overnight. The aqueous supernatant was decanted away from the red gum, and the gum was dissolved in ethyl acetate. This solution was washed with water, dried (sodium sulfate), filtered, evaporated, and purified by chromatography using a Waters Sep-Pak® column, eluting with 20% ethyl acetate/hexanes to elute 2-(4-chloro-phenyl)-3-methoxy-7,8,8-trimethyl-4,5,6,7-tetrahydro-2H-4,7-methano-indazole, and then a step gradient of 50% ethyl acetate/hexanes, 66% ethyl acetate/hexanes, and finally 4% methanol/ethyl acetate to give (4S,7R)-2-(4-chloro-phenyl)-1,7,8,8-tetramethyl-1,2,4,5,6,7-hexahydro-4,7-methano-indazol-3-one (18 mg, 7%). ES(+)-MS (M+H) 317.

Example 12

(4S,7R)-2-(2-Fluoro-phenyl)-1,7,8,8-tetramethyl-1,2,4,5,6,7-hexahydro-4,7-methano-indazol-3-one

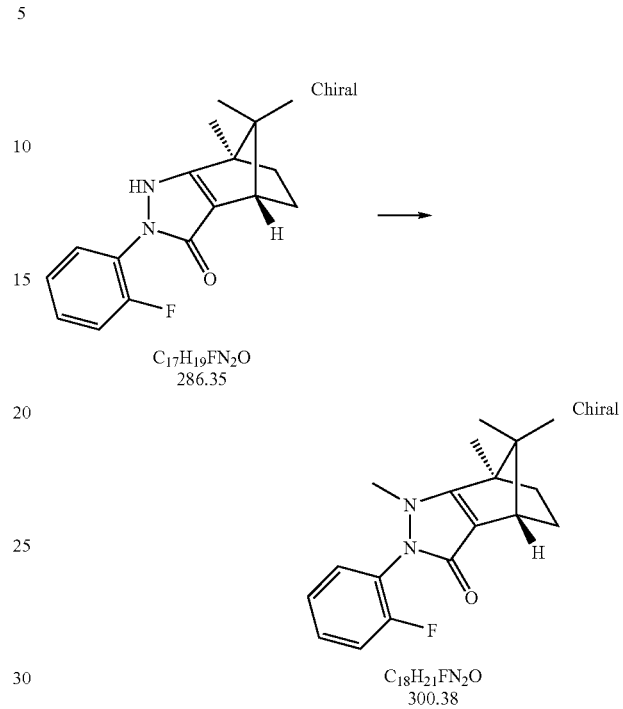

A mixture of a (4S,7R)-2-(2-fluoro-phenyl)-7,8,8-trimethyl-1,2,4,5,6,7-hexahydro-4,7-methano-indazol-3-one (Intermediate 12; 1.06 g, 3.7 mmol) and iodomethane (450 µL, 7.2 mmol) in N,N-dimethylformamide (20 mL) in a sealed tube was heated to 98° C. and stirred for 5 h. The reaction mixture was allowed to cool and water (20 mL) and saturated sodium bicarbonate solution (200 mL) were added. The solution was extracted with ethyl acetate (200 mL), and the organic layer was washed with brine (200 mL), dried (sodium sulfate), filtered, and evaporated. The residue was triturated with hexanes (4×5 mL) and the solid was recrystallized twice from ethyl acetate/hexanes to give (4S,7R)-2-(2-fluoro-phenyl)-1,7,8,8-tetramethyl-1,2,4,5,6,7-hexahydro-4,7-methano-indazol-3-one (451 mg, 41%) as white needles. ES(+)-MS (M+H) 301.

Example 13

(4S,7R)-2-(2-Fluoro-phenyl)-7,8,8-trimethyl-1-propyl-1,2,4,5,6,7-hexahydro-4,7-methano-indazol-3-one

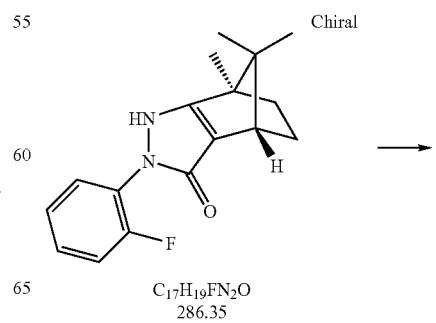

-continued

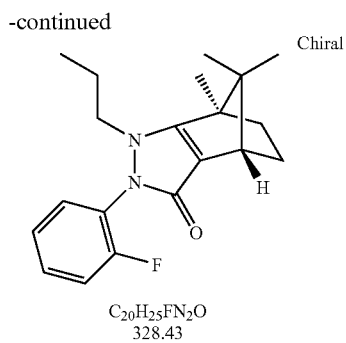

C₂₀H₂₅FN₂O
328.43

A mixture of a (4S,7R)-2-(2-fluoro-phenyl)-7,8,8-trimethyl-1,2,4,5,6,7-hexahydro-4,7-methano-indazol-3-one (Intermediate 12; 150 mg, 0.52 mmol) and 1-iodopropane (103 μL, 1.05 mmol) in N,N-dimethylformamide (2 mL) in a microwave reaction tube was heated to 100° C. and stirred for 18 h. The reaction mixture was allowed to cool, diluted with saturated sodium bicarbonate, and extracted twice with ethyl acetate. The organic extracts were combined, washed with water and brine, dried (magnesium sulfate), filtered, evaporated, and purified using an ISCO CombiFlash® Sg100c chromatography system with an Isco 12 g column, eluting with 25-100% ethyl acetate/hexanes to give (4S,7R)-2-(2-fluoro-phenyl)-7,8,8-trimethyl-1-propyl-1,2,4,5,6,7-hexahydro-4,7-methano-indazol-3-one (59.7 mg, 35%) as an orange oil. ES(+)-MS (M+H) 329.

Example 14

(4S,7R)-1-Allyl-2-(2-Fluoro-phenyl)-7,8,8-trimethyl-1,2,4,5,6,7-hexahydro-4,7-methano-indazol-3-one

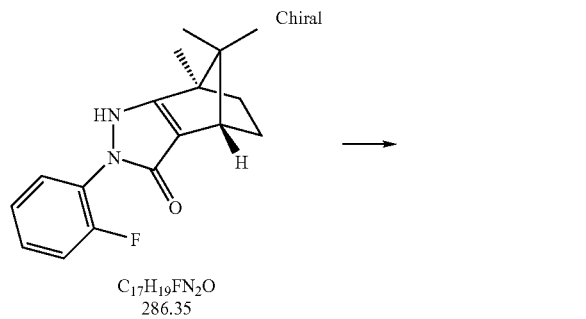

C₁₇H₁₉FN₂O
286.35

C₂₀H₂₃FN₂O
326.42

A mixture of a (4S,7R)-2-(2-fluoro-phenyl)-7,8,8-trimethyl-1,2,4,5,6,7-hexahydro-4,7-methano-indazol-3-one (Intermediate 12; 150 mg, 0.52 mmol) and allyl iodide (100 μL, 1.1 mmol) in N,N-dimethylformamide (2 mL) in a microwave reaction tube was heated to 100° C. and stirred for 18 h. The reaction mixture was allowed to cool, diluted with saturated sodium bicarbonate, and extracted twice with ethyl acetate. The organic extracts were combined, washed with water and brine, dried (magnesium sulfate), filtered, evaporated, and purified using an ISCO CombiFlash® Sg100c chromatography system with an Isco 12 g column, eluting with 25-100% ethyl acetate/hexanes to give (4S,7R)-1-allyl-2-(2-fluoro-phenyl)-7,8,8-trimethyl-1,2,4,5,6,7-hexahydro-4,7-methano-indazol-3-one (56 mg, 33%) as an orange solid. ES(+)-MS (M+H) 327.

Example 15

(4S,7R)-2-(2-Fluoro-phenyl)-1-isopropyl-7,8,8-trimethyl-1,2,4,5,6,7-hexahydro-4,7-methano-indazol-3-one

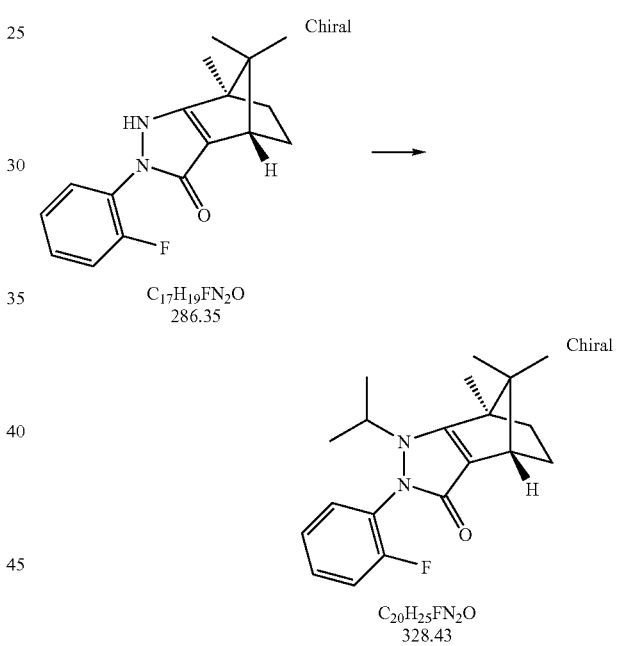

C₁₇H₁₉FN₂O
286.35

C₂₀H₂₅FN₂O
328.43

A mixture of a (4S,7R)-2-(2-fluoro-phenyl)-7,8,8-trimethyl-1,2,4,5,6,7-hexahydro-4,7-methano-indazol-3-one (Intermediate 12; 150 mg, 0.52 mmol) and 2-iodopropane (105 μL, 1.05 mmol) in N,N-dimethylformamide (2 mL) in a microwave reaction tube was heated to 100° C. and stirred for 18 h. The reaction mixture was allowed to cool, diluted with saturated sodium bicarbonate, and extracted twice with ethyl acetate. The organic extracts were combined, washed with water and brine, dried (magnesium sulfate), filtered, evaporated, and purified using an ISCO CombiFlash® Sg100c chromatography system with an Isco 12 g column, eluting with 25-100% ethyl acetate/hexanes followed by crystallization from dichloromethane to give (4S,7R)-2-(2-fluoro-phenyl)-1-isopropyl-7,8,8-trimethyl-1,2,4,5,6,7-hexahydro-4,7-methano-indazol-3-one (7 mg, 4%) as an yellow solid. ES(+)-MS (M+H) 329.

Example 16

(4S,7R)-1-Benzyl-2-(2-fluoro-phenyl)-7,8,8-trimethyl-1,2,4,5,6,7-hexahydro-4,7-methano-indazol-3-one

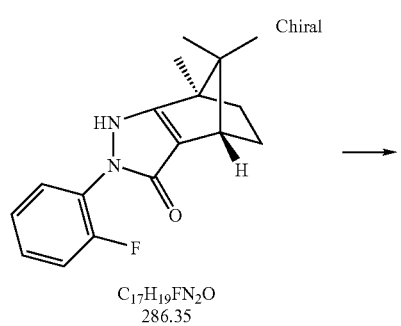

C₁₇H₁₉FN₂O
286.35

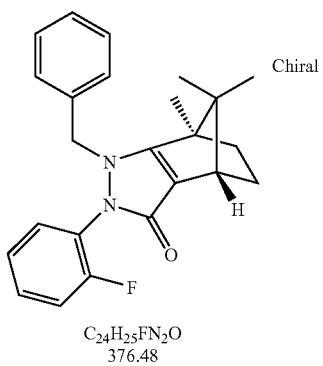

C₂₄H₂₅FN₂O
376.48

A mixture of a (4S,7R)-2-(2-fluoro-phenyl)-7,8,8-trimethyl-1,2,4,5,6,7-hexahydro-4,7-methano-indazol-3-one (Intermediate 12; 150 mg, 0.52 mmol) and benzyl bromide (130 μL, 1.09 mmol) in N,N-dimethylformamide (2 mL) in a microwave reaction tube was heated to 100° C. and stirred for 18 h. The reaction mixture was allowed to cool, diluted with saturated sodium bicarbonate, and extracted twice with ethyl acetate. The organic extracts were combined, washed with water and brine, dried (magnesium sulfate), filtered, evaporated, and purified using an ISCO CombiFlash® Sg100c chromatography system with an Isco 12 g column, eluting with 25-100% ethyl acetate/hexanes to give (4S,7R)-1-benzyl-2-(2-fluoro-phenyl)-7,8,8-trimethyl-1,2,4,5,6,7-hexahydro-4,7-methano-indazol-3-one (59 mg, 30%) as an light brown solid. ES(+)-MS (M+H) 377.

Example 17

(4S,7R)-2-(4-Fluoro-phenyl)-1,7,8,8-tetramethyl-1,2,4,5,6,7-hexahydro-4,7-methano-indazol-3-one

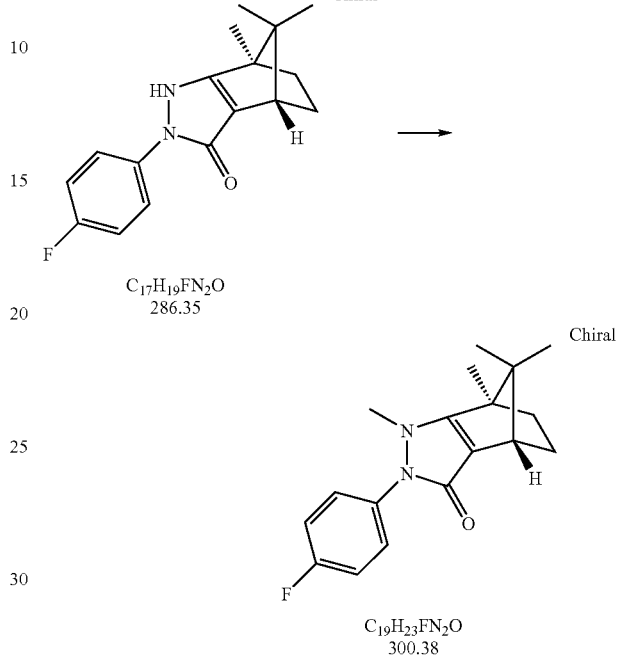

C₁₇H₁₉FN₂O
286.35

C₁₉H₂₃FN₂O
300.38

A mixture of dimethyl sulfate (1.1 mL, 11.6 mmol) and (4S,7R)-2-(4-fluoro-phenyl)-7,8,8-trimethyl-1,2,4,5,6,7-hexahydro-4,7-methano-indazol-3-one (Intermediate 13; 1.65 g, 5.8 mmol) in 1 M NaOH (25 mL) was heated at 50 degrees overnight, and then allowed to stand at room temperature over the weekend. The precipitate was filtered off, washed with water, and recrystallized from ethyl acetate to give (4S,7R)-2-(4-fluoro-phenyl)-1,7,8,8-tetramethyl-1,2,4,5,6,7-hexahydro-4,7-methano-indazol-3-one (239 mg, 14%) as a white solid. ES(+)-MS (M+H) 301.

Example 18

(4S,7R)-2-(2,4-Difluoro-phenyl)-1,7,8,8-tetramethyl-1,2,4,5,6,7-hexahydro-4,7-methano-indazol-3-one

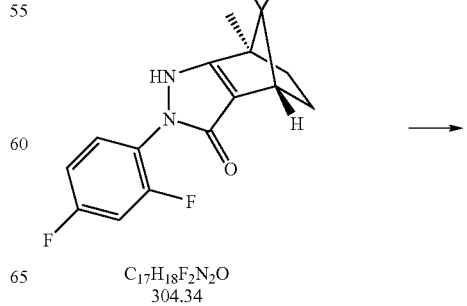

C₁₇H₁₈F₂N₂O
304.34

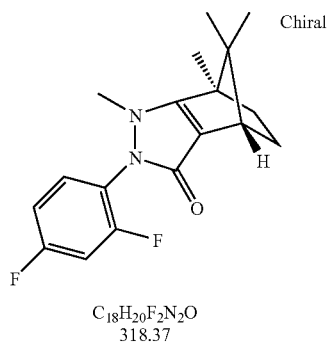

C₁₈H₂₀F₂N₂O
318.37

A mixture of dimethyl sulfate (0.56 mL, 5.9 mmol) and (4S,7R)-2-(2,4-difluoro-phenyl)-7,8,8-trimethyl-1,2,4,5,6,7-hexahydro-4,7-methano-indazol-3-one (Intermediate 14; 1.82 g, 6.0 mmol) in 1 M NaOH (25 mL) was heated at 45 degrees for 4.5 h, then a further portion of dimethyl sulfate (0.56 mL, 5.9 mmol) was added and the reaction was heated at 45 degrees overnight. NaOH was added and the mixture was extracted twice with ethyl acetate. The combined organic layers were evaporated and purified by column chromatography, eluting with 10-50% ethyl acetate/dichloromethane followed by recrystallization from ethyl acetate/hexanes to give (4S,7R)-2-(2,4-difluoro-phenyl)-1,7,8,8-tetramethyl-1,2,4,5,6,7-hexahydro-4,7-methano-indazol-3-one (199 mg, 11%) as a white solid. ES(+)-MS (M+H) 319.

Example 19

(4S,7R)-1-Benzyl-2-(2,4-Difluoro-phenyl)-7,8,8-trimethyl-1,2,4,5,6,7-hexahydro-4,7-methano-indazol-3-one

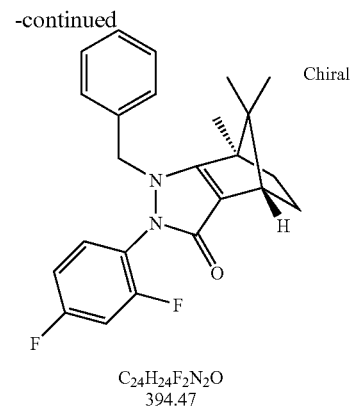

C₂₄H₂₄F₂N₂O
394.47

A mixture of (4S,7R)-2-(2,4-difluoro-phenyl)-7,8,8-trimethyl-1,2,4,5,6,7-hexahydro-4,7-methano-indazol-3-one (Intermediate 14; 1.28 g, 4.2 mmol) and benzyl bromide (0.5 mL, 4.2 mmol) in N,N-dimethylformamide (10 mL) was stirred at room temperature overnight and then heated at 60° C. for 3 h. A further portion of benzyl bromide (0.5 mL, 4.2 mmol) was added and the reaction mixture was heated overnight at 60° C., and then at 80° C. for a further 24 hours. The reaction mixture was diluted with water (60 mL) and extracted with dichloromethane (60 mL). The organic layer was washed with water, saturated sodium bicarbonate, and brine, then dried (sodium sulfate), filtered, and concentrated to give a viscous red oil. This was co-evaporated with petroleum ether then hexanes and then ether. Trituration with ether gave 0.48 g of pink solid. The supernatant was concentrated and then coevaporated with petroleum ether and then hexanes. Trituration with hexanes gave 0.61 g of pink solid. The supernatant was concentrated and passed through a plug of silica gel (38 g) eluting with 25-75% ethyl acetate/hexanes. The resulting crude product was combined with the two previously obtained pink solids and the purified using an ISCO CombiFlash® Sg100c chromatography system eluting with 10-100% ethyl acetate/hexanes to give (4S,7R)-1-benzyl-2-(2,4-difluoro-phenyl)-7,8,8-trimethyl-1,2,4,5,6,7-hexahydro-4,7-methano-indazol-3-one (1.01 g, 61%) as a pale pink solid. ES(+)-MS (M+H) 395.

Example 20

(4S,7R)-2-(2,6-Dichloro-phenyl)-7,8,8-trimethyl-1,2,4,5,6,7-hexahydro-4,7-methano-indazol-3-one

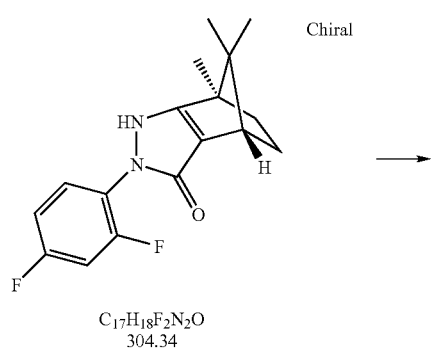

C₁₇H₁₈F₂N₂O
304.34

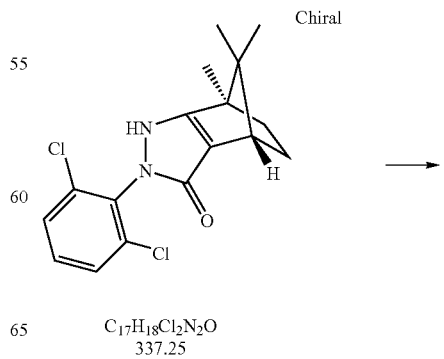

C₁₇H₁₈Cl₂N₂O
337.25

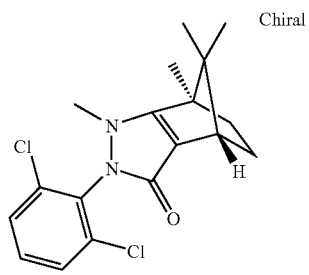

C₁₈H₂₀Cl₂N₂O
351.28

A mixture of (4S,7R)-2-(2,6-dichloro-phenyl)-7,8,8-trimethyl-1,2,4,5,6,7-hexahydro-4,7-methano-indazol-3-one (Intermediate 15; 1.2 g, 3.6 mmol) and iodomethane (0.45 mL, 8.0 mmol) in N,N-dimethylformamide (20 mL) was heated to 80° C. and stirred for 4.5 h. The reaction mixture was allowed to cool and water (200 mL) was added. A solid precipitated. Water (100 mL) was added, and the mixture was extracted with ethyl acetate (200 mL). The organic layer was washed with saturated sodium bicarbonate and brine, dried (sodium sulfate), filtered, concentrated and purified by chromatography, eluting with 5-80% ethyl acetate/dichloromethane. Fractions containing the product were combined, evaporated, and recrystallized from ethyl acetate/hexanes to give (4S,7R)-2-(2,6-dichloro-phenyl)-1,7,8,8-tetramethyl-1,2,4,5,6,7-hexahydro-4,7-methano-indazol-3-one (220 mg 18%) as a light tan solid. ES(+)-MS (M+H) 351

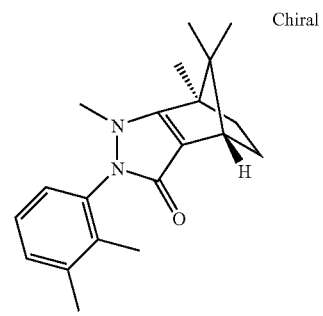

C₂₀H₂₆N₂O
310.44

A mixture of (4S,7R)-2-(2,3-dimethyl-phenyl)-7,8,8-trimethyl-1,2,4,5,6,7-hexahydro-4,7-methano-indazol-3-one (Intermediate 16; 4.07 g, 13.8 mmol) and iodomethane (1.5 mL, 24.1 mmol) in N,N-dimethylformamide (60 mL) in a sealed tube was heated to 105° C. and stirred for 1.5 h. The reaction mixture was allowed to cool and saturated sodium bicarbonate solution (200 mL) was added. A solid precipitated. Water (100 mL) was added, and the mixture was extracted with ethyl acetate (300 mL). The organic layer was washed with brine (300 mL), concentrated and purified by chromatography, eluting with 60-100% ethyl acetate/dichloromethane. Fractions containing the product were combined, evaporated, and recrystallized from ethyl acetate/hexanes to give (4S,7R)-2-(2,3-dimethyl-phenyl)-1,7,8,8-tetramethyl-1,2,4,5,6,7-hexahydro-4,7-methano-indazol-3-one (2.12 g 49%) as a white solid. ES(+)-MS (M+H) 311.

Example 21

(4S,7R)-2-(2,3-Dimethyl-phenyl)-1,7,8,8-tetramethyl-1,2,4,5,6,7-hexahydro-4,7-methano-indazol-3-one Example 22

(4S,7R)-2-(3-Bromo-phenyl)-1,7,8,8-tetramethyl-1,2,4,5,6,7-hexahydro-4,7-methano-indazol-3-one

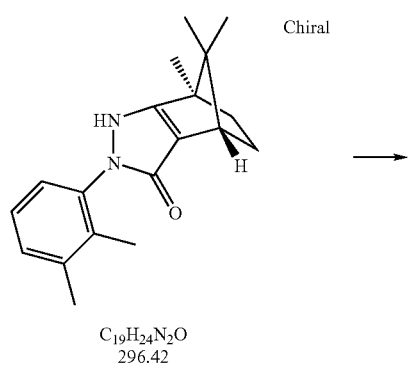

C₁₉H₂₄N₂O
296.42

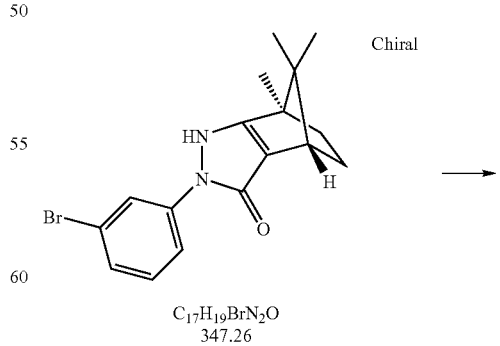

C₁₇H₁₉BrN₂O
347.26

-continued

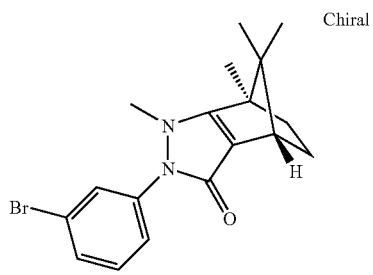

C₁₈H₂₁BrN₂O
361.29

-continued

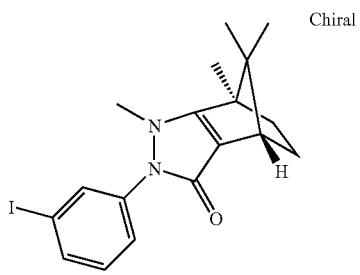

C₁₈H₂₁IN₂O
408.29

Dimethyl sulfate (0.26 mL, 2.7 mmol) was added to (4S,7R)-2-(3-bromo-phenyl)-7,8,8-trimethyl-1,2,4,5,6,7-hexahydro-4,7-methano-indazol-3-one (Intermediate 17; 770 mg, 2.2 mmol) in 1 M NaOH (12 mL) at 40-45 degrees. The mixture was stirred at room temperature overnight and then a further portion of dimethyl sulfate (0.35 mL, 3.7 mmol) was added and the reaction mixture was stirred at 40-45 degrees for 2 h. A further portion of dimethyl sulfate (0.35 mL, 3.7 mmol) was added and the reaction mixture was stirred at room temperature overnight. The aqueous supernatant was decanted away from a light brown/tan gum and the gum was dissolved in ethyl acetate, washed with water and brine, dried (sodium sulfate), filtered, and evaporated to give 0.73 g of light brown gum which LC/MS confirms contains the mass, and which RP-HPLC indicates contains 2 major products. This material was combined with the product of a second run using 1 g of the starting material. The combined crude products were purified using an ISCO CombiFlash® Sg100c chromatography system with an RS-120 column, eluting with 0-75% ethyl acetate/hexanes to give (4S,7R)-2-(3-bromo-phenyl)-1,7,8,8-tetramethyl-1,2,4,5,6,7-hexahydro-4,7-methano-indazol-3-one (32 mg, 2%). ES(+)-MS (M+H) 361.

Dimethyl sulfate (0.6 mL, 6.3 mmol) was added to a mixture of (4S,7R)-2-(3-iodo-phenyl)-7,8,8-trimethyl-1,2,4,5,6,7-hexahydro-4,7-methano-indazol-3-one (Intermediate 18; 1.62 g, 4.1 mmol) in methanol (10 mL) and 1 M NaOH (20 mL). The mixture was stirred at room temperature overnight and then further portions of dimethyl sulfate (0.6 mL, 6.3 mmol) were added immediately, after 2 h, and after 5 h. The mixture was stirred at room temperature over the weekend, and it was then diluted with water and extracted with ethyl acetate (2×125 mL). The combined organic layers were washed with water (100 mL) and brine (100 mL), dried (magnesium sulfate), filtered, evaporated, and purified using an Analogix Intelliflash 280 system (Analogix, Inc., Burlington, Wis.) with an RS-90 column, eluting with 0-100% ethyl acetate/hexanes to give (4S,7R)-2-(3-iodo-phenyl)-1,7,8,8-tetramethyl-1,2,4,5,6,7-hexahydro-4,7-methano-indazol-3-one (620 mg, 38%), as a white solid, (4S,7R)-2-(3-iodo-phenyl)-3-methoxy-7,8,8-trimethyl-4,5,6,7-tetrahydro-2H-4,7-methano-indazole (606 mg, 37%) as a yellow solid and unreacted starting material (140 mg, 9%). ES(+)-MS (M+H) 409

Example 23

(4S,7R)-2-(3-Iodo-phenyl)-1,7,8,8-tetramethyl-1,2,4,5,6,7-hexahydro-4,7-methano-indazol-3-one Example 24

(4S,7R)-2-(Pyridin-2-yl)-1,7,8,8-tetramethyl-1,2,4,5,6,7-hexahydro-4,7-methano-indazol-3-one

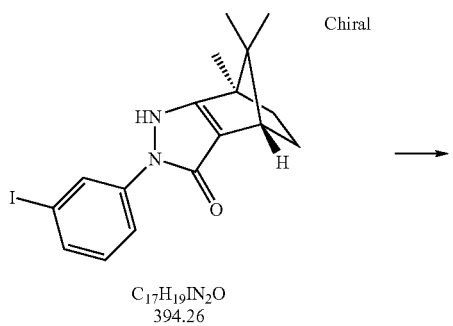

C₁₇H₁₉IN₂O
394.26

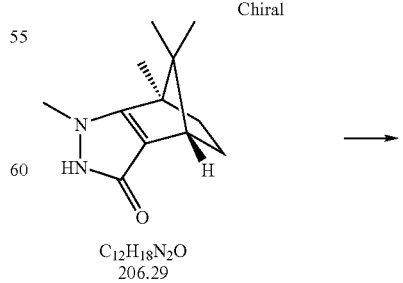

C₁₂H₁₈N₂O
206.29

-continued

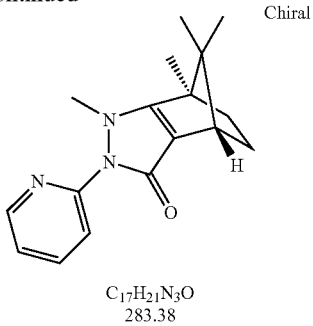

C<sub>17</sub>H<sub>21</sub>N<sub>3</sub>O
283.38

A mixture of (4S,7R)-1,7,8,8-tetramethyl-1,2,4,5,6,7-hexahydro-4,7-methano-indazol-3-one (Intermediate 19; 412 mg, 2 mmol), 2-bromo-pyridine (175 µL, 1.8 mmol), copper(I) iodide (19 mg, 0.1 mmol), picolinic acid (49 mg, 0.4 mmol), and potassium bicarbonate (280 mg, 2.8 mmol) in N,N-dimethylformamide (10 mL) was irradiated in a microwave oven at 220° C. for 30 min. The reaction mixture was diluted with 0.1 M HCl (200 mL) and then extracted with ethyl acetate (200 mL). The organic layer was washed with 0.1 M HCl, 0.25 M NaOH, and brine, then dried (magnesium sulfate), filtered, evaporated and purified using an ISCO system, eluting with 5-60% ethyl acetate/dichloromethane to give (4S,7R)-2-(pyridin-2-yl)-1,7,8,8-tetramethyl-1,2,4,5,6,7-hexahydro-4,7-methano-indazol-3-one (132 mg, 23%) as a white solid. ES(+)-MS (M+H) 284.

Example 25

(4S,7R)-2-(3-Methoxy-phenyl)-1,7,8,8-tetramethyl-1,2,4,5,6,7-hexahydro-4,7-methano-indazol-3-one

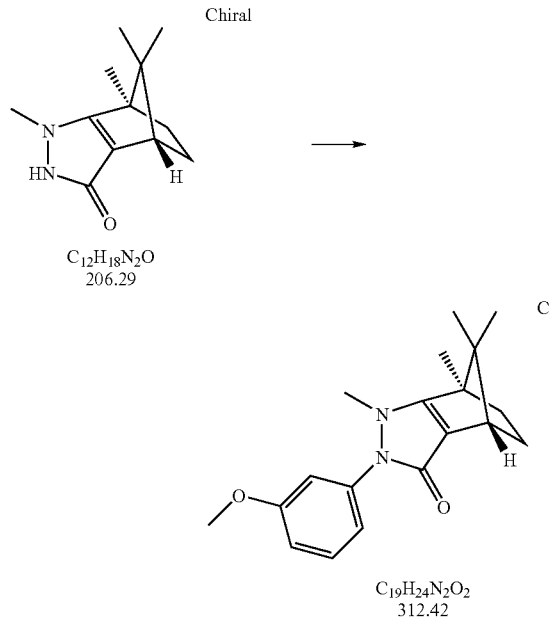

A mixture of (4S,7R)-1,7,8,8-tetramethyl-1,2,4,5,6,7-hexahydro-4,7-methano-indazol-3-one (Intermediate 19; 412 mg, 2 mmol), 3-iodo-methoxy-benzene (264 µL, 2.2 mmol), copper(I) iodide (19 mg, 0.1 mmol), picolinic acid (49 mg, 0.4 mmol), and potassium bicarbonate (280 mg, 2.8 mmol) in N,N-dimethylformamide (10 mL) was irradiated in a microwave oven at 220° C. for 30 min. The reaction mixture was diluted with 0.1 M HCl (200 mL) and then extracted with ethyl acetate (200 mL). The organic layer was washed with 0.1 M HCl, 0.25 M NaOH, and brine, then dried (magnesium sulfate), filtered, evaporated and purified using an ISCO system, eluting with 5-60% ethyl acetate/dichloromethane to give a tan semi-solid. This was dissolved in ethyl acetate (30 mL) and washed with 0.1 M HCl (30 mL), then dried, filtered, evaporated and triturated with petroleum ether to give (4S,7R)-2-(3-methoxy-phenyl)-1,7,8,8-tetramethyl-1,2,4,5,6,7-hexahydro-4,7-methano-indazol-3-one (107 mg, 20%) as a white solid. ES(+)-MS (M+H) 313.

Example 26

4-((4S,7R)-1,7,8,8-Tetramethyl-3-oxo-1,3,4,5,6,7-hexahydro-4,7-methano-indazol-2-yl)-benzoic acid methyl ester

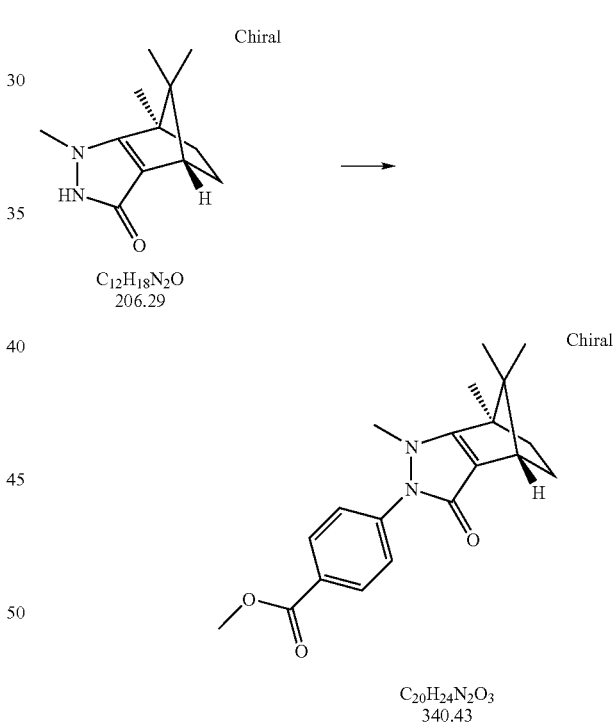

A mixture of (4S,7R)-1,7,8,8-tetramethyl-1,2,4,5,6,7-hexahydro-4,7-methano-indazol-3-one (Intermediate 19; 100 mg, 0.48 mmol), 4-methoxycarbonyl-phenyl-boronic acid (180 mg, 0.97 mmol), and copper(II) acetate (133 mg, 0.73 mmol) in dichloromethane (1 mL) and pyridine (0.8 mL) was stirred at room temperature for 2 days. The reaction mixture was evaporated and purified using an Analogix Intelliflash 280 system (Analogix, Inc., Burlington, Wis.) with an Isco 12 g column, eluting with 10-60% ethyl acetate/hexanes to give 4-((4S,7R)-1,7,8,8-tetramethyl-3-oxo-1,3,4,5,6,7- hexahydro-4,7-methano-indazol-2-yl)-benzoic acid methyl ester (48.2 mg, 29%) as an off-white solid. ES(+)-MS (M+H) 341.

Example 27

(4S,7R)-2-Benzyl-1,7,8,8-tetramethyl-1,2,4,5,6,7-hexahydro-4,7-methano-indazol-3-one

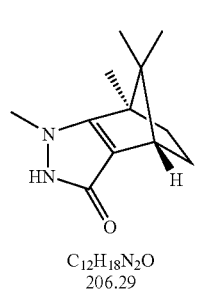

C₁₂H₁₈N₂O
206.29

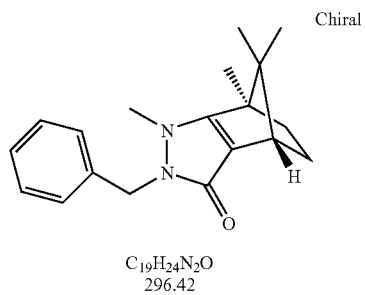

C₁₉H₂₄N₂O
296.42

A mixture of (4S,7R)-1,7,8,8-tetramethyl-1,2,4,5,6,7-hexahydro-4,7-methano-indazol-3-one (Intermediate 19; 100 mg, 0.49 mmol) and benzyl bromide (52 µL, 0.44 mmol) in N,N-dimethylformamide (4.5 mL) was heated at 100° C. overnight. The reaction mixture was evaporated and the residue was purified using a Biotage 40S system, eluting with 0-1% methanol/chloroform, followed by drying under high vacuum to give (4S,7R)-2-benzyl-1,7,8,8-tetramethyl-1,2,4,5,6,7-hexahydro-4,7-methano-indazol-3-one (71.5 mg, 55%) as an off-white solid. APCI-MS (M+H) 297.

Example 28

(4S,7R)-1,7,8,8-Tetramethyl-2-(2-trifluoromethyl-benzyl)-1,2,4,5,6,7-hexahydro-4,7-methano-indazol-3-one

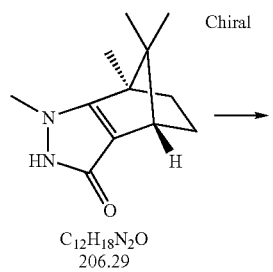

C₁₂H₁₈N₂O
206.29

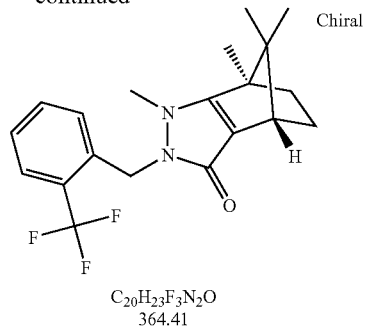

C₂₀H₂₃F₃N₂O
364.41

A mixture of (4S,7R)-1,7,8,8-tetramethyl-1,2,4,5,6,7-hexahydro-4,7-methano-indazol-3-one (Intermediate 19; 100 mg, 0.49 mmol) and 2-trifluoromethyl-benzyl bromide (77 µL, 0.51 mmol) in N,N-dimethylformamide (5 mL) was heated at 100° C. overnight. The reaction mixture was evaporated and the residue was purified using a Biotage 40S system, eluting with 0-1% methanol/chloroform, followed by drying under high vacuum to give (4S,7R)-1,7,8,8-tetramethyl-2-(2-trifluoromethyl-benzyl)-1,2,4,5,6,7-hexahydro-4,7-methano-indazol-3-one (55.3 mg, 32%) as a light yellow solid. APCI-MS (M+H) 365.

Example 29

(4S,7R)-2-(3,4-Dichloro-benzyl)-1,7,8,8-tetramethyl-1,2,4,5,6,7-hexahydro-4,7-methano-indazol-3-one

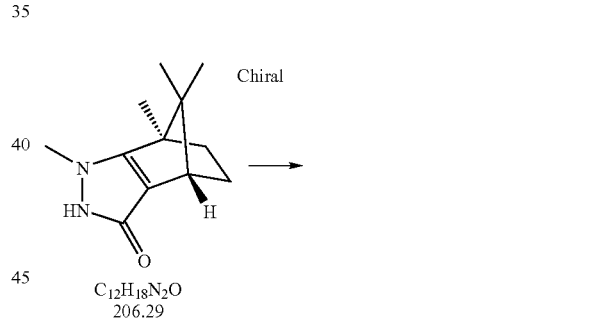

C₁₂H₁₈N₂O
206.29

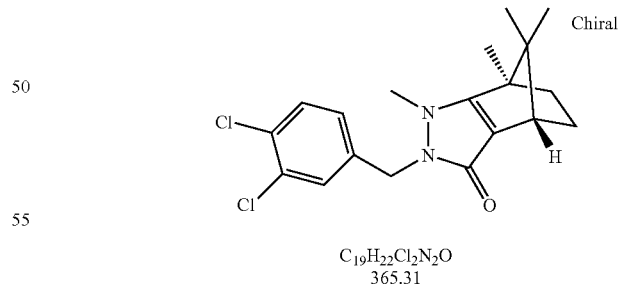

C₁₉H₂₂Cl₂N₂O
365.31

A mixture of (4S,7R)-1,7,8,8-tetramethyl-1,2,4,5,6,7-hexahydro-4,7-methano-indazol-3-one (Intermediate 19; 100 mg, 0.49 mmol) and 3,4-dichloro-benzyl bromide (116 mg, 0.48 mmol) in N,N-dimethylformamide (5 mL) was heated at 100° C. overnight. The reaction mixture was evaporated and the residue was purified using a Biotage 40S system, eluting with 0-1% methanol/chloroform, followed by drying under high vacuum to give (4S,7R)-2-(3,4-dichlorobenzyl)-1,7,8,8-tetramethyl-1,2,4,5,6,7-hexahydro-4,7-methano-indazol-3-one (104 mg, 59%) as a light yellow solid. APCI-MS (M+H) 365.

Example 30

(4S,7R)-2-(2,4-Difluoro-benzyl)-1,7,8,8-tetramethyl-1,2,4,5,6,7-hexahydro-4,7-methano-indazol-3-one

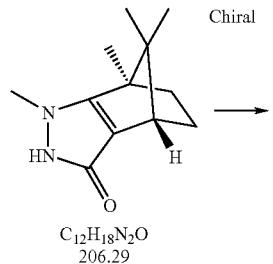

C$_{12}$H$_{18}$N$_2$O
206.29

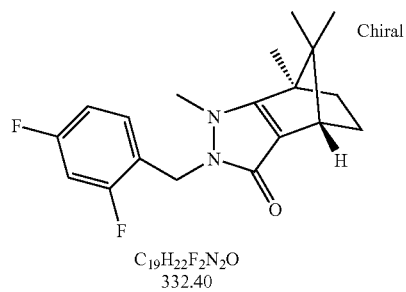

C$_{19}$H$_{22}$F$_2$N$_2$O
332.40

A mixture of (4S,7R)-1,7,8,8-tetramethyl-1,2,4,5,6,7-hexahydro-4,7-methano-indazol-3-one (Intermediate 19; 100 mg, 0.49 mmol) and 2,4-difluoro-benzyl bromide (62 µL, 0.48 mmol) in N,N-dimethylformamide (5 mL) was heated at 100° C. overnight. The reaction mixture was evaporated and the residue was purified using a Biotage 40S system, eluting with 0-1% methanol/chloroform, followed by drying under high vacuum to give (4S,7R)-2-(2,4-difluoro-benzyl)-1,7,8,8-tetramethyl-1,2,4,5,6,7-hexahydro-4,7-methano-indazol-3-one (82 mg, 51%) as an off-white solid. APCI-MS (M+H) 333.

Example 31

(4S,7R)-2-(2-Fluoro-benzyl)-1,7,8,8-tetramethyl-1,2,4,5,6,7-hexahydro-4,7-methano-indazol-3-one

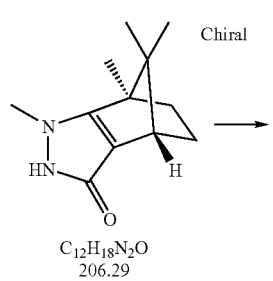

C$_{12}$H$_{18}$N$_2$O
206.29

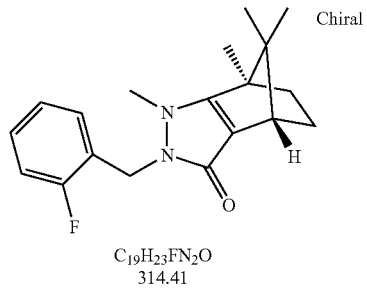

C$_{19}$H$_{23}$FN$_2$O
314.41

A mixture of (4S,7R)-1,7,8,8-tetramethyl-1,2,4,5,6,7-hexahydro-4,7-methano-indazol-3-one (Intermediate 19; 100 mg, 0.49 mmol) and 2-fluoro-benzyl bromide (58 µL, 0.48 mmol) in N,N-dimethylformamide (5 mL) was heated at 100° C. overnight and then allowed to stand at room temperature for five days. The reaction mixture was evaporated and the residue was purified using a Biotage 40S system, eluting with 0-1% methanol/chloroform, followed by drying under high vacuum to give (4S,7R)-2-(2-fluoro-benzyl)-1,7,8,8-tetramethyl-1,2,4,5,6,7-hexahydro-4,7-methano-indazol-3-one (63 mg, 42%) as a white solid. APCI-MS (M+H) 315.

Example 32

(4S,7R)-2-(3-Fluoro-benzyl)-1,7,8,8-tetramethyl-1,2,4,5,6,7-hexahydro-4,7-methano-indazol-3-one

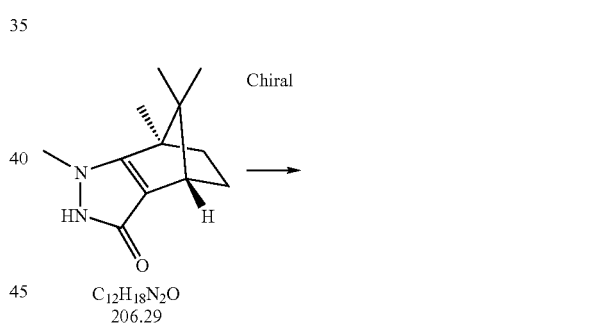

C$_{12}$H$_{18}$N$_2$O
206.29

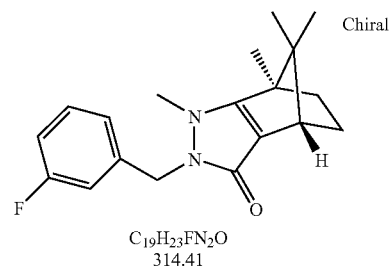

C$_{19}$H$_{23}$FN$_2$O
314.41

A mixture of (4S,7R)-1,7,8,8-tetramethyl-1,2,4,5,6,7-hexahydro-4,7-methano-indazol-3-one (Intermediate 19; 100 mg, 0.49 mmol) and 3-fluoro-benzyl bromide (59 µL, 0.48 mmol) in N,N-dimethylformamide (5 mL) was heated at 100° C. overnight. The reaction mixture was evaporated and the residue was purified using a Biotage 40S system, eluting with 0-1% methanol/chloroform, followed by drying under high vacuum to give (4S,7R)-2-(3-fluoro-benzyl)-1,7,8,8-tetramethyl-1,2,4,5,6,7-hexahydro-4,7-methano-indazol-3-one (64 mg, 42%) as a white solid. APCI-MS (M+H) 315.

Example 33

(4S,7R)-2-(4-Fluoro-benzyl)-1,7,8,8-tetramethyl-1,2,4,5,6,7-hexahydro-4,7-methano-indazol-3-one

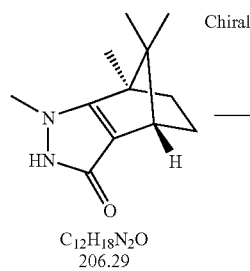

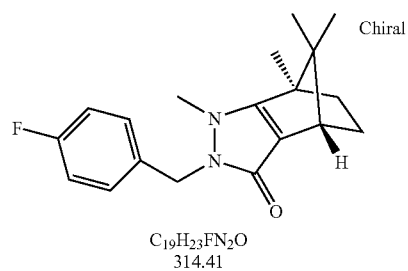

A mixture of (4S,7R)-1,7,8,8-tetramethyl-1,2,4,5,6,7-hexahydro-4,7-methano-indazol-3-one (Intermediate 19; 100 mg, 0.49 mmol) and 4-fluoro-benzyl bromide (60 µL, 0.48 mmol) in N,N-dimethylformamide (5 mL) was heated at 100° C. overnight. The reaction mixture was evaporated and the residue was purified using a Biotage 40S system, eluting with 0-1% methanol/chloroform, followed by drying under high vacuum to give (4S,7R)-2-(4-fluoro-benzyl)-1,7,8,8-tetramethyl-1,2,4,5,6,7-hexahydro-4,7-methano-indazol-3-one (61 mg, 41%) as a white solid. APCI-MS (M+H) 315.

Example 34

(4S,7R)-2-(3-Methoxy-benzyl)-1,7,8,8-tetramethyl-1,2,4,5,6,7-hexahydro-4,7-methano-indazol-3-one

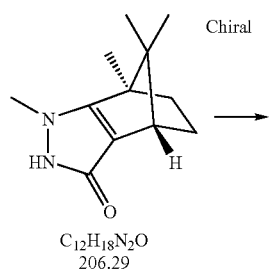

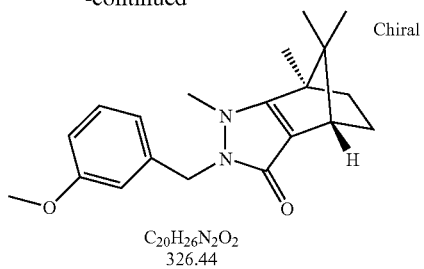

A mixture of (4S,7R)-1,7,8,8-tetramethyl-1,2,4,5,6,7-hexahydro-4,7-methano-indazol-3-one (Intermediate 19; 100 mg, 0.49 mmol) and 3-methoxy-benzyl bromide (67 µL, 0.48 mmol) in N,N-dimethylformamide (5 mL) was heated at 100° C. overnight. The reaction mixture was evaporated and the residue was purified using a Biotage 40S system, eluting with 0-1% methanol/chloroform, followed by drying under high vacuum to give (4S,7R)-2-(3-methoxy-benzyl)-1,7,8,8-tetramethyl-1,2,4,5,6,7-hexahydro-4,7-methano-indazol-3-one (65 mg, 42%) as a light yellow oil. APCI-MS (M+H) 327.

Example 35

(4S,7R)-2-(4-Methoxy-benzyl)-1,7,8,8-tetramethyl-1,2,4,5,6,7-hexahydro-4,7-methano-indazol-3-one

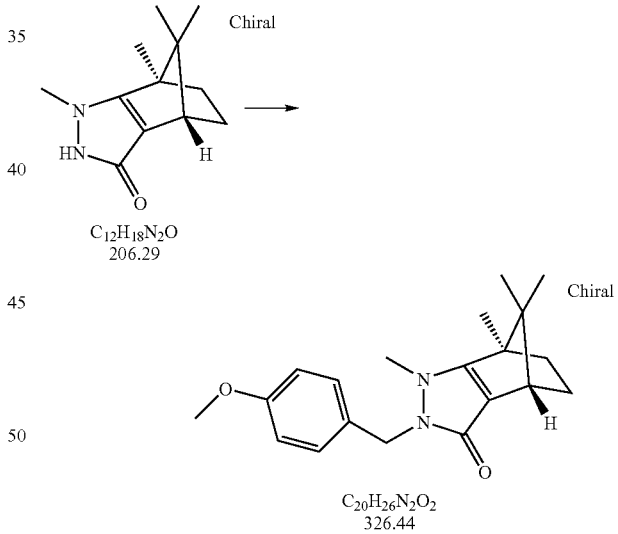

A mixture of (4S,7R)-1,7,8,8-tetramethyl-1,2,4,5,6,7-hexahydro-4,7-methano-indazol-3-one (Intermediate 19; 102 mg, 0.49 mmol) and 4-methoxy-benzyl bromide (73 µL, 0.50 mmol) in N,N-dimethylformamide (5 mL) was stirred at room temperature overnight, then heated to 100° C. and left over the weekend. At this time it was found that the heating bath had failed and the reaction mixture was at room temperature. The reaction mixture was evaporated and the residue was purified using a Biotage 40S system, eluting with 0-1% methanol/chloroform, followed by drying under high vacuum to give (4S,7R)-2-(4-methoxy-benzyl)-1,7,8,8-tetramethyl-1,2,4,5,6,7-hexahydro-4,7-methano-indazol-3-one (48 mg, 30%) as a white solid. APCI-MS (M+H) 327.

Example 36

(4S,7R)-2-(3-Trifluoromethyl-benzyl)-1,7,8,8-tetramethyl-1,2,4,5,6,7-hexahydro-4,7-methano-indazol-3-one

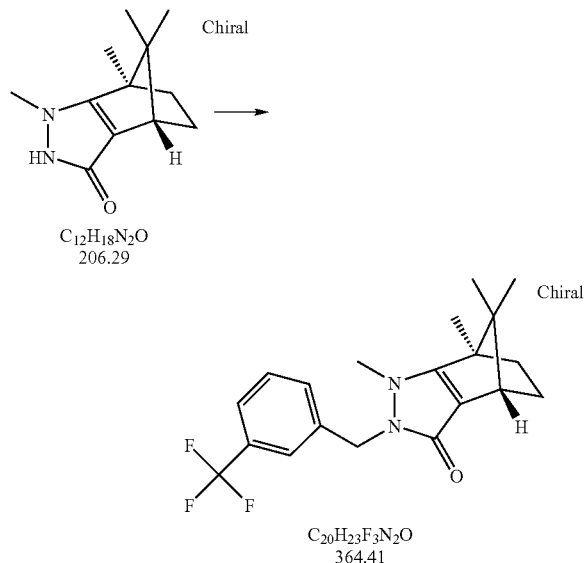

A mixture of (4S,7R)-1,7,8,8-tetramethyl-1,2,4,5,6,7-hexahydro-4,7-methano-indazol-3-one (Intermediate 19; 100 mg, 0.49 mmol) and 3-trifluoromethyl-benzyl bromide (75 μL, 0.49 mmol) in N,N-dimethylformamide (5 mL) was heated at 100° C. overnight. The reaction mixture was evaporated and the residue was purified using a Biotage 40S system, eluting with 0-1% methanol/chloroform, followed by drying under high vacuum to give (4S,7R)-2-(3-trifluoromethyl-benzyl)-1,7,8,8-tetramethyl-1,2,4,5,6,7-hexahydro-4,7-methano-indazol-3-one (64 mg, 36%) as an off-white solid. APCI-MS (M+H) 365.

Example 37

(4S,7R)-2-(4-Fluoro-2-trifluoromethyl-benzyl)-1,7,8,8-tetramethyl-1,2,4,5,6,7-hexahydro-4,7-methano-indazol-3-one

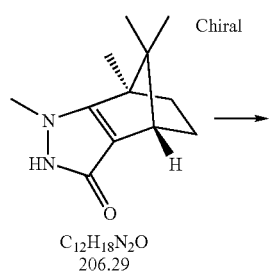

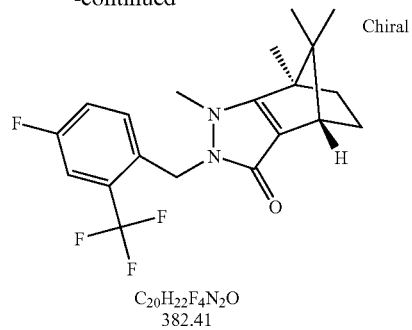

A mixture of (4S,7R)-1,7,8,8-tetramethyl-1,2,4,5,6,7-hexahydro-4,7-methano-indazol-3-one (Intermediate 19; 210 mg, 1.02 mmol) and 4-fluoro-2-trifluoromethyl-benzyl bromide (470 μL, 3.04 mmol) in N,N-dimethylformamide (10 mL) was heated at 100° C. overnight. The reaction mixture was evaporated and the residue was purified using a Biotage 40M system, eluting with 0-0.5% methanol/chloroform, followed by drying under high vacuum to give (4S,7R)-2-(4-fluoro-2-trifluoromethyl-benzyl)-1,7,8,8-tetramethyl-1,2,4,5,6,7-hexahydro-4,7-methano-indazol-3-one (215 mg, 55%) as an off-white solid. APCI-MS (M+H) 383.

Example 38

(4S,7R)-2-(4-Trifluoromethoxy-benzyl)-1,7,8,8-tetramethyl-1,2,4,5,6,7-hexahydro-4,7-methano-indazol-3-one

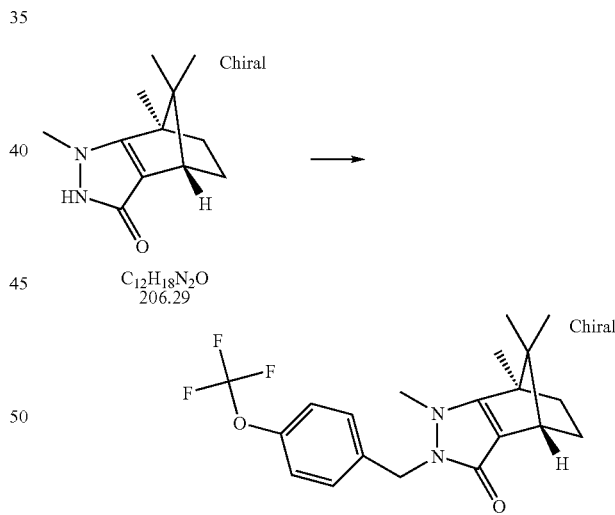

A mixture of (4S,7R)-1,7,8,8-tetramethyl-1,2,4,5,6,7-hexahydro-4,7-methano-indazol-3-one (Intermediate 19; 100 mg, 0.49 mmol) and 4-trifluoromethoxy-benzyl bromide (77 μL, 0.48 mmol) in N,N-dimethylformamide (5 mL) was heated at 100° C. overnight. The reaction mixture was evaporated and the residue was purified using a Biotage 40S system, eluting with 0-1% methanol/chloroform, followed by drying under high vacuum to give (4S,7R)-2-(4-trifluoromethoxy-benzyl)-1,7,8,8-tetramethyl-1,2,4,5,6,7-hexahydro-4,7-methano-indazol-3-one (110 mg, 60%) as a light yellow oil. APCI-MS (M+H) 381.

Example 39

(4S,7R)-4-(1,7,8,8-Tetramethyl-3-oxo-1,3,4,5,6,7-hexahydro-4,7-methano-indazol-2-ylmethyl)-benzamide

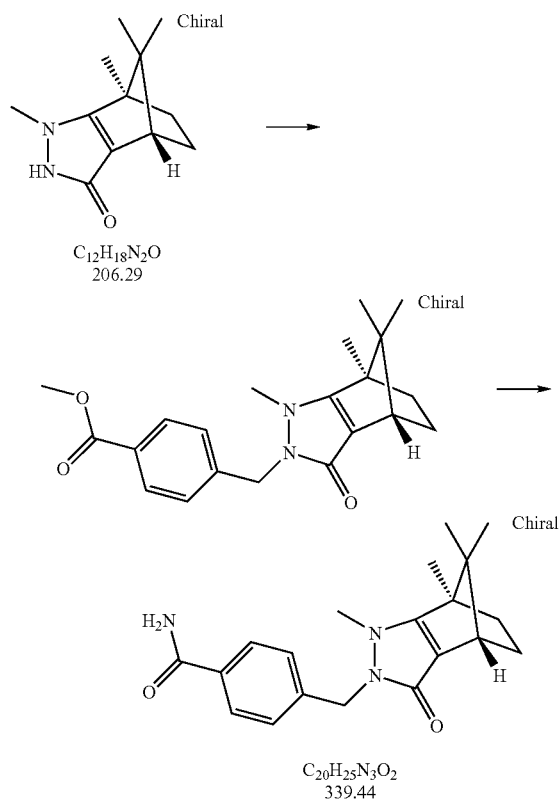

C$_{12}$H$_{18}$N$_2$O
206.29

C$_{20}$H$_{25}$N$_3$O$_2$
339.44

Step 1: (4S,7R)-4-(1,7,8,8-Tetramethyl-3-oxo-1,3,4,5,6,7-hexahydro-4,7-methano-indazol-2-ylmethyl)-benzoic acid methyl ester A mixture of (4S,7R)-1,7,8,8-tetramethyl-1,2,4,5,6,7-hexahydro-4,7-methano-indazol-3-one (Intermediate 19; 250 mg, 1.21 mmol) and methyl 4-(bromomethyl)-benzoate (0.27 g, 1.18 mmol) in N,N-dimethylformamide (12 mL) was heated at 100° C. overnight. The reaction mixture was evaporated and the residue was purified using a Biotage 40S system, eluting with 0-1% methanol/chloroform, followed by drying under high vacuum to give (4S,7R)-4-(1,7,8,8-tetramethyl-3-oxo-1,3,4,5,6,7-hexahydro-4,7-methano-indazol-2-ylmethyl)-benzoic acid methyl ester (256 mg, 61%) as a light yellow oil.

Step 2: (4S,7R)-4-(1,7,8,8-Tetramethyl-3-oxo-1,3,4, 5,6,7-hexahydro-4,7-methano-indazol-2-ylmethyl)-benzoic acid 1 M NaOH (1.1 mL, 1.1 mmol) was added to a solution of (4S,7R)-4-(1,7,8,8-tetramethyl-3-oxo-1,3,4,5,6,7-hexahydro-4,7-methano-indazol-2-ylmethyl)-benzoic acid methyl ester (228 mg, 0.644 mmol) in methanol (0.9 mL) and tetrahydrofuran (1.8 mL). The reaction mixture was stirred at room temperature overnight, and it was then partitioned between water (100 mL) and ether (100 mL). The aqueous layer was acidified with 1 M HCl to pH<3 and the resulting mixture was extracted with chloroform (100 mL). The chloroform extract was washed with brine (100 mL), dried (magnesium sulfate), filtered, and evaporated to give (4S,7R)-4-(1,7,8,8-tetramethyl-3-oxo-1,3,4,5,6,7-hexahydro-4,7-methano-indazol-2-ylmethyl)-benzoic acid (168 mg, 77%) as a white solid.

Step 3: (4S,7R)-4-(1,7,8,8-Tetramethyl-3-oxo-1,3,4, 5,6,7-hexahydro-4,7-methano-indazol-2-ylmethyl)-benzamide A mixture of 4-(1,7,8,8-tetramethyl-3-oxo-1,3,4,5,6,7-hexahydro-4,7-methano-indazol-2-ylmethyl)-benzoic acid (50 mg, 0.147 mmol) and dichloromethane (1.5 mL) was cooled to 0° C. and oxalyl chloride (26.6 µL, 0.29 mmol) and N,N-dimethylformamide (one drop) were added. The reaction mixture was stirred at ~0° C. for 30 min and then at room temperature for 2.5 h. The reaction mixture was evaporated and the residue was co-evaporated three times with dichloromethane to remove residual oxalyl chloride. Dichloromethane (1.5 mL) was added and the mixture was cooled to 0° C. Anhydrous ammonia gas was passed through a calcium carbonate drying tube and bubbled into the solution at ~0° C. for 15 min. The flask was capped and the mixture was stirred at ~0° C. for 50 min and then at room temperature overnight. The reaction mixture was partitioned between water (25 mL) and chloroform (25 mL). The organic layer was washed with saturated sodium bicarbonate (25 mL) and brine (25 mL), dried (magnesium sulfate), filtered, evaporated and purified using a Biotage 40S system, eluting with 0-7% methanol/chloroform, followed by drying under high vacuum to give (4S,7R)-4-(1,7,8,8-tetramethyl-3-oxo-1,3,4,5,6,7-hexahydro-4,7-methano-indazol-2-ylmethyl)-benzamide (35 mg, 70%) as a white solid. APCI-MS (M+H) 340.

Example 40

(4S,7R)-1,7,8,8-Tetramethyl-2-(3-trifluoromethyl-1H-pyrazol-4-ylmethyl)-1,2,4,5,6,7-hexahydro-4,7-methano-indazol-3-one

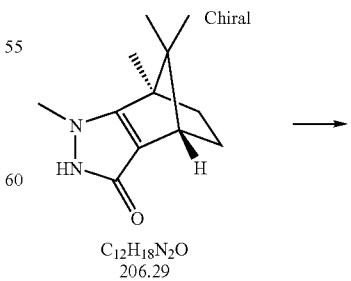

C$_{12}$H$_{18}$N$_2$O
206.29

107

-continued

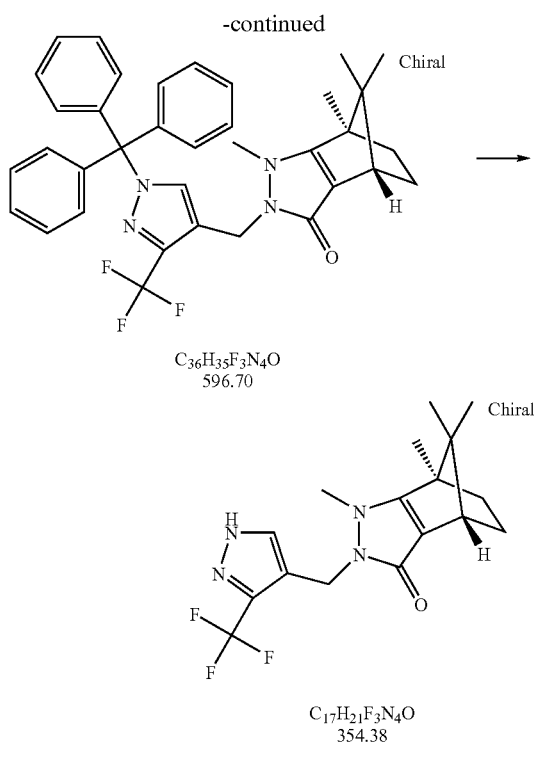

C36H35F3N4O
596.70

C17H21F3N4O
354.38

Step 1: (4S,7R)-1,7,8,8-Tetramethyl-2-(3-trifluoromethyl-1-trityl-1H-pyrazol-4-ylmethyl)-1,2,4,5,6,7-hexahydro-4,7-methano-indazol-3-one A mixture of (4S,7R)-1,7,8,8-tetramethyl-1,2,4,5,6,7-hexahydro-4,7-methano-indazol-3-one (Intermediate 19; 100 mg, 0.49 mmol) and 4-bromomethyl-3-trifluoromethyl-1-trityl-1H-pyrazole (0.23 g, 0.49 mmol) in N,N-dimethylformamide (5 mL) was heated at 100° C. over the weekend. The reaction mixture was evaporated and the residue was purified by flash chromatography, eluting with 3% methanol/dichloromethane, followed by drying under high vacuum to give (4S,7R)-1,7,8,8-tetramethyl-2-(3-trifluoromethyl-1-trityl-1H-pyrazol-4-ylmethyl)-1,2,4,5,6,7-hexahydro-4,7-methano-indazol-3-one (213 mg, 73%).

Step 2: (4S,7R)-1,7,8,8-Tetramethyl-2-(3-trifluoromethyl-1H-pyrazol-4-ylmethyl)-1,2,4,5,6,7-hexahydro-4,7-methano-indazol-3-one Trifluoroacetic acid (2 mL) was added to a solution of (4S,7R)-1,7,8,8-tetramethyl-2-(3-trifluoromethyl-1-trityl-1H-pyrazol-4-ylmethyl)-1,2,4,5,6,7-hexahydro-4,7-methano-indazol-3-one (210 mg, 0.35 mmol) in dichloromethane (2 mL) and the resulting solution was stirred at room temperature for 3.5 h. Triethylsilane (56 μL, 0.35 mmol) was added and the solution was stirred for 5 min, and then evaporated and held under high vacuum overnight. The residue was taken up in dichloromethane and water and the pH was adjusted to ~7 by adding saturated sodium bicarbonate solution. The layers were separated and the organic layer was dried (magnesium sulfate), filtered, evaporated, and chromatographed, eluting with 1-3% methanol/ethyl acetate to give (4S,7R)-1,7,8,8-Tetramethyl-2-(3-trifluoromethyl-

108

1H-pyrazol-4-ylmethyl)-1,2,4,5,6,7-hexahydro-4,7-methano-indazol-3-one (86 mg, 69%). ES(+)-MS (M+H) 355.

Example 41

(4S,7R)-1,7,8,8-Tetramethyl-2-(5-trifluoromethyl-furan-2-ylmethyl)-1,2,4,5,6,7-hexahydro-4,7-methano-indazol-3-one

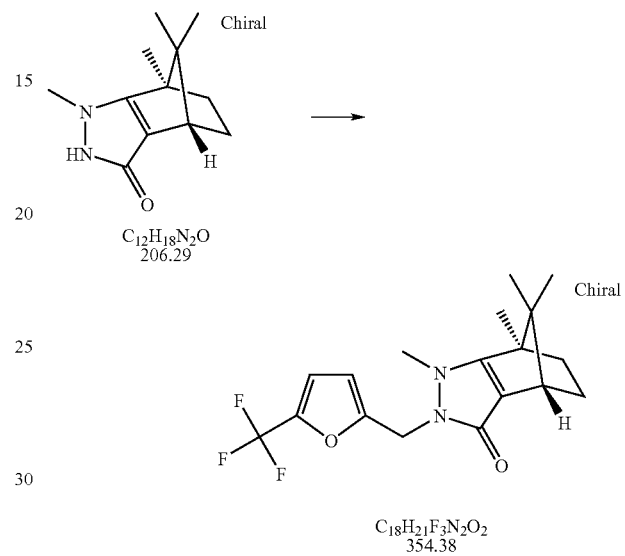

C12H18N2O
206.29

C18H21F3N2O2
354.38

A mixture of (4S,7R)-1,7,8,8-tetramethyl-1,2,4,5,6,7-hexahydro-4,7-methano-indazol-3-one (Intermediate 19; 100 mg, 0.49 mmol) and 2-bromomethyl-5-trifluoromethyl-furan (144 mg, 0.63 mmol) in N,N-dimethylformamide (5 mL) was heated at 110° C. for 2 days. The reaction mixture was evaporated and the residue was dissolved in ethyl acetate (50 mL), washed with water (2×25 mL) and brine (25 mL), dried (magnesium sulfate), filtered, evaporated, and purified by flash chromatography, eluting with 2-3% methanol/dichloromethane to give (4S,7R)-1,7,8,8-tetramethyl-2-(5-trifluoromethyl-furan-2-ylmethyl)-1,2,4,5,6,7-hexahydro-4,7-methano-indazol-3-one (136 mg, 78%) as a white solid. APCI-MS (M+H) 355.

Example 42

(4S,7R)-2-(3,5-Dimethyl-isoxazol-4-ylmethyl)-1,7,8,8-tetramethyl-1,2,4,5,6,7-hexahydro-4,7-methano-indazol-3-one

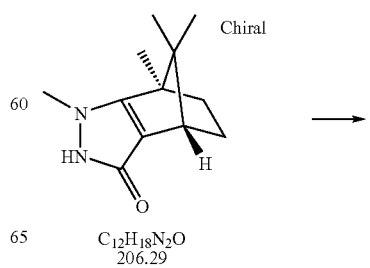

C12H18N2O
206.29

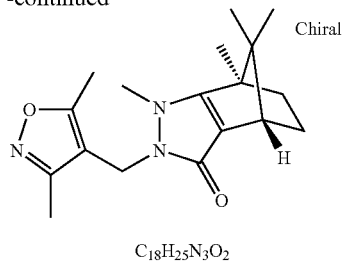

C₁₈H₂₅N₃O₂
315.42

A mixture of (4S,7R)-1,7,8,8-tetramethyl-1,2,4,5,6,7-hexahydro-4,7-methano-indazol-3-one (Intermediate 19; 100 mg, 0.49 mmol) and 4-chloromethyl-3,5-dimethyl-isoxazole (60 μL, 0.48 mmol) in N,N-dimethylformamide (5 mL) was heated at 100° C. overnight. A further portion of and 4-chloromethyl-3,5-dimethyl-isoxazole (30 μL, 0.24 mmol) was added and the solution was heated at 100° C. for 2 h. The reaction mixture was evaporated and the residue was diluted with water and extracted with chloroform. The chloroform layer was washed with water, dried (magnesium sulfate), filtered, evaporated, and purified by flash chromatography, eluting with 3% methanol/dichloromethane to give (4S,7R)-2-(3,5-Dimethyl-isoxazol-4-ylmethyl)-1,7,8,8-tetramethyl-1,2,4,5,6,7-hexahydro-4,7-methano-indazol-3-one (62 mg, 41%) as an off-white solid. ES(+)-MS (M+H) 316.

Example 43

(4S,7R)-2-Biphenyl-3-yl-1,7,8,8-tetramethyl-1,2,4,5,6,7-hexahydro-4,7-methano-indazol-3-one

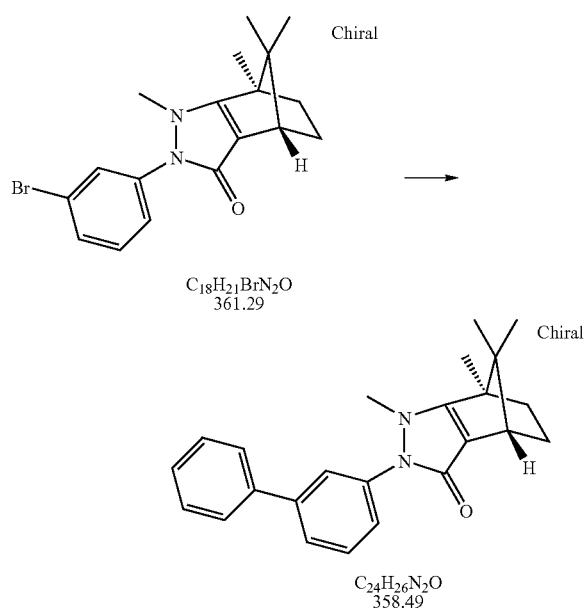

A degassed mixture of 2-(3-bromo-phenyl)-1,7,8,8-tetramethyl-1,2,4,5,6,7-hexahydro-4,7-methano-indazol-3-one (Example 22; 75 mg, 0.2 mmol), phenyl-boronic acid (38 mg, 0.3 mmol), potassium phosphate (132 mg, 0.62 mmol) and [1,1'-bis(diphenylphosphino)ferrocene]dichloropalladium (II) (17 mg, 0.024 mmol) in dimethoxyethane (3 mL) was sealed under argon and heated at 80 degrees overnight and then at 60 degrees over the weekend. The reaction mixture was filtered and the residue was washed with dimethoxyethane. The solvent was evaporated from the filtrate and the residue was purified by chromatography on a Sep-Pak column, eluting with 15% ethyl acetate/hexanes to give (4S,7R)-2-biphenyl-3-yl-1,7,8,8-tetramethyl-1,2,4,5,6,7-hexahydro-4,7-methano-indazol-3-one (13 mg, 17%) as a white solid. ES(+)-MS (M+H) 359.

Example 44

(4S,7R)-1,7,8,8-Tetramethyl-2-(2'-chloro-biphenyl-3-yl)-1,2,4,5,6,7-hexahydro-4,7-methano-indazol-3-one

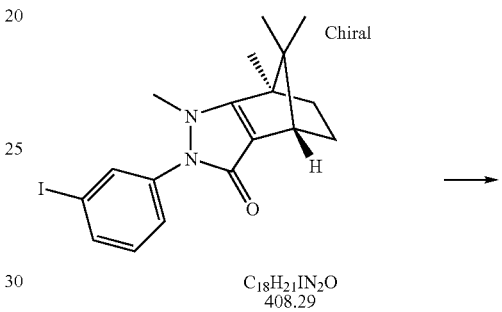

C₁₈H₂₁IN₂O
408.29

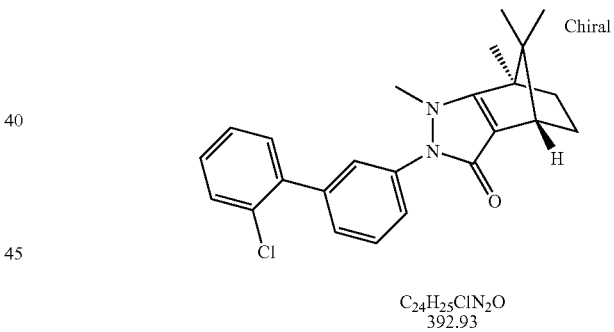

C₂₄H₂₅ClN₂O
392.93

A mixture of 2-(3-iodo-phenyl)-1,7,8,8-tetramethyl-1,2,4,5,6,7-hexahydro-4,7-methano-indazol-3-one (Example 23; 80 mg, 0.2 mmol), 2-chloro-phenyl-boronic acid (46 mg, 0.29 mmol), potassium carbonate (66 mg, 0.47 mmol) and [1,1'-bis(diphenylphosphino)ferrocene]dichloropalladium(II) (10 mg, 0.014 mmol) in dimethoxyethane (4 mL) was sealed under argon and heated at 80 degrees overnight and then at 90 degrees over the weekend. The reaction mixture was diluted with dichloromethane, filtered through a cotton plug and frit, evaporated, and purified using an Analogix Intelliflash 280 system (Analogix, Inc., Burlington, Wis.) with an RS-12 column, eluting with 0-75% ethyl acetate/hexanes to give (4S,7R)-2-(2'-chloro-biphenyl-3-yl)-1,7,8,8-tetramethyl-1,2,4,5,6,7-hexahydro-4,7-methano-indazol-3-one (23 mg, 30%) as a light brown solid and unreacted starting material (37 mg, 46%). ES(+)-MS (M+H) 393.

Example 45

(4S,7R)-1,7,8,8-Tetramethyl-2-(2'-methoxy-biphenyl-3-yl)-1,2,4,5,6,7-hexahydro-4,7-methano-indazol-3-one

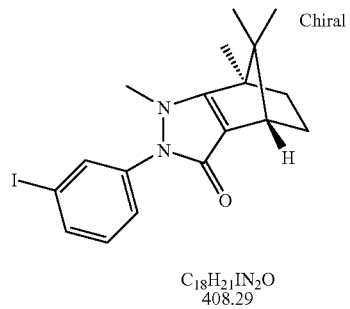

C₁₈H₂₁IN₂O
408.29

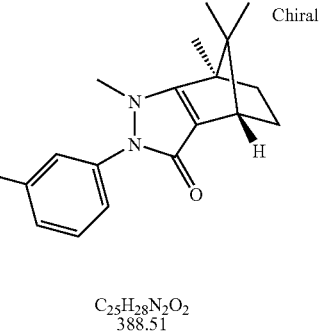

C₂₅H₂₈N₂O₂
388.51

A mixture of 2-(3-iodo-phenyl)-1,7,8,8-tetramethyl-1,2,4,5,6,7-hexahydro-4,7-methano-indazol-3-one (Example 23; 80 mg, 0.2 mmol), 2-methoxy-phenyl-boronic acid (46 mg, 0.29 mmol), potassium carbonate (66 mg, 0.47 mmol) and [1,1'-bis(diphenylphosphino)ferrocene]dichloropalladium (II) (10 mg, 0.014 mmol) in dimethoxyethane (4 mL) was sealed under argon and heated at 80 degrees overnight and then at 90 degrees over the weekend. The reaction mixture was diluted with dichloromethane, filtered through a cotton plug and frit, evaporated, and purified using an Analogix Intelliflash 280 system (Analogix, Inc., Burlington, Wis.) with an RS-12 column, eluting with 0-80% ethyl acetate/hexanes to give (4S,7R)-2-(2'-methoxy-biphenyl-3-yl)-1,7,8,8-tetramethyl-1,2,4,5,6,7-hexahydro-4,7-methano-indazol-3-one (8 mg, 10%) as a white solid and unreacted starting material (54 mg, 67%). ES(+)-MS (M+H) 389.

Example 46

(4S,7R)-1,7,8,8-Tetramethyl-2-(2'-methyl-biphenyl-3-yl)-1,2,4,5,6,7-hexahydro-4,7-methano-indazol-3-one

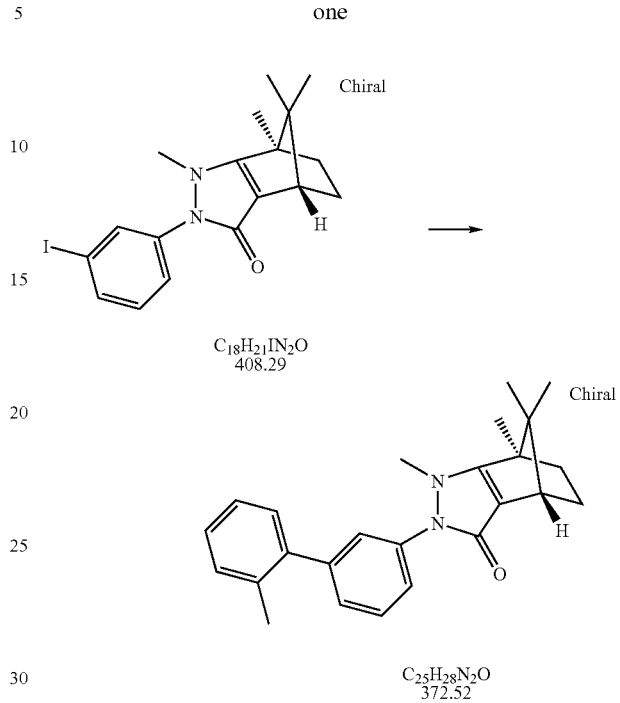

C₁₈H₂₁IN₂O
408.29

C₂₅H₂₈N₂O
372.52

A mixture of 2-(3-iodo-phenyl)-1,7,8,8-tetramethyl-1,2,4,5,6,7-hexahydro-4,7-methano-indazol-3-one (Example 23; 80 mg, 0.2 mmol), 2-methyl-phenyl-boronic acid (40 mg, 0.29 mmol), potassium carbonate (66 mg, 0.47 mmol) and [1,1'-bis(diphenylphosphino)ferrocene]dichloropalladium (II) (10 mg, 0.014 mmol) in dimethoxyethane (4 mL) was sealed under argon and heated at 80 degrees overnight and then at 90 degrees over the weekend. The reaction mixture was diluted with dichloromethane, filtered through a cotton plug and frit, evaporated, and purified using an Analogix Intelliflash 280 system (Analogix, Inc., Burlington, Wis.) with an RS-12 column, eluting with 0-35% ethyl acetate/hexanes to give (4S,7R)-1,7,8,8-tetramethyl-2-(2'-methyl-biphenyl-3-yl)-1,2,4,5,6,7-hexahydro-4,7-methano-indazol-3-one (32 mg, 44%) as a light brown solid. ES(+)-MS (M+H) 373.

Example 47

(4S,7R)-2-(2'-Acetyl-biphenyl-3-yl)-1,7,8,8-tetramethyl-1,2,4,5,6,7-hexahydro-4,7-methano-indazol-3-one

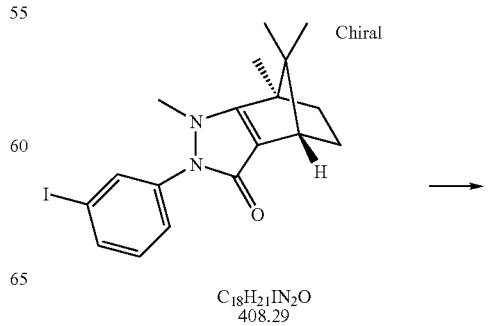

C₁₈H₂₁IN₂O
408.29

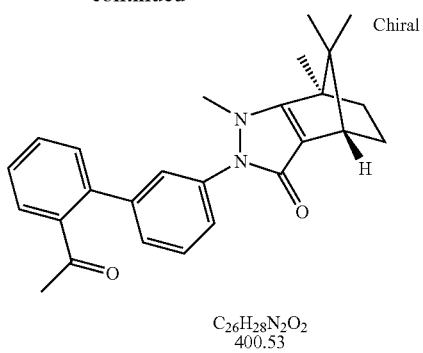

C26H28N2O2
400.53

A mixture of 2-(3-iodo-phenyl)-1,7,8,8-tetramethyl-1,2,4,5,6,7-hexahydro-4,7-methano-indazol-3-one (Example 23; 80 mg, 0.2 mmol), 2-acetyl-phenyl-boronic acid (49 mg, 0.29 mmol), potassium carbonate (66 mg, 0.47 mmol) and [1,1'-bis(diphenylphosphino)ferrocene]dichloropalladium(II) (10 mg, 0.014 mmol) in dimethoxyethane (4 mL) was sealed under argon and heated at 80 degrees overnight and then at 90 degrees over the weekend. The reaction mixture was diluted with dichloromethane, filtered through a cotton plug and frit, evaporated, and purified using an Analogix Intelliflash 280 system (Analogix, Inc., Burlington, Wis.) with an RS-12 column, eluting with 0-80% ethyl acetate/hexanes to give (4S,7R)-2-(2'-acetyl-biphenyl-3-yl)-1,7,8,8-tetramethyl-1,2,4,5,6,7-hexahydro-4,7-methano-indazol-3-one and unreacted starting material (40 mg, 50%). The product was further purified by preparative HPLC (Gilson 215 collector, Shimadzu prep HPLC system, Leap autoinjector. Solvent (A) 0.05% TFA/H2O (B) 0.035% TFA/ACN, using a linear gradient of 20-80% solvent B in 10 minutes, with a C-18 column, 2.0×10 cm eluting at 20 ml/min and UV-directed collection) followed by lyophilization to give (4S,7R)-2-(2'-acetyl-biphenyl-3-yl)-1,7,8,8-tetramethyl-1,2,4,5,6,7-hexahydro-4,7-methano-indazol-3-one (9 mg, 11%) as a white solid. ES(+)-MS (M+H) 401.

Example 48

(4S,7R)-2-(3'-methoxy-biphenyl-3-yl)-1,7,8,8-tetramethyl-1,2,4,5,6,7-hexahydro-4,7-methano-indazol-3-one

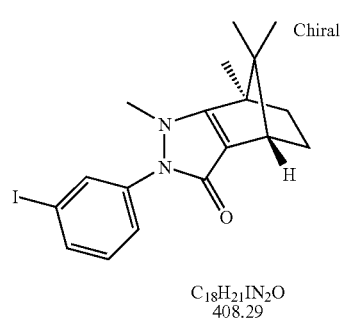

C18H21IN2O
408.29

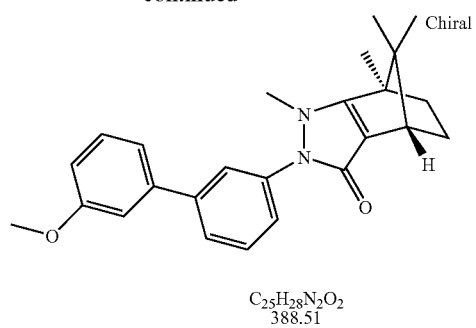

C25H28N2O2
388.51

A mixture of 2-(3-iodo-phenyl)-1,7,8,8-tetramethyl-1,2,4,5,6,7-hexahydro-4,7-methano-indazol-3-one (Example 23; 80 mg, 0.2 mmol), 3-methoxy-phenyl-boronic acid (46 mg, 0.29 mmol), potassium carbonate (66 mg, 0.47 mmol) and [1,1'-bis(diphenylphosphino)ferrocene]dichloropalladium (II) (10 mg, 0.014 mmol) in dimethoxyethane (4 mL) was sealed under argon and heated at 80 degrees overnight and then at 90 degrees over the weekend. The reaction mixture was diluted with dichloromethane, filtered through a cotton plug and frit, evaporated, and purified using an Analogix Intelliflash 280 system (Analogix, Inc., Burlington, Wis.) with an RS-12 column, eluting with 0-60% ethyl acetate/hexanes to give (4S,7R)-2-(3'-methoxy-biphenyl-3-yl)-1,7,8,8-tetramethyl-1,2,4,5,6,7-hexahydro-4,7-methano-indazol-3-one and unreacted starting material (54 mg, 67%). The product was further purified by preparative HPLC (Gilson 215 collector, Shimadzu prep HPLC system, Leap autoinjector. Solvent (A) 0.05% TFA/H2O (B) 0.035% TFA/ACN, using a linear gradient of 20-80% solvent B in 10 minutes, with a C-18 column, 2.0×10 cm eluting at 20 ml/min and UV-directed collection) followed by lyophilization to give (4S,7R)-2-(3'-methoxy-biphenyl-3-yl)-1,7,8,8-tetramethyl-1,2,4,5,6,7-hexahydro-4,7-methano-indazol-3-one (13 mg, 17%) as a white solid. ES(+)-MS (M+H) 389.

Example 49

(4S,7R)-1,7,8,8-tetramethyl-2-(3'-methyl-biphenyl-3-yl)-1,2,4,5,6,7-hexahydro-4,7-methano-indazol-3-one

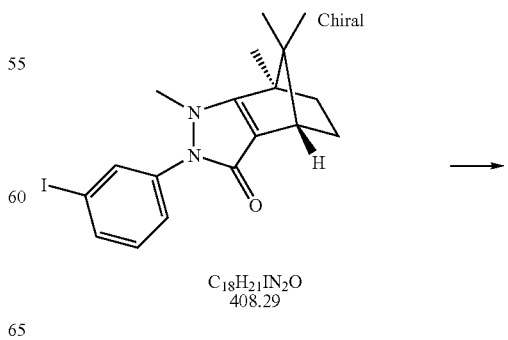

C18H21IN2O
408.29

A mixture of 2-(3-iodo-phenyl)-1,7,8,8-tetramethyl-1,2,4,5,6,7-hexahydro-4,7-methano-indazol-3-one (Example 23; 80 mg, 0.2 mmol), 3-methyl-phenyl-boronic acid (41 mg, 0.29 mmol), potassium carbonate (66 mg, 0.47 mmol) and [1,1'-bis(diphenylphosphino)ferrocene]dichloropalladium (II) (10 mg, 0.014 mmol) in dimethoxyethane (4 mL) was sealed under argon and heated at 80 degrees overnight and then at 90 degrees over the weekend. The reaction mixture was diluted with dichloromethane, filtered through a cotton plug and frit, evaporated, and purified using an Analogix Intelliflash 280 system (Analogix, Inc., Burlington, Wis.) with an RS-12 column, eluting with 0-35% ethyl acetate/hexanes to give (4S,7R)-1,7,8,8-tetramethyl-2-(3'-methyl-biphenyl-3-yl)-1,2,4,5,6,7-hexahydro-4,7-methano-indazol-3-one (15 mg, 20%) as a brown solid. ES(+)-MS (M+H) 373.

Example 50

(4S,7R)-2-Benzyl-7,8,8-trimethyl-1-phenyl-1,2,4,5,6,7-hexahydro-4,7-methano-indazol-3-one A mixture of (4S,7R)-1-phenyl-7,8,8-trimethyl-1,2,4,5,6,7-hexahydro-4,7-methano-indazol-3-one (Intermediate 8; 1.00 g, 3.7 mmol) and benzyl bromide (0.9 mL, 7.6 mmol) in N,N-dimethylformamide (30 mL) was heated at 100° C. overnight. The reaction mixture was diluted with water and extracted twice with ethyl acetate. The organic extracts were combined, washed with water and brine, dried (magnesium sulfate), filtered, evaporated, and purified using an Analogix Intelliflash 280 system (Analogix, Inc., Burlington, Wis.) with an Isco 80 g column, eluting with 5-75% ethyl acetate/hexanes to give (4S,7R)-2-benzyl-7,8,8-trimethyl-1-phenyl-1,2,4,5,6,7-hexahydro-4,7-methano-indazol-3-one (1.01 g, 76%) as a brown oil. ES(+)-MS (M+H) 359.

Example 51

(4R,7S)-2-(4-Iodo-benzyl)-1,7,8,8-tetramethyl-1,2,4,5,6,7-hexahydro-4,7-methano-indazol-3-one A mixture of (4R,7S)-1,7,8,8-tetramethyl-1,2,4,5,6,7-hexahydro-4,7-methano-indazol-3-one (Intermediate 19; 104 mg, 0.50 mmol) and 4-iodo-benzyl bromide (163.5 mg, 0.55 mmol) in N,N-dimethylformamide (5 mL) was heated at 80° C. over the weekend and then allowed to stand at room temperature for three days. The reaction mixture was evaporated and the residue was purified using a Biotage 40S system, eluting with 0-1% methanol/chloroform, followed by drying under high vacuum to give (4R,7S)-2-(4-iodo-benzyl)-1,7,8,8-tetramethyl-1,2,4,5,6,7-hexahydro-4,7-methano-indazol-3-one (144 mg, 68%) as an off-white solid. APCI-MS (M+H) 423.

Example 52

(4S,7R)-1-Cyclopropylmethyl-7,8,8-trimethyl-2-phenyl-1,2,4,5,6,7-hexahydro-4,7-methano-indazol-3-one

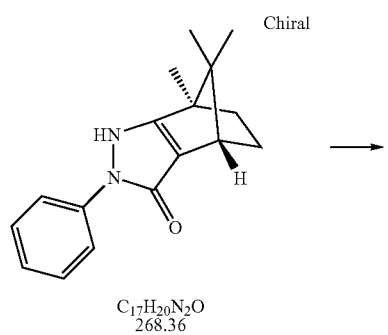

$C_{17}H_{20}N_2O$
268.36

↓

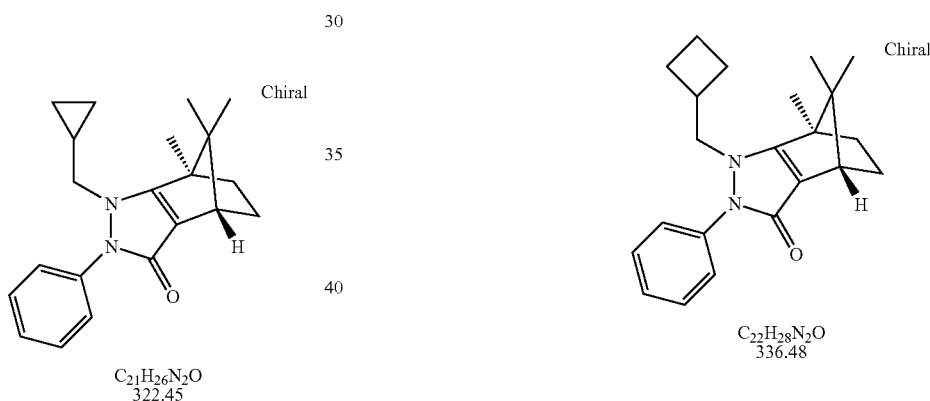

$C_{21}H_{26}N_2O$
322.45

A mixture of (bromomethyl)cyclopropane (263 µL, 2.75 mmol), (4R,7S)-2-phenyl-7,8,8-trimethyl-1,2,4,5,6,7-hexahydro-4,7-methano-indazol-3-one (Intermediate 6; 184 mg, 0.69 mmol) and tetra-n-butylammonium iodide (1.02 g, 2.75 mmol) in N,N-dimethylformamide (4.3 mL) was heated in an oil-bath at 100° C. for 16 h. The solvent was evaporated and dichloromethane (100 mL) and water were added. The aqueous layer was extracted with dichloromethane (2×100 mL) and the combined organic layers were washed with water (5×100 mL) and then with sodium thiosulfate solution (100 mL). The solvent was evaporated and the residue purified on an Isco 120 g column, eluting with 33-100% ethyl acetate/hexanes to give (4R,7S)-1-(cyclopropyl)methyl-7,8,8-trimethyl-2-phenyl-1,2,4,5,6,7-hexahydro-4,7-methano-indazol-3-one (108 mg, 49%) as an off-white/tan oil. APCI-MS (M+H) 323.

Example 53

(4S,7R)-1-Cyclobutylmethyl-7,8,8-trimethyl-2-phenyl-1,2,4,5,6,7-hexahydro-4,7-methano-indazol-3-one

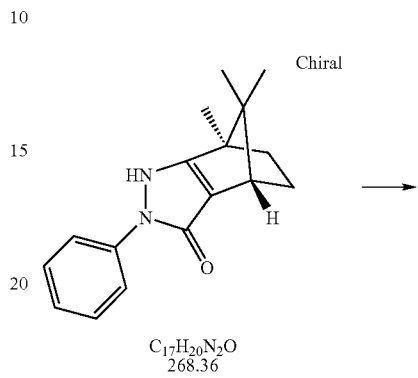

$C_{17}H_{20}N_2O$
268.36

↓

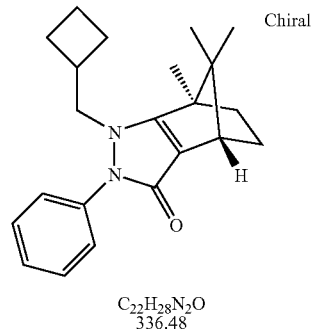

$C_{22}H_{28}N_2O$
336.48

A mixture of (bromomethyl)cyclobutane (1.7 mL, 15.1 mmol), (4R,7S)-2-phenyl-7,8,8-trimethyl-1,2,4,5,6,7-hexahydro-4,7-methano-indazol-3-one (Intermediate 6; 393 mg, 1.46 mmol) and tetra-n-butylammonium iodide (400 mg, 1.08 mmol) in N,N-dimethylformamide (7 mL) was heated in an oil-bath at 100° C. for 16 h. Additional quantities of (bromomethyl)cyclobutane (1.7 mL, 8.9 mmol) and tetra-n-butylammonium iodide (400 mg, 1.08 mmol) were added and the mixture was heated in an oil-bath at 135° C. for 6 days. The reaction mixture was allowed to cool and it was then diluted with dichloromethane (75 mL) and water (30 mL). The layers were separated and the aqueous layer was extracted with dichloromethane (2×30 mL). The combined organic layers were washed with water (5×30 mL), sodium thiosulfate solution (30 mL) and brine (30 mL). The organic extract was dried (magnesium sulfate), filtered, evaporated, and the residue purified on an Isco 40 g column, eluting with 15-75% ethyl acetate/hexanes and then held under high vacuum to give (4R,7S)-1-(cyclobutyl)methyl-7,8,8-trimethyl-2-phenyl-1,2,4,5,6,7-hexahydro-4,7-methano-indazol-3-one (52 mg, 11%) as a yellow gum. ES(+)-MS (M+H) 337.

Example 54

(4S,7R)-1-Cyclopentylmethyl-7,8,8-trimethyl-2-phenyl-1,2,4,5,6,7-hexahydro-4,7-methano-indazol-3-one

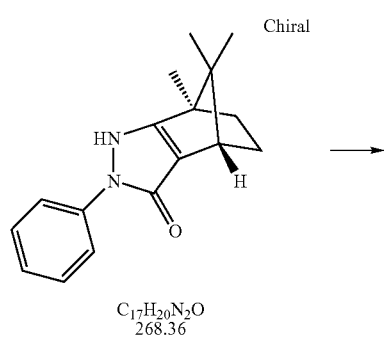

C₁₇H₂₀N₂O
268.36

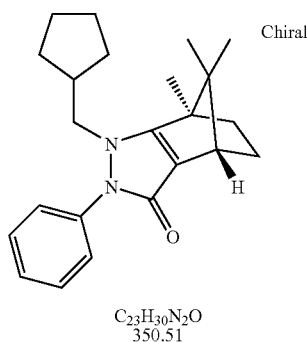

C₂₃H₃₀N₂O
350.51

A mixture of (iodomethyl)cyclopentane (prepared according to W. L. Corbett US 20040067939; 352 mg, 1.68 mmol) and (4R,7S)-2-phenyl-7,8,8-trimethyl-1,2,4,5,6,7-hexahydro-4,7-methano-indazol-3-one (Intermediate 6; 90 mg, 0.34 mmol) was heated in an oil-bath at 100° C. for 6 days. The reaction mixture was allowed to cool and it was then diluted with dichloromethane (200 mL) and washed with water (5×30 mL), aqueous sodium thiosulfate solution (2×30 mL) and brine (30 mL). The organic extract was dried (magnesium sulfate), filtered, evaporated, and the residue purified on an Isco 40 g column, eluting with 30-100% ethyl acetate/hexanes and then held under high vacuum to give (4R,7S)-1-(cyclopentyl)methyl-7,8,8-trimethyl-2-phenyl-1,2,4,5,6,7-hexahydro-4,7-methano-indazol-3-one (4.5 mg, 4%) as a semi-solid. ES(+)-MS (M+H) 351.

Example 55

(4S,7R)-1-Cyclohexylmethyl-7,8,8-trimethyl-2-phenyl-1,2,4,5,6,7-hexahydro-4,7-methano-indazol-3-one

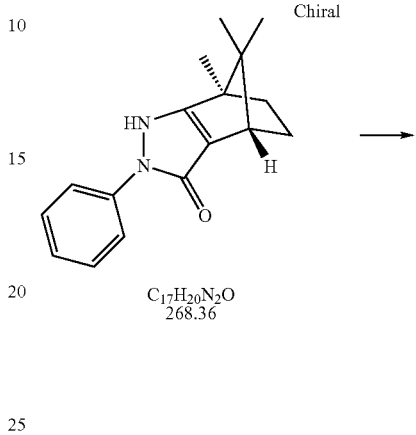

C₁₇H₂₀N₂O
268.36

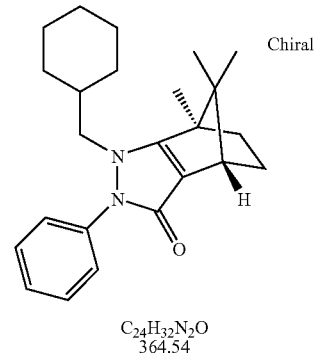

C₂₄H₃₂N₂O
364.54

A mixture of cyclohexylmethyl bromide (2.1 mL, 15 mmol), (4R,7S)-2-phenyl-7,8,8-trimethyl-1,2,4,5,6,7-hexahydro-4,7-methano-indazol-3-one (Intermediate 6; 395 mg, 1.47 mmol) and tetra-n-butylammonium iodide (400 mg, 1.08 mmol) in N,N-dimethylformamide (4 mL) was heated in an oil-bath at 100° C. for 64 h. Additional quantities of in N,N-dimethylformamide (2 mL), cyclohexylmethyl bromide (2.1 mL, 15 mmol), and tetra-n-butylammonium iodide (400 mg, 1.08 mmol) were added and the mixture was heated at 135° C. for 20 h. An additional quantity of cyclohexylmethyl bromide (2.1 mL, 15 mmol) was added and the mixture was heated at 135° C. for 6 days. The reaction mixture to cooled to room temperature and then diluted with dichloromethane (150 mL) and washed with water (5×30 mL), aqueous sodium thiosulfate solution (2×30 mL) and brine (30 mL). The organic extract was dried (magnesium sulfate), filtered, evaporated, and the residue purified on an Isco 40 g column, eluting with 15-100% ethyl acetate/hexanes and then held under high vacuum to give an orange gum. This was treated with charcoal in methanol in a warm water bath, and the resulting mixture was filtered, evaporated and held under high vacuum to give (4R,7S)-1-(cyclohexyl)methyl-7,8,8-trimethyl-2-phenyl-1,2,4,5,6,7-hexahydro-4,7-methano-indazol-3-one (22 mg, 4%) as a yellow gum. ES(+)-MS (M+H) 365.

Example 56

(4S,7R)-1-Cyclopropylmethyl-2-(2,4-difluoro-phenyl)-7,8,8-trimethyl-1,2,4,5,6,7-hexahydro-4,7-methano-indazol-3-one

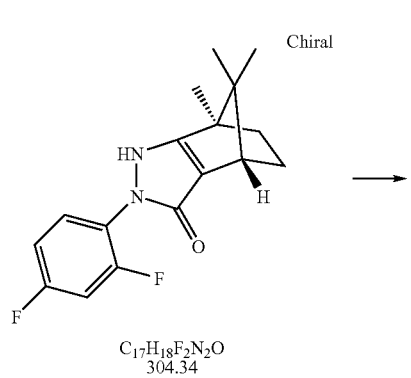

A mixture of (bromomethyl)cyclopropane (2 mL, 20.6 mmol), (4R,7S)-2-(2,4-difluoro-phenyl)-7,8,8-trimethyl-1,2,4,5,6,7-hexahydro-4,7-methano-indazol-3-one (Intermediate 14; 414 mg, 1.36 mmol) and tetra-n-butylammonium iodide (0.80 g, 2.2 mmol) in N,N-dimethylformamide (5 mL) was heated in a sealed tube in an oil-bath at 100° C. for 20 h. The reaction mixture was cooled to room temperature and then diluted with dichloromethane (200 mL). The solution was washed with water (5×30 mL), aqueous sodium thiosulfate solution (2×30 mL) and brine (30 mL), then dried (magnesium sulfate), filtered, and evaporated, and the residue was purified on an Isco 120 g column, eluting with 30-100% ethyl acetate/hexanes to give (4S,7R)-1-(cyclopropyl)methyl-7,8,8-trimethyl-2-(2,4-difluoro-phenyl)-1,2,4,5,6,7-hexahydro-4,7-methano-indazol-3-one (209 mg, 43%) as an pale yellow gum. APCI-MS (M+H) 359.

Example 57

(4S,7R)-1-Cyclobutylmethyl-2-(2,4-difluoro-phenyl)-7,8,8-trimethyl-1,2,4,5,6,7-hexahydro-4,7-methano-indazol-3-one

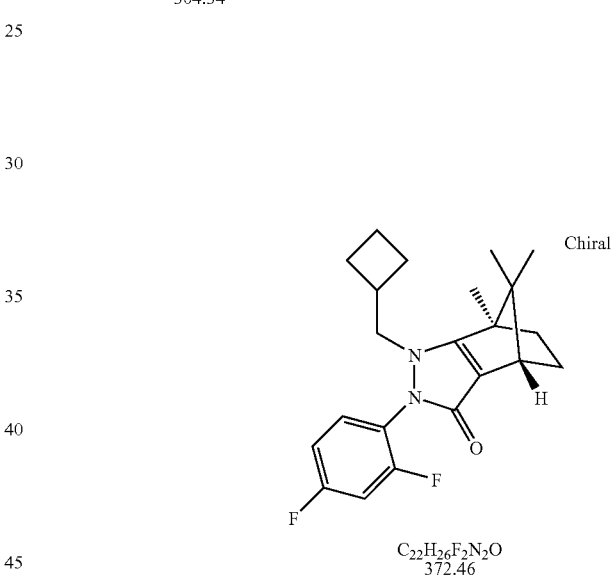

A mixture of (bromomethyl)cyclobutane (2 mL, 17.8 mmol), (4R,7S)-2-(2,4-difluoro-phenyl)-7,8,8-trimethyl-1,2,4,5,6,7-hexahydro-4,7-methano-indazol-3-one (Intermediate 14; 402 mg, 1.3 mmol) and tetra-n-butylammonium iodide (830 mg, 2.25 mmol) in N,N-dimethylformamide (5 mL) was heated in an oil-bath at 135° C. for 42 h. The reaction mixture was cooled to room temperature and then diluted with dichloromethane (200 mL). The solution was washed with water (5×30 mL), aqueous sodium thiosulfate solution (2×30 mL) and brine (30 mL), then dried (magnesium sulfate), filtered, and evaporated, and the residue was purified on an Isco 120 g column, eluting with 30-100% ethyl acetate/hexanes to give a brown gum (145 mg). This was dissolved in methanol and ethyl acetate, treated with charcoal, stirred for 20 min in warm water, filtered through celite, concentrated, co-evaporated twice with dichloromethane, and held under high vacuum to give (4S,7R)-1-cyclobutylmethyl-2-(2,4-difluoro-phenyl)-7,8,8-trimethyl-1,2,4,5,6,7-hexahydro-4,7-methano-indazol-3-one (120 mg, 24%) as a pale yellow gum. ES(+)-MS (M+H) 373.

Example 58

(4S,7R)-2-(2-Chloro-4-fluoro-phenyl)-1,7,8,8-tetramethyl-1,2,4,5,6,7-hexahydro-4,7-methano-indazol-3-one

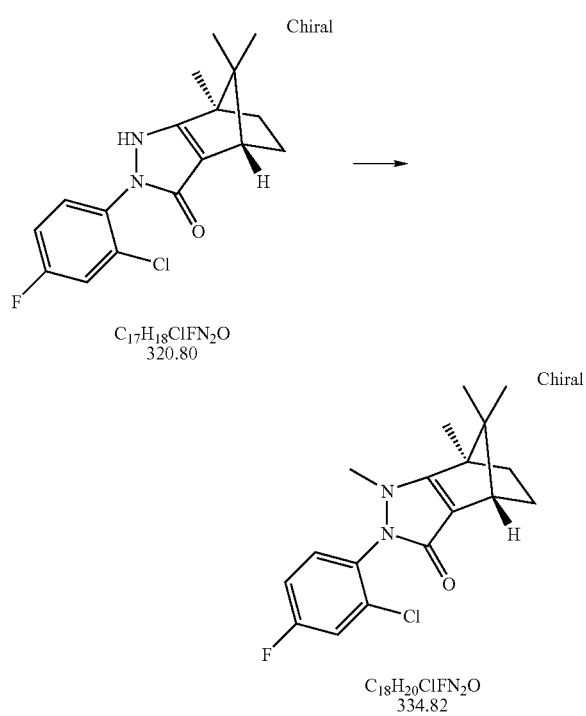

A mixture of (4S,7R)-2-(2-chloro-4-fluoro-phenyl)-7,8,8-trimethyl-1,2,4,5,6,7-hexahydro-4,7-methano-indazol-3-one (Intermediate 21; 290 mg, 0.90 mmol) and iodomethane (0.15 mL, 2.3 mmol) in N,N-dimethylformamide (5 mL) was heated at 100° C. overnight. Water was added and the reaction mixture was extracted three times with ethyl acetate. The combined organic extracts were washed with water and brine, dried (magnesium sulfate), filtered, and evaporated to give (4S,7R)-2-(2-chloro-4-fluoro-phenyl)-1,7,8,8-tetramethyl-1,2,4,5,6,7-hexahydro-4,7-methano-indazol-3-one (260 mg, 86%) as a yellow solid. ES(+)-MS (M+H) 335.

Example 59

(4S,7R)-7,8,8-Trimethyl-1,2-diphenyl-1,2,4,5,6,7-hexahydro-4,7-methano-indazol-3-one

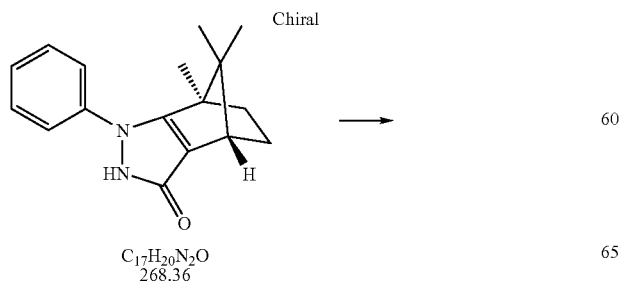

-continued

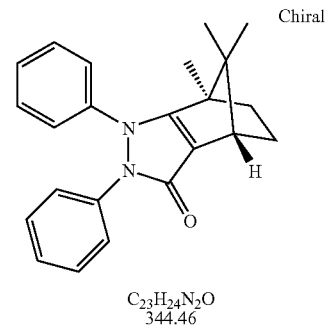

A mixture of (4S,7R)-1-phenyl-7,8,8-trimethyl-1,2,4,5,6,7-hexahydro-4,7-methano-indazol-3-one (Intermediate 8; 1.00 g, 3.7 mmol), phenyl-boronic acid (0.94 g, 7.5 mmol), and copper(II) acetate (1.03 g, 5.6 mmol) in dichloromethane (10 mL) and pyridine (0.6 mL, 7.5 mmol) was stirred at room temperature for 2 days and then heated at reflux for 2 h. The reaction mixture was diluted with water and dichloromethane. The aqueous layer was extracted twice with dichloromethane, and the combined organic layers were washed with water, 10% copper(II) sulfate solution, water, and brine. The solution was then dried (magnesium sulfate), filtered, evaporated and purified using an Analogix Intelliflash 280 system (Analogix, Inc., Burlington, Wis.) with an Analytical Sales Aspire 90 g column, eluting with 10-50% ethyl acetate/hexanes to give (4S,7R)-7,8,8-trimethyl-1,2-diphenyl-1,2,4,5,6,7-hexahydro-4,7-methano-indazol-3-one (0.57 g, 44%) as a light brown solid. ES(+)-MS (M+H) 345.

Example 60

(4S,7R)-1,7,8,8-Tetramethyl-2-(2-trifluoromethyl-phenyl)-1,2,4,5,6,7-hexahydro-4,7-methano-indazol-3-one

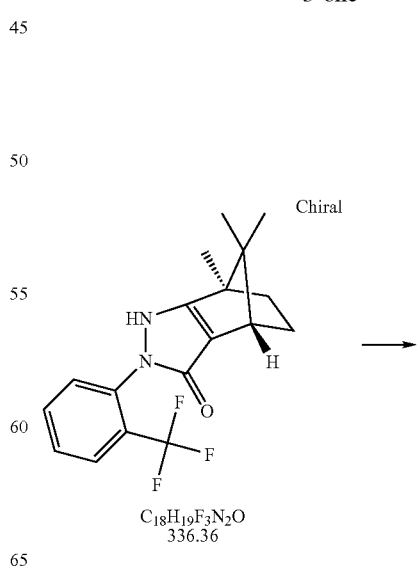

-continued

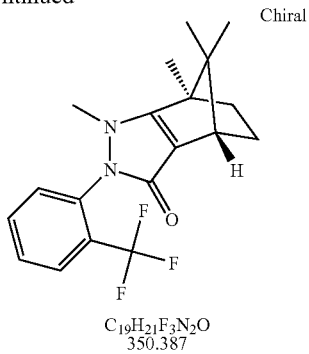

C₁₉H₂₁F₃N₂O
350.387

A mixture of (4S,7R)-7,8,8-trimethyl-2-(2-trifluoromethyl-phenyl)-1,2,4,5,6,7-hexahydro-4,7-methano-indazol-3-one (Intermediate 22; 710 mg, 2.1 mmol) and iodomethane (0.33 mL, 5.3 mmol) in N,N-dimethylformamide (5 mL) in a sealed tube was heated at 100° C. overnight. Water was added and the reaction mixture was extracted three times with ethyl acetate. The combined organic extracts were washed with water and brine, dried (magnesium sulfate), filtered, evaporated, and purified using an Analogix Intelliflash 280 system (Analogix, Inc., Burlington, Wis.) with an Analytical Sales Aspire 90 g column, eluting with 25-100% ethyl acetate/hexanes. Fractions homogeneous for the product were evaporated, dissolved in ethyl acetate and heated at reflux with activated charcoal for 10 min. The mixture was filtered through Celite® and evaporated to give (4S,7R)-1,7,8,8-tetramethyl-2-(2-trifluoromethyl-phenyl)-1,2,4,5,6,7-hexahydro-4,7-methano-indazol-3-one (602 mg, 81%) as a light yellow solid. ES(+)-MS (M+H) 351.

Example 61

(4S,7R)-1,2-Dibenzyl-7,8,8-trimethyl-1,2,4,5,6,7-hexahydro-4,7-methano-indazol-3-one

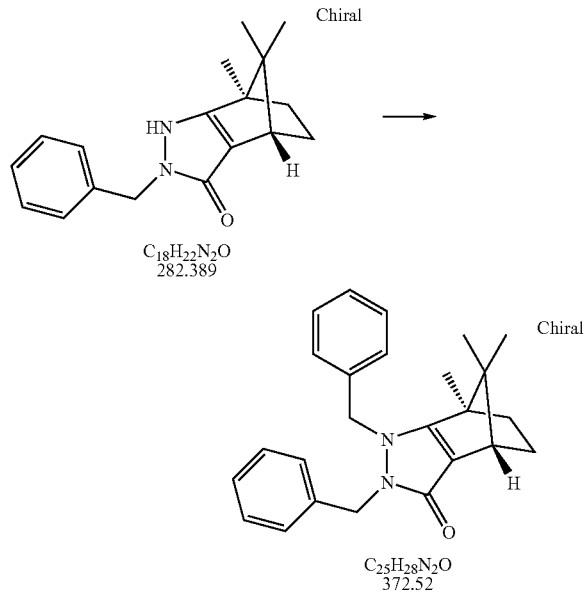

C₁₈H₂₂N₂O
282.389

C₂₅H₂₈N₂O
372.52

A mixture of benzyl bromide (300 μL, 2.5 mmol), (4S,7R)-2-benzyl-7,8,8-trimethyl-1,2,4,5,6,7-hexahydro-4,7-methano-indazol-3-one (Intermediate 23; 159 mg, 0.56 mmol), and tetra-n-butylammonium iodide (160 mg, 0.43 mmol) in N,N-dimethylformamide (2 mL) was heated in an oil-bath at 100° C. for 17 h. The reaction mixture was cooled to room temperature and diluted with dichloromethane (125 mL). The solution was washed with water (5×25 mL) and sodium thiosulfate solution (25 mL), dried (magnesium sulfate), filtered, and evaporated and the residue was purified on an Isco 40 g column, eluting with 20-100% ethyl acetate/hexanes to give (4S,7R)-1,2-dibenzyl-7,8,8-trimethyl-1,2,4,5,6,7-hexahydro-4,7-methano-indazol-3-one (89 mg, 42%) as a yellow gum. ES(+)-MS (M+H) 373.

Example 62

(4S,7R)-2-(2,4-Difluoro-phenyl)-7,8,8-trimethyl-1-phenethyl-1,2,4,5,6,7-hexahydro-4,7-methano-indazol-3-one

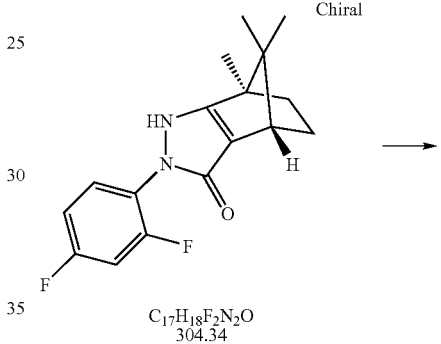

C₁₇H₁₈F₂N₂O
304.34

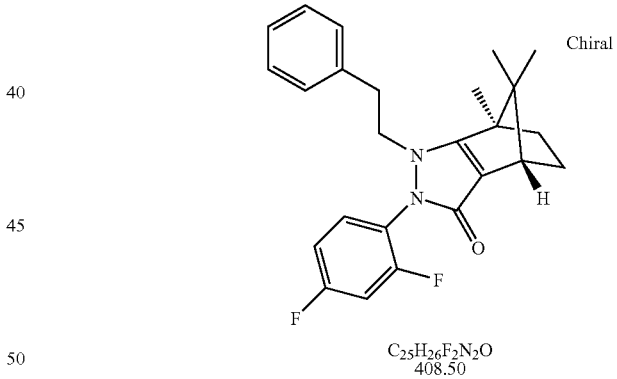

C₂₅H₂₆F₂N₂O
408.50

A mixture of (2-bromoethyl)benzene (200 μL, 1.46 mmol), (4R,7S)-2-(2,4-difluoro-phenyl)-7,8,8-trimethyl-1,2,4,5,6,7-hexahydro-4,7-methano-indazol-3-one (Intermediate 14; 100 mg, 0.33 mmol) and tetra-n-butylammonium iodide (94 mg, 0.25 mmol) in N,N-dimethylformamide (1 mL) was heated in a pressure tube in an oil-bath at 100° C. for 18 h. Additional portions of (2-bromoethyl)benzene (200 μL, 2.2 mmol) and tetra-n-butylammonium iodide (100 mg, 0.27 mmol) were added and the reaction mixture was heated at 100° C. for 3 days, and then allowed to stand overnight at room temperature. The reaction mixture was diluted with dichloromethane (100 mL), washed with water (5×25 mL) and sodium thiosulfate solution (25 mL), dried (magnesium sulfate), filtered, and evaporated and the residue was purified on an Isco 40 g column, eluting with 40-100% ethyl acetate/ hexanes to give (4S,7R)-2-(2,4-difluoro-phenyl)-7,8,8-trimethyl-1-phenethyl-1,2,4,5,6,7-hexahydro-4,7-methano-indazol-3-one (37 mg, 28%) as a pale yellow oil that solidified on standing. ES(+)-MS (M+H) 409.

Example 63

(4S,7R)-7,8,8-Trimethyl-1-(3-methyl-but-2-enyl)-2-phenyl-1,2,4,5,6,7-hexahydro-4,7-methano-indazol-3-one

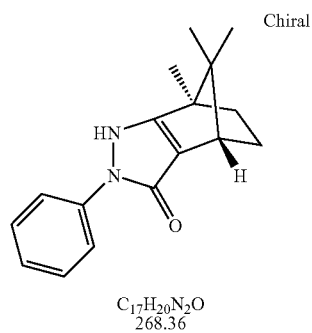

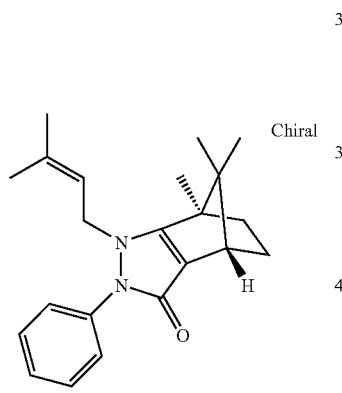

A mixture of (4S,7R)-7,8,8-trimethyl-2-phenyl-1,2,4,5,6,7-hexahydro-4,7-methano-indazol-3-one (Intermediate 6; 420 mg, 1.57 mmol), tetrabutylammonium iodide (2.31 g, 6.26 mmol) and 4-bromo-2-methyl-2-butene (720 µL, 6.26 mmol) in dimethylformamide (5 mL) was heated in an oil-bath at 100° C. for 8 h. The solvent was evaporated and the residue was partitioned between dichloromethane and water. The aqueous layer was extracted with dichloromethane (2×100 mL) and the combined organic layers were washed with water (5×100 mL) and aqueous sodium thiosulfate (100 mL). The solvent was evaporated and the residue was purified using an ISCO 40 g column, eluting with 90-100% ethyl acetate/hexanes to give (4S,7R)-7,8,8-trimethyl-1-(3-methyl-but-2-enyl)-2-phenyl-1,2,4,5,6,7-hexahydro-4,7-methano-indazol-3-one (38 mg, 7%) as a viscous yellow oil. APCI(+)-MS (M+H) 337.

Example 64

(4S,7R)-1-Cyclopropyl-7,8,8-trimethyl-2-phenyl-1,2,4,5,6,7-hexahydro-4,7-methano-indazol-3-one

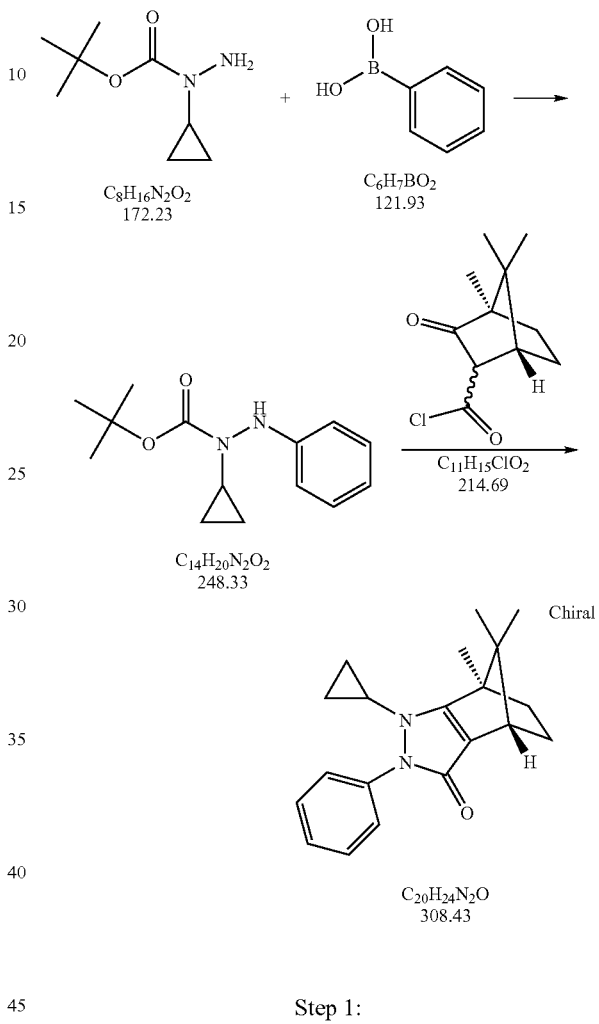

Step 1:
N-Cyclopropyl-N'-phenyl-hydrazinecarboxylic acid tert-butyl ester

A mixture of N-cyclopropyl-hydrazinecarboxylic acid tert-butyl ester (Intermediate 28; 0.111 g, 0.64 mmol), phenylboronic acid (Aldrich; 156 mg, 1.3 mmol), copper(II) acetate (116 mg, 0.64 mmol) and triethylamine (180 µL, 1.3 mmol) in 1,2-dichloroethane (3 mL) was heated in an oil bath at 50° C. for 16 h. The mixture was allowed to cool, and it was then adsorbed onto silica gel and purified by chromatography using an ISCO 40 g column, eluting with 5-40% ethyl acetate/hexanes, to give N-cyclopropyl-N'-phenyl-hydrazinecarboxylic acid tert-butyl ester (72 mg, 45%) as a pale yellow solid.

Step 2: (4S,7R)-1-Cyclopropyl-7,8,8-trimethyl-2-phenyl-1,2,4,5,6,7-hexahydro-4,7-methano-indazol-3-one Triethylamine (120 µL, 0.86 mmol) was added dropwise to a cooled (0° C.) solution of (1R,4R)-4,7,7-trimethyl-3-oxo-bicyclo[2.2.1]heptane-2-carbonyl chloride (Intermediate 20;

90 mg, 0.42 mmol) in 1,2-dichloroethane (1 mL) over 1 min. A solution of N-cyclopropyl-N'-phenyl-hydrazinecarboxylic acid tert-butyl ester (66 mg, 0.27 mmol) in 1,2-dichloroethane (4 mL) was added. The reaction mixture was stirred at 0° C. for 15 min, at room temperature for 15 min, and then in an oil bath at 50° C. for 90 min. The reaction mixture was cooled. A solution of HCl in dioxane (4 M; 4 mL, 16 mmol) was added and the mixture was heated in an oil bath at 100° C. for 1 h. A further portion of HCl in dioxane (4 M; 10 mL, 40 mmol) was added and the mixture was heated in an oil bath at 100° C. for 2 h. The solvent was evaporated. Dichloromethane (30 mL) was added and the mixture was washed with 1:1 water/brine (10 mL), dried (magnesium sulfate), filtered, evaporated, and purified using an ISCO 40 g column, eluting with 25-100% ethyl acetate/hexanes. Fractions homogeneous for the product were evaporated, and then co-evaporated with dichloromethane and then petroleum ether. The residue was dried under high vacuum at 75° C. overnight to give (4S,7R)-1-cyclopropyl-7,8,8-trimethyl-2-phenyl-1,2,4,5,6,7-hexahydro-4,7-methano-indazol-3-one (35 mg, 43%) as a light yellow solid. APCI(+)-MS (M+H) 309.

Example 65

(4S,7R)-1-(2-Methoxy-ethyl)-7,8,8-trimethyl-2-phenyl-1,2,4,5,6,7-hexahydro-4,7-methano-indazol-3-one

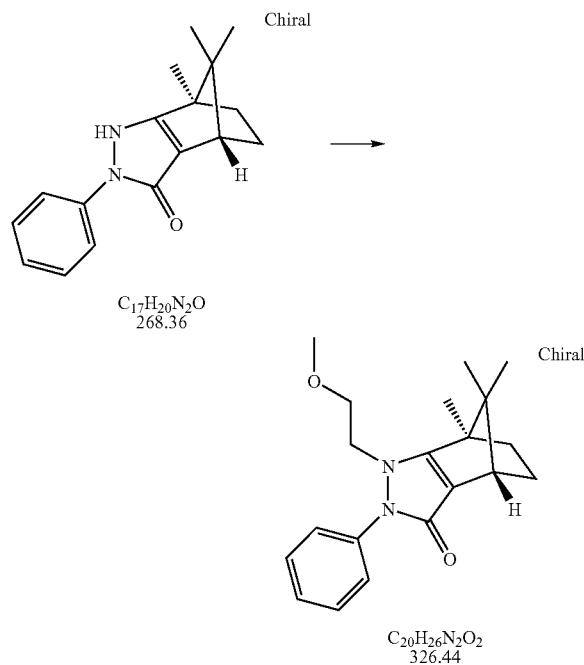

A mixture of (4S,7R)-7,8,8-trimethyl-2-phenyl-1,2,4,5,6,7-hexahydro-4,7-methano-indazol-3-one (Intermediate 6; 150 mg, 0.56 mmol), tetrabutylammonium iodide (207 mg, 0.56 mmol) and 2-bromoethyl methyl ether (540 µL, 5.75 mmol) in dimethylformamide (3 mL) was heated in an oil-bath at 100° C. for 17 h. An additional portion of 2-bromoethyl methyl ether (540 µL, 5.75 mmol) was added and the mixture was heated at 100° C. for 3 days. Dichloromethane (75 mL) and water (25 mL) were added, and the aqueous layer was back-extracted with dichloromethane (2×30 mL). The combined organic layers were washed with water (4×20 mL), aqueous sodium thiosulfate (20 mL), and brine (30 mL). The solution was dried (magnesium sulfate), filtered, evaporated and the residue was purified using an ISCO 40 g column, eluting with 20-100% ethyl acetate/hexanes to give an orange oil. This was treated with charcoal in methanol and the mixture was filtered through Celite. The solvent was evaporated to give (4S,7R)-1-(2-methoxy-ethyl)-7,8,8-trimethyl-2-phenyl-1,2,4,5,6,7-hexahydro-4,7-methano-indazol-3-one (10.3 mg, 6%) as an orange oil. The purity of the sample was assessed at 88% by 1H NMR. ES(+)-MS (M+H) 327.

Example 66

(4S,7R)-7,8,8-Trimethyl-1-phenethyl-2-phenyl-1,2,4,5,6,7-hexahydro-4,7-methano-indazol-3-one

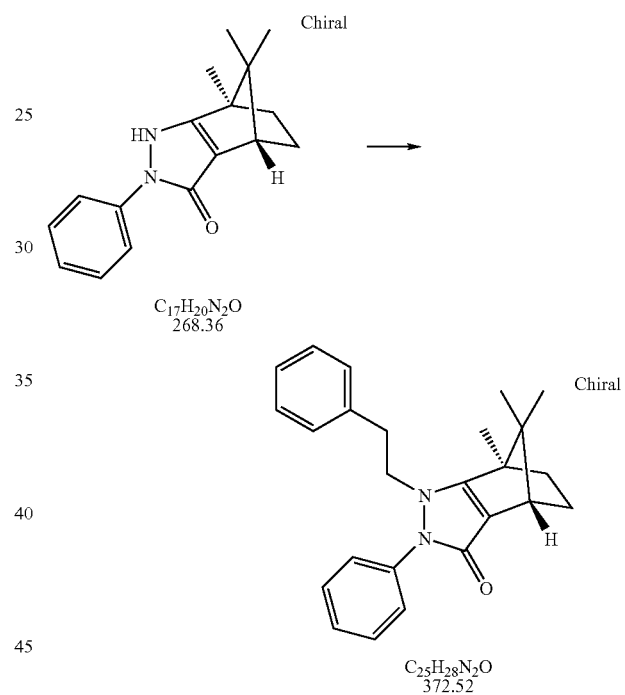

A mixture of (4S,7R)-7,8,8-trimethyl-2-phenyl-1,2,4,5,6,7-hexahydro-4,7-methano-indazol-3-one (Intermediate 6; 150 mg, 0.56 mmol), tetrabutylammonium iodide (200 mg, 0.54 mmol) and (2-bromoethyl)benzene (500 µL, 3.7 mmol) in dimethylformamide (1.5 mL) was heated in a pressure tube in an oil-bath at 100° C. for 2 days. Dichloromethane (100 mL) was added and the solution was washed with water (4×25 mL) and aqueous sodium thiosulfate (25 mL), dried (magnesium sulfate), filtered, evaporated and purified using an ISCO 40 g column, eluting with 60-100% ethyl acetate/hexanes. Fractions homogeneous for the product were evaporated and co-evaporated successively with dichloromethane/petroleum ether and then methanol, and dried under high vacuum over the weekend at room temperature and then at 80° C. for 4 h. The residue was treated with petroleum ether to give a solid. The solvent was evaporated and the solid was dried overnight at 70° C. to give (4S,7R)-7,8,8-trimethyl-1-phenethyl-2-phenyl-1,2,4,5,6,7-hexahydro-4,7-methano-indazol-3-one (30 mg, 14%) as a pale yellow solid. ES(+)-MS (M+H) 373.

Example 67

(4R,7S)-1-Benzyl-2-(2-fluoro-phenyl)-7,8,8-trimethyl-1,2,4,5,6,7-hexahydro-4,7-methano-indazol-3-one Procedure A

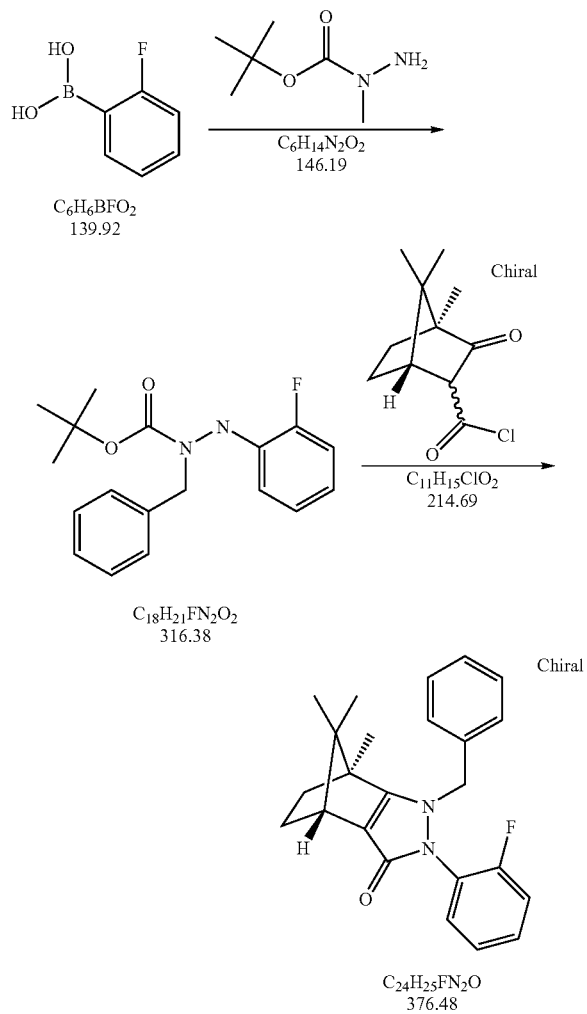

Step 1: N-Benzyl-N'-(2-Fluoro-phenyl)-hydrazinecarboxylic acid tert-butyl ester A mixture of N-benzyl-hydrazinecarboxylic acid tert-butyl ester (Intermediate 27; 444 mg, 2 mmol), 2-fluorophenylboronic acid (Matrix; 274 mg, 2.01 mmol), copper(II) acetate (363 mg, 2.0 mmol) and triethylamine (280 µL, 2.0 mmol) in 1,2-dichloroethane (3 mL) was heated in an oil bath at 50° C. for 2 h. The mixture was allowed to cool, and it was then adsorbed onto silica gel and purified by chromatography using an ISCO 40 g column, eluting with 20-40% ethyl acetate/hexanes, to give N-benzyl-N'-(2-fluoro-phenyl)-hydrazinecarboxylic acid tert-butyl ester (242 mg, 38%) as a colorless oil.

Step 2: (4R,7S)-1-Benzyl-2-(2-fluoro-phenyl)-7,8,8-trimethyl-1,2,4,5,6,7-hexahydro-4,7-methano-indazol-3-one Triethylamine (440 µL, 3.2 mmol) was added dropwise to a solution of (1S,4S)-4,7,7-trimethyl-3-oxo-bicyclo[2.2.1]heptane-2-carbonyl chloride (Intermediate 25; 318 mg, 1.5 mmol) in 1,2-dichloroethane (4 mL) over 1 min. Then a solution of N-benzyl-N'-(2-fluoro-phenyl)-hydrazinecarboxylic acid tert-butyl ester (242 mg, 0.77 mmol) in 1,2-dichloroethane (8 mL) was added over 2 min. The reaction mixture was stirred at room temperature for 15 min and then heated in an oil bath at 100° C. for 45 min. A solution of HCl in dioxane (4 M; 4 mL, 16 mmol) was added and the mixture was heated in an oil-bath at 100° C. for 1 h. A further portion of HCl in dioxane (4 M; 2 mL, 8 mmol) was added and the mixture was heated in an oil-bath at 100° C. for 2 h. The reaction mixture was allowed to cool to room temperature and dichloromethane (100 mL) was added. The mixture was washed with 1:1 water/brine (20 mL), dried (magnesium sulfate), filtered, evaporated, and purified on an ISCO system using a 40 g column, eluting with 50-100% ethyl acetate/hexanes. Fractions homogeneous for the product were evaporated, co-evaporated with diethyl ether and petroleum ether, and then dried under high vacuum at 90° C. to give (4R,7S)-1-benzyl-2-(2-fluoro-phenyl)-7,8,8-trimethyl-1,2,4,5,6,7-hexahydro-4,7-methano-indazol-3-one (40 mg, 14%) as a pale yellow solid. ES(+)-MS (M+H) 377.

Procedure B

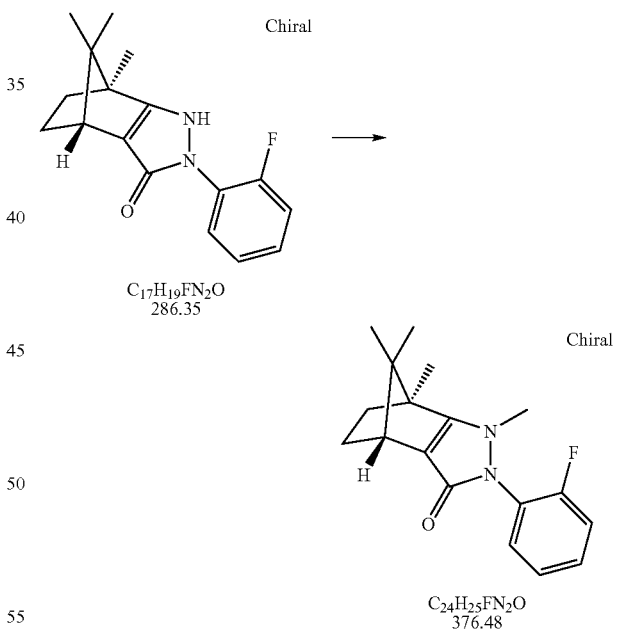

A solution of (4R,7S)-2-(2-fluoro-phenyl)-7,8,8-trimethyl-1,2,4,5,6,7-hexahydro-4,7-methano-indazol-3-one (Intermediate 38; 890 mg, 3.11 mmol), terabutylammonium iodide (860 mg, 2.33 mmol) and benzyl bromide (1.7 mL, 14.3 mmol) in dimethylformamide (15 mL) was heated in an oil-bath at 100° C. for 3 h. The reaction mixture was cooled to room temperature and the solvent was evaporated. Dichloromethane (100 µL) was added and the solution was washed with water (5×25 mL), aqueous sodium thiosulfate (25 mL), and brine (25 mL), dried (magnesium sulfate, filtered, and evaporated. The residue was purified using an ISCO 120 g column, eluting with 60-100% ethyl acetate/hexanes. Fractions containing the product were concentrated and then co-evaporated with ether. Petroleum ether was added and the mixture was scratched to give a solid. The solvent was evaporated and the residue was co-evaporated three times with ethanol, and then dried under high vacuum at 65° C. and then at 75° C. to give (4R,7S)-1-benzyl-2-(2-fluoro-phenyl)-7,8,8-trimethyl-1,2,4,5,6,7-hexahydro-4,7-methano-indazol-3-one (462 mg, 39%) as a pale yellow solid. ES(+)-MS (M+H) 377.

Example 68

(4S,7R)-2-(3-Fluoro-phenyl)-1,7,8,8-tetramethyl-1,2,4,5,6,7-hexahydro-4,7-methano-indazol-3-one

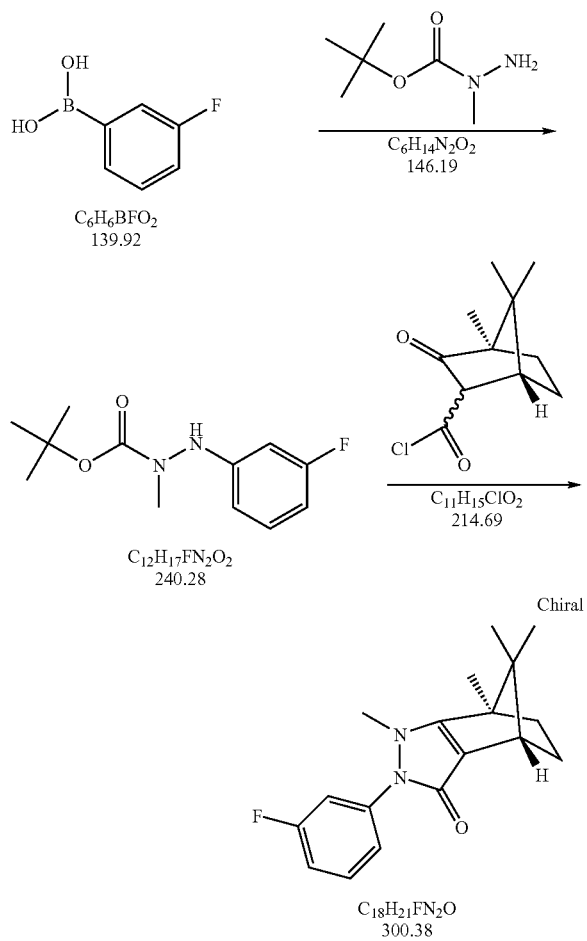

Step 1: N'-(3-Fluoro-phenyl)-N-methyl-hydrazinecarboxylic acid tert-butyl ester

A mixture of N-methyl-hydrazinecarboxylic acid tert-butyl ester (Intermediate 1; 570 mg, 4.1 mmol), 3-fluorophenylboronic acid (Aldrich; 673 mg, 4.6 mmol), copper(II) acetate (750 mg, 4.1 mmol) and triethylamine (1.4 mL, 10.0 mmol) in 1,2-dichloroethane (20 mL) was heated in an oil bath at 60° C. for 1.5 h. The mixture was allowed to cool, and it was then adsorbed onto silica gel and purified by chromatography using an ISCO 120 g column, eluting with 10-20% ethyl acetate/hexanes, to give N'-(3-fluoro-phenyl)-N-methyl-hydrazinecarboxylic acid tert-butyl ester (386 mg, 39%) as a pale yellow oil.

Step 2: (4S,7R)-2-(3-Fluoro-phenyl)-1,7,8,8-tetramethyl-1,2,4,5,6,7-hexahydro-4,7-methano-indazol-3-one Triethylamine (1.1 mL, 7.9 mmol) was added dropwise to a cooled (0° C.) solution of N'-(3-fluoro-phenyl)-N-methyl-hydrazinecarboxylic acid tert-butyl ester (380 mg, 1.58 mmol) in 1,2-dichloroethane (8 mL) over 1 min. A solution of (1R,4R)-4,7,7-trimethyl-3-oxo-bicyclo[2.2.1]heptane-2-carbonyl chloride (Intermediate 20; 980 mg, 4.56 mmol) in 1,2-dichloroethane (16 mL) was added. The reaction mixture was stirred at 0° C. for 15 min, at room temperature for 15 min, and then in an oil bath at 50° C. for 2 h. The reaction mixture was cooled. A solution of HCl in dioxane (4 M; 8 mL, 32 mmol) was added and the mixture was heated in an oil bath at 100° C. for 1 h. Dichloromethane (100 mL) was added and the mixture was washed with 1:1 water/brine (20 mL), dried (magnesium sulfate), filtered, evaporated, and purified using an ISCO 40 g column, eluting with 20-50% ethyl acetate/hexanes. Fractions homogeneous for the product were evaporated, and then co-evaporated with dichloromethane and then petroleum ether. The residue was dried under high vacuum at 70° C. overnight to give (4S,7R)-2-(3-fluoro-phenyl)-1,7,8,8-tetramethyl-1,2,4,5,6,7-hexahydro-4,7-methano-indazol-3-one (130 mg, 27%) as an off-white solid. ES(+)-MS (M+H) 301.

Example 69

(4R,7S)-2-(2-Chloro-phenyl)-1,7,8,8-tetramethyl-1,2,4,5,6,7-hexahydro-4,7-methano-indazol-3-one

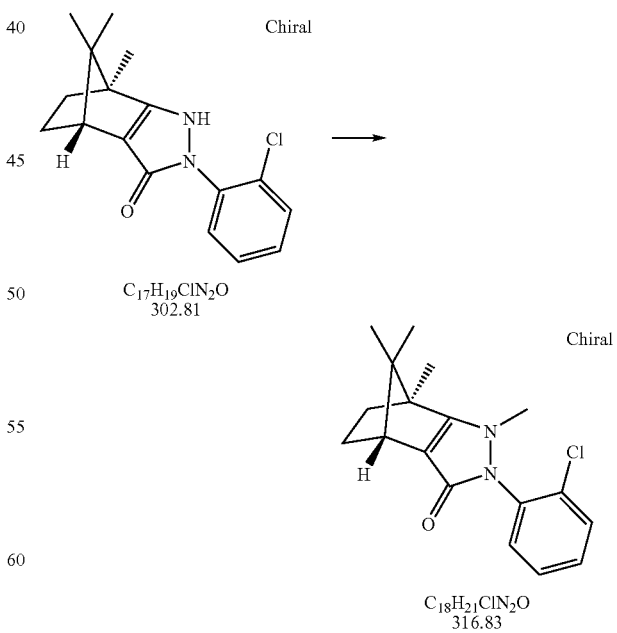

A solution of (4R,7S)-2-(2-chloro-phenyl)-7,8,8-trimethyl-1,2,4,5,6,7-hexahydro-4,7-methano-indazol-3-one (Intermediate 39; 151.5 mg, 0.5 mmol) and iodomethane (0.16 mL, 2.55 mmol) in N-methylpyrrolidine (1 mL) was heated at 100° C. in a sealed tube for 2 h. The reaction mixture was purified by preparative HPLC to give (4R,7S)-2-(2-chloro-phenyl)-1,7,8,8-tetramethyl-1,2,4,5,6,7-hexahydro-4,7-methano-indazol-3-one (106 mg, 67%) as an off-white solid. ES(+)-MS (M+H) 317.

Example 70

(4R,7S)-2-(2-Chloro-phenyl)-1-ethyl-7,8,8-trimethyl-1,2,4,5,6,7-hexahydro-4,7-methano-indazol-3-one

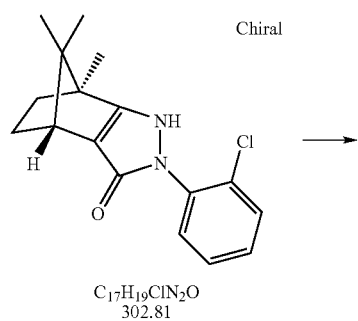

A solution of (4R,7S)-2-(2-chloro-phenyl)-7,8,8-trimethyl-1,2,4,5,6,7-hexahydro-4,7-methano-indazol-3-one (Intermediate 39; 151 mg, 0.5 mmol) and iodoethane (0.21 mL, 2.58 mmol) in N-methylpyrrolidine (1 mL) was heated at 100° C. in a sealed tube overnight. The reaction mixture was purified by preparative HPLC to give a brown gum which was dissolved in ethyl acetate. The solution was washed with 10% aqueous sodium thiosulfate (three times) and brine, dried (sodium sulfate), filtered, evaporated, and dried under high vacuum to give (4R,7S)-2-(2-chloro-phenyl)-1-ethyl-7,8,8-trimethyl-1,2,4,5,6,7-hexahydro-4,7-methano-indazol-3-one (76 mg, 46%) as an off-white foam. ES(+)-MS (M+H) 331.

Example 71

(4R,7S)-2-(2-Chloro-phenyl)-7,8,8-trimethyl-1-propyl-1,2,4,5,6,7-hexahydro-4,7-methano-indazol-3-one

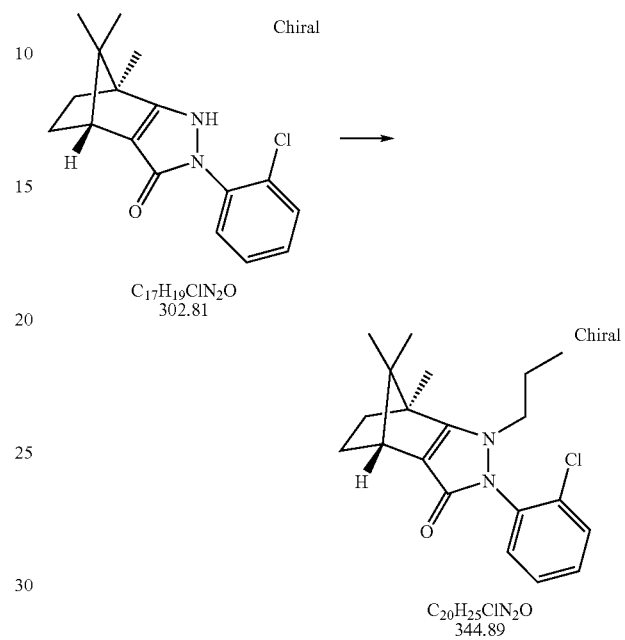

A solution of (4R,7S)-2-(2-chloro-phenyl)-7,8,8-trimethyl-1,2,4,5,6,7-hexahydro-4,7-methano-indazol-3-one (Intermediate 39; 151 mg, 0.5 mmol) and iodopropane (0.25 mL, 2.54 mmol) in N-methylpyrrolidine (1 mL) was heated at 100° C. in a sealed tube overnight. The reaction mixture was purified by preparative HPLC to give a brown gum which was dissolved in ethyl acetate. The solution was washed with 10% aqueous sodium thiosulfate (three times) and brine, dried (sodium sulfate), filtered, evaporated, and dried under high vacuum to give (4R,7S)-2-(2-chloro-phenyl)-7,8,8-trimethyl-1-propyl-1,2,4,5,6,7-hexahydro-4,7-methano-indazol-3-one (44 mg, 26%) as a light brown gum. ES(+)-MS (M+H) 345.

Example 72

(4S,7R)-2-(2-Chloro-phenyl)-1-cyclopropylmethyl-7,8,8-trimethyl-1,2,4,5,6,7-hexahydro-4,7-methano-indazol-3-one

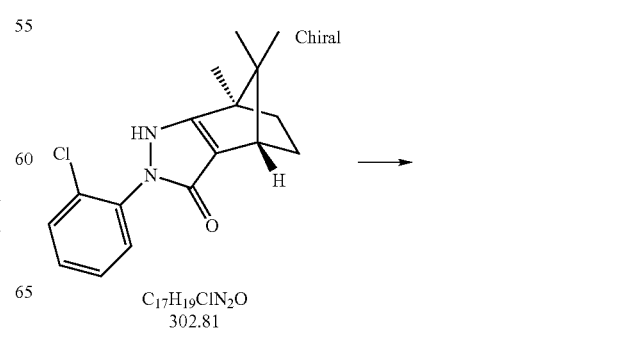

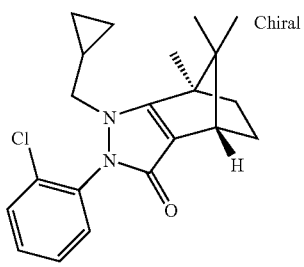

C₂₁H₂₅ClN₂O
356.90

A mixture of (4S,7R)-2-(2-chloro-phenyl)-7,8,8-trimethyl-1,2,4,5,6,7-hexahydro-4,7-methano-indazol-3-one (Intermediate 10; 154 mg, 0.51 mmol), tetrabutylammonium iodide (752 mg, 2.0 mmol), and (bromomethyl)cyclopropane (Lancaster; 195 μL, 2.0 mmol) in dimethylformamide (4.3 mL) was heated in an oil-bath at 100° C. for 16 h. The solvent was evaporated and the residue was partitioned between dichloromethane and water. The aqueous layer was extracted with dichloromethane (2×100 mL) and the combined organic layers were washed with water (5×100 mL) and aqueous sodium thiosulfate (100 mL). The solvent was evaporated and the residue was purified using an ISCO 120 g column, eluting with 65-100% ethyl acetate/hexanes to give (4S,7R)-2-(2-chloro-phenyl)-1-cyclopropylmethyl-7,8,8-trimethyl-1,2,4,5,6,7-hexahydro-4,7-methano-indazol-3-one (60 mg, 33%) as a yellow gum. ES(+)-MS (M+H) 357.

Example 73

2-((4S,7R)-1,7,8,8-Tetramethyl-3-oxo-1,3,4,5,6,7-hexahydro-4,7-methano-indazol-2-yl)-benzonitrile

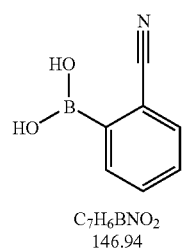

C₇H₆BNO₂
146.94

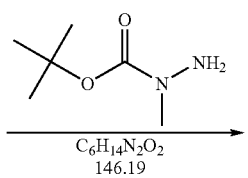

C₆H₁₄N₂O₂
146.19

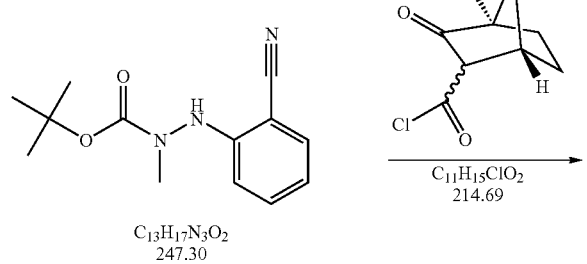

C₁₃H₁₇N₃O₂
247.30

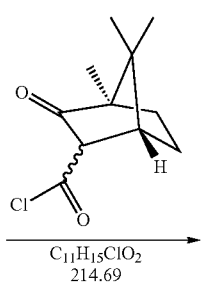

C₁₁H₁₅ClO₂
214.69

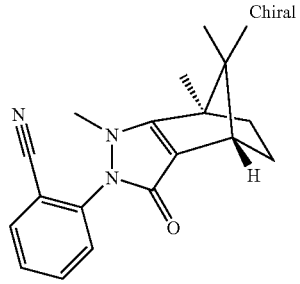

C₁₉H₂₁N₃O
307.40

Step 1: N'-(2-Cyano-phenyl)-N-methyl-hydrazinecarboxylic acid tert-butyl ester

A mixture of N-methyl-hydrazinecarboxylic acid tert-butyl ester (Intermediate 1; 890 mg, 6.06 mmol), 2-cyanophenylboronic acid (CombiBlock; 1.00 g, 6.8 mmol), copper(II) acetate (1.25 g, 6.9 mmol) and triethylamine (2 mL, 14.4 mmol) in 1,2-dichloroethane (30 mL) was heated in an oil bath at 60° C. for 3 h. The mixture was allowed to cool, and it was then adsorbed onto silica gel and purified by chromatography using an ISCO 40 g column, eluting with 10-20% ethyl acetate/hexanes, to give N'-(2-cyano-phenyl)-N-methyl-hydrazinecarboxylic acid tert-butyl ester (439 mg, 29%) as a pale yellow oil.

Step 2: 2-((4S,7R)-1,7,8,8-Tetramethyl-3-oxo-1,3,4,5,6,7-hexahydro-4,7-methano-indazol-2-yl)-benzonitrile Triethylamine (0.82 mL, 5.9 mmol) was added dropwise to a cooled (0° C.) solution of (1R,4R)-4,7,7-trimethyl-3-oxobicyclo[2.2.1]heptane-2-carbonyl chloride (Intermediate 20; 690 mg, 3.21 mmol) in 1,2-dichloroethane (6 mL) over 1 min. A solution of N'-(2-cyano-phenyl)-N-methyl-hydrazinecarboxylic acid tert-butyl ester (435 mg, 1.76 mmol) in 1,2-dichloroethane (10 mL) was added. The reaction mixture was stirred at 0° C. for 15 min, at room temperature for 15 min, and then in an oil bath at 50° C. for 1 h. The reaction mixture was cooled. A solution of HCl in dioxane (4 M; 6 mL, 24 mmol) was added and the mixture was heated in an oil bath at 50° C. for 30 min and then at 100° C. for 1 h and allowed to cool. Dichloromethane (150 mL) was added and the mixture was washed with 1:1 water/brine (30 mL), dried (magnesium sulfate), filtered, evaporated, and purified by flash chromatography, eluting with 50-100% ethyl acetate/hexanes. Fractions homogeneous for the product were evaporated, and then co-evaporated with methanol and then diethyl ether. The residue was dried under high vacuum at 70° C. to give 2-((4S,7R)-1,7,8,8-tetramethyl-3-oxo-1,3,4,5,6,7-hexahydro-4,7-methano-indazol-2-yl)-benzonitrile (55 mg, 10%) as an off-white solid. ES(+)-MS (M+H) 308.

Example 74

(4S,7R)-2-(2-Ethoxy-phenyl)-1,7,8,8-tetramethyl-1,2,4,5,6,7-hexahydro-4,7-methano-indazol-3-one

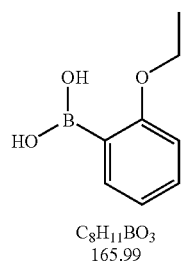
C₈H₁₁BO₃
165.99

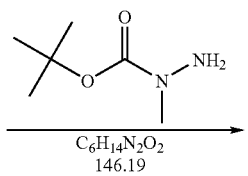
C₆H₁₄N₂O₂
146.19

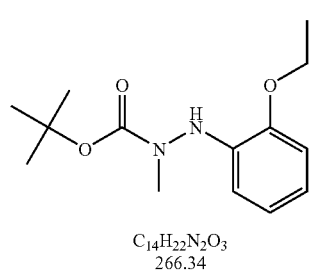
C₁₄H₂₂N₂O₃
266.34

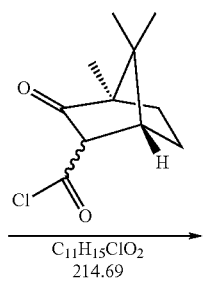
C₁₁H₁₅ClO₂
214.69

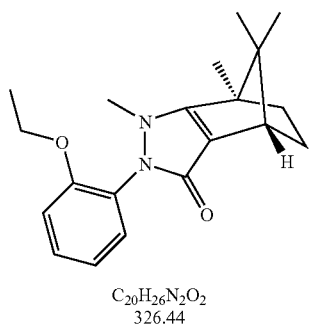
C₂₀H₂₆N₂O₂
326.44

Step 1: N'-(2-Ethoxy-phenyl)-N-methyl-hydrazinecarboxylic acid tert-butyl ester A mixture of N-methyl-hydrazinecarboxylic acid tert-butyl ester (Intermediate 1; 1.00 g, 6.8 mmol), 2-ethoxyphenylboronic acid (Combiblock; 1.12 g, 6.8 mmol), copper(II) acetate (1.24 g, 6.8 mmol) and triethylamine (960 µL, 6.8 mmol) in 1,2-dichloroethane (15 mL) was heated in an oil bath at 50° C. overnight. The mixture was allowed to cool, and it was then adsorbed onto silica gel and purified by chromatography using an ISCO 120 g column, eluting with 20-25% ethyl acetate/hexanes, to give N'-(2-ethoxy-phenyl)-N-methyl-hydrazinecarboxylic acid tert-butyl ester (751 mg, 38%) as an off-white solid.

Step 2: (4S,7R)-2-(2-Ethoxy-phenyl)-1,7,8,8-tetramethyl-1,2,4,5,6,7-hexahydro-4,7-methano-indazol-3-one Triethylamine (944 µL, 6.7 mmol) was added dropwise to a cooled (0° C.) solution of (1R,4R)-4,7,7-trimethyl-3-oxo-bicyclo[2.2.1]heptane-2-carbonyl chloride (Intermediate 20; 693 mg, 3.23 mmol) in 1,2-dichloroethane (3 mL) over 1 min. The reaction mixture was stirred for 5 min and then a solution of N'-(2-ethoxy-phenyl)-N'-methyl-hydrazinecarboxylic acid tert-butyl ester (544 mg, 2.04 mmol) in 1,2-dichloroethane (6 mL) was added over 2 min. The reaction mixture was stirred at 0° C. for 15 min, at room temperature for 30 min, and then in an oil bath at 50° C. for 2 h. A solution of HCl in dioxane (4 M; 8 mL, 32 mmol) was added and the mixture was heated in an oil bath at 100° C. for 1 h and then allowed to cool to room temperature. Dichloromethane (100 mL) was added and the mixture was washed with 1:1 water/brine (20 mL), dried (magnesium sulfate), filtered, evaporated, and purified using an ISCO 40 g column, eluting with 20-50% ethyl acetate/hexanes. Fractions homogeneous for the product were evaporated, and then co-evaporated with ether and then petroleum ether. The residue was triturated with hexanes, and the solid was dried overnight under high vacuum at 70° C. and then at 85° C. for 1 h to give (4S,7R)-2-(2-ethoxy-phenyl)-1,7,8,8-tetramethyl-1,2,4,5,6,7-hexahydro-4,7-methano-indazol-3-one (200 mg, 30%) as an off-white solid. ES(+)-MS (M+H) 327.

Example 75

(4S,7R)-2-(3-Isopropyl-phenyl)-1,7,8,8-tetramethyl-1,2,4,5,6,7-hexahydro-4,7-methano-indazol-3-one

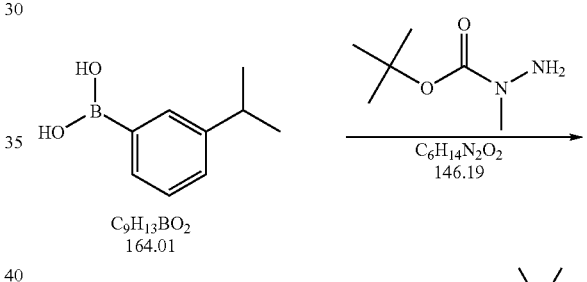
C₉H₁₃BO₂
164.01
C₆H₁₄N₂O₂
146.19

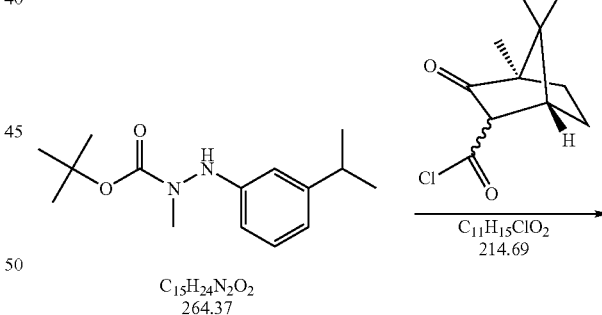
C₁₅H₂₄N₂O₂
264.37
C₁₁H₁₅ClO₂
214.69

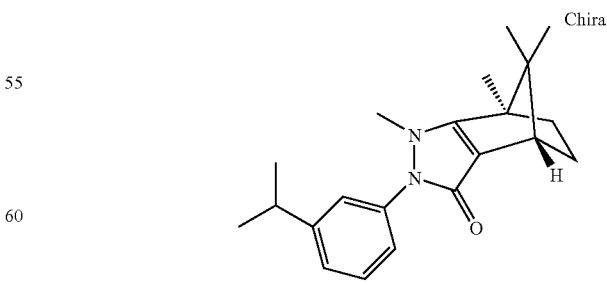
Chiral
C₂₁H₂₈N₂O
324.47

Step 1: N'-(3-Isopropyl-phenyl)-N-methyl-hydrazinecarboxylic acid tert-butyl ester A mixture of N-methyl-hydrazinecarboxylic acid tert-butyl ester (Intermediate 1; 300 mg, 2.05 mmol), 2-isopropylphenylboronic acid (Lancaster; 330 mg, 2.01 mmol), copper (II) acetate (373 mg, 2.05 mmol) and triethylamine (287 µL, 2.05 mmol) in 1,2-dichloroethane (4 mL) was heated in an oil bath at 50° C. for 3 h. The mixture was allowed to cool, and it was then adsorbed onto silica gel and purified by chromatography using an ISCO 40 g column, eluting with 5% ethyl acetate/hexanes, to give N'-(3-isopropyl-phenyl)-N-methyl-hydrazinecarboxylic acid tert-butyl ester (142 mg, 26%) as an oil.

Step 2: (4S,7R)-2-(3-Isopropyl-phenyl)-1,7,8,8-tetramethyl-1,2,4,5,6,7-hexahydro-4,7-methano-indazol-3-one Triethylamine (0.38 mL, 2.73 mmol) was added dropwise to a cooled (0° C.) solution of (1R,4R)-4,7,7-trimethyl-3-oxo-bicyclo[2.2.1]heptane-2-carbonyl chloride (Intermediate 20; 330 mg, 1.54 mmol) in 1,2-dichloroethane (4 mL) over 1 min. A solution of N'-(3-isopropyl-phenyl)-N-methyl-hydrazinecarboxylic acid tert-butyl ester (142 mg, 0.54 mmol) in 1,2-dichloroethane (8 mL) was added. The reaction mixture was stirred at 0° C. for 15 min, at room temperature for 15 min, and then in an oil bath at 50° C. for 1 h. The reaction mixture was cooled. A solution of HCl in dioxane (4 M; 5 mL, 20 mmol) was added and the mixture was heated in an oil bath at 100° C. for 1 h and allowed to cool. Dichloromethane (100 mL) was added and the mixture was washed with 1:1 water/brine (20 mL), dried (magnesium sulfate), filtered, evaporated, and purified by flash chromatography, eluting with 50% ethyl acetate/hexanes. Fractions homogeneous for the product were evaporated, and then co-evaporated with methanol and then diethyl ether. The residue was dried under high vacuum at 70° C. overnight to give (4S,7R)-2-(3-isopropyl-phenyl)-1,7,8,8-tetramethyl-1,2,4,5,6,7-hexahydro-4,7-methano-indazol-3-one (51 mg, 29%) as a pale yellow solid. ES(+)-MS (M+H) 325.

Example 76

(4S,7R)-2-(4-Hydroxy-phenyl)-1,7,8,8-tetramethyl-1,2,4,5,6,7-hexahydro-4,7-methano-indazol-3-one

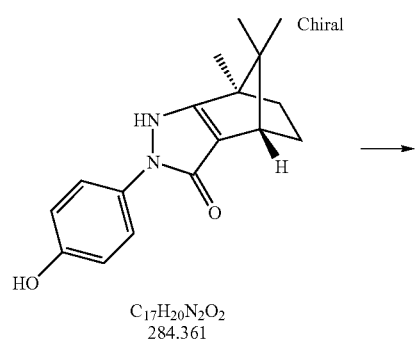

$C_{17}H_{20}N_2O_2$
284.361

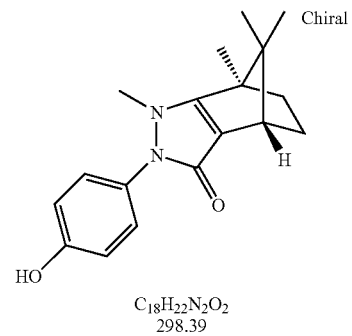

$C_{18}H_{22}N_2O_2$
298.39

A mixture of (4S,7R)-2-(4-hydroxy-phenyl)-7,8,8-trimethyl-1,2,4,5,6,7-hexahydro-4,7-methano-indazol-3-one (Intermediate 41; 1.60 g, 5.6 mmol) and iodomethane (1.1 mL, 17.7 mmol) in dimethylformamide (50 mL) was heated in a sealed tube at about 100° C. for 2.5 h. The reaction mixture was allowed to cool to room temperature. The tube was carefully opened, and the contents were allowed to stand at room temperature over a weekend. The solvent was evaporated and dichloromethane (250 mL) was added. The solution was washed with water (100 mL), saturated sodium thiosulfate (100 mL), water (100 mL), and brine (100 mL). The organic layer was dried (magnesium sulfate), filtered, and evaporated. The residue was triturated with ethyl acetate and the solid was filtered off and washed with 20% ethyl acetate/hexanes and then hexanes, and then purified using a Biotage 40M system, eluting with 3-5% methanol/dichloromethane to give (4S,7R)-2-(4-Hydroxy-phenyl)-1,7,8,8-tetramethyl-1,2,4,5,6,7-hexahydro-4,7-methano-indazol-3-one (1.26 g, 75%) as a light yellow solid. APCI(+)-MS (M+H) 299.

Example 77

(4S,7R)-2-(4-Methoxy-phenyl)-1,7,8,8-tetramethyl-1,2,4,5,6,7-hexahydro-4,7-methano-indazol-3-one

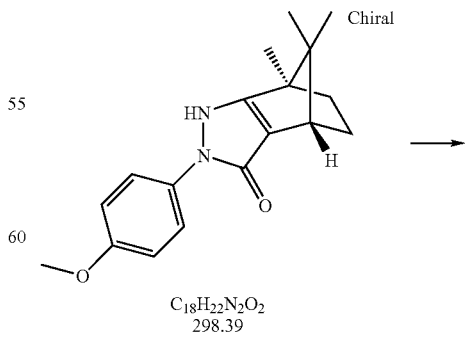

$C_{18}H_{22}N_2O_2$
298.39

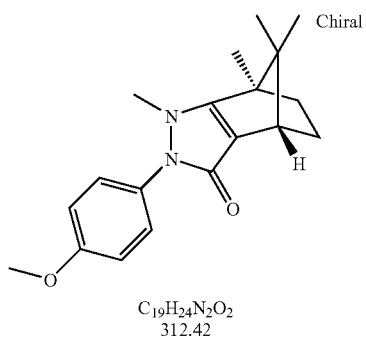

C19H24N2O2
312.42

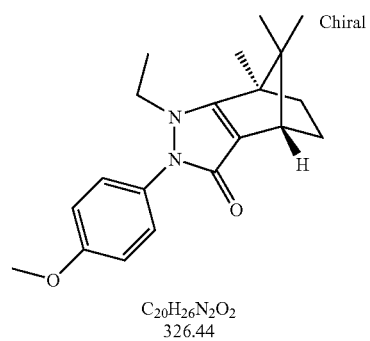

C20H26N2O2
326.44

A mixture of (4S,7R)-2-(4-methoxy-phenyl)-7,8,8-trimethyl-1,2,4,5,6,7-hexahydro-4,7-methano-indazol-3-one (Intermediate 40; 300 mg, 1.0 mmol) and iodomethane (315 μL, 5.1 mmol) in dimethylformamide (9 mL) was heated in a sealed tube at ~100° C. for 1 h 40 min. The reaction mixture was allowed to cool to room temperature, diluted with dichloromethane (100 mL), transferred to a round-bottomed flask and evaporated. Ethyl acetate (100 mL) and dichloromethane (50 mL) were added and the solution was washed with water, concentrated aqueous sodium thiosulfate (50 mL; 50% w/v), saturated aqueous sodium hydrogen carbonate (50 mL) and brine (50 mL). The solution was dried (magnesium sulfate), filtered, evaporated, and purified using a Biotage 40S system, eluting with 3% methanol/dichloromethane. Fractions homogeneous for the product were evaporated, co-evaporated with ethanol and dried under high vacuum to give (4S,7R)-2-(4-methoxy-phenyl)-1,7,8,8-tetramethyl-1,2,4,5,6,7-hexahydro-4,7-methano-indazol-3-one (235 mg, 75%) as an off-white solid. APCI(+)-MS (M+H) 313.

A mixture of (4S,7R)-2-(4-methoxy-phenyl)-7,8,8-trimethyl-1,2,4,5,6,7-hexahydro-4,7-methano-indazol-3-one (Intermediate 40; 300 mg, 1.0 mmol) and iodoethane (405 μL, 5.0 mmol) in dimethylformamide (9 mL) was heated in a sealed tube at ~100° C. overnight. The reaction mixture was allowed to cool to room temperature, diluted with dichloromethane (100 mL), transferred to a round-bottomed flask and evaporated. Ethyl acetate (100 mL) was added and the solution was washed with water, concentrated aqueous sodium thiosulfate (50 mL; 50% w/v), saturated aqueous sodium hydrogen carbonate (50 mL) and brine (50 mL). The solution was dried (magnesium sulfate), filtered, evaporated, and purified using a Biotage 40S system, eluting with 3% methanol/dichloromethane. Fractions homogeneous for the product were evaporated, co-evaporated with ethanol and dried under high vacuum to give (4S,7R)-1-ethyl-2-(4-methoxy-phenyl)-7,8,8-trimethyl-1,2,4,5,6,7-hexahydro-4,7-methano-indazol-3-one (152 mg, 46%) as a light yellow solid. APCI(+)-MS (M+H) 327.

Example 78

(4S,7R)-1-Ethyl-2-(4-methoxy-phenyl)-7,8,8-trimethyl-1,2,4,5,6,7-hexahydro-4,7-methano-indazol-3-one Example 79

(4S,7R)-1-Benzyl-2-(4-methoxy-phenyl)-7,8,8-trimethyl-1,2,4,5,6,7-hexahydro-4,7-methano-indazol-3-one

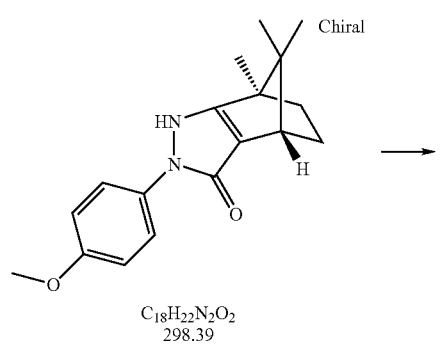

C18H22N2O2
298.39

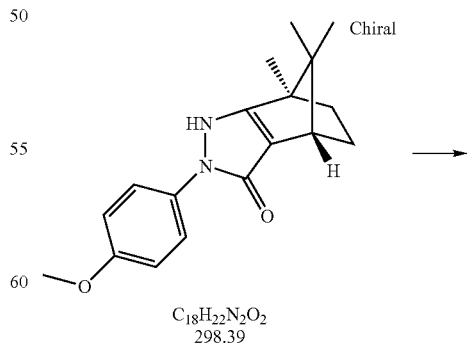

C18H22N2O2
298.39

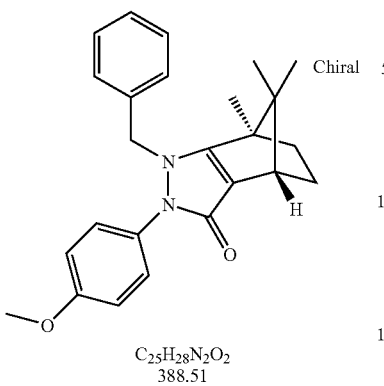

C<sub>25</sub>H<sub>28</sub>N<sub>2</sub>O<sub>2</sub>
388.51

A mixture of (4S,7R)-2-(4-methoxy-phenyl)-7,8,8-trimethyl-1,2,4,5,6,7-hexahydro-4,7-methano-indazol-3-one (Intermediate 40; 300 mg, 1.0 mmol), tetrabutylammonium iodide (371 mg, 1.0 mmol) and benzyl bromide (478 μL, 4.0 mmol) in dimethylformamide (10 mL) was heated at ~100° C. overnight. The solvent was evaporated. Dichloromethane (150 mL) was added and the solution was washed with brine (150 mL), saturated aqueous sodium thiosulfate (150 mL; 50% w/v), saturated aqueous sodium hydrogen carbonate (150 mL) and brine (150 mL). The solution was dried (sodium sulfate), filtered, evaporated, and purified using a Biotage 40S system, eluting with 0.5-2% methanol/dichloromethane to give a partially purified product that still contained some tetrabutylammonium iodide (according to 1H NMR). The solid was dissolved in dichloromethane, washed with saturated sodium thiosulfate and brine, and then evaporated to dryness. The solid was passed through a plug of silica, eluting with 0-5% methanol/dichloromethane, to give (4S,7R)-1-Benzyl-2-(4-methoxy-phenyl)-7,8,8-trimethyl-1,2,4,5,6,7-hexahydro-4,7-methano-indazol-3-one (54.5 mg, 14%). APCI(+)-MS (M+H) 389.

Example 80

(4S,7R)-2-(2,3-Difluoro-phenyl)-1,7,8,8-tetramethyl-1,2,4,5,6,7-hexahydro-4,7-methano-indazol-3-one

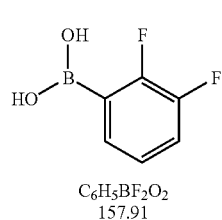

C<sub>6</sub>H<sub>5</sub>BF<sub>2</sub>O<sub>2</sub>
157.91

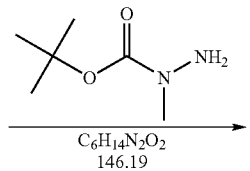

C<sub>6</sub>H<sub>14</sub>N<sub>2</sub>O<sub>2</sub>
146.19

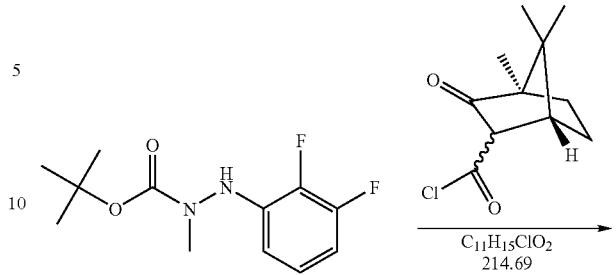

C<sub>12</sub>H<sub>16</sub>F<sub>2</sub>N<sub>2</sub>O<sub>2</sub>
258.27

C<sub>11</sub>H<sub>15</sub>ClO<sub>2</sub>
214.69

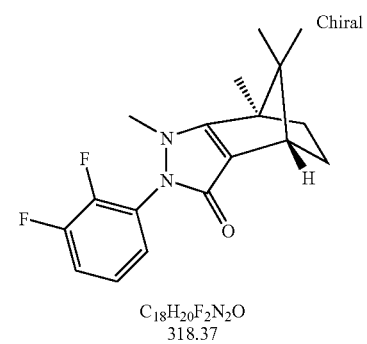

C<sub>18</sub>H<sub>20</sub>F<sub>2</sub>N<sub>2</sub>O
318.37

Step 1: N'-(2,3-Difluoro-phenyl)-N-methyl-hydrazinecarboxylic acid tert-butyl ester A mixture of N-methyl-hydrazinecarboxylic acid tert-butyl ester (Intermediate 1; 500 mg, 3.4 mmol), 2,3-difluorophenylboronic acid (Aldrich; 529 mg, 3.35 mmol), copper (II) acetate (621 mg, 3.4 mmol) and triethylamine (480 μL, 3.4 mmol) in 1,2-dichloroethane (4 mL) was heated in an oil bath at 50° C. for 3 h. The mixture was allowed to cool, and it was then adsorbed onto silica gel and purified by chromatography using an ISCO 40 g column, eluting with 20-40% ethyl acetate/hexanes, to give N'-(2,3-difluoro-phenyl)-N-methyl-hydrazinecarboxylic acid tert-butyl ester (450 mg, 39%) as a colorless oil.

Step 2: (4S,7R)-2-(2,3-Difluoro-phenyl)-1,7,8,8-tetramethyl-1,2,4,5,6,7-hexahydro-4,7-methano-indazol-3-one Triethylamine (1 mL, 7.2 mmol) was added dropwise to a solution of N'-(2,3-difluoro-phenyl)-N'-methyl-hydrazinecarboxylic acid tert-butyl ester (360 mg, 1.4 mmol) in 1,2-dichloroethane (6 mL) over 1 min. The reaction mixture was stirred for 5 min and then a solution of (1R,4R)-4,7,7-trimethyl-3-oxo-bicyclo[2.2.1]heptane-2-carbonyl chloride (Intermediate 20; 800 mg, 3.72 mmol) in 1,2-dichloroethane (14 mL) was added over 2 min. The reaction mixture was heated in an oil bath at 50° C. for 1 h. The solution was allowed to cool and a solution of HCl in dioxane (4 M; 6 mL, 24 mmol) was added and the mixture was heated at reflux for 1.5 h and then allowed to cool to room temperature. The solvent was evaporated and the residue was purified by preparative HPLC and dried under high vacuum to give (4S,7R)-2-(2,3-difluoro-phenyl)-1,7,8,8-tetramethyl-1,2,4,5,6,7-hexahydro-4,7-methano-indazol-3-one (129 mg, 29%) as a white solid. ES(+)-MS (M+H) 319.

Example 81

(4R,7S)-2-(2,4-Difluoro-phenyl)-1,7,8,8-tetramethyl-1,2,4,5,6,7-hexahydro-4,7-methano-indazol-3-one

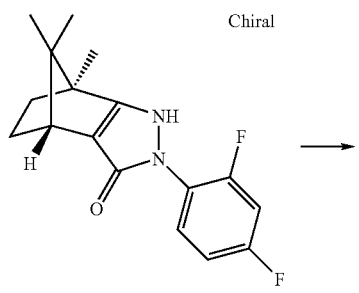

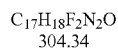

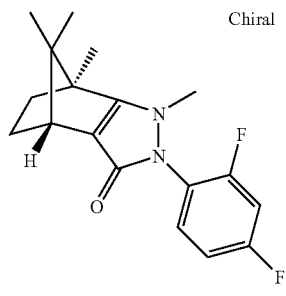

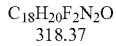

A solution of (4R,7S)-2-(2,4-difluoro-phenyl)-7,8,8-trimethyl-1,2,4,5,6,7-hexahydro-4,7-methano-indazol-3-one (Intermediate 42; 153 mg, 0.5 mmol) and iodomethane (0.16 mL, 2.55 mmol) in N-methylpyrrolidine (1 mL) was heated at 100° C. in a sealed tube overnight. The reaction mixture was purified by preparative HPLC to give a brown semi-solid which was dissolved in ethyl acetate. The solution was washed with 10% aqueous sodium thiosulfate (three times) and brine, dried (sodium sulfate), filtered, and evaporated to give (4R,7S)-2-(2,4-difluoro-phenyl)-1,7,8,8-tetramethyl-1,2,4,5,6,7-hexahydro-4,7-methano-indazol-3-one (104 mg, 65%) as an off-white solid. ES(+)-MS (M+H) 319.

Example 82

(4R,7S)-2-(2,4-Difluoro-phenyl)-1-ethyl-7,8,8-trimethyl-1,2,4,5,6,7-hexahydro-4,7-methano-indazol-3-one

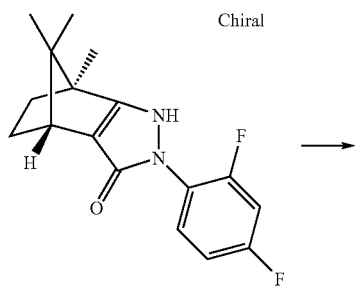

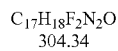

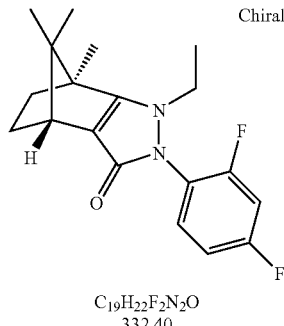

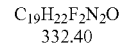

A solution of (4R,7S)-2-(2,4-difluoro-phenyl)-7,8,8-trimethyl-1,2,4,5,6,7-hexahydro-4,7-methano-indazol-3-one (Intermediate 42; 153 mg, 0.5 mmol) and iodoethane (0.21 mL, 2.6 mmol) in N-methylpyrrolidine (1 mL) was heated at 100° C. in a sealed tube for 17 h. The reaction mixture was purified by preparative HPLC to give a brown semi-solid which was dissolved in ethyl acetate. The solution was washed with 10% aqueous sodium thiosulfate (three times) and brine, dried (sodium sulfate), filtered, evaporated, and dried under high vacuum to give (4R,7S)-2-(2,4-difluoro-phenyl)-1-ethyl-7,8,8-trimethyl-1,2,4,5,6,7-hexahydro-4,7-methano-indazol-3-one (66 mg, 39%) as a pale yellow foam. ES(+)-MS (M+H) 333.

Example 83

(4S,7R)-2-(2,4-Difluoro-phenyl)-1-ethyl-7,8,8-trimethyl-1,2,4,5,6,7-hexahydro-4,7-methano-indazol-3-one

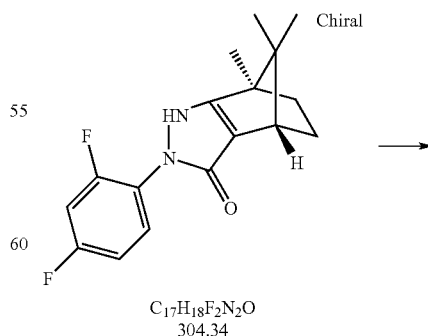

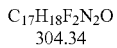

-continued

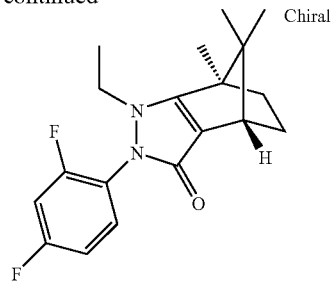

C19H22F2N2O
332.40

A mixture of (4S,7R)-2-(2,4-difluoro-phenyl)-7,8,8-trimethyl-1,2,4,5,6,7-hexahydro-4,7-methano-indazol-3-one (Intermediate 14; 200 mg, 0.65 mmol) and ethyl iodide (262 μL, 3.3 mmol) in dimethylformamide (2 mL) was heated at 100° C. over the weekend. The solvent was evaporated and ethyl acetate was added. The solution was washed twice with saturated aqueous sodium thiosulfate, and three times with water. The solution was dried (magnesium sulfate), filtered, evaporated, and purified by column chromatography, eluting with 75% ethyl acetate/petroleum ether, to give (4S,7R)-2-(2,4-difluoro-phenyl)-1-ethyl-7,8,8-trimethyl-1,2,4,5,6,7-hexahydro-4,7-methano-indazol-3-one (145 mg, 67%) as a white solid. IR 1667 cm$^{-1}$.

Example 84

(4R,7S)-2-(2,4-Difluoro-phenyl)-7,8,8-trimethyl-1-propyl-1,2,4,5,6,7-hexahydro-4,7-methano-indazol-3-one

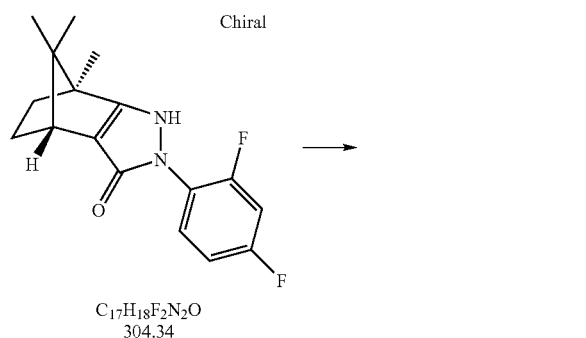

C17H18F2N2O
304.34

C20H24F2N2O
346.42

A solution of (4R,7S)-2-(2,4-difluoro-phenyl)-7,8,8-trimethyl-1,2,4,5,6,7-hexahydro-4,7-methano-indazol-3-one (Intermediate 42; 153 mg, 0.5 mmol) and iodopropane (0.25 mL, 2.54 mmol) in N-methylpyrrolidine (1 mL) was heated at 100° C. in a sealed tube overnight. The reaction mixture was purified by preparative HPLC to give a brown gum which was dissolved in ethyl acetate. The solution was washed with 10% aqueous sodium thiosulfate (three times) and brine, dried (sodium sulfate), filtered, evaporated, and dried under high vacuum to give (4R,7S)-2-(2,4-difluoro-phenyl)-7,8,8-trimethyl-1-propyl-1,2,4,5,6,7-hexahydro-4,7-methano-indazol-3-one (75 mg, 39%) as a beige foam. ES(+)-MS (M+H) 347.

Example 85

(4R,7S)-1-Allyl-2-(2,4-difluoro-phenyl)-7,8,8-trimethyl-1,2,4,5,6,7-hexahydro-4,7-methano-indazol-3-one

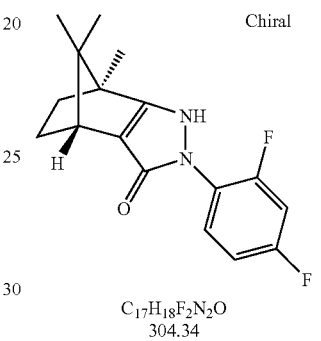

C17H18F2N2O
304.34

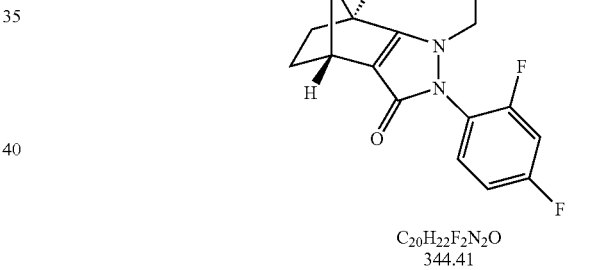

C20H22F2N2O
344.41

A mixture of (4R,7S)-2-(2,4-difluoro-phenyl)-7,8,8-trimethyl-1,2,4,5,6,7-hexahydro-4,7-methano-indazol-3-one (Intermediate 42; 989 mg, 3.25 mmol), tetrabutylammonium iodide (600 mg, 1.63 mmol) and allyl iodide (1.05 mL, 9.75 mmol) in dimethylformamide (5.7 mL) was heated in an oil-bath at 100° C. overnight. The solvent was evaporated and dichloromethane (400 mL) was added. The solution was washed with aqueous sodium thiosulfate (2×100 mL) and the combined aqueous washes were back-extracted with dichloromethane (2×100 mL). The combined organic layers were washed with water (100 mL) and brine (100 mL), dried (magnesium sulfate), filtered, and purified using an ISCO 40 g column, eluting with 20-50% ethyl acetate/hexanes. Fractions homogeneous for the product were evaporated, and then co-evaporated successively with methanol, ether, and petroleum ether. The residue was triturated with hexane and the solid was dried under high vacuum at 70° C. overnight and then at 85° C. for 1 h to give (4R,7S)-1-allyl-2-(2,4-difluoro-phenyl)-7,8,8-trimethyl-1,2,4,5,6,7-hexahydro-4,7-methano-indazol-3-one (334 mg, 30%) as an off-white solid. APCI(+)-MS (M+H) 345.

Example 86

(4S,7R)-1-Allyl-2-(2,4-difluoro-phenyl)-7,8,8-trimethyl-1,2,4,5,6,7-hexahydro-4,7-methano-indazol-3-one

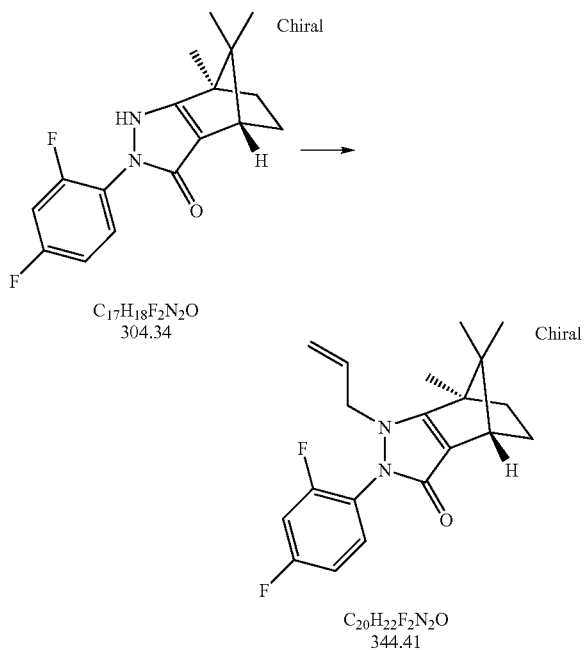

A mixture of (4S,7R)-2-(2,4-difluoro-phenyl)-7,8,8-trimethyl-1,2,4,5,6,7-hexahydro-4,7-methano-indazol-3-one (Intermediate 14; 420 mg, 1.38 mmol) and allyl iodide (600 μL, 5.5 mmol) in dimethylformamide (5 mL) was heated in an oil-bath at 100° C. for 8 h. The solvent was evaporated and the residue was partitioned between dichloromethane and water. The aqueous layer was extracted with dichloromethane (2×100 mL) and the combined organic layers were washed with water (5×100 mL) and aqueous sodium thiosulfate (100 mL). The solvent was evaporated and the residue was purified using an ISCO 40 g column, eluting with 90-100% ethyl acetate/hexanes to give (4S,7R)-1-allyl-2-(2,4-difluoro-phenyl)-7,8,8-trimethyl-1,2,4,5,6,7-hexahydro-4,7-methano-indazol-3-one (313 mg, 66%) as a white solid. APCI(+)-MS (M+H) 345.

Example 87

(4S,7R)-2-(2,4-Difluoro-phenyl)-7,8,8-trimethyl-1-(3-methyl-butyl)-1,2,4,5,6,7-hexahydro-4,7-methano-indazol-3-one

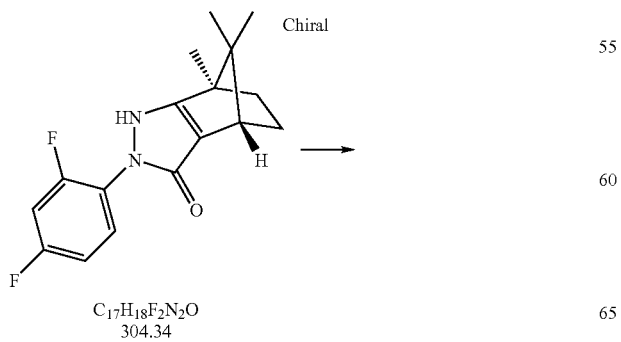

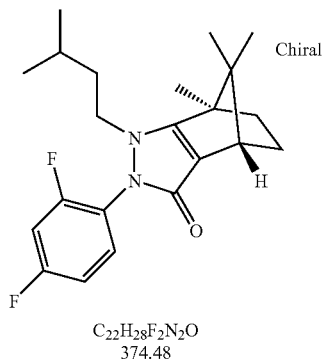

A mixture of (4S,7R)-2-(2,4-difluoro-phenyl)-7,8,8-trimethyl-1,2,4,5,6,7-hexahydro-4,7-methano-indazol-3-one (Intermediate 14; 600 mg, 1.97 mmol), tetrabutylammonium iodide (770 mg, 2.1 mmol) and 1-bromo-3-methyl-butane (2 mL, 16.7 mmol) in dimethylformamide (6 mL) was heated in an oil-bath at 120° C. for 18 h. The solvent was evaporated and dichloromethane (75 mL) was added. The solution was washed with water (5×20 mL) and aqueous sodium thiosulfate (20 mL), dried (magnesium sulfate), filtered, and evaporated. The residue was purified using an ISCO 40 g column, eluting with 20-90% ethyl acetate/hexanes to give (4S,7R)-2-(2,4-difluoro-phenyl)-7,8,8-trimethyl-1-(3-methyl-butyl)-1,2,4,5,6,7-hexahydro-4,7-methano-indazol-3-one (204 mg, 28%) as a white solid. ES(+)-MS (M+H) 375.

Example 88

(4S,7R)-2-(2,4-Difluoro-phenyl)-7,8,8-trimethyl-1-(3,3,3-trifluoro-propyl)-1,2,4,5,6,7-hexahydro-4,7-methano-indazol-3-one

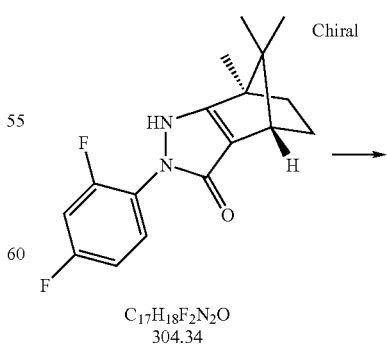

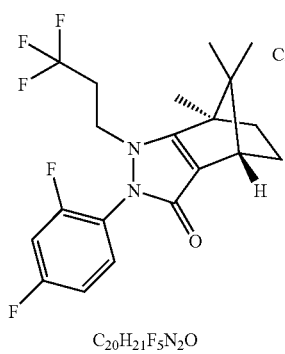

C₂₀H₂₁F₅N₂O
400.40

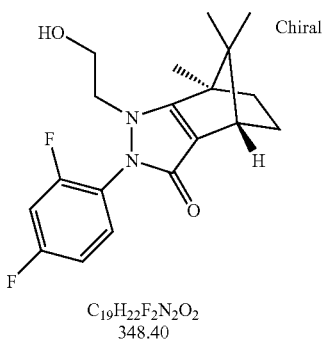

C₁₉H₂₂F₂N₂O₂
348.40

A mixture of (4S,7R)-2-(2,4-difluoro-phenyl)-7,8,8-trimethyl-1,2,4,5,6,7-hexahydro-4,7-methano-indazol-3-one (Intermediate 14; 200 mg, 0.66 mmol), tetrabutylammonium iodide (190 mg, 0.51 mmol) and 3-bromo-1,1,1-trifluoropropane (Aldrich; 5.00 g, 28.25 mmol) in dimethylformamide (2 mL) was heated in a pressure tube in an oil-bath at 100° C. for 4 days. An additional portion of tetrabutylammoiun iodide (190 mg, 0.51 mmol) was added and the reaction mixture was heated at 100° C. for 3 days and then cooled to room temperature. Dichloromethane (150 mL) was added and the solution was washed with water (5×25 mL) and aqueous sodium thiosulfate (25 mL), dried (magnesium sulfate), filtered, evaporated and purified using an ISCO 40 g column, eluting with 30-100% ethyl acetate/hexanes. Fractions homogeneous for the product were evaporated and the residue was triturated with petroleum ether. The mixture was evaporated again and dried at 70° C. under high vacuum to give (4S,7R)-2-(2,4-difluoro-phenyl)-7,8,8-trimethyl-1-(3,3,3-trifluoro-propyl)-1,2,4,5,6,7-hexahydro-4,7-methano-indazol-3-one (46 mg, 17%) as a light yellow solid. ES(+)-MS (M+H) 401.

Example 89

(4S,7R)-2-(2,4-Difluoro-phenyl)-1-(2-hydroxy-ethyl)-7,8,8-trimethyl-1,2,4,5,6,7-hexahydro-4,7-methano-indazol-3-one A solution of lithium aluminum hydride in tetrahydrofuran (Aldrich; 2 M; 80 µL; 0.16 mmol) was added to a solution of [(4S,7R)-2-(2,4-difluoro-phenyl)-7,8,8-trimethyl-3-oxo-2,3,4,5,6,7-hexahydro-4,7-methano-indazol-1-yl]-acetic acid ethyl ester (Example 92; 57 mg, 0.15 mmol) in dry tetrahydrofuran (EMScience DriSolve; 700 µL) over 1 min, and the solution was stirred at room temperature for 18 h. Water (4 mL) was added and the mixture was stirred for 10 min. 2M aqueous sodium hydroxide solution (4 mL, 8 mmol) was added and the mixture was stirred for 10 min. The mixture was extracted with dichloromethane (50 mL) and the organic extract was dried (magesium sulfate), filtered, evaporated, and purified using an ISCO 4 g column, eluting with 0-10% methanol/ethyl acetate. Fractions containing the product were combined, evaporated, co-evaporated successively with methanol and ether, and then dried under high vacuum at 75° C. to give (4S,7R)-2-(2,4-difluoro-phenyl)-1-(2-hydroxy-ethyl)-7,8,8-trimethyl-1,2,4,5,6,7-hexahydro-4,7-methano-indazol-3-one (8 mg, 16%) as a white solid. ES(+)-MS (M+H) 349.

Example 90

(4S,7R)-2-(2,4-Difluoro-phenyl)-1-(3-hydroxy-propyl)-7,8,8-trimethyl-1,2,4,5,6,7-hexahydro-4,7-methano-indazol-3-one

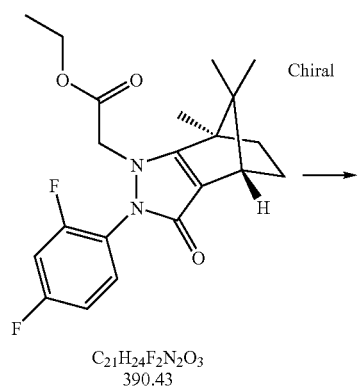

C₂₁H₂₄F₂N₂O₃
390.43

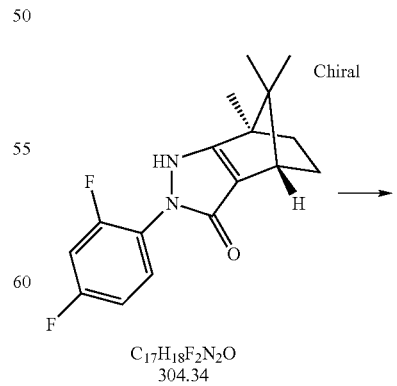

C₁₇H₁₈F₂N₂O
304.34

-continued

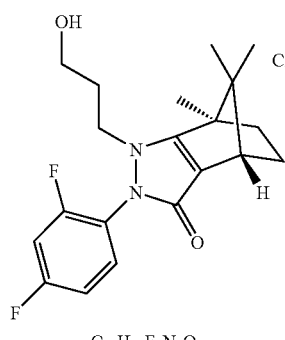

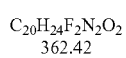

-continued

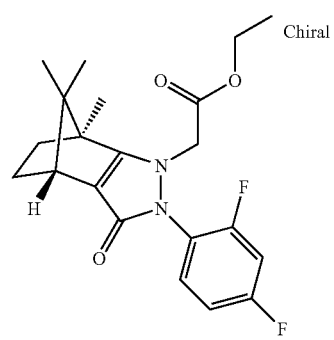

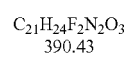

A mixture of (4S,7R)-2-(2,4-difluoro-phenyl)-7,8,8-trimethyl-1,2,4,5,6,7-hexahydro-4,7-methano-indazol-3-one (Intermediate 14; 355 mg, 1.17 mmol), tetrabutylammonium iodide (220 mg, 0.60 mmol) and 3-bromo-1-propanol (450 μL, 5.0 mmol) in dimethylformamide (4 mL) was heated at 100° C. for 21 h. Dichloromethane (100 mL), and the solution was washed with aqueous sodium thiosulfate (25 mL), and water (4×25 mL). The solution was dried (magnesium sulfate), and filtered. Silica gel was added and the solvent was evaporated. The resulting material was purified using an ISCO 12 g column, eluting with 0-5% methanol/ethyl acetate. Fractions containing the product were combined, evaporated, and dried under high vacuum at 95° C. overnight to give a gum that solidified on scratching. In this way was obtained (4S,7R)-2-(2,4-difluoro-phenyl)-1-(3-hydroxy-propyl)-7,8,8-trimethyl-1,2,4,5,6,7-hexahydro-4,7-methano-indazol-3-one (21 mg, 9%) as a light brown solid. APCI(+)-MS (M+H) 363.

A mixture of (4R,7S)-2-(2,4-difluoro-phenyl)-7,8,8-trimethyl-1,2,4,5,6,7-hexahydro-4,7-methano-indazol-3-one (Intermediate 42; 355 mg, 1.16 mmol) and ethyl iodoacetate (700 μL, 5.91 mmol) in dimethylformamide (5 mL) was heated at 100° C. for 2 h. The solvent was evaporated, dichloromethane (50 mL) was added and the solution was washed with 1:1 water/aqueous sodium thiosulfate (25 mL). The aqueous layer was back-extracted with dichloromethane (2×25 mL) and the combined organic layers were washed with brine (25 mL). The solution was dried (magnesium sulfate), filtered, evaporated, purified using an ISCO 12 g column, eluting with 40-100% ethyl acetate/petroleum ether, and dried under high vacuum at 75° C. to give [(4R,7S)-2-(2,4-difluoro-phenyl)-7,8,8-trimethyl-3-oxo-2,3,4,5,6,7-hexahydro-4,7-methano-indazol-1-yl]-acetic acid ethyl ester (269 mg, 59%) as an off-white solid. ES(+)-MS (M+H) 391.

Example 91

[(4R,7S)-2-(2,4-Difluoro-phenyl)-7,8,8-trimethyl-3-oxo-2,3,4,5,6,7-hexahydro-4,7-methano-indazol-1-yl]-acetic acid ethyl ester Example 92

[(4S,7R)-2-(2,4-Difluoro-phenyl)-7,8,8-trimethyl-3-oxo-2,3,4,5,6,7-hexahydro-4,7-methano-indazol-1-yl]-acetic acid ethyl ester

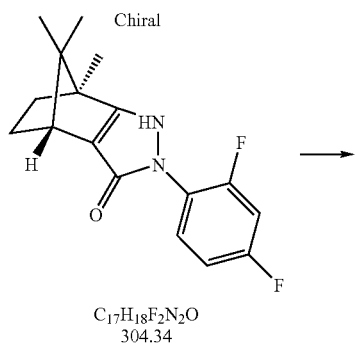

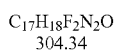

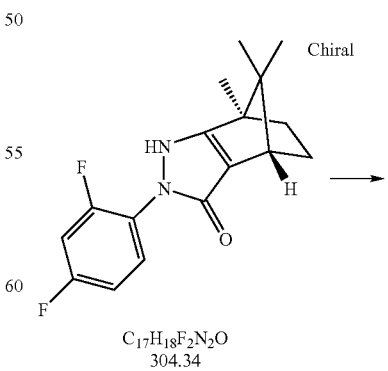

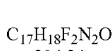

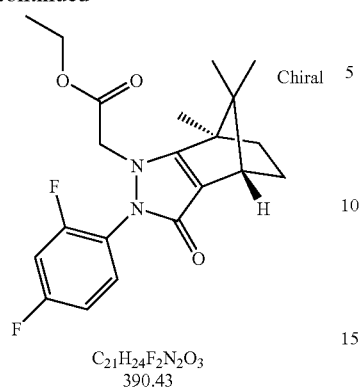

C21H24F2N2O3
390.43

A mixture of (4S,7R)-2-(2,4-difluoro-phenyl)-7,8,8-trimethyl-1,2,4,5,6,7-hexahydro-4,7-methano-indazol-3-one (Intermediate 14; 256 mg, 0.84 mmol) and ethyl iodoacetate (500 μL, 4.22 mmol) in dimethylformamide (5 mL) was heated at 100° C. for 2 h. The solvent was evaporated, dichloromethane (75 mL) was added and the solution was washed with 1:1 water/aqueous sodium thiosulfate (25 mL). The aqueous layer was back-extracted with dichloromethane (25 mL) and the combined organic layers were washed with brine (25 mL). The solution was dried (magnesium sulfate), filtered, evaporated, purified using an ISCO 12 g column, eluting with 40-100% ethyl acetate/petroleum ether, and dried under high vacuum at 70° C. overnight to give [(4S,7R)-2-(2,4-difluoro-phenyl)-7,8,8-trimethyl-3-oxo-2,3,4,5,6,7-hexahydro-4,7-methano-indazol-1-yl]-acetic acid ethyl ester (130 mg, 40%) as a light yellow solid. APCI(+)-MS (M+H) 391.

Example 93

(4R,7S)-1-Benzyl-2-(2,4-difluoro-phenyl)-7,8,8-trimethyl-1,2,4,5,6,7-hexahydro-4,7-methano-indazol-3-one

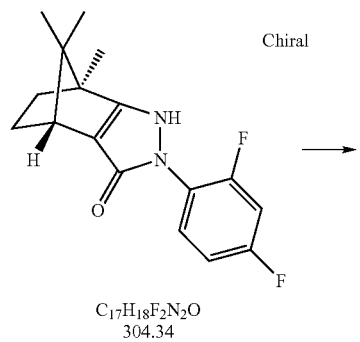

C17H18F2N2O
304.34

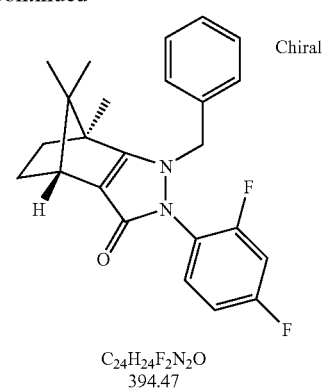

C24H24F2N2O
394.47

A solution of (4R,7S)-2-(2,4-difluoro-phenyl)-7,8,8-trimethyl-1,2,4,5,6,7-hexahydro-4,7-methano-indazol-3-one (Intermediate 42; 213 mg, 0.7 mmol), tetrabutylammonium iodide (271 mg, 0.7 mmol) and benzyl bromide (0.45 mL, 3.7 mmol) in dimethylformamide (1.4 mL) was heated at 100° C. in a sealed tube for 24 h and then left at room temperature for a further 24 h. The solvent was evaporated and ethyl acetate was added. The solution was washed with 10% aqueous sodium thiosulfate and brine, dried (sodium sulfate), filtered, evaporated, and purified using an Analogix Intelliflash 280 system (Analogix, Inc. Burlington, Wis.) with a RS-12G silica gel column, eluting with 10-100% ethyl acetate/hexanes, to give a light brown foam. This was dissolved in ethanol and the solution was treated with activated carbon (15 mg) and heated at 50° C. for 1 h. The mixture was filtered through Celite and the Celite was washed with ethanol. The combined filtrates were evaporated and the resulting foam was dried under high vacuum to give (4R,7S)-1-benzyl-2-(2,4-difluoro-phenyl)-7,8,8-trimethyl-1,2,4,5,6,7-hexahydro-4,7-methano-indazol-3-one (220 mg, 80%) as an off-white solid. ES(+)-MS (M+H) 395.

Example 94

(4S,7R)-2-(2,4-Difluoro-phenyl)-1-(2-fluoro-benzyl)-7,8,8-trimethyl-1,2,4,5,6,7-hexahydro-4,7-methano-indazol-3-one

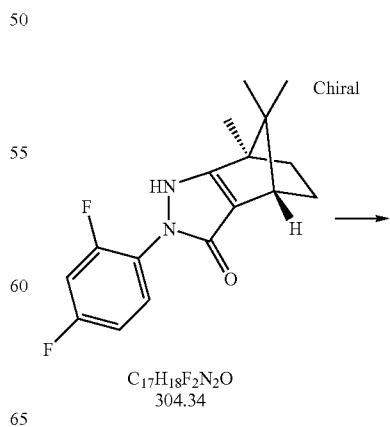

C17H18F2N2O
304.34

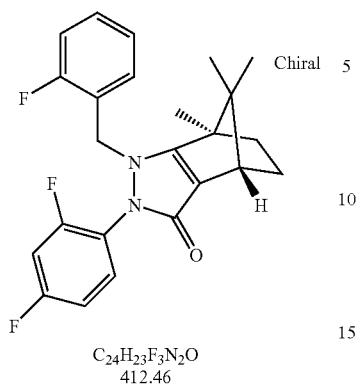

C₂₄H₂₃F₃N₂O
412.46

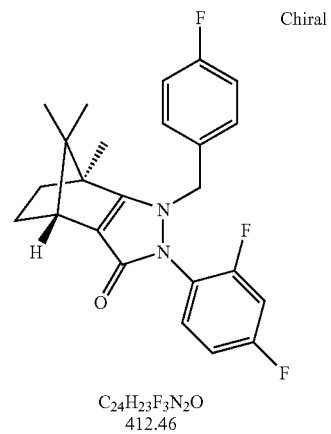

C₂₄H₂₃F₃N₂O
412.46

A mixture of (4S,7R)-2-(2,4-difluoro-phenyl)-7,8,8-trimethyl-1,2,4,5,6,7-hexahydro-4,7-methano-indazol-3-one (Intermediate 14; 100 mg, 0.33 mmol), tetrabutylammonium iodide (85 mg, 0.23 mmol) and 2-fluoro-benzyl bromide (164 µL, 1.3 mmol) in dimethylformamide (2 mL) was heated at 100° C. overnight. Dichloromethane (50 mL) and a mixture of water (13 mL) and brine (6 mL) were added. The organic layer was washed with 10% aqueous sodium thiosulfate (20 µL), and brine (20 mL). The solution was dried (magnesium sulfate), filtered, evaporated, and purified by column chromatography, eluting with 50-60% ethyl acetate/petroleum ether, to give (4S,7R)-2-(2,4-difluoro-phenyl)-1-(2-fluoro-benzyl)-7,8,8-trimethyl-1,2,4,5,6,7-hexahydro-4,7-methano-indazol-3-one (106 mg, 78%) as a pale solid. ES(+)-MS (M+H) 413.

Example 95

(4R,7S)-2-(2,4-Difluoro-phenyl)-1-(4-fluoro-benzyl)-7,8,8-trimethyl-1,2,4,5,6,7-hexahydro-4,7-methano-indazol-3-one A solution of (4R,7S)-2-(2,4-difluoro-phenyl)-7,8,8-trimethyl-1,2,4,5,6,7-hexahydro-4,7-methano-indazol-3-one (Intermediate 42; 152 mg, 0.5 mmol), tetrabutylammonium iodide (195 mg, 0.52 mmol) and 4-fluorobenzyl bromide (0.33 mL, 2.57 mmol) in dimethylformamide (1 mL) was heated at 100° C. in a sealed tube for 9 h. The solvent was evaporated and ethyl acetate was added. The solution was washed with 10% aqueous sodium thiosulfate and brine, dried (sodium sulfate), filtered, evaporated, and purified using an Analogix Intelliflash 280 system (Analogix, Inc. Burlington, Wis.) with a RS-12G silica gel column, eluting with 20-100% ethyl acetate/hexanes, to give (4R,7S)-2-(2,4-difluoro-phenyl)-1-(4-fluoro-benzyl)-7,8,8-trimethyl-1,2,4,5,6,7-hexahydro-4,7-methano-indazol-3-one (167 mg, 81%) as an off-white solid. ES(+)-MS (M+H) 395.

Example 96

(4S,7R)-2-(2,4-Difluoro-phenyl)-1-(4-fluoro-benzyl)-7,8,8-trimethyl-1,2,4,5,6,7-hexahydro-4,7-methano-indazol-3-one

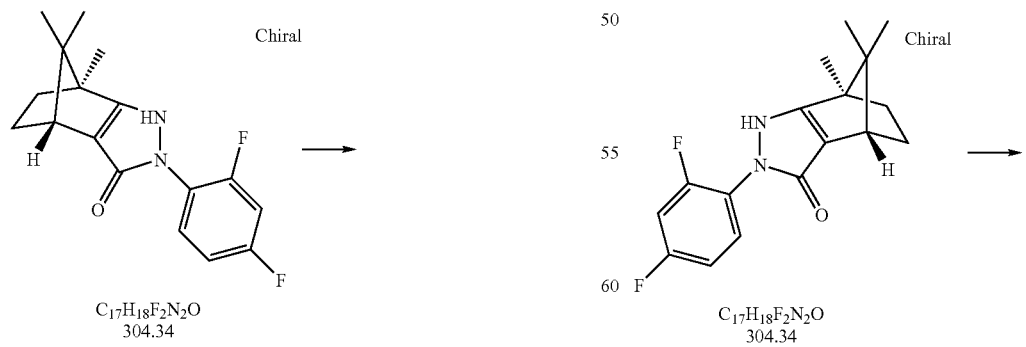

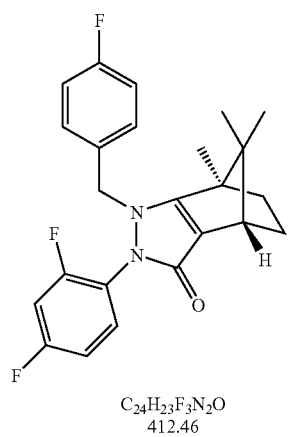

C24H23F3N2O
412.46

A mixture of (4S,7R)-2-(2,4-difluoro-phenyl)-7,8,8-trimethyl-1,2,4,5,6,7-hexahydro-4,7-methano-indazol-3-one (Intermediate 14; 100 mg, 0.33 mmol), tetrabutylammonium iodide (85 mg, 0.23 mmol) and 4-fluoro-benzyl bromide (164 μL, 1.3 mmol) in dimethylformamide (2 mL) was heated at 100° C. overnight. Dichloromethane (50 mL) and a mixture of water (10 mL) and brine (10 mL) were added. The organic layer was washed with 10% aqueous sodium thiosulfate (20 mL), and brine (20 mL). The solution was dried (magnesium sulfate), filtered, evaporated, and purified by column chromatography, eluting with 50-60% ethyl acetate/petroleum ether, to give (4S,7R)-2-(2,4-difluoro-phenyl)-1-(4-fluoro-benzyl)-7,8,8-trimethyl-1,2,4,5,6,7-hexahydro-4,7-methano-indazol-3-one (105 mg, 78%) as an off-white solid. ES(+)-MS (M+H) 413.

Example 97

(4S,7R)-1-(4-Chloro-benzyl)-2-(2,4-difluoro-phenyl)-7,8,8-trimethyl-1,2,4,5,6,7-hexahydro-4,7-methano-indazol-3-one

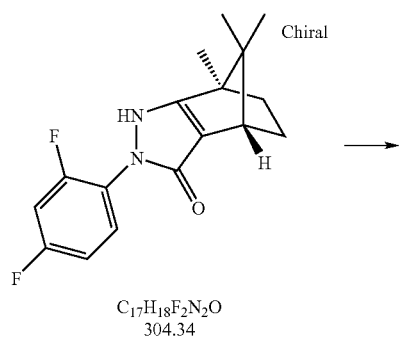

C17H18F2N2O
304.34

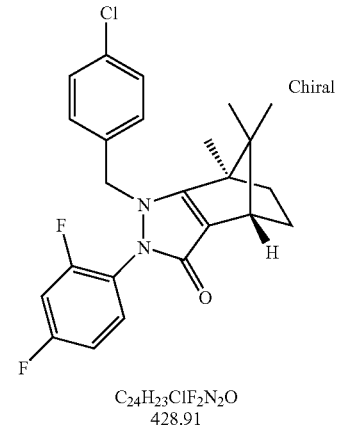

C24H23ClF2N2O
428.91

A mixture of (4S,7R)-2-(2,4-difluoro-phenyl)-7,8,8-trimethyl-1,2,4,5,6,7-hexahydro-4,7-methano-indazol-3-one (Intermediate 14; 150 mg, 0.49 mmol), tetrabutylammonium iodide (181 mg, 0.49 mmol) and 4-chlorobenzyl bromide (400 mg, 1.95 mmol) in dimethylformamide (3 mL) was heated at 80° C. for 4 days. The solvent was evaporated, dichloromethane (50 mL) was added and the solution was washed with water (2×20 mL), saturated aqueous sodium thiosulfate (20 mL), and brine (20 mL). The solution was dried (magnesium sulfate), filtered, evaporated, and purified by column chromatography, eluting with 60-70% ethyl acetate/petroleum ether, and dried under high vacuum overnight to give an off-white solid. This was dissolved in ethanol and the solution was treated with charcoal, then filtered through Celite and evaporated. 1H NMR indicated that there was some tetrabutylammonium iodide present. The residue was dissolved in ethyl acetate (50 mL) and the solution was washed with saturated aqueous sodium thiosulfate (25 mL), dried (magnesium sulfate), filtered, evaporated and chromatographed, eluting with 75% ethyl acetate/petroleum ether, to give (4S,7R)-1-(4-chloro-benzyl)-2-(2,4-difluorophenyl)-7,8,8-trimethyl-1,2,4,5,6,7-hexahydro-4,7-methano-indazol-3-one (100 mg, 48%). APCI(+)-MS (M+H) 429.

Example 98

(4S,7R)-1-(4-tert-Butyl-benzyl)-2-(2,4-difluoro-phenyl)-7,8,8-trimethyl-1,2,4,5,6,7-hexahydro-4,7-methano-indazol-3-one

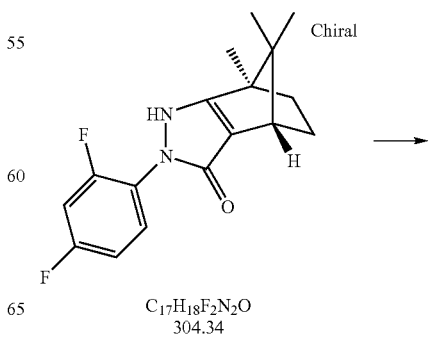

C17H18F2N2O
304.34

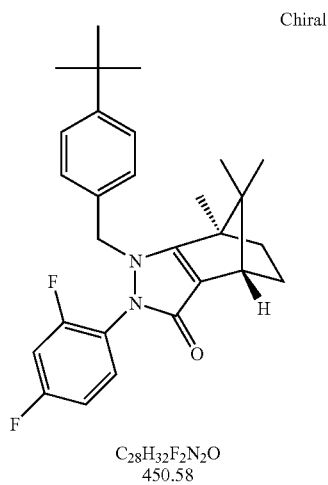

C₂₈H₃₂F₂N₂O
450.58

A mixture of (4S,7R)-2-(2,4-difluoro-phenyl)-7,8,8-trimethyl-1,2,4,5,6,7-hexahydro-4,7-methano-indazol-3-one (Intermediate 14; 150 mg, 0.49 mmol), tetrabutylammonium iodide (181 mg, 0.49 mmol) and 4-tert-butylbenzyl bromide (360 µL, 1.96 mmol) in dimethylformamide (3 mL) was heated at 80° C. for 4 days. The solvent was evaporated, dichloromethane (50 mL) was added and the solution was washed with water (2×20 mL), saturated aqueous sodium thiosulfate (20 mL), and brine (20 mL). The solution was dried (magnesium sulfate), filtered, evaporated, and purified by column chromatography, eluting with 60-70% ethyl acetate/petroleum ether, and dried under high vacuum overnight to give a pale yellow foam. This was dissolved in ethanol and treated with charcoal. The mixture was filtered through Celite, and the filtrate was evaporated and dried under high vacuum to give (4S,7R)-1-(4-tert-butyl-benzyl)-2-(2,4-difluoro-phenyl)-7,8,8-trimethyl-1,2,4,5,6,7-hexahydro-4,7-methano-indazol-3-one (151 mg, 68%). APCI(+)-MS (M+H) 451.

Example 99

(4S,7R)-2-(2,4-Difluoro-phenyl)-1-(4-methoxy-benzyl)-7,8,8-trimethyl-1,2,4,5,6,7-hexahydro-4,7-methano-indazol-3-one

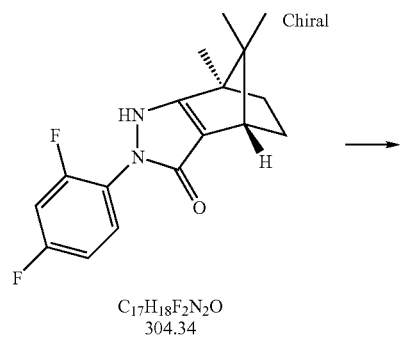

C₁₇H₁₈F₂N₂O
304.34

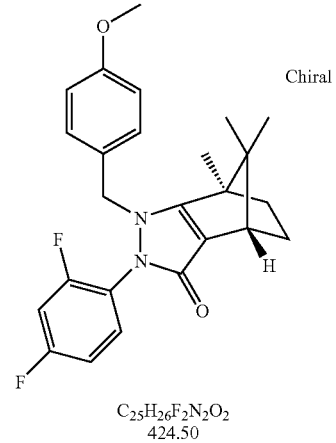

C₂₅H₂₆F₂N₂O₂
424.50

A mixture of (4S,7R)-2-(2,4-difluoro-phenyl)-7,8,8-trimethyl-1,2,4,5,6,7-hexahydro-4,7-methano-indazol-3-one (Intermediate 14; 150 mg, 0.49 mmol), tetrabutylammonium iodide (181 mg, 0.49 mmol) and 4-methoxybenzyl bromide (280 µL, 1.94 mmol) in dimethylformamide (3 mL) was heated at 80° C. overnight. The solvent was evaporated, dichloromethane (50 mL) was added and the solution was washed with water (2×20 mL), saturated aqueous sodium thiosulfate (20 mL), and brine (20 mL). The solution was dried (magnesium sulfate), filtered, evaporated, and purified by column chromatography, eluting with 60-75% ethyl acetate/petroleum ether, and dried under high vacuum overnight to give (4S,7R)-2-(2,4-difluoro-phenyl)-1-(4-methoxy-benzyl)-7,8,8-trimethyl-1,2,4,5,6,7-hexahydro-4,7-methano-indazol-3-one (162 mg, 78%). APCI(+)-MS (M+H) 425.

Example 100

(4R,7S)-2-(2,4-Difluoro-phenyl)-1-(4-hydroxymethyl-benzyl)-7,8,8-trimethyl-1,2,4,5,6,7-hexahydro-4,7-methano-indazol-3-one

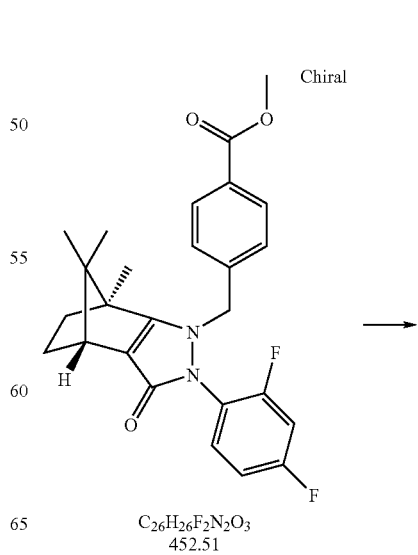

C₂₆H₂₆F₂N₂O₃
452.51

165

-continued

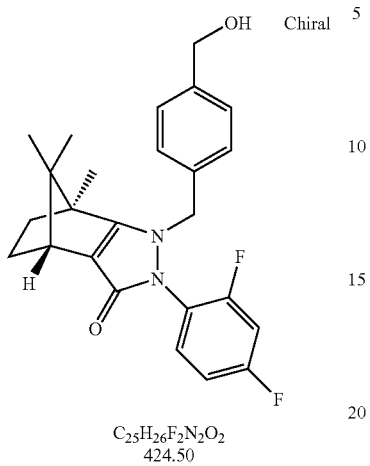

C25H26F2N2O2
424.50

A mixture of 4-[(4R,7S)-2-(2,4-difluoro-phenyl)-7,8,8-trimethyl-3-oxo-2,3,4,5,6,7-hexahydro-4,7-methano-indazol-1-ylmethyl]-benzoic acid methyl ester (Example 104; 189 mg, 0.42 mmol) and pulverized sodium borohydride (102 mg, 2.7 mmol) in tetrahydrofuran (2 mL) was heated at 65° C. for 15 min. Methanol (2 mL) was added dropwise over a period of 2 min and gas evolution was noted. The mixture was heated at 65° C. for 1 h, and then an additional portion of methanol (1 mL) was added. The mixture was heated at 65° C. for 1 h, and then an additional portion of sodium borohydride (ca. 50 mg) was added. The mixture was heated at 65° C. for 1 h, and then an additional portion of sodium borohydride (ca. 50 mg) was added. The mixture was heated at 65° C. for 1 h, and then it was cooled to room temperature. Saturated aqueous ammonium chloride (6 mL) and dichloromethane (30 mL) were added. The mixture was stirred at room temperature for 10 min. 1:1 Water/brine (20 mL) was added and the mixture was extracted with dichloromethane (3×30 mL). The combined organic extracts were dried (magnesium sulfate), filtered, and evaporated. The residue was purified using an ISCO 12 g column, eluting with 75-100% ethyl acetate/hexanes. Fractions containing the product were concentrated, co-evaporated with ether and petroleum ether, and then dried under high vacuum at 50° C. overnight give (4R,7S)-2-(2,4-difluoro-phenyl)-1-(4-hydroxymethyl-benzyl)-7,8,8-trimethyl-1,2,4,5,6,7-hexahydro-4,7-methano-indazol-3-one (76 mg, 43%) as a white solid. ES(+)-MS (M+H) 425.

166

Example 101

(4S,7R)-2-(2,4-Difluoro-phenyl)-7,8,8-trimethyl-1-(2-trifluoromethyl-benzyl)-1,2,4,5,6,7-hexahydro-4,7-methano-indazol-3-one

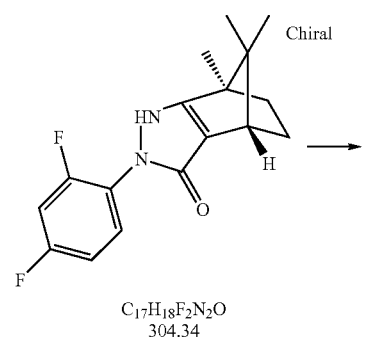

C17H18F2N2O
304.34

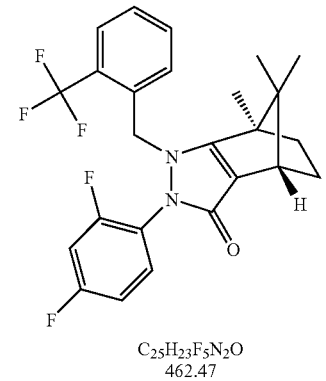

C25H23F5N2O
462.47

A mixture of (4S,7R)-2-(2,4-difluoro-phenyl)-7,8,8-trimethyl-1,2,4,5,6,7-hexahydro-4,7-methano-indazol-3-one (Intermediate 14; 100 mg, 0.33 mmol), tetrabutylammonium iodide (120 mg, 0.32 mmol) and 2-(trifluoromethyl)benzyl bromide (200 µL, 1.3 mmol) in dimethylformamide (2 mL) was heated at 100° C. overnight. Dichloromethane (50 mL) was added and the solution was washed with 1:1 water/brine (20 mL), aqueous sodium thiosulfate, water, and brine. The solution was dried (magnesium sulfate), filtered, evaporated, and purified by column chromatography, eluting with 50-70% ethyl acetate/petroleum ether, to give (4S,7R)-2-(2,4-difluoro-phenyl)-7,8,8-trimethyl-1-(2-trifluoromethyl-benzyl)-1,2,4,5,6,7-hexahydro-4,7-methano-indazol-3-one (52 mg, 34%) as a white solid. APCI(+)-MS (M+H) 463.

Example 102

(4S,7R)-2-(2,4-Difluoro-phenyl)-7,8,8-trimethyl-1-(3-trifluoromethyl-benzyl)-1,2,4,5,6,7-hexahydro-4,7-methano-indazol-3-one

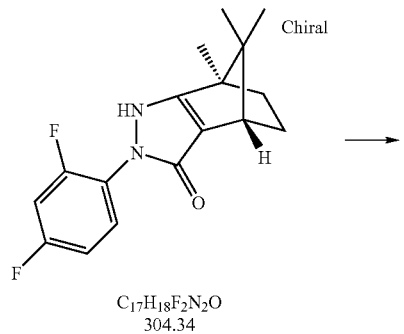

$C_{17}H_{18}F_2N_2O$
304.34

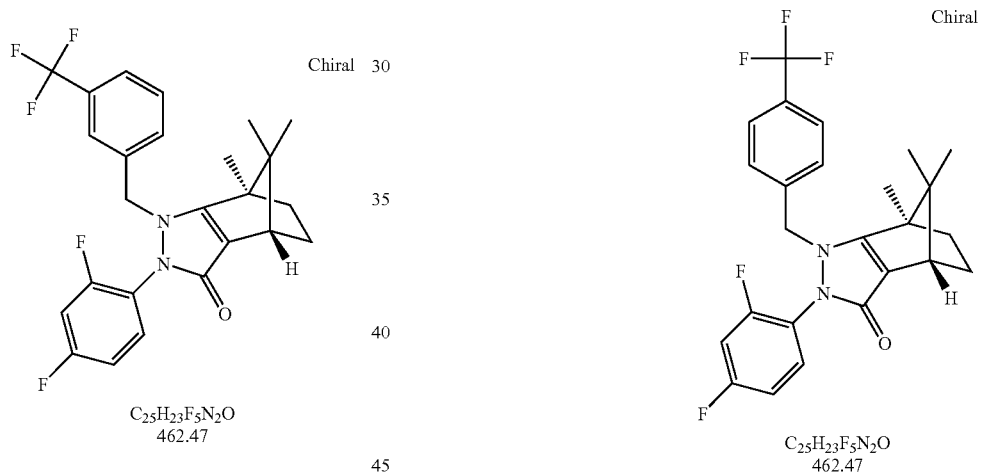

$C_{25}H_{23}F_5N_2O$
462.47

A mixture of (4S,7R)-2-(2,4-difluoro-phenyl)-7,8,8-trimethyl-1,2,4,5,6,7-hexahydro-4,7-methano-indazol-3-one (Intermediate 14; 100 mg, 0.33 mmol), tetrabutylammonium iodide (85 mg, 0.23 mmol) and 3-(trifluoromethyl)benzyl bromide (200 μL, 1.3 mmol) in dimethylformamide (2 mL) was heated at 100° C. overnight. Dichloromethane (50 mL) was added and the solution was washed with water (3×20 mL), 50% aqueous sodium thiosulfate (20 mL), and brine (20 mL). The solution was dried (magnesium sulfate), filtered, evaporated, and purified by column chromatography, eluting with 50-100% ethyl acetate/petroleum ether, to give (4S,7R)-2-(2,4-difluoro-phenyl)-7,8,8-trimethyl-1-(3-trifluoromethyl-benzyl)-1,2,4,5,6,7-hexahydro-4,7-methano-indazol-3-one (108 mg, 71%) as a white solid. APCI(+)-MS (M+H) 463.

Example 103

(4S,7R)-2-(2,4-Difluoro-phenyl)-7,8,8-trimethyl-1-(4-trifluoromethyl-benzyl)-1,2,4,5,6,7-hexahydro-4,7-methano-indazol-3-one

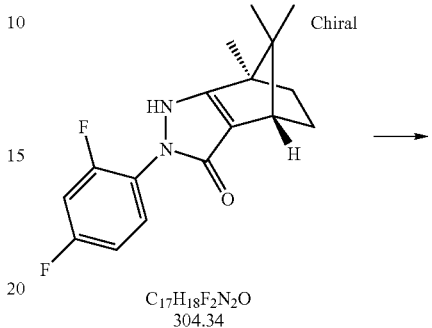

$C_{17}H_{18}F_2N_2O$
304.34

$C_{25}H_{23}F_5N_2O$
462.47

A mixture of (4S,7R)-2-(2,4-difluoro-phenyl)-7,8,8-trimethyl-1,2,4,5,6,7-hexahydro-4,7-methano-indazol-3-one (Intermediate 14; 100 mg, 0.33 mmol), tetrabutylammonium iodide (85 mg, 0.23 mmol) and 4-(trifluoromethyl)benzyl bromide (315 mg, 1.3 mmol) in dimethylformamide (2 mL) was heated at 100° C. overnight. Dichloromethane (50 mL) and a mixture of water (13 mL) and brine (6 mL) were added. The organic layer was washed with 10% aqueous sodium thiosulfate (20 mL), and brine (20 mL). The solution was dried (magnesium sulfate), filtered, evaporated, and purified by column chromatography, eluting with 50% ethyl acetate/petroleum ether, to give (4S,7R)-2-(2,4-difluoro-phenyl)-7,8,8-trimethyl-1-(4-trifluoromethyl-benzyl)-1,2,4,5,6,7-hexahydro-4,7-methano-indazol-3-one (58 mg, 38%) as a white solid. ES(+)-MS (M+H) 463.

Example 104

4-[(4R,7S)-2-(2,4-Difluoro-phenyl)-7,8,8-trimethyl-3-oxo-2,3,4,5,6,7-hexahydro-4,7-methano-indazol-1-ylmethyl]-benzoic acid methyl ester

Example 105

(4R,7S)-1-(2,4-Difluoro-benzyl)-2-(2,4-difluoro-phenyl)-7,8,8-trimethyl-1,2,4,5,6,7-hexahydro-4,7-methano-indazol-3-one

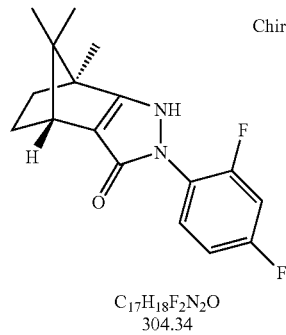

$C_{17}H_{18}F_2N_2O$
304.34

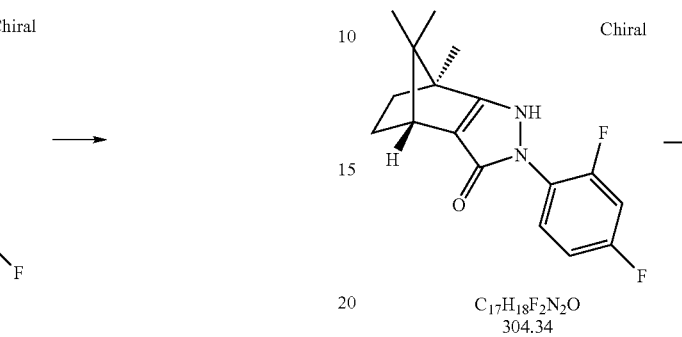

$C_{17}H_{18}F_2N_2O$
304.34

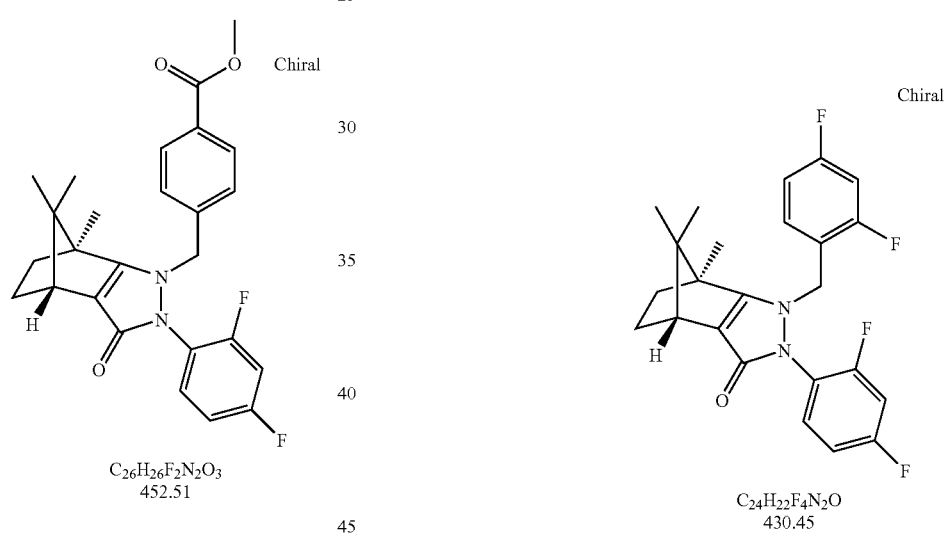

$C_{26}H_{26}F_2N_2O_3$
452.51

$C_{24}H_{22}F_4N_2O$
430.45

A solution of (4R,7S)-2-(2,4-difluoro-phenyl)-7,8,8-trimethyl-1,2,4,5,6,7-hexahydro-4,7-methano-indazol-3-one (Intermediate 42; 300 mg, 0.99 mmol), tetrabutylammonium iodide (270 mg, 0.7 mmol) and methyl 4-(bromomethyl)benzoate (1.00 g, 4.37 mmol) in dimethylformamide (10 mL) was heated at 100° C. for 3 h. The reaction mixture was allowed to cool. Dichloromethane (100 mL) was added, and the solution was washed with (5×25 mL), aqueous sodium thiosulfate (25 mL), and brine (25 mL), dried (magnesium sulfate, filtered, and evaporated. The residue was purified using an ISCO 40 g column, eluting with 50-100% ethyl acetate/hexanes. Fractions containing the product were concentrated and then dried under high vacuum at 50° C. give 4-[(4R,7S)-2-(2,4-difluoro-phenyl)-7,8,8-trimethyl-3-oxo-2,3,4,5,6,7-hexahydro-4,7-methano-indazol-1-ylmethyl]-benzoic acid methyl ester (219 mg, 49%) as a pale yellow solid. ES(+)-MS (M+H) 453.

A solution of (4R,7S)-2-(2,4-difluoro-phenyl)-7,8,8-trimethyl-1,2,4,5,6,7-hexahydro-4,7-methano-indazol-3-one (Intermediate 42; 101 mg, 0.33 mmol), sodium iodide (53 mg, 0.35 mmol) and 2,4-difluorobenzyl bromide (0.22 mL, 1.68 mmol) in dimethylformamide (0.8 mL) was heated under microwave irradiation at 150° C. for 1 h. Ethyl acetate was added and the solution was washed with 10% aqueous sodium thiosulfate (three times), dried (sodium sulfate), filtered, evaporated, and purified on an RS-4g silica gel column, eluting with 20-100% ethyl acetate/hexanes to give (4R,7S)-1-(2,4-Difluoro-benzyl)-2-(2,4-difluoro-phenyl)-7,8,8-trimethyl-1,2,4,5,6,7-hexahydro-4,7-methano-indazol-3-one (82 mg, 58%) as a light brown foam. ES(+)-MS (M+H) 431.

Example 106

(4S,7R)-1-(2,4-Difluoro-benzyl)-2-(2,4-difluoro-phenyl)-7,8,8-trimethyl-1,2,4,5,6,7-hexahydro-4,7-methano-indazol-3-one

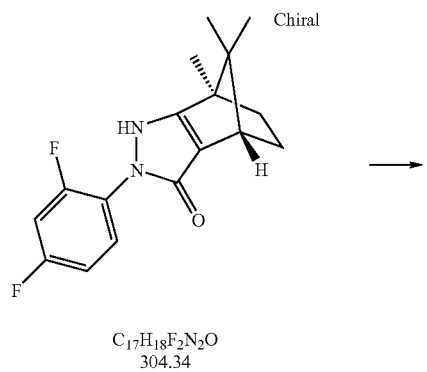

$C_{17}H_{18}F_2N_2O$
304.34

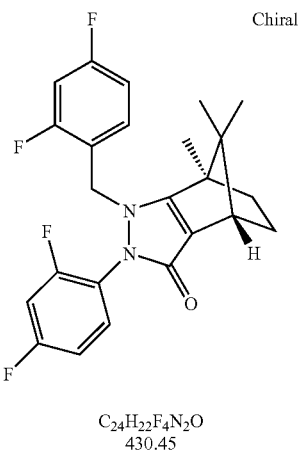

$C_{24}H_{22}F_4N_2O$
430.45

A mixture of (4S,7R)-2-(2,4-difluoro-phenyl)-7,8,8-trimethyl-1,2,4,5,6,7-hexahydro-4,7-methano-indazol-3-one (Intermediate 14; 500 mg, 1.64 mmol), tetrabutylammonium iodide (605 mg, 1.64 mmol) and 2,4-difluorobenzyl bromide (840 µL, 6.54 mmol) in dimethylformamide (10 mL) was heated at 100° C. overnight. Dichloromethane (250 mL) was added and the solution was washed with water (3×100 mL), aqueous sodium thiosulfate (100 mL), and brine (100 mL). The solution was dried (magnesium sulfate), filtered, evaporated, and purified by column chromatography, eluting with 45-50% ethyl acetate/petroleum ether. Fractions homogeneous for the product were concentrated to give an oil which was co-evaporated with ethanol and then held under high vacuum to give (4S,7R)-1-(2,4-difluoro-benzyl)-2-(2,4-difluoro-phenyl)-7,8,8-trimethyl-1,2,4,5,6,7-hexahydro-4,7-methano-indazol-3-one (508 mg, 71%). APCI(+)-MS (M+H) 431.

Example 107

(4S,7R)-2-(2,4-Difluoro-phenyl)-1-(3-fluoro-5-trifluoromethyl-benzyl)-7,8,8-trimethyl-1,2,4,5,6,7-hexahydro-4,7-methano-indazol-3-one

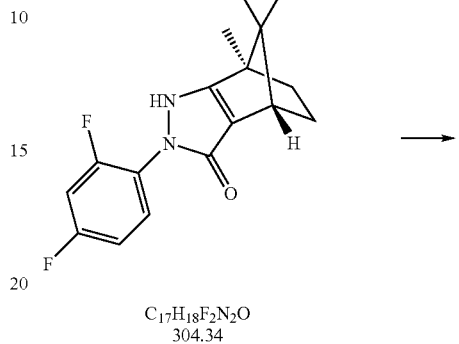

$C_{17}H_{18}F_2N_2O$
304.34

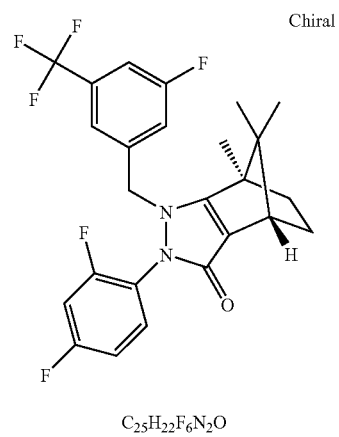

$C_{25}H_{22}F_6N_2O$
480.46

A mixture of (4S,7R)-2-(2,4-difluoro-phenyl)-7,8,8-trimethyl-1,2,4,5,6,7-hexahydro-4,7-methano-indazol-3-one (Intermediate 14; 25 mg, 0.08 mmol), tetrabutylammonium iodide (30 mg, 0.08 mmol) and 3-fluoro-5-trifluoromethyl-benzyl bromide (75 mg, 0.29 mmol) in dimethylformamide (1 mL) was heated at 100° C. overnight. The reaction mixture was diluted with dichloromethane (50 mL) and the solution was washed with water/brine (1:1; 20 mL), water (2×20 mL), sodium thiosulfate (20 mL) and brine (20 mL). The solution was dried (magnesium sulfate), filtered, concentrated and purified by chromatography, eluting with 50% ethyl acetate/petroleum ether, to give (4S,7R)-2-(2,4-difluoro-phenyl)-1-(3-fluoro-5-trifluoromethyl-benzyl)-7,8,8-trimethyl-1,2,4,5,6,7-hexahydro-4,7-methano-indazol-3-one (21 mg, 53%) as an off-white solid. APCI(+)-MS (M+H) 481.

Example 108

(4S,7R)-2-(2,4-Difluoro-phenyl)-1-(4-fluoro-2-trifluoromethyl-benzyl)-7,8,8-trimethyl-1,2,4,5,6,7-hexahydro-4,7-methano-indazol-3-one

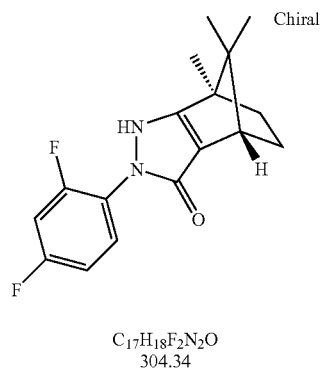

$C_{17}H_{18}F_2N_2O$
304.34

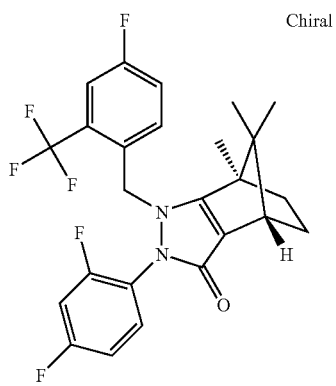

$C_{25}H_{22}F_6N_2O$
480.46

A mixture of (4S,7R)-2-(2,4-difluoro-phenyl)-7,8,8-trimethyl-1,2,4,5,6,7-hexahydro-4,7-methano-indazol-3-one (Intermediate 14; 100 mg, 0.33 mmol), tetrabutylammonium iodide (120 mg, 0.32 mmol) and 4-fluoro-2-(trifluoromethyl) benzyl bromide (204 μL, 1.3 mmol) in dimethylformamide (2 mL) was heated at 100° C. overnight. Dichloromethane (50 mL) was added and the solution was washed with 1:1 water/brine (2×25 mL), aqueous sodium thiosulfate, water, and brine. The solution was dried (magnesium sulfate), filtered, evaporated, and purified by column chromatography, eluting with 50% ethyl acetate/petroleum ether, to give an orange oil. 1H NMR showed that this oil contained some dimethyl formamide. The oil was dissolved in ethyl acetate and the solution was washed with water (3×10 mL), dried (magnesium sulfate), filtered, evaporated, then co-evaporated with ethyl ether and dichlormethane, and held under high vacuum to give (4S,7R)-2-(2,4-difluoro-phenyl)-1-(4-fluoro-2-trifluoromethyl-benzyl)-7,8,8-trimethyl-1,2,4,5,6,7-hexahydro-4,7-methano-indazol-3-one (63 mg, 40%) as a pale foam. APCI (+)-MS (M+H) 481.

Example 109

(4S,7R)-1-(3,5-Bis-trifluoromethyl-benzyl)-2-(2,4-difluoro-phenyl)-7,8,8-trimethyl-1,2,4,5,6,7-hexahydro-4,7-methano-indazol-3-one

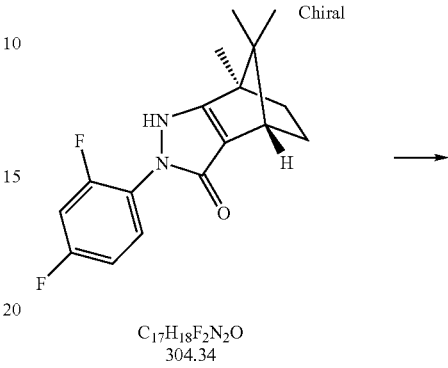

$C_{17}H_{18}F_2N_2O$
304.34

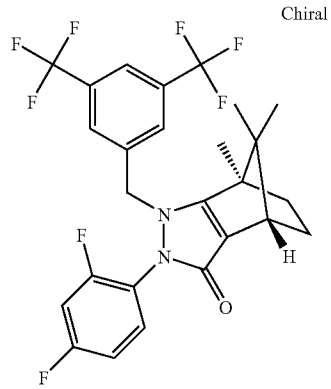

$C_{26}H_{22}F_8N_2O$
530.47

A mixture of (4S,7R)-2-(2,4-difluoro-phenyl)-7,8,8-trimethyl-1,2,4,5,6,7-hexahydro-4,7-methano-indazol-3-one (Intermediate 14; 100 mg, 0.33 mmol), tetrabutylammonium iodide (120 mg, 0.32 mmol) and 3,5-bis(trifluoromethyl)benzyl bromide (240 μL, 1.3 mmol) in dimethylformamide (2 mL) was heated at 100° C. overnight. Dichloromethane (50 mL) was added and the solution was washed with 1:1 water/brine (20 mL), water (2×20 mL), aqueous sodium thiosulfate (20 mL), and brine (20 mL). The solution was dried (magnesium sulfate), filtered, evaporated, and purified by column chromatography, eluting with 45-50% ethyl acetate/petroleum ether, to give an oil. The oil was co-evaporated with ethanol, and the residue was held under high vacuum to give (4S,7R)-1-(3,5-bis-trifluoromethyl-benzyl)-2-(2,4-difluoro-phenyl)-7,8,8-trimethyl-1,2,4,5,6,7-hexahydro-4,7-methano-indazol-3-one (128 mg, 73%) as a white solid. APCI (+)-MS (M+H) 531.

Example 110

(4S,7R)-2-(2,4-Difluoro-phenyl)-7,8,8-trimethyl-1-(3-oxo-3-phenyl-propyl)-1,2,4,5,6,7-hexahydro-4,7-methano-indazol-3-one

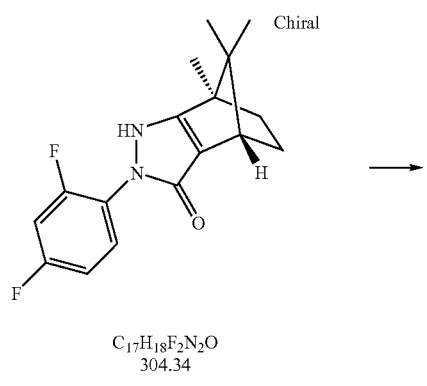

C$_{17}$H$_{18}$F$_2$N$_2$O
304.34

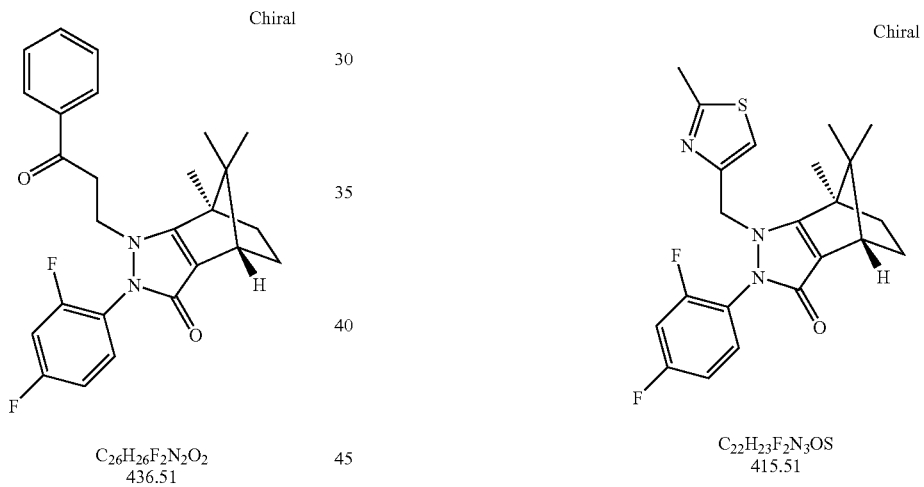

C$_{26}$H$_{26}$F$_2$N$_2$O$_2$
436.51

A mixture of (4S,7R)-2-(2,4-difluoro-phenyl)-7,8,8-trimethyl-1,2,4,5,6,7-hexahydro-4,7-methano-indazol-3-one (Intermediate 14; 330 mg, 1.08 mmol), tetrabutylammonium iodide (400 mg, 1.08 mmol) and 3-chloropropiophenone (Acros; 820 mg, 4.86 mmol) in dimethylformamide (6 mL) was heated at 100° C. for 3.5 h. The reaction mixture was cooled to room temperature. Dichloromethane (100 mL) was added and the solution was washed with water (4×25 mL), aqueous sodium thiosulfate (25 mL), and brine (25 mL). The solution was dried (magnesium sulfate), filtered, evaporated, and purified using an ISCO 40 g column, eluting with 50-100% ethyl acetate/hexane. The resulting material was dried under high vacuum at 70° C. for 3 h to give (4S,7R)-2-(2,4-difluoro-phenyl)-7,8,8-trimethyl-1-(3-oxo-3-phenyl-propyl)-1,2,4,5,6,7-hexahydro-4,7-methano-indazol-3-one (290 mg, 61%) as a tan solid. APCI(+)-MS (M+H) 437.

Example 111

(4S,7R)-2-(2,4-Difluoro-phenyl)-7,8,8-trimethyl-1-(2-methyl-thiazol-4-ylmethyl)-1,2,4,5,6,7-hexahydro-4,7-methano-indazol-3-one

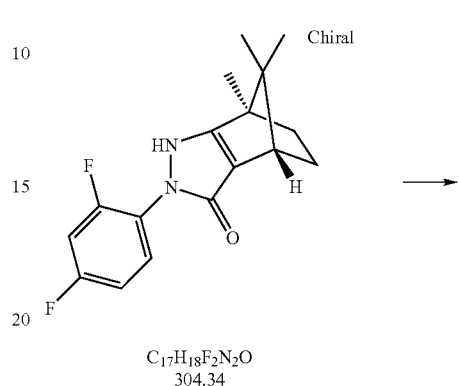

C$_{17}$H$_{18}$F$_2$N$_2$O
304.34

C$_{22}$H$_{23}$F$_2$N$_3$OS
415.51

A mixture of (4S,7R)-2-(2,4-difluoro-phenyl)-7,8,8-trimethyl-1,2,4,5,6,7-hexahydro-4,7-methano-indazol-3-one (Intermediate 14; 100 mg, 0.33 mmol), tetrabutylammonium iodide (120 mg, 0.32 mmol) and 4-(chloromethyl)-2-methylthiazole (Maybridge plc, Tintagel, Cornwall, UK; 197 mg, 1.3 mmol) in dimethylformamide (2 mL) was heated at 100° C. overnight. Dichloromethane (50 mL) was added and the solution was washed with 1:1 water/brine (2×25 mL) and the combined aqueous washes were back-extracted with dichloromethane (50 mL). The combined organic extracts were washed with saturated aqueous sodium thiosulfate (50 mL), and brine (50 mL). The solution was dried (magnesium sulfate), filtered, evaporated, and purified by column chromatography, eluting with 50-70% ethyl acetate/petroleum ether, to give (4S,7R)-2-(2,4-difluoro-phenyl)-7,8,8-trimethyl-1-(2-methyl-thiazol-4-ylmethyl)-1,2,4,5,6,7-hexahydro-4,7-methano-indazol-3-one (59 mg, 43%) as a light tan solid. APCI(+)-MS (M+H) 416.

Example 112

(4R,7S)-2-(2,4-Difluoro-phenyl)-1-(2-hydroxy-pyridin-3-ylmethyl)-7,8,8-trimethyl-1,2,4,5,6,7-hexahydro-4,7-methano-indazol-3-one

Example 113

(4R,7S)-2-(2,4-Difluoro-phenyl)-1-(2-methoxy-pyridin-3-ylmethyl)-7,8,8-trimethyl-1,2,4,5,6,7-hexahydro-4,7-methano-indazol-3-one

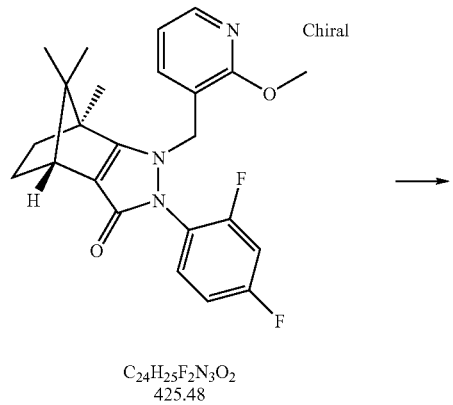

$C_{24}H_{25}F_2N_3O_2$
425.48

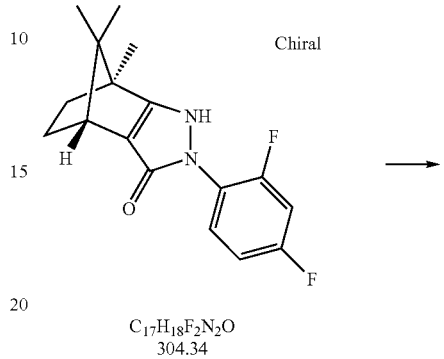

$C_{17}H_{18}F_2N_2O$
304.34

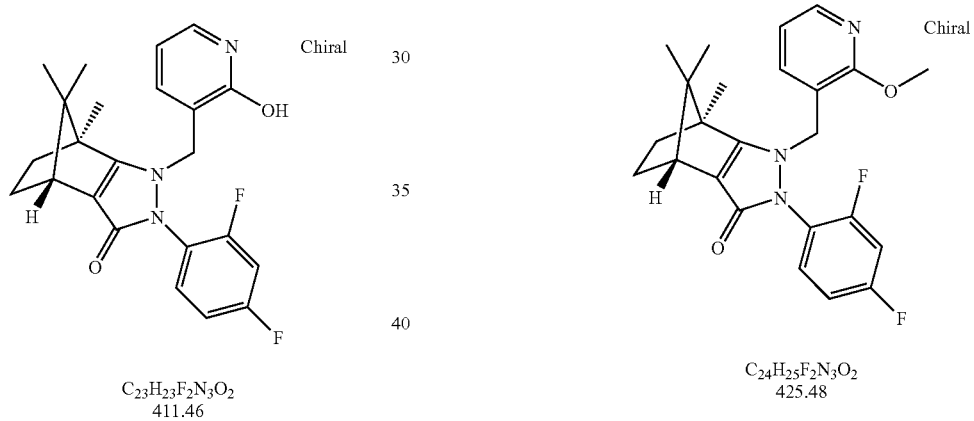

$C_{23}H_{23}F_2N_3O_2$
411.46

$C_{24}H_{25}F_2N_3O_2$
425.48

A mixture of (4R,7S)-2-(2,4-difluoro-phenyl)-1-(2-methoxy-pyridin-3-ylmethyl)-7,8,8-trimethyl-1,2,4,5,6,7-hexahydro-4,7-methano-indazol-3-one (Example 113; 149 mg, 0.35 mmol), ethanol (440 µL) and concentrated aqueous hydrochloric acid (440 µL) was heated at 75° C. overnight, and then at ~100° C. for 40 min. Water (10 mL) was added and the mixture was neutralized to pH 7-8 by the dropwise addition of saturated aqueous sodium hydrogen carbonate solution. The resulting mixture was extracted with dichloromethane (2×25 mL). The combined organic layers were washed with brine (10 mL), dried (magnesium sulfate), filtered, evaporated, purified using a Biotage 40S system, eluting with 3-4% methanol/dichcloromethane, and then dried in a vacuum overn for 3 days to give (4R,7S)-2-(2,4-difluoro-phenyl)-1-(2-hydroxy-pyridin-3-ylmethyl)-7,8,8-trimethyl-1,2,4,5,6,7-hexahydro-4,7-methano-indazol-3-one (108 mg, 75%) as an off-white solid. APCI(+)-MS (M+H) 412.

A mixture of (4R,7S)-2-(2,4-difluoro-phenyl)-7,8,8-trimethyl-1,2,4,5,6,7-hexahydro-4,7-methano-indazol-3-one (Intermediate 42; 476 mg, 1.56 mmol), 3-chloromethyl-2-methoxy-pyridine (Intermediate 51; 989 mg, 6.3 mmol) and tetrabutylammonium iodide (580 mg, 1.6 mmol) in dimethylformamide (16 mL) was heated at 100° C. for 48 h. The solvent was evaporated and dichloromethane (250 mL) was added. The solution was washed with concentrated aqueous sodium thiosulfate (2×100 mL), saturated aqueous sodium hydrogen carbonate (100 mL), water (6×500 mL) and brine (100 mL), dried (magnesium sulfate), filtered, evaporated and purified using a Biotage 40L system, eluting with 1-2% methanol/dichcloromethane to give an oily material. This material was dried on a vacuum pump, co-evaporated three times with ethanol, and finally held again under high vacuum to give (4R,7S)-2-(2,4-difluoro-phenyl)-1-(2-methoxy-pyridin-3-ylmethyl)-7,8,8-trimethyl-1,2,4,5,6,7-hexahydro-4,7-methano-indazol-3-one (201 mg, 30%) as an off-white solid. ES(+)-MS (M+H) 426.

Example 114

(4R,7S)-2-(2,4-Difluoro-phenyl)-1-(6-methoxy-pyridin-3-ylmethyl)-7,8,8-trimethyl-1,2,4,5,6,7-hexahydro-4,7-methano-indazol-3-one

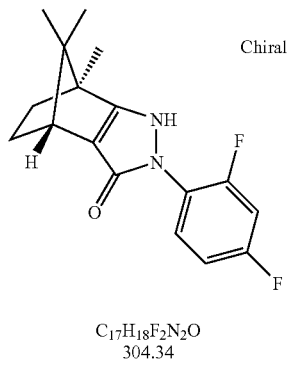

A mixture of (4R,7S)-2-(2,4-difluoro-phenyl)-7,8,8-trimethyl-1,2,4,5,6,7-hexahydro-4,7-methano-indazol-3-one (Intermediate 42; 480 mg, 1.6 mmol), 5-chloromethyl-2-methoxy-pyridine (Intermediate 50; 995 mg, 6.3 mmol) and tetrabutylammonium iodide (583 mg, 1.6 mmol) in dimethylformamide (63 mL) was heated at 100° C. for 48 h. The solvent was evaporated and dichloromethane (150 mL) was added. The solution was washed with saturated aqueous sodium thiosulfate (200 mL), saturated aqueous sodium hydrogen carbonate (200 mL) and brine (200 mL), dried (sodium sulfate), filtered, evaporated and purified using a Biotage 40M system, eluting with 20-50% ethyl acetate/hexanes and then 2% methanol/dichloromethane, to give a crude product that contains some tetrabutylammonium iodide. This material was taken up in dichloromethane (50 mL) and washed with 5% dimethylformamide in water (2×100 mL) and water (5×100 mL). The organic phase was dried (sodium sulfate), filtered and evaporated to give (4R,7S)-2-(2,4-difluoro-phenyl)-1-(6-methoxy-pyridin-3-ylmethyl)-7,8,8-trimethyl-1,2,4,5,6,7-hexahydro-4,7-methano-indazol-3-one (59 mg, 9%). APCI(+)-MS (M+H) 426.

Example 115

(4S,7R)-2-(2,5-Difluoro-phenyl)-1,7,8,8-tetramethyl-1,2,4,5,6,7-hexahydro-4,7-methano-indazol-3-one

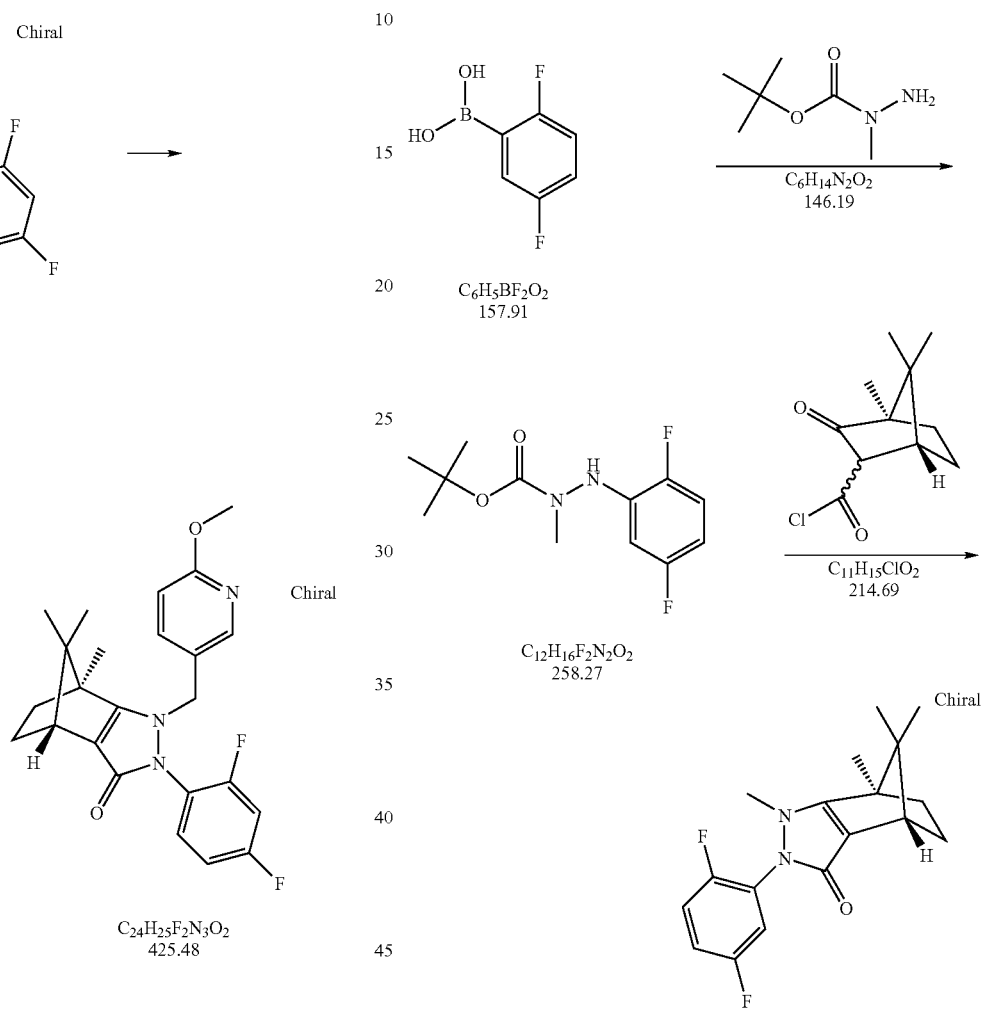

Step 1: N-(2,5-Difluoro-phenyl)-N-methyl-hydrazinecarboxylic acid tert-butyl ester A mixture of N-methyl-hydrazinecarboxylic acid tert-butyl ester (Intermediate 1; 500 mg, 3.4 mmol), 2,5-difluorophenylboronic acid (Aldrich; 529 mg, 3.35 mmol), copper (II) acetate (621 mg, 3.4 mmol) and triethylamine (480 µL, 3.4 mmol) in 1,2-dichloroethane (4 mL) was heated in an oil bath at 50° C. for 3 h. The mixture was allowed to cool, and it was then adsorbed onto silica gel and purified by chromatography using an ISCO 40 g column, eluting with 20-40% ethyl acetate/hexanes, to give N'-(2,5-difluoro-phenyl)-N-methyl-hydrazinecarboxylic acid tert-butyl ester (305 mg, 35%) as a colorless oil.

Step 2: (4S,7R)-2-(2,5-Difluoro-phenyl)-1,7,8,8-tetramethyl-1,2,4,5,6,7-hexahydro-4,7-methano-indazol-3-one Triethylamine (1 mL, 7.2 mmol) was added dropwise to a solution of N'-(2,5-difluoro-phenyl)-N'-methyl-hydrazinecarboxylic acid tert-butyl ester (305 mg, 1.2 mmol) in 1,2-dichloroethane (6 mL) over 1 min. The reaction mixture was stirred for 5 min and then a solution of (1R,4R)-4,7,7-trimethyl-3-oxo-bicyclo[2.2.1]heptane-2-carbonyl chloride (Intermediate 20; 800 mg, 3.7 mmol) in 1,2-dichloroethane (14 mL) was added over 2 min. The reaction mixture was heated in an oil bath at 50° C. for 1 h. The solution was allowed to cool and a solution of HCl in dioxane (4 M; 6 mL, 24 mmol) was added and the mixture was heated at reflux for 1.5 h and then allowed to cool to room temperature. The solvent was evaporated and the residue was purified by preparative HPLC to give a yellow foam. This was taken up in ethyl acetate and washed with water. The organic layer was evaporated and the residue was further purified on an ISCO system, eluting with 50-90% ethyl acetate/hexanes. Fractions homogeneous for the product were evaporated, co-evaporated successively with methanol, and diethyl ether, and then dried under high vacuum at 75° C. overnight to give (4S,7R)-2-(2,5-difluoro-phenyl)-1,7,8,8-tetramethyl-1,2,4,5,6,7-hexahydro-4,7-methano-indazol-3-one (105 mg, 27%) as a white solid. ES(+)-MS (M+H) 319.

Example 116

(4S,7R)-2-(2,6-Difluoro-phenyl)-1,7,8,8-tetramethyl-1,2,4,5,6,7-hexahydro-4,7-methano-indazol-3-one

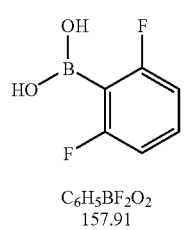

$C_6H_5BF_2O_2$
157.91

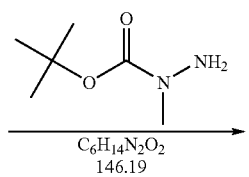

$C_6H_{14}N_2O_2$
146.19

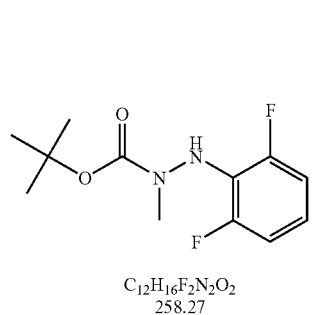

$C_{12}H_{16}F_2N_2O_2$
258.27

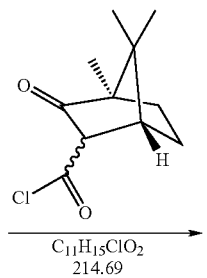

$C_{11}H_{15}ClO_2$
214.69

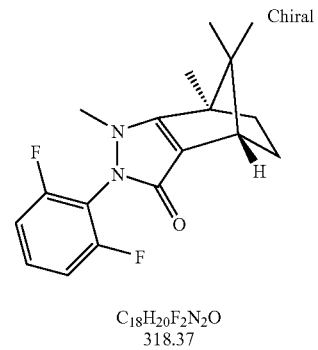

$C_{18}H_{20}F_2N_2O$
318.37

Step 1: N'-(2,6-Difluoro-phenyl)-N-methyl-hydrazinecarboxylic acid tert-butyl ester A mixture of N-methyl-hydrazinecarboxylic acid tert-butyl ester (Intermediate 1; 1.00 g, 6.8 mmol), 2,6-difluorophenylboronic acid (Aldrich; 1.07 g, 6.8 mmol), copper(II) acetate (1.24 g, 6.8 mmol) and triethylamine (960 µL, 6.8 mmol) in 1,2-dichloroethane (15 mL) was heated in an oil bath at 50° C. overnight. The mixture was allowed to cool, and it was then adsorbed onto silica gel and purified by chromatography using an ISCO 120 g column, eluting with 20-25% ethyl acetate/hexanes, to give N'-(2,6-difluoro-phenyl)-N-methyl-hydrazinecarboxylic acid tert-butyl ester (167 mg, 9%) as a colorless oil.

Step 2: (4S,7R)-2-(2,6-Difluoro-phenyl)-1,7,8,8-tetramethyl-1,2,4,5,6,7-hexahydro-4,7-methano-indazol-3-one Triethylamine (300 µL, 2.15 mmol) was added dropwise to a cooled (0° C.) solution of (1R,4R)-4,7,7-trimethyl-3-oxo-bicyclo[2.2.1]heptane-2-carbonyl chloride (Intermediate 20; 220 mg, 1.03 mmol) in 1,2-dichloroethane (3 mL) over 1 min. The reaction mixture was stirred for 5 min and then a solution of N-(2,6-difluoro-phenyl)-N'-methyl-hydrazinecarboxylic acid tert-butyl ester (167 mg, 0.65 mmol) in 1,2-dichloroethane (6 mL) was added over 2 min. The reaction mixture was stirred at 0° C. for 15 min, at room temperature for 30 min, and then in an oil bath at 50° C. for 1 h. The solution was allowed to cool and a solution of HCl in dioxane (4 M; 4 mL, 16 mmol) was added and the mixture was heated at reflux for 1.5 h and then allowed to cool to room temperature. Dichloromethane (100 mL) was added and the mixture was washed with 1:1 water/brine (20 mL), dried (magnesium sulfate), filtered, evaporated, and purified using an ISCO 40 g column, eluting with 20-100% ethyl acetate/hexanes. Fractions homogeneous for the product were evaporated, and co-evaporated successively with methanol and diethyl ether. The residue was dried overnight under high vacuum at 70° C. to give (4S,7R)-2-(2,6-difluoro-phenyl)-1,7,8,8-tetramethyl-1,2,4,5,6,7-hexahydro-4,7-methano-indazol-3-one (97 mg, 47%) as an off-white solid. ES(+)-MS (M+H) 319.

Example 117

(4S,7R)-2-(2-Chloro-4-fluoro-phenyl)-1-ethyl-7,8,8-trimethyl-1,2,4,5,6,7-hexahydro-4,7-methano-indazol-3-one

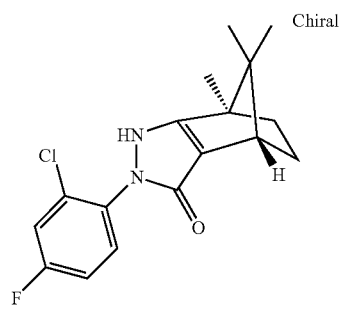

C₁₇H₁₈ClFN₂O
320.80

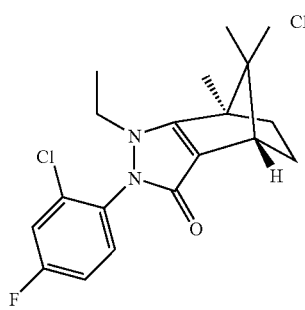

C₁₉H₂₂ClFN₂O
348.85

A mixture of (4S,7R)-2-(2-chloro-4-fluoro-phenyl)-7,8,8-trimethyl-1,2,4,5,6,7-hexahydro-4,7-methano-indazol-3-one (Intermediate 21; 200 mg, 0.62 mmol) and iodoethane (250 μL, 3.1 mmol) in dimethylformamide (4 mL) was heated at 95° C. overnight and then stirred at room temperature over the weekend. The solvent was evaporated and dichloromethane (50 mL) was added. The solution was washed with water (2×20 mL), saturated aqueous sodium thiosulfate (20 mL), and brine (20 mL), dried (magnesium sulfate), filtered, concentrated and purified by chromatography, eluting with 60-75% ethyl acetate/petroleum ether, to give (4S,7R)-2-(2-chloro-4-fluoro-phenyl)-1-ethyl-7,8,8-trimethyl-1,2,4,5,6,7-hexahydro-4,7-methano-indazol-3-one (62 mg, 29%) as an off-white solid. APCI(+)-MS (M+H) 349.

Example 118

(4R,7S)-2-(2-Chloro-4-fluoro-phenyl)-7,8,8-trimethyl-1-(3-methyl-butyl)-1,2,4,5,6,7-hexahydro-4,7-methano-indazol-3-one

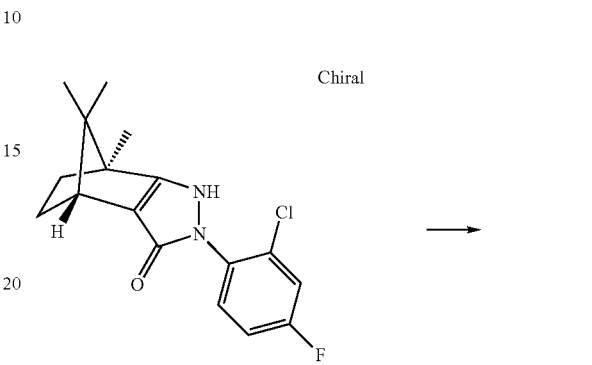

C₁₇H₁₈ClFN₂O
320.80

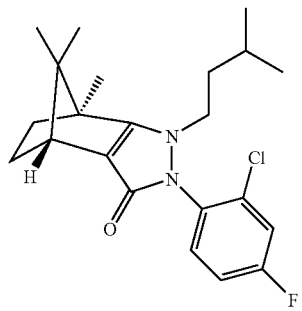

C₂₂H₂₈ClFN₂O
390.93

A mixture of (4R,7S)-2-(2-chloro-4-fluoro-phenyl)-7,8,8-trimethyl-1,2,4,5,6,7-hexahydro-4,7-methano-indazol-3-one (Intermediate 43; 150 mg, 0.47 mmol), tetrabutylammonium iodide (174 mg, 0.47 mmol) and 1-iodo-3-methylbutane (230 μL, 1.75 mmol) in dimethylformamide (3 mL) was heated at 80° C. for 4 days. The solvent was evaporated and dichloromethane (50 mL) was added. The solution was washed with water (2×20 mL), saturated aqueous sodium thiosulfate (20 mL), and brine (20 mL), dried (magnesium sulfate), filtered, concentrated, purified by chromatography, eluting with 60-80% ethyl acetate/petroleum ether, and dried under high vacuum overnight to give (4R,7S)-2-(2-chloro-4-fluoro-phenyl)-7,8,8-trimethyl-1-(3-methyl-butyl)-1,2,4,5,6,7-hexahydro-4,7-methano-indazol-3-one (31 mg, 17%) as a tacky oil. APCI(+)-MS (M+H) 391.

Example 119

(4S,7R)-2-(2-Chloro-4-fluoro-phenyl)-7,8,8-trimethyl-1-(3-methyl-butyl)-1,2,4,5,6,7-hexahydro-4,7-methano-indazol-3-one

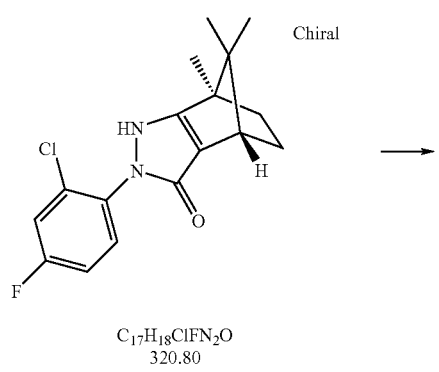

C₁₇H₁₈ClFN₂O
320.80

C₂₂H₂₈ClFN₂O
390.93

A mixture of (4S,7R)-2-(2-chloro-4-fluoro-phenyl)-7,8,8-trimethyl-1,2,4,5,6,7-hexahydro-4,7-methano-indazol-3-one (Intermediate 21; 200 mg, 0.62 mmol) and 1-iodo-3-methylbutane (410 µL, 3.1 mmol) in dimethylformamide (4 mL) was heated at 100° C. overnight and then stirred at room temperature over the weekend. The solvent was evaporated and dichloromethane (50 mL) was added. The solution was washed with water (2×20 mL), saturated aqueous sodium thiosulfate (20 mL), and brine (20 mL), dried (magnesium sulfate), filtered, concentrated, purified by chromatography, eluting with 65% ethyl acetate/petroleum ether, and dried under high vacuum over the weekend to give (4S,7R)-2-(2-chloro-4-fluoro-phenyl)-7,8,8-trimethyl-1-(3-methyl-butyl)-1,2,4,5,6,7-hexahydro-4,7-methano-indazol-3-one (91 mg, 38%) as an off-white solid. APCI(+)-MS (M+H) 391.

Example 120

(4R,7S)-1-Benzyl-2-(2-chloro-4-fluoro-phenyl)-7,8,8-trimethyl-1,2,4,5,6,7-hexahydro-4,7-methano-indazol-3-one

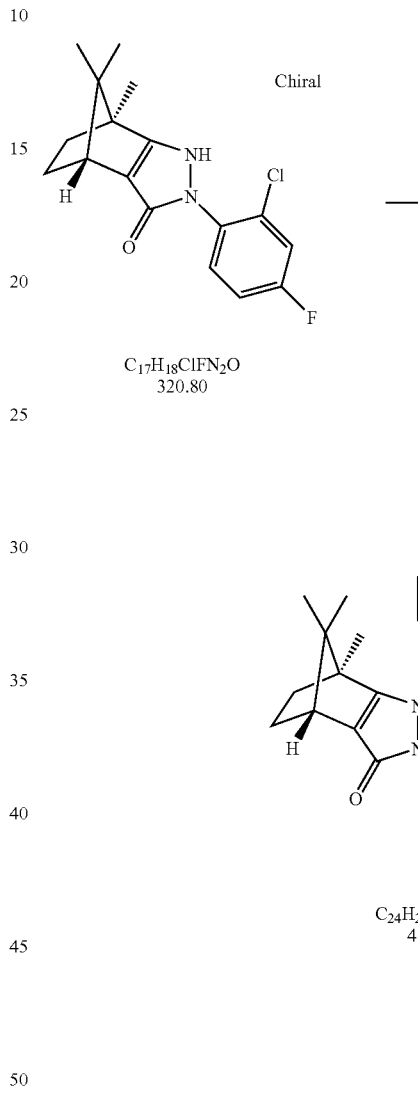

C₁₇H₁₈ClFN₂O
320.80

C₂₄H₂₄ClFN₂O
410.92

A mixture of (4R,7S)-2-(2-chloro-4-fluoro-phenyl)-7,8,8-trimethyl-1,2,4,5,6,7-hexahydro-4,7-methano-indazol-3-one (Intermediate 43; 150 mg, 0.47 mmol), tetrabutylammonium iodide (174 mg, 0.47 mmol) and benzyl bromide (223 µL, 1.9 mmol) in dimethylformamide (3 mL) was heated at 80° C. overnight and then stirred at room temperature over the weekend. The solvent was evaporated and dichloromethane (50 mL) was added. The solution was washed with water (2×20 mL), saturated aqueous sodium thiosulfate (20 mL), and brine (20 mL), dried (magnesium sulfate), filtered, concentrated, purified by chromatography, eluting with 60-70% ethyl acetate/petroleum ether, and dried under high vacuum overnight to give (4R,7S)-1-benzyl-2-(2-chloro-4-fluoro-phenyl)-7,8,8-trimethyl-1,2,4,5,6,7-hexahydro-4,7-methano-indazol-3-one (92 mg, 38%) as a light tan solid. APCI(+)-MS (M+H) 411.

Example 121

(4R,7S)-2-(2-Chloro-4-fluoro-phenyl)-1-(4-fluoro-benzyl)-7,8,8-trimethyl-1,2,4,5,6,7-hexahydro-4,7-methano-indazol-3-one

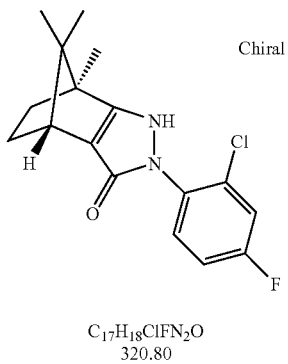

C$_{17}$H$_{18}$ClFN$_2$O
320.80

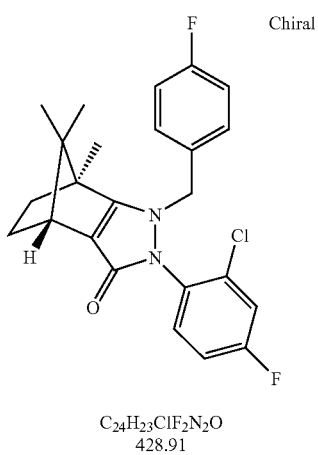

C$_{24}$H$_{23}$ClF$_2$N$_2$O
428.91

A mixture of (4R,7S)-2-(2-chloro-4-fluoro-phenyl)-7,8,8-trimethyl-1,2,4,5,6,7-hexahydro-4,7-methano-indazol-3-one (Intermediate 43; 150 mg, 0.47 mmol), tetrabutylammonium iodide (174 mg, 0.47 mmol) and 4-fluorobenzyl bromide (230 µL, 1.85 mmol) in dimethylformamide (3 mL) was heated at 80° C. overnight. The solvent was evaporated and dichloromethane (50 mL) was added. The solution was washed with water (2×20 mL), saturated aqueous sodium thiosulfate (20 mL), and brine (20 mL), dried (magnesium sulfate), filtered, concentrated, purified by chromatography, eluting with 50-60% ethyl acetate/petroleum ether, and dried under high vacuum for 2 days to give (4R,7S)-2-(2-chloro-4-fluoro-phenyl)-1-(4-fluoro-benzyl)-7,8,8-trimethyl-1,2,4,5,6,7-hexahydro-4,7-methano-indazol-3-one (103 mg, 51%) as a light brown solid. APCI(+)-MS (M+H) 429.

Example 122

(4R,7S)-2-(2-Chloro-4-fluoro-phenyl)-1-(2,4-difluoro-benzyl)-7,8,8-trimethyl-1,2,4,5,6,7-hexahydro-4,7-methano-indazol-3-one

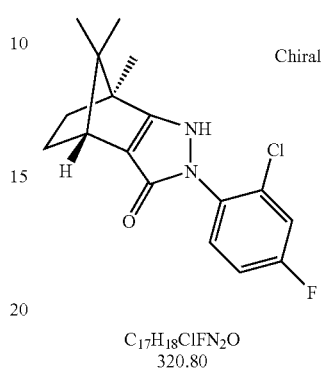

C$_{17}$H$_{18}$ClFN$_2$O
320.80

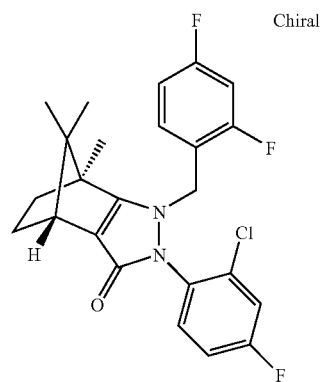

C$_{24}$H$_{22}$ClF$_3$N$_2$O
446.90

A mixture of (4R,7S)-2-(2-chloro-4-fluoro-phenyl)-7,8,8-trimethyl-1,2,4,5,6,7-hexahydro-4,7-methano-indazol-3-one (Intermediate 43; 150 mg, 0.47 mmol), tetrabutylammonium iodide (174 mg, 0.47 mmol) and 2,4-difluorobenzyl bromide (240 µL, 1.9 mmol) in dimethylformamide (3 mL) was heated at 80° C. overnight. The solvent was evaporated and dichloromethane (50 mL) was added. The solution was washed with water (2×20 mL), saturated aqueous sodium thiosulfate (20 mL), and brine (20 mL), dried (magnesium sulfate), filtered, concentrated, purified by chromatography, eluting with 50-60% ethyl acetate/petroleum ether, and dried under high vacuum overnight to give (4R,7S)-2-(2-chloro-4-fluoro-phenyl)-1-(2,4-difluoro-benzyl)-7,8,8-trimethyl-1,2,4,5,6,7-hexahydro-4,7-methano-indazol-3-one (123 mg, 59%) as a light brown solid. APCI(+)-MS (M+H) 447.

Example 123

(4S,7R)-2-(2-Chloro-4-fluoro-phenyl)-1-(2,4-difluoro-benzyl)-7,8,8-trimethyl-1,2,4,5,6,7-hexahydro-4,7-methano-indazol-3-one

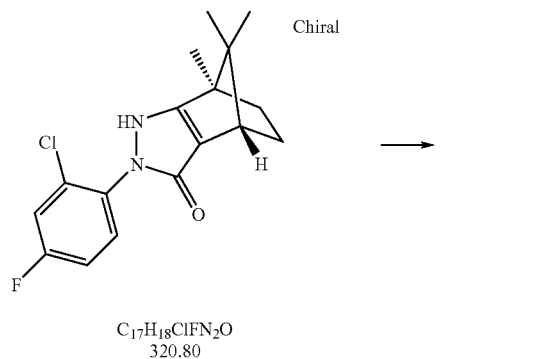

A mixture of (4S,7R)-2-(2-chloro-4-fluoro-phenyl)-7,8,8-trimethyl-1,2,4,5,6,7-hexahydro-4,7-methano-indazol-3-one (Intermediate 21; 200 mg, 0.62 mmol), tetrabutylammonium iodide (229 mg, 0.62 mmol) and 2,4-difluorobenzyl bromide (320 μL, 2.5 mmol) in dimethylformamide (4 mL) was heated at 80° C. overnight. The solvent was evaporated and dichloromethane (50 mL) was added. The solution was washed with water (2×20 mL), saturated aqueous sodium thiosulfate (20 mL), and brine (20 mL), dried (magnesium sulfate), filtered, concentrated and purified by chromatography, eluting with 60-70% ethyl acetate/petroleum ether, to give (4S,7R)-2-(2-chloro-4-fluoro-phenyl)-1-(2,4-difluoro-benzyl)-7,8,8-trimethyl-1,2,4,5,6,7-hexahydro-4,7-methano-indazol-3-one (182 mg, 68%) as an off-white solid. APCI(+)-MS (M+H) 447.

Example 124

(4S,7R)-2-(2-Chloro-5-fluoro-phenyl)-1,7,8,8-tetramethyl-1,2,4,5,6,7-hexahydro-4,7-methano-indazol-3-one

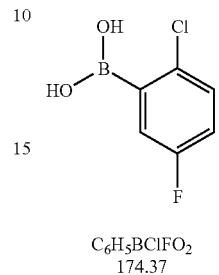

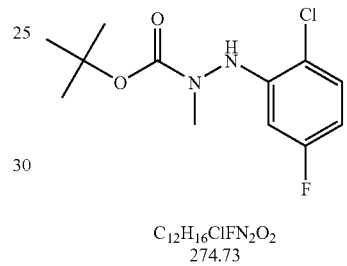

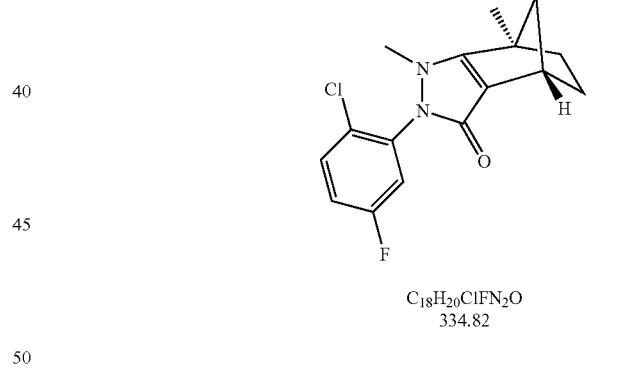

Step 1: N'-(2-Chloro-5-fluoro-phenyl)-N-methyl-hydrazinecarboxylic acid tert-butyl ester A mixture of N-methyl-hydrazinecarboxylic acid tert-butyl ester (Intermediate 1; 650 mg, 4.4 mmol), 2-chloro-5-fluorophenylboronic acid (Aldrich; 760 mg, 4.35 mmol), copper(II) acetate (807 mg, 4.4 mmol) and triethylamine (623 μL, 4.4 mmol) in 1,2-dichloroethane (4.5 mL) was heated in an oil bath at 50° C. for 3 h. The mixture was allowed to cool, and it was then adsorbed onto silica gel and purified by chromatography using an ISCO 40 g column, eluting with 20-40% ethyl acetate/hexanes, to give N'-(2-chloro-5-fluoro-phenyl)-N-methyl-hydrazinecarboxylic acid tert-butyl ester (322 mg, 27%) as a colorless oil.

Step 2: (4S,7R)-2-(2-Chloro-5-fluoro-phenyl)-1,7,8,8-tetramethyl-1,2,4,5,6,7-hexahydro-4,7-methano-indazol-3-one Triethylamine (1 mL, 7.2 mmol) was added dropwise to a solution of (1R,4R)-4,7,7-trimethyl-3-oxo-bicyclo[2.2.1]heptane-2-carbonyl chloride (Intermediate 20; 800 mg, 3.7 mmol) in 1,2-dichloroethane (6 mL) over 1 min. The reaction mixture was stirred for 5 min and then a solution of N'-(2-chloro-5-fluoro-phenyl)-M-methyl-hydrazinecarboxylic acid tert-butyl ester (322 mg, 1.2 mmol) in 1,2-dichloroethane (14 mL) was added over 2 min. The reaction mixture was heated in an oil bath at 50° C. for 1 h. The solution was allowed to cool and a solution of HCl in dioxane (4 M; 6 mL, 24 mmol) was added and the mixture was heated at reflux for 1.5 h and then allowed to cool to room temperature. The solvent was evaporated and the residue was purified on an ISCO system, eluting with 50-100% ethyl acetate/hexanes. Fractions homogeneous for the product were evaporated, and the residue was treated with ether containing a small amount of methanol. The solid was filtered off. 1H NMR showed product plus triethylamine hydrochloride. This material was dissolved in dichloromethane and washed five times with water, and then with saturated aqueous sodium carbonate, and finally with brine. The solution was dried (magnesium sulfate), filtered, evaporated, and dried under high vacuum to give (4S,7R)-2-(2-chloro-5-fluoro-phenyl)-1,7,8,8-tetramethyl-1,2,4,5,6,7-hexahydro-4,7-methano-indazol-3-one (219 mg, 55%) as a white solid. ES(+)-MS (M+H) 335.

Example 125

(4S,7R)-2-(3-Chloro-2-fluoro-phenyl)-1,7,8,8-tetramethyl-1,2,4,5,6,7-hexahydro-4,7-methano-indazol-3-one

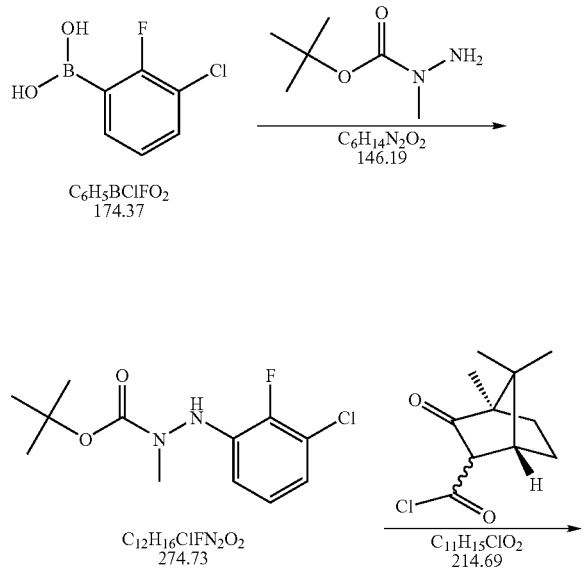

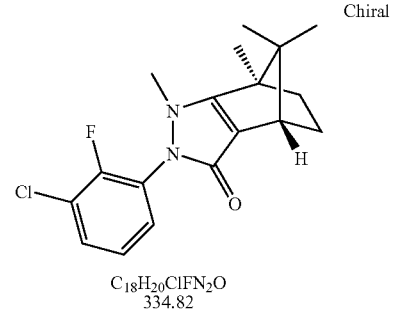

$C_{18}H_{20}ClFN_2O$
334.82

Step 1: N'-(3-Chloro-2-fluoro-phenyl)-N-methyl-hydrazinecarboxylic acid tert-butyl ester A mixture of N-methyl-hydrazinecarboxylic acid tert-butyl ester (Intermediate 1; 500 mg, 3.4 mmol), 3-chloro-2-fluorophenylboronic acid (Aldrich; 584 mg, 3.35 mmol), copper(II) acetate (621 mg, 3.4 mmol) and triethylamine (480 μL, 3.4 mmol) in 1,2-dichloroethane (4 mL) was heated in an oil bath at 50° C. for 3 h. The mixture was allowed to cool, and it was then adsorbed onto silica gel and purified by chromatography using an ISCO 40 g column, eluting with 20-40% ethyl acetate/hexanes, to give N'-(3-chloro-2-fluoro-phenyl)-N-methyl-hydrazinecarboxylic acid tert-butyl ester (434 mg, 46%) as a colorless oil which solidified on standing.

Step 2: (4S,7R)-2-(3-Chloro-2-fluoro-phenyl)-1,7,8,8-tetramethyl-1,2,4,5,6,7-hexahydro-4,7-methano-indazol-3-one Triethylamine (1 mL, 7.2 mmol) was added dropwise to a solution of N'-(3-chloro-2-fluoro-phenyl)-N'-methyl-hydrazinecarboxylic acid tert-butyl ester (434 mg, 1.6 mmol) in 1,2-dichloroethane (6 mL) over 1 min. The reaction mixture was stirred for 5 min and then a solution of (1R,4R)-4,7,7-trimethyl-3-oxo-bicyclo[2.2.1]heptane-2-carbonyl chloride (Intermediate 20; 800 mg, 3.7 mmol) in 1,2-dichloroethane (14 mL) was added over 2 min. The reaction mixture was heated in an oil bath at 50° C. for 1 h. The solution was allowed to cool and a solution of HCl in dioxane (4 M; 6 mL, 24 mmol) was added and the mixture was heated at reflux for 1.5 h and then allowed to cool to room temperature. The solvent was evaporated and the residue was purified on an ISCO system, eluting with 30-100% ethyl acetate/hexanes. Fractions homogeneous for the product were evaporated, and co-evaporated with methanol. The residue was triturated with ether/hexane and the solvent was removed with a pipet. The solid was drie under high vacuum at 90° C. to give (4S,7R)-2-(3-chloro-2-fluoro-phenyl)-1,7,8,8-tetramethyl-1,2,4,5,6,7-hexahydro-4,7-methano-indazol-3-one (37 mg, 7%) as a white solid. ES(+)-MS (M+H) 335.

Example 126

(4S,7R)-2-(2,3-Dichloro-phenyl)-1,7,8,8-tetramethyl-1,2,4,5,6,7-hexahydro-4,7-methano-indazol-3-one

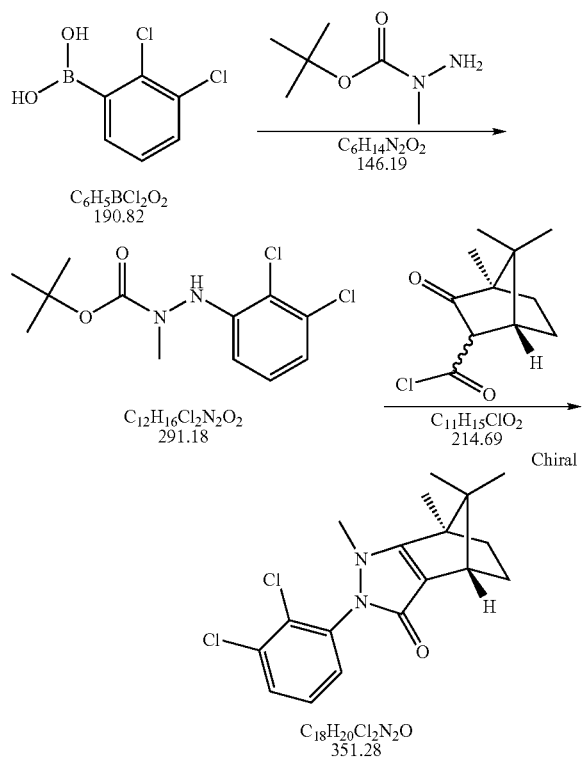

Step 1: N'-(2,3-Dichloro-phenyl)-N-methyl-hydrazinecarboxylic acid tert-butyl ester A mixture of N-methyl-hydrazinecarboxylic acid tert-butyl ester (Intermediate 1; 1.00 g, 6.8 mmol), 2,3-dichlorophenylboronic acid (Lancaster; 1.29 g, 6.8 mmol), copper(II) acetate (1.24 g, 6.8 mmol) and triethylamine (960 µL, 6.8 mmol) in 1,2-dichloroethane (15 mL) was heated in an oil bath at 50° C. for 3 h. The mixture was allowed to cool, and it was then adsorbed onto silica gel and purified by chromatography using an ISCO 40 g column, eluting with 10% ethyl acetate/hexanes, to give N'-(2,3-dichloro-phenyl)-N-methyl-hydrazinecarboxylic acid tert-butyl ester (775 mg, 39%) as a solid.

Step 2: (4S,7R)-2-(2,3-Dichloro-phenyl)-1,7,8,8-tetramethyl-1,2,4,5,6,7-hexahydro-4,7-methano-indazol-3-one Triethylamine (1.3 mL, 9.33 mmol) was added dropwise to a cooled (0° C.) solution of (1R,4R)-4,7,7-trimethyl-3-oxobicyclo[2.2.1]heptane-2-carbonyl chloride (Intermediate 20; 905 mg, 4.22 mmol) in 1,2-dichloroethane (8 mL) over 1 min. A solution of N'-(2,3-dichloro-phenyl)-N-methyl-hydrazinecarboxylic acid tert-butyl ester (775.8 mg, 2.66 mmol) in 1,2-dichloroethane (14 mL) was added. The reaction mixture was stirred at 0° C. for 15 min, at room temperature for 15 min, and then in an oil bath at 50° C. for 30 min. The reaction mixture was cooled. A solution of HCl in dioxane (4 M; 10 mL, 40 mmol) was added and the mixture was heated at reflux for 1 h and allowed to cool. Dichloromethane (150 mL) was added and the mixture was washed with 1:1 water/brine (30 mL), dried (magnesium sulfate), filtered, evaporated, and purified using an ISCO 120 g column, eluting with 20-100% ethyl acetate/hexanes. Fractions homogeneous for the product were evaporated, and then co-evaporated with methanol and then diethyl ether. The residue was dried under high vacuum at 70° C. overnight to give (4S,7R)-2-(2,3-dichloro-phenyl)-1,7,8,8-tetramethyl-1,2,4,5,6,7-hexahydro-4,7-methano-indazol-3-one (332 mg, 36%) as a white solid. ES(+)-MS (M+H) 351.

Example 127

(4S,7R)-2-(2,4-Dichloro-phenyl)-1,7,8,8-tetramethyl-1,2,4,5,6,7-hexahydro-4,7-methano-indazol-3-one

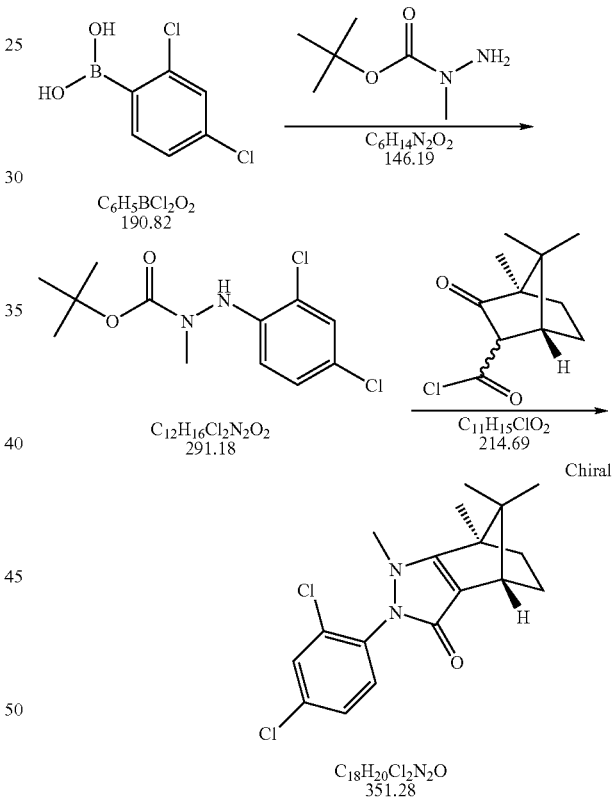

Step 1: N'-(2,4-Dichloro-phenyl)-N-methyl-hydrazinecarboxylic acid tert-butyl ester A mixture of N-methyl-hydrazinecarboxylic acid tert-butyl ester (Intermediate 1; 0.50 g, 3.4 mmol), 2,4-dichlorophenylboronic acid (Lancaster; 645 mg, 3.4 mmol), copper(II) acetate (621 mg, 3.4 mmol) and triethylamine (480 µL, 3.4 mmol) in 1,2-dichloroethane (15 mL) was heated in an oil bath at 50° C. for 2 h. The mixture was allowed to cool, and it was then adsorbed onto silica gel and purified by chromatography using an ISCO 40 g column, eluting with 10% ethyl acetate/hexanes, to give N'-(2,4-dichloro-phenyl)-N-methyl-hydrazinecarboxylic acid tert-butyl ester (380 mg, 34%) as a colorless oil.

Step 2: (4S,7R)-2-(2,4-Dichloro-phenyl)-1,7,8,8-tetramethyl-1,2,4,5,6,7-hexahydro-4,7-methano-indazol-3-one Triethylamine (450 µL, 3.2 mmol) was added dropwise to a cooled (0° C.) solution of (1R,4R)-4,7,7-trimethyl-3-oxo-bicyclo[2.2.1]heptane-2-carbonyl chloride (Intermediate 20; 361 mg, 1.68 mmol) in 1,2-dichloroethane (3 mL) over 1 min. The reaction mixture was stirred for 5 min and then a solution of N'-(2,4-dichloro-phenyl)-N'-methyl-hydrazinecarboxylic acid tert-butyl ester (310 mg, 1.07 mmol) in 1,2-dichloroethane (6 mL) was added over 2 min. The reaction mixture was stirred at 0° C. for 15 min, at room temperature for 30 min, and then in an oil bath at 50° C. for 2 h. A solution of HCl in dioxane (4 M; 8 mL, 32 mmol) was added and the mixture was heated in an oil bath at 100° C. for 1 h and then allowed to cool to room temperature. Dichloromethane (100 mL) was added and the mixture was washed with 1:1 water/brine (20 mL), dried (magnesium sulfate), filtered, evaporated, and purified using an ISCO 40 g column, eluting with 20-50% ethyl acetate/hexanes. Fractions homogeneous for the product were evaporated, and co-evaporated successively with methanol, diethyl ether and petroleum ether. The residue was triturated with hexanes, and the solid was dried overnight under high vacuum at 70° C. and then at 85° C. for 1 h to give (4S,7R)-2-(2,4-dichloro-phenyl)-1,7,8,8-tetramethyl-1,2,4,5,6,7-hexahydro-4,7-methano-indazol-3-one (175 mg, 45%) as an off-white solid. ES(+)-MS (M+H) 351.

Example 128

(4R,7S)-2-(2,5-Dichloro-phenyl)-1,7,8,8-tetramethyl-1,2,4,5,6,7-hexahydro-4,7-methano-indazol-3-one

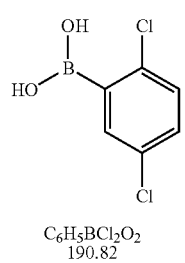

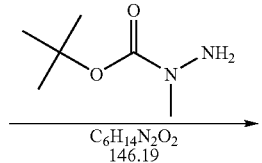

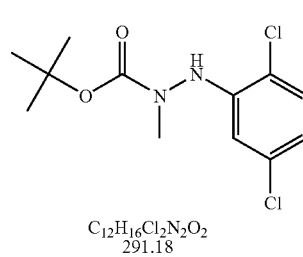

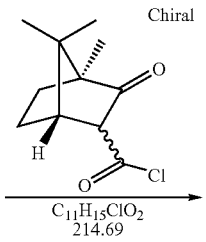

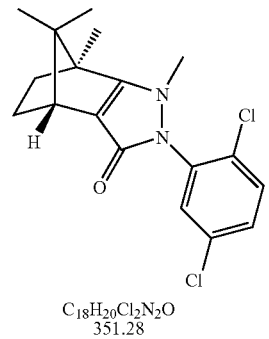

Step 1: N'-(2,5-Dichloro-phenyl)-N-methyl-hydrazinecarboxylic acid tert-butyl ester A mixture of N-methyl-hydrazinecarboxylic acid tert-butyl ester (Intermediate 1; 650 mg, 4.45 mmol), 2,5-dichlorophenylboronic acid (Aldrich; 831 mg, 4.36 mmol), copper (II) acetate (807 mg, 4.45 mmol) and triethylamine (623 µL, 4.45 mmol) in 1,2-dichloroethane (4.5 mL) was heated in an oil bath at 50° C. for 3 h. The mixture was allowed to cool, and it was then adsorbed onto silica gel and purified by chromatography using an ISCO 40 g column, eluting with 20-40% ethyl acetate/hexanes, to give N'-(2,5-dichloro-phenyl)-N-methyl-hydrazinecarboxylic acid tert-butyl ester (592 mg, 46%) as a yellow oil that solidified on standing.

Step 2: (4R,7S)-2-(2,5-Dichloro-phenyl)-1,7,8,8-tetramethyl-1,2,4,5,6,7-hexahydro-4,7-methano-indazol-3-one Triethylamine (440 µL, 3.2 mmol) was added to solution of (1S,4S)-4,7,7-trimethyl-3-oxo-bicyclo[2.2.1]heptane-2-carbonyl chloride (Intermediate 25; 329 mg, 1.5 mmol) in 1,2-dichloroethane (4 mL) over 1 min. Then a solution of N'-(2,5-dichloro-phenyl)-N-methyl-hydrazinecarboxylic acid tert-butyl ester (300 mg, 1.03 mmol) in 1,2-dichloroethane (8 mL) was added over 2 min. The reaction mixture was stirred at room temperature for 15 min and then heated in an oil bath at 50° C. for 30 min. An additional portion of N'-(2,5-dichloro-phenyl)-N-methyl-hydrazinecarboxylic acid tert-butyl ester (290 mg, 1.0 mmol) in 1,2-dichloroethane (4 mL) was added and the mixture was heated in an oil bath at 50° C. for 1.5 h. A solution of HCl in dioxane (4 M; 8 mL, 32 mmol) was added and the mixture was heated in an oil-bath at 100° C. for 1 h. The reaction mixture was allowed to cool, silica gel was added, the solvent was evaporated and the mixture was purified using an ISCO 40 g column, eluting with 60-100% ethyl acetate/hexanes. Fractions homogeneous for the product were evaporated, co-evaporated successively with methanol and diethyl ether, and then dried under high vacuum at 95° C. to give (4R,7S)-2-(2,5-dichloro-phenyl)-1,7,8,8-tetramethyl-1,2,4,5,6,7-hexahydro-4,7-methano-indazol-3-one (24 mg, 37%) as a pale yellow solid. ES(+)-MS (M+H) 351.

Example 129

(4S,7R)-2-(2,5-Dichloro-phenyl)-1,7,8,8-tetramethyl-1,2,4,5,6,7-hexahydro-4,7-methano-indazol-3-one Procedure A

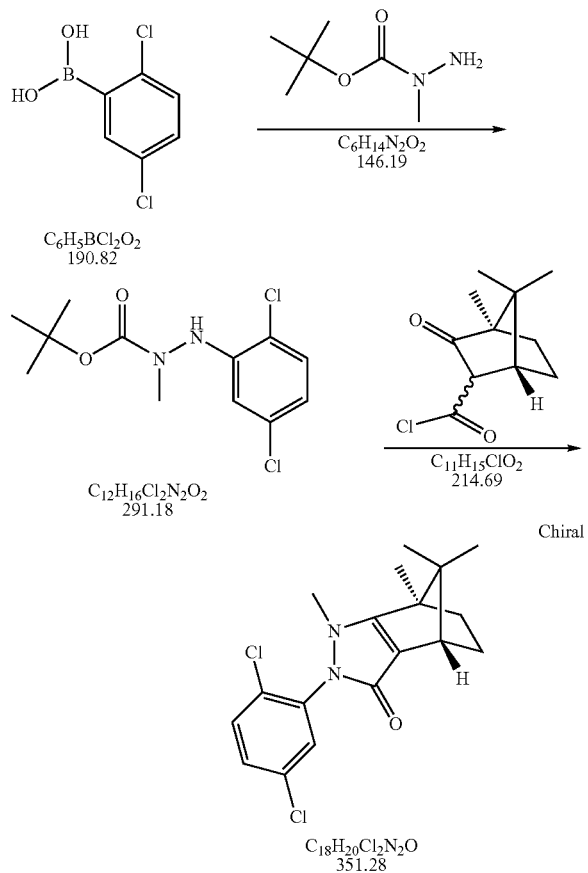

Step 1: N'-(2,5-Dichloro-phenyl)-N-methyl-hydrazinecarboxylic acid tert-butyl ester A mixture of N-methyl-hydrazinecarboxylic acid tert-butyl ester (Intermediate 1; 1.00 g, 6.8 mmol), 2,5-dichlorophenylboronic acid (Aldrich; 1.28 g, 6.7 mmol), copper(II) acetate (1.24 g, 6.8 mmol) and triethylamine (0.96 mL, 6.8 mmol) in 1,2-dichloroethane (7 mL) was heated in an oil bath at 50° C. overnight. The mixture was allowed to cool, and it was then adsorbed onto silica gel and purified by chromatography using an ISCO 120 g column, eluting with 20-25% ethyl acetate/hexanes, to give N'-(2,5-dichloro-phenyl)-N-methyl-hydrazinecarboxylic acid tert-butyl ester (750 mg, 38%) as an off-white solid.

Step 2: (4S,7R)-2-(2,5-Dichloro-phenyl)-1,7,8,8-tetramethyl-1,2,4,5,6,7-hexahydro-4,7-methano-indazol-3-one Triethylamine (1.2 mL, 8.6 mmol) was added dropwise to a cooled (0° C.) solution of (1R,4R)-4,7,7-trimethyl-3-oxobicyclo[2.2.1]heptane-2-carbonyl chloride (Intermediate 20; 880 mg, 4.1 mmol) in 1,2-dichloroethane (8 mL) over 1 min. The reaction mixture was stirred for 5 min and then a solution of N'-(2,5-dichloro-phenyl)-N'-methyl-hydrazinecarboxylic acid tert-butyl ester (751 mg, 2.58 mmol) in 1,2-dichloroethane (14 mL) was added over 2 min. The reaction mixture was stirred at 0° C. for 15 min, at room temperature for 30 min, and then in an oil bath at 50° C. for 30 min. A solution of HCl in dioxane (4 M; 8 mL, 32 mmol) was added and the mixture was heated at reflux for 1 h and then allowed to cool to room temperature. Dichloromethane (150 mL) was added and the mixture was washed with 1:1 water/brine (30 mL), dried (magnesium sulfate), filtered, evaporated, and purified using an ISCO 120 g column, eluting with 20-100% ethyl acetate/hexanes. Fractions homogeneous for the product were evaporated, and co-evaporated successively with methanol and diethyl ether. The residue was dried overnight under high vacuum at 70° C. to give (4S,7R)-2-(2,5-dichloro-phenyl)-1,7,8,8-tetramethyl-1,2,4,5,6,7-hexahydro-4,7-methano-indazol-3-one (400 mg, 44%) as a white solid. ES(+)-MS (M+H) 351.

Procedure B

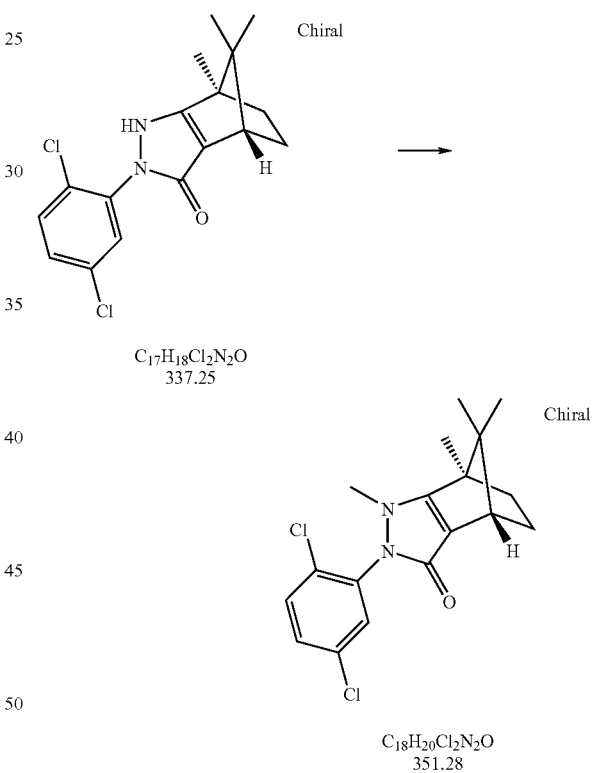

A mixture of (4S,7R)-2-(2,5-dichloro-phenyl)-7,8,8-trimethyl-1,2,4,5,6,7-hexahydro-4,7-methano-indazol-3-one (Intermediate 44; 12.55 g, 37.2 mmol) and iodomethane (12 mL, 193 mmol) in dimethylformamide (75 mL) was heated at 100° C. for 3 h and then cooled to room temperature. The solvent was evaporated, dichloromethane (300 mL) was added and the solution was washed with saturated aqueous sodium thiosulfate (100 mL), water (2×100 mL), and brine (100 mL). The solution was dried (magnesium sulfate), filtered, evaporated, and purified by flash column chromatography, eluting with 50-100% ethyl acetate/petroleum ether. Fractions homogeneous for the product were evaporated and ethyl acetate (100 mL) was added. The mixture was stirred at room temperature for 10 min and then hexane (300 mL) was added. The mixture was stirred at room temperature for 10 min and then cooled to 0° C. and filtered. The filter cake was washed with hexane and dried. The solid was dissolved in ethanol (100 mL) and treated with activated charcoal (0.8 g). The mixture was stirred at room temperature for 30 min, filtered through celite, and then evaporated. The residue was dried at 70° C. overnight to give (4S,7R)-2-(2,5-dichloro-phenyl)-1,7,8,8-tetramethyl-1,2,4,5,6,7-hexahydro-4,7-methano-indazol-3-one (9.18 g, 70%) as a white solid. ES(+)-MS (M+H) 351.

Example 130

(4R,7S)-1-Benzyl-2-(2,5-dichloro-phenyl)-7,8,8-trimethyl-1,2,4,5,6,7-hexahydro-4,7-methano-indazol-3-one

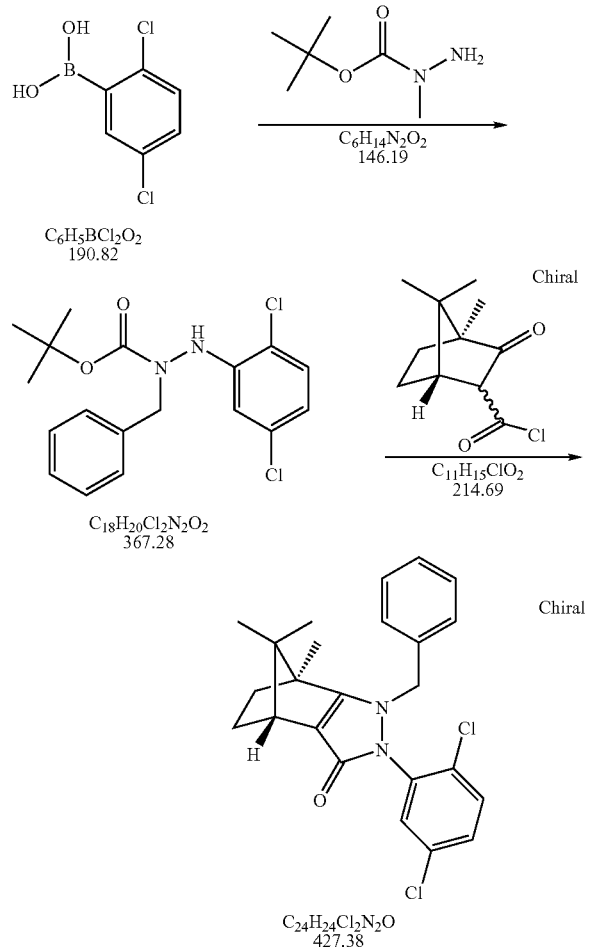

Step 1: N-Benzyl-N'-(2,5-dichloro-phenyl)-hydrazinecarboxylic acid tert-butyl ester A mixture of N-benzyl-hydrazinecarboxylic acid tert-butyl ester (Intermediate 27; 444 mg, 2.0 mmol), 2,5-dichlorophenylboronic acid (Aldrich; 274 mg, 1.44 mmol), copper(II) acetate (363 mg, 2.0 mmol) and triethylamine (280 µL, 2.0 mmol) in 1,2-dichloroethane (3 mL) was heated in an oil bath at 50° C. for 3 h. The mixture was allowed to cool, and it was then adsorbed onto silica gel and purified by chromatography using an ISCO 40 g column, eluting with 20-40% ethyl acetate/hexanes, to give N-benzyl-N'-(2,5-dichloro-phenyl)-hydrazinecarboxylic acid tert-butyl ester (265 mg, 50%) as a colorless oil.

Step 2: (4R,7S)-1-Benzyl-2-(2,5-dichloro-phenyl)-7,8,8-trimethyl-1,2,4,5,6,7-hexahydro-4,7-methano-indazol-3-one Triethylamine (380 µL, 2.7 mmol) was added dropwise to a solution of (1S,4S)-4,7,7-trimethyl-3-oxo-bicyclo[2.2.1]heptane-2-carbonyl chloride (Intermediate 25; 318 mg, 1.5 mmol) in 1,2-dichloroethane (4 mL) over 1 min. Then a solution of N-benzyl-N'-(2,5-dichloro-phenyl)-hydrazinecarboxylic acid tert-butyl ester (265 mg, 0.72 mmol) in 1,2-dichloroethane (8 mL) was added over 2 min. The reaction mixture was stirred at room temperature for 15 min and then heated in an oil bath at 100° C. for 45 min. A solution of HCl in dioxane (4 M; 4 mL, 16 mmol) was added and the mixture was heated in an oil-bath at 100° C. for 1 h. An additional portion of HCl in dioxane (4 M; 2 mL, 8 mmol) was added and the mixture was heated in an oil-bath at 100° C. for 2 h. The reaction mixture was allowed to cool to room temperature and dichloromethane (100 mL) was added. The mixture was washed with 1:1 water/brine (20 mL), dried (magnesium sulfate), filtered, evaporated, and purified on an ISCO system using a 12 g column, eluting with 33-100% ethyl acetate/hexanes. Fractions homogeneous for the product were evaporated, co-evaporated with diethyl ether and petroleum ether, and then dried under high vacuum at 90° C. to give (4R,7S)-1-benzyl-2-(2,5-dichloro-phenyl)-7,8,8-trimethyl-1,2,4,5,6,7-hexahydro-4,7-methano-indazol-3-one (10 mg, 3%) as a pale yellow solid. ES(+)-MS (M+H) 427.

Example 131

4-Fluoro-3-((4S,7R)-1,7,8,8-tetramethyl-3-oxo-1,3,4,5,6,7-hexahydro-4,7-methano-indazol-2-yl)-benzonitrile

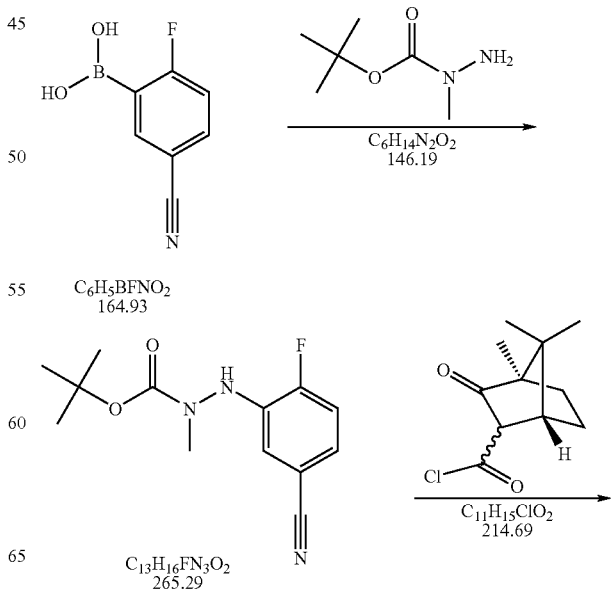

-continued

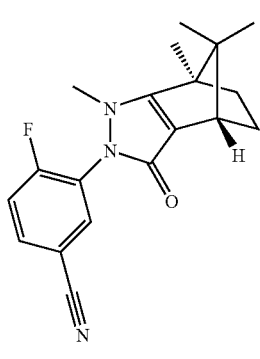

C₁₉H₂₀FN₃O
325.39

Step 1: N'-(5-Cyano-2-fluoro-phenyl)-N-methylhydrazinecarboxylic acid tert-butyl ester A mixture of N-methyl-hydrazinecarboxylic acid tert-butyl ester (Intermediate 1; 1.00 g, 6.1 mmol), 5-cyano-2-fluorophenylboronic acid (CombiBlocks; 1.00 g, 6.84 mmol), copper(II) acetate (1.1 g, 6.1 mmol) and triethylamine (2.1 mL, 15.1 mmol) in 1,2-dichloroethane (30 mL) was heated in an oil bath at 60° C. for 3 h. The mixture was allowed to cool, and it was then adsorbed onto silica gel and purified by chromatography using an ISCO 120 g column, eluting with 10-50% ethyl acetate/hexanes, to give N'-(5-cyano-2-fluorophenyl)-N-methyl-hydrazinecarboxylic acid tert-butyl ester (700 mg, 44%) as a colorless oil.

Step 2: 4-Fluoro-3-((4S,7R)-1,7,8,8-tetramethyl-3-oxo-1,3,4,5,6,7-hexahydro-4,7-methano-indazol-2-yl)-benzonitrile Triethylamine (1 mL, 7.2 mmol) was added dropwise to a solution (1R,4R)-4,7,7-trimethyl-3-oxo-bicyclo[2.2.1]heptane-2-carbonyl chloride (Intermediate 20; 1.00 g, 4.7 mmol) of in 1,2-dichloroethane (6 mL) over 1 min. The reaction mixture was stirred for 5 min and then a solution of N'-(5-cyano-2-fluoro-phenyl)-N'-methyl-hydrazinecarboxylic acid tert-butyl ester (700 mg, 2.6 mmol) in 1,2-dichloroethane (14 mL) was added over 2 min. The reaction mixture was heated in an oil bath at 50° C. for 1 h. The solution was allowed to cool and a solution of HCl in dioxane (4 M; 6 mL, 24 mmol) was added and the mixture was heated at reflux for 1.5 h and then allowed to cool to room temperature. The solvent was evaporated and the residue was purified by preparative HPLC to give a yellow foam. This was triturated with ether and then petroleum ether and the solvent was removed. The residue was co-evaporated with methanol and the petroleum ether and then further purified on an ISCO system, eluting with 50-100% ethyl acetate/hexanes. Fractions homogeneous for the product were evaporated, co-evaporated successively with methanol, diethyl ether, and petroleum ether, and then dried under high vacuum at room temperature to give 4-fluoro-3-((4S,7R)-1,7,8,8-tetramethyl-3-oxo-1,3,4,5,6,7-hexahydro-4,7-methano-indazol-2-yl)-benzonitrile (84 mg, 10%) as a white foam. APCI(+)-MS (M+H) 326.

Example 132

(4S,7R)-2-(2-Fluoro-5-trifluoromethyl-phenyl)-1,7,8,8-tetramethyl-1,2,4,5,6,7-hexahydro-4,7-methano-indazol-3-one

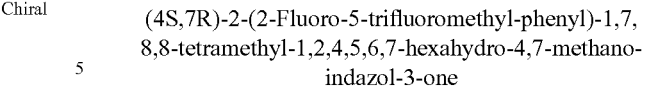

C₇H₅BF₄O₂
207.92

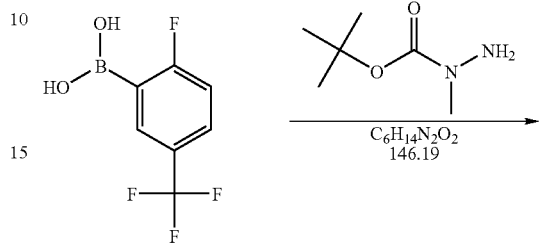

C₁₃H₁₆F₄N₂O₂
308.28

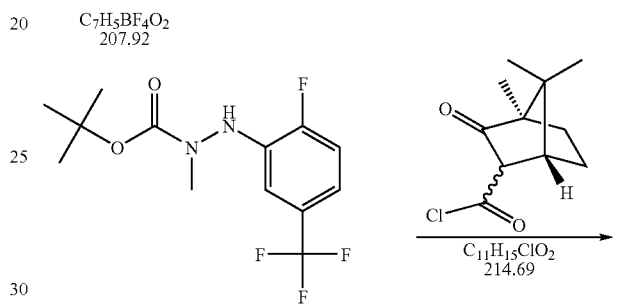

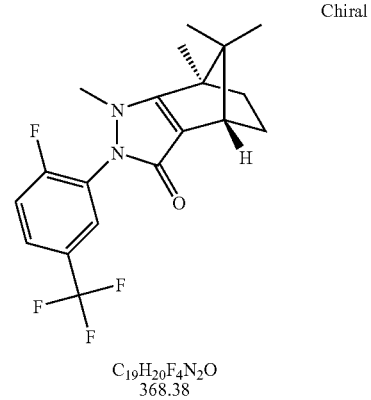

C₁₉H₂₀F₄N₂O
368.38

Step 1: N'-(2-Fluoro-5-trifluoromethyl-phenyl)-N-methyl-hydrazinecarboxylic acid tert-butyl ester A mixture of N-methyl-hydrazinecarboxylic acid tert-butyl ester (Intermediate 1; 0.50 g, 3.4 mmol), 2-fluoro-5-(trifluoromethyl)phenylboronic acid (Aldrich; 561 mg, 3.4 mmol), copper(II) acetate (621 mg, 3.4 mmol) and triethylamine (480 μL, 3.4 mmol) in 1,2-dichloroethane (15 mL) was heated in an oil bath at 50° C. for 2 h. The mixture was allowed to cool, and it was then adsorbed onto silica gel and purified by chromatography using an ISCO 40 g column, eluting with 10% ethyl acetate/hexanes, to give N'-(2-fluoro-5-trifluoromethyl-phenyl)-N-methyl-hydrazinecarboxylic acid tert-butyl ester (310 mg, 31%) as a colorless oil that solidified.

Step 2: (4S,7R)-2-(2-Fluoro-5-trifluoromethyl-phenyl)-1,7,8,8-tetramethyl-1,2,4,5,6,7-hexahydro-4,7-methano-indazol-3-one Triethylamine (518 μL, 3.7 mmol) was added dropwise to a cooled (0° C.) solution (1R,4R)-4,7,7-trimethyl-3-oxo-bicyclo[2.2.1]heptane-2-carbonyl chloride (418 mg, 1.95 mmol) of in 1,2-dichloroethane (3 mL) over 1 min. The reaction mixture was stirred for 5 min and then a solution of N'-(2-fluoro-5-trifluoromethyl-phenyl)-N-methyl-hydrazinecarboxylic acid tert-butyl ester (380 mg, 1.23 mmol) in 1,2-dichloroethane (6 mL) was added over 2 min. The reaction mixture was stirred at 0° C. for 15 min, at room temperature for 30 min, and then in an oil bath at 50° C. for 2 h. A solution of HCl in dioxane (4 M; 8 mL, 32 mmol) was added and the mixture was heated in an oil bath at 100° C. for 1 h and then allowed to cool to room temperature. Dichloromethane (100 mL) was added and the mixture was washed with 1:1 water/brine (20 mL), dried (magnesium sulfate), filtered, evaporated, and purified using an ISCO 40 g column, eluting with 20-50% ethyl acetate/hexanes. Fractions homogeneous for the product were evaporated, and then co-evaporated with ether and then petroleum ether. The residue was triturated with hexanes, and the solid was dried under high vacuum at 70° C. overnight and then at 85° C. for 1 h to give (4S,7R)-2-(2-fluoro-5-trifluoromethyl-phenyl)-1,7,8,8-tetramethyl-1,2,4,5,6,7-hexahydro-4,7-methano-indazol-3-one (142 mg, 30%) as a light yellow solid. ES(+)-MS (M+H) 369.

Example 133

(4S,7R)-2-(5-Fluoro-2-trifluoromethyl-phenyl)-1,7,8,8-tetramethyl-1,2,4,5,6,7-hexahydro-4,7-methano-indazol-3-one

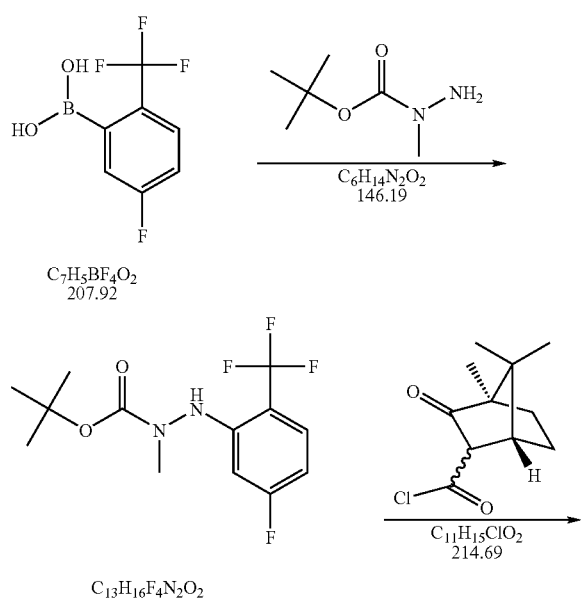

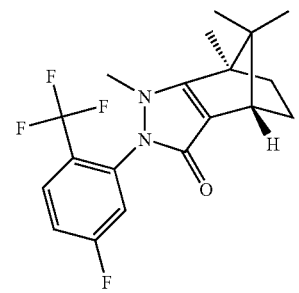

$C_{19}H_{20}F_4N_2O$
368.38

Step 1: N'-(5-Fluoro-2-trifluoromethyl-phenyl)-N-methyl-hydrazinecarboxylic acid tert-butyl ester A mixture of N-methyl-hydrazinecarboxylic acid tert-butyl ester (Intermediate 1; 400 mg, 2.74 mmol), 5-fluoro-2-(trifluoromethyl)phenylboronic acid (Cuschem, Inc., Yonkers, N.Y.; 512 mg, 2.46 mmol), copper(II) acetate (497 mg, 2.74 mmol) and triethylamine (380 μL, 2.7 mmol) in 1,2-dichloroethane (18 mL) was heated in an oil bath at 50° C. for 2 h. The mixture was allowed to cool, and it was then adsorbed onto silica gel and purified by chromatography using an ISCO 40 g column, eluting with 10% ethyl acetate/hexanes, to give N'-(5-fluoro-2-trifluoromethyl-phenyl)-N-methyl-hydrazinecarboxylic acid tert-butyl ester (348 mg, 41%) as a colorless oil that solidified.

Step 2: (4S,7R)-2-(5-Fluoro-2-trifluoromethyl-phenyl)-1,7,8,8-tetramethyl-1,2,4,5,6,7-hexahydro-4,7-methano-indazol-3-one A solution of (1R,4R)-4,7,7-trimethyl-3-oxo-bicyclo[2.2.1]heptane-2-carbonyl chloride (Intermediate 20; 349 mg, 1.62 mmol) in 1,2-dichloroethane (9 mL) was added to a cooled (0° C.) solution of triethylamine (320 μL, 2.30 mmol) and N'-(5-fluoro-2-trifluoromethyl-phenyl)-N-methyl-hydrazinecarboxylic acid tert-butyl ester (348 mg, 1.13 mmol) in 1,2-dichloroethane (6 mL) over a period of 1 min. The reaction mixture was stirred for 10 min at room temperature and then in an oil bath at 50° C. for 1 h. A solution of HCl in dioxane (4 M; 8 mL, 32 mmol) was added and the mixture was heated at reflux for 1 h and then allowed to cool to room temperature. Silica gel was added and the solvent was evaporated. The residue was purified using an ISCO 40 g column, eluting with 50-100% ethyl acetate/hexanes and then with 10% methanol/ethyl acetate. Fractions homogeneous for the product were evaporated, and the residue was dissolved in dichloromethane (75 mL), and washed with 1:1 water/saturated aqueous sodium thiosulfate (20 mL) and brine (20 mL). The solution was dried (magnesium sulfate), filtered, evaporated, and dried under high vacuum at 95° C. to give (4S,7R)-2-(5-fluoro-2-trifluoromethyl-phenyl)-1,7,8,8-tetramethyl-1,2,4,5,6,7-hexahydro-4,7-methano-indazol-3-one (127 mg, 31%) as a white solid. ES(+)-MS (M+H) 369.

Example 134

(4S,7R)-2-(3,5-Dichloro-phenyl)-1,7,8,8-tetramethyl-1,2,4,5,6,7-hexahydro-4,7-methano-indazol-3-one

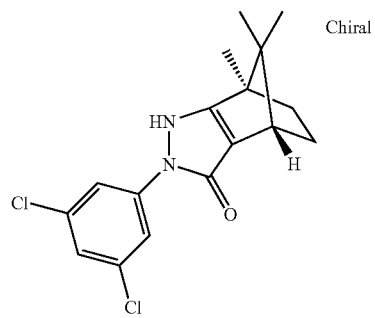

C₁₇H₁₈Cl₂N₂O
337.25

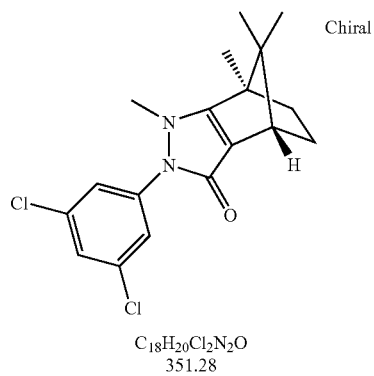

C₁₈H₂₀Cl₂N₂O
351.28

A mixture of (4S,7R)-2-(3,5-dichloro-phenyl)-7,8,8-trimethyl-1,2,4,5,6,7-hexahydro-4,7-methano-indazol-3-one (Intermediate 45; 200 mg, 0.59 mmol) and iodomethane (180 μL, 2.9 mmol) in dimethylformamide (3 mL) was heated at 95° C. for 7 h and then stirred overnight at room temperature. The solvent was evaporated, dichloromethane (50 mL) was added and the solution was washed with water (3×25 mL), saturated aqueous sodium thiosulfate (25 mL), and brine (25 mL). The solution was dried (magnesium sulfate), filtered, evaporated, and purified by column chromatography, eluting with 20% ethyl acetate/petroleum ether, and dried under high vacuum overnight to give a pale orange solid. This was dissolved in ethanol and the solution was treated with charcoal, then filtered through Celite (washing the Celite well with ethanol) and evaporated to give a brown solid. The brown solid was dissolved in ethyl ether and the solution was cooled in a freezer for 1 h. The solid was filtered off and washed with ether to give (4S,7R)-2-(3,5-dichloro-phenyl)-1,7,8,8-tetramethyl-1,2,4,5,6,7-hexahydro-4,7-methano-indazol-3-one (39 mg, 19%). ES(+)-MS (M+H) 351.

Example 135

(4S,7R)-2-(3,5-Dichloro-phenyl)-1-ethyl-7,8,8-trimethyl-1,2,4,5,6,7-hexahydro-4,7-methano-indazol-3-one

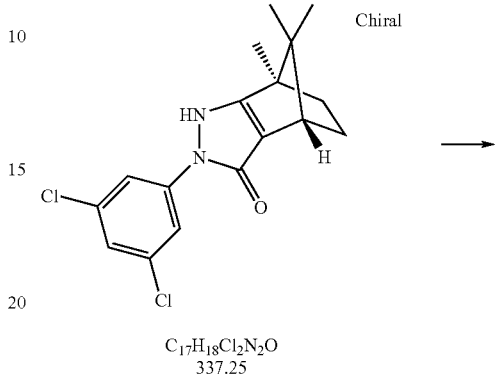

C₁₇H₁₈Cl₂N₂O
337.25

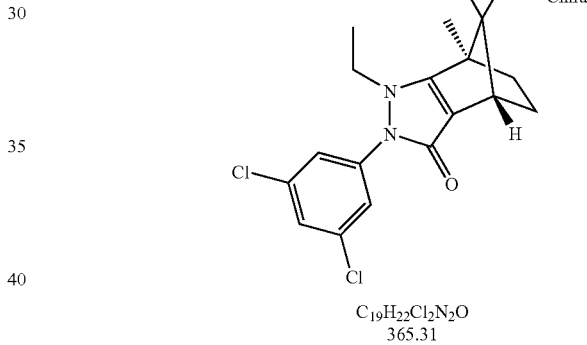

C₁₉H₂₂Cl₂N₂O
365.31

A mixture of (4S,7R)-2-(3,5-dichloro-phenyl)-7,8,8-trimethyl-1,2,4,5,6,7-hexahydro-4,7-methano-indazol-3-one (Intermediate 45; 400 mg, 1.2 mmol) and iodoethane (480 μL, 5.95 mmol) in dimethylformamide (5 mL) was heated at 95° C. for 7 h and then a further portion of iodoethane (480 μL, 5.95 mmol) was added. The solution was heated at 95° C. overnight. The solvent was evaporated, dichloromethane (100 mL) was added and the solution was washed with water (3×50 mL), saturated aqueous sodium thiosulfate (50 mL), and brine (50 mL). The solution was dried (magnesium sulfate), filtered, evaporated, and purified by column chromatography, eluting with 20% ethyl acetate/petroleum ether, and dried under high vacuum over the weekend to give a pale orange solid. The solid was stirred in a small amount of ether, and the insoluble material was filtered off and dried under high vacuum overnight to give (4S,7R)-2-(3,5-dichloro-phenyl)-1-ethyl-7,8,8-trimethyl-1,2,4,5,6,7-hexahydro-4,7-methano-indazol-3-one (30 mg, 7%). ES(+)-MS (M+H) 351.

Example 136

(4S,7R)-1,7,8,8-Tetramethyl-2-(2,3,5-trichloro-phenyl)-1,2,4,5,6,7-hexahydro-4,7-methano-indazol-3-one

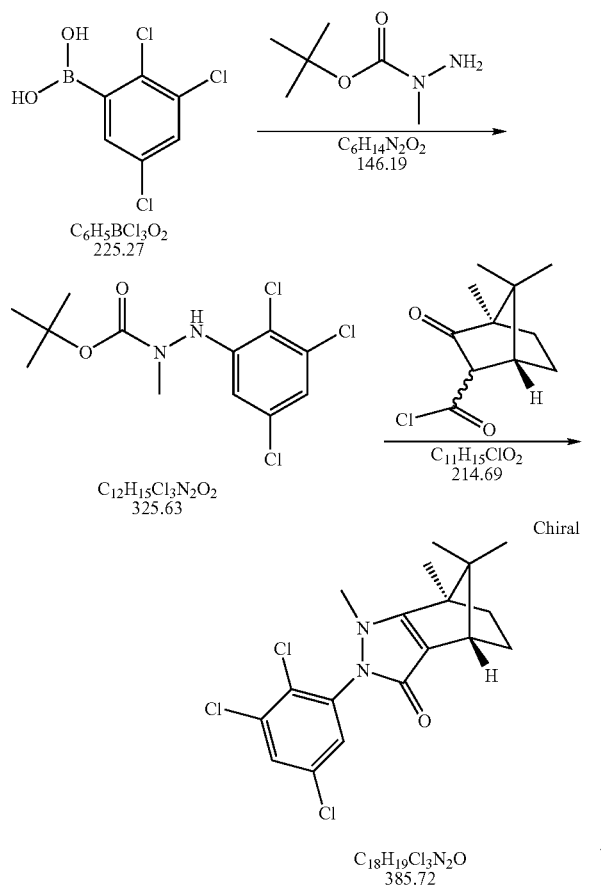

Step 1: N-Methyl-N'-(2,3,5-trichloro-phenyl)-hydrazinecarboxylic acid tert-butyl ester A mixture of N-methyl-hydrazinecarboxylic acid tert-butyl ester (Intermediate 1; 500 mg, 3.4 mmol), 2,3,5-trichlorophenylboronic acid (Aldrich; 751 mg, 3.35 mmol), copper (II) acetate (621 mg, 3.4 mmol) and triethylamine (480 μL, 3.4 mmol) in 1,2-dichloroethane (4 mL) was heated in an oil bath at 50° C. for 3 h. The mixture was allowed to cool, and it was then adsorbed onto silica gel and purified by chromatography using an ISCO 40 g column, eluting with 20-40% ethyl acetate/hexanes, to give N-methyl-N'-(2,3,5-trichloro-phenyl)-hydrazinecarboxylic acid tert-butyl ester (592 mg, 53%) as a colorless oil that solidified on standing.

Step 2: (4S,7R)-1,7,8,8-Tetramethyl-2-(2,3,5-trichloro-phenyl)-1,2,4,5,6,7-hexahydro-4,7-methano-indazol-3-one Triethylamine (1 mL, 7.2 mmol) was added dropwise to a solution of (1R,4R)-4,7,7-trimethyl-3-oxo-bicyclo[2.2.1]heptane-2-carbonyl chloride (Intermediate 20; 1.00 g, 4.66 mmol) in 1,2-dichloroethane (6 mL) over 1 min. The reaction mixture was stirred for 5 min and then a solution of M-(2,3,5-trichloro-phenyl)-N'-methyl-hydrazinecarboxylic acid tert-butyl ester (592 mg, 1.8 mmol) in 1,2-dichloroethane (14 mL) was added over 2 min. The reaction mixture was heated in an oil bath at 50° C. for 1 h. The solution was allowed to cool and a solution of HCl in dioxane (4 M; 6 mL, 24 mmol) was added and the mixture was heated at reflux for 1.5 h and then allowed to cool to room temperature. The solvent was evaporated and the residue was purified by preparative HPLC and then on an ISCO system, eluting with 40-70% ethyl acetate/hexanes. Fractions homogeneous for the product were evaporated, and then dried under high vacuum to give (4S,7R)-2-(2,3,5-trichloro-phenyl)-1,7,8,8-tetramethyl-1,2,4,5,6,7-hexahydro-4,7-methano-indazol-3-one (317 mg, 46%) as a white solid. ES(+)-MS (M+H) 385.

Example 137

(4R,7S)-1-Benzyl-2-(2,3-dimethyl-phenyl)-7,8,8-trimethyl-1,2,4,5,6,7-hexahydro-4,7-methano-indazol-3-one

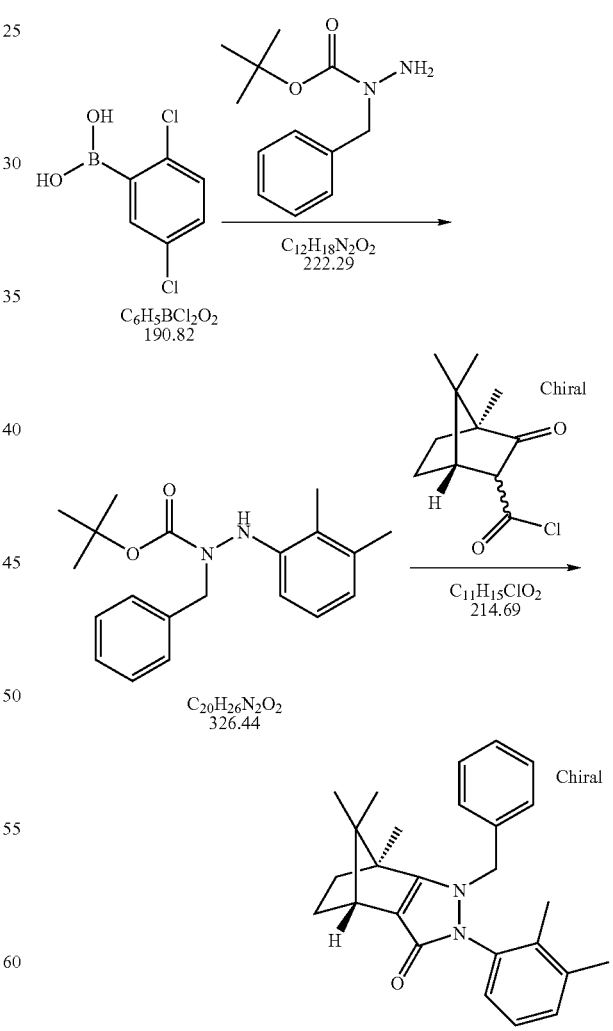

Step 1: N-Benzyl-N'-(2,3-dimethyl-phenyl)-hydrazinecarboxylic acid tert-butyl ester A mixture of N-benzyl-hydrazinecarboxylic acid tert-butyl ester (Intermediate 27; 790 mg, 3.55 mmol), 2,3-dimethylphenylboronic acid (Aldrich; 522 mg, 3.48 mmol), copper (II) acetate (646 mg, 3.55 mmol) and triethylamine (500 µL, 3.55 mmol) in 1,2-dichloroethane (5.5 mL) was heated in an oil bath at 50° C. for 2 h. The mixture was allowed to cool, and it was then adsorbed onto silica gel and purified by chromatography using an ISCO 40 g column, eluting with 20-40% ethyl acetate/hexanes, to give N-benzyl-N'-(2,3-dimethyl-phenyl)-hydrazinecarboxylic acid tert-butyl ester (450 mg, 39%) as a yellow oil.

Step 2: (4R,7S)-1-Benzyl-2-(2,3-dimethyl-phenyl)-7,8,8-trimethyl-1,2,4,5,6,7-hexahydro-4,7-methano-indazol-3-one Triethylamine (440 µL, 3.2 mmol) was added to solution of (1S,4S)-4,7,7-trimethyl-3-oxo-bicyclo[2.2.1]heptane-2-carbonyl chloride (Intermediate 25; 329 mg, 1.5 mmol) in 1,2-dichloroethane (6 mL) over 1 min. Then a solution of N-benzyl-N'-(2,3-dimethyl-phenyl)-hydrazinecarboxylic acid tert-butyl ester (450 mg, 1.38 mmol) in 1,2-dichloroethane (12 mL) was added over 2 min. The reaction mixture was stirred at room temperature for 15 min and then heated in an oil bath at 50° C. for 2 h and then at 60° C. for 1 h. A solution of HCl in dioxane (4 M; 8 mL, 32 mmol) was added and the mixture was heated in an oil-bath at 100° C. for 1 h. The reaction mixture was allowed to cool, silica gel was added, the solvent was evaporated and the mixture was purified using an ISCO 40 g column, eluting with 60-100% ethyl acetate/hexanes and then 5% methanol/dichloromethane. Fractions homogeneous for the product were evaporated, and then treated with methanol and charcoal. This mixture was stirred for 20 min, filtered through Celite and evaporated to give an orange gum. The gum was purified for a second time using an ISCO 40 g column, eluting with 2-4% methanol/dichloromethane. Fractions homogeneous for the product were evaporated, co-evaporated with diethyl ether and petroleum ether, and then dried under high vacuum at room temperature to give (4R,7S)-1-benzyl-2-(2,3-dimethyl-phenyl)-7,8,8-trimethyl-1,2,4,5,6,7-hexahydro-4,7-methano-indazol-3-one (57 mg, 11%) as an off-white foam. ES(+)-MS (M+H) 387.

Example 138

(4S,7R)-2-(2,4-Bis-trifluoromethyl-phenyl)-1,7,8,8-tetramethyl-1,2,4,5,6,7-hexahydro-4,7-methano-indazol-3-one

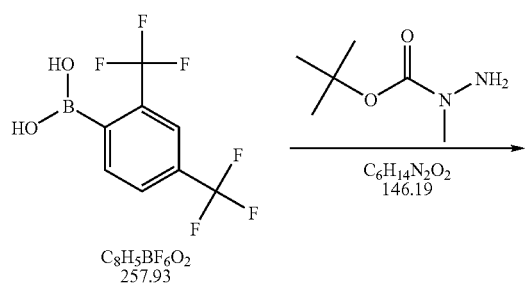

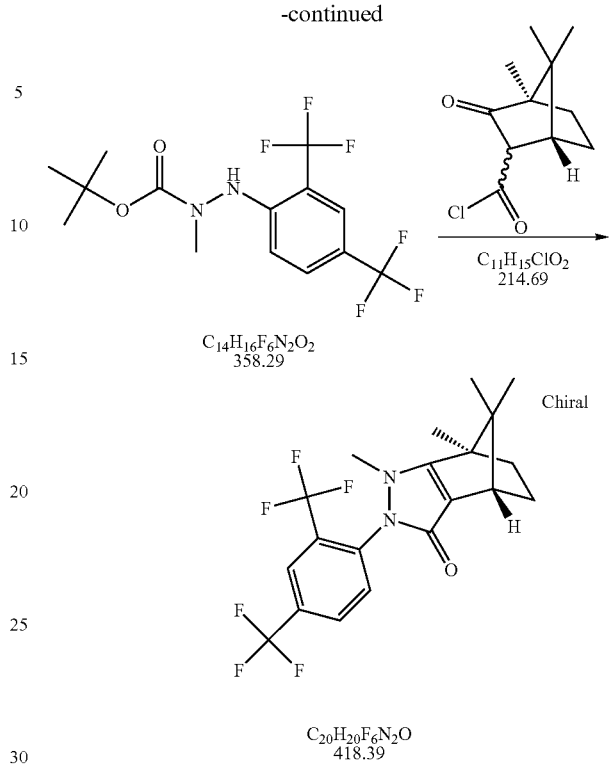

Step 1: N'-(2,4-Bis-trifluoromethyl-phenyl)-N-methyl-hydrazinecarboxylic acid tert-butyl ester A mixture of N-methyl-hydrazinecarboxylic acid tert-butyl ester (Intermediate 1; 1.00 g, 6.8 mmol), 2,4-bis(trifluoromethyl)phenylboronic acid (Ryscor; 1.75 g, 6.8 mmol), copper(II) acetate (1.24 g, 6.8 mmol) and triethylamine (960 µL, 6.8 mmol) in 1,2-dichloroethane (15 mL) was heated in an oil bath at 50° C. for 3 h. The mixture was allowed to cool, and it was then adsorbed onto silica gel and purified by chromatography using an ISCO 40 g column, eluting with 10% ethyl acetate/hexanes, to give N'-(2,4-bis-trifluoromethyl-phenyl)-N-methyl-hydrazinecarboxylic acid tert-butyl ester (646 mg, 36%) as a solid.

Step 2: (4S,7R)-2-(2,4-Bis-trifluoromethyl-phenyl)-1,7,8,8-tetramethyl-1,2,4,5,6,7-hexahydro-4,7-methano-indazol-3-one Triethylamine (840 µL, 6.0 mmol) was added to a cooled (0° C.) solution of (1R,4R)-4,7,7-trimethyl-3-oxo-bicyclo [2.2.1]heptane-2-carbonyl chloride (Intermediate 20; 612 mg, 2.9 mmol) in 1,2-dichloroethane (8 mL) over 1 min. The reaction mixture was stirred for 5 min and then a solution of N'-(2,4-bis-trifluoromethyl-phenyl)-N-methyl-hydrazinecarboxylic acid tert-butyl ester (646 mg, 1.8 mmol) in 1,2-dichloroethane (14 mL) was added. The reaction mixture was stirred at 0° C. for 15 min, at room temperature for 30 min, and then in an oil bath at 50° C. for 30 min. An additional portion of (1R,4R)-4,7,7-trimethyl-3-oxo-bicyclo[2.2.1]heptane-2-carbonyl chloride (Intermediate 20; 0.6 g, 2.8 mmol) in 1,2-dichloroethane (6 mL) was added and the mixture was heated at 50° C. for 45 min. The reaction mixture was allowed to cool. A solution of HCl in dioxane (4 M; 8 mL, 32 mmol)

was added and the reaction mixture was heated at reflux for 1 h, allowed to cool, poured into water (200 mL) and extracted with ethyl acetate (3×50 mL). The combined organic layers were dried (magnesium sulfate), filtered, evaporated, and chromatographed, eluting with 40% ethyl acetate/hexanes) to give (4S,7R)-2-(2,4-bis-trifluoromethyl-phenyl)-1,7,8,8-tetramethyl-1,2,4,5,6,7-hexahydro-4,7-methano-indazol-3-one (501 mg, 66%) as an off-white solid. APCI(+)-MS (M+H) 419.

Example 139

(4S,7R)-2-(2,5-Bis-trifluoromethyl-phenyl)-1,7,8,8-tetramethyl-1,2,4,5,6,7-hexahydro-4,7-methano-indazol-3-one

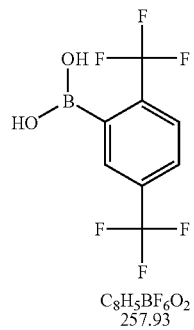

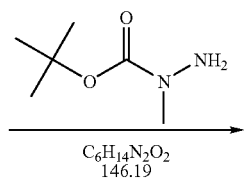

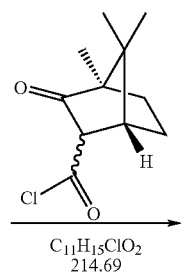

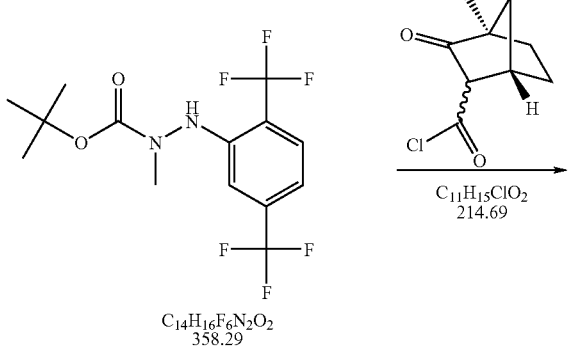

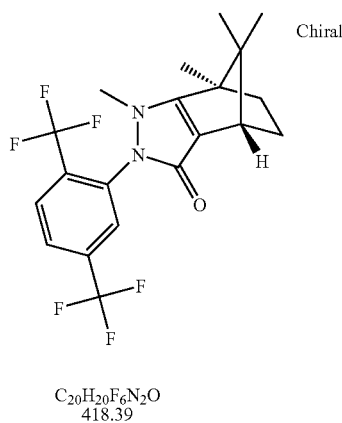

Step 1: N'-(2,5-Bis-trifluoromethyl-phenyl)-N-methyl-hydrazinecarboxylic acid tert-butyl ester A mixture of N-methyl-hydrazinecarboxylic acid tert-butyl ester (Intermediate 1; 600 mg, 3.4 mmol), 2,5-bis(trifluoromethyl)phenylboronic acid (ChemFocus, LLC, East Brunswick, N.J., USA; 953 mg, 3.7 mmol), copper(II) acetate (746 mg, 4.1 mmol) and triethylamine (575 μL, 4.1 mmol) in 1,2-dichloroethane (18 mL) was heated in an oil bath at 50° C. for 2 h. The mixture was allowed to cool, and it was then adsorbed onto silica gel and purified by chromatography using an ISCO 40 g column, eluting with 10% ethyl acetate/hexanes, to give N'-(2,5-bis-trifluoromethyl-phenyl)-N-methyl-hydrazinecarboxylic acid tert-butyl ester (480 mg, 33%) as a colorless oil that solidified.

Step 2: (4S,7R)-2-(2,5-Bis-trifluoromethyl-phenyl)-1,7,8,8-tetramethyl-1,2,4,5,6,7-hexahydro-4,7-methano-indazol-3-one A solution of (1R,4R)-4,7,7-trimethyl-3-oxo-bicyclo[2.2.1]heptane-2-carbonyl chloride (Intermediate 20; 415 mg, 1.93 mmol) in 1,2-dichloroethane (12 mL) was added to a cooled (0° C.) solution of triethylamine (380 μL, 2.73 mmol) and N'-(2,5-bis-trifluoromethyl-phenyl)-N-methyl-hydrazinecarboxylic acid tert-butyl ester (480 mg, 1.34 mmol) in 1,2-dichloroethane (8 mL) over a period of 1 min. The reaction mixture was stirred for 10 min at room temperature and then in an oil bath at 50° C. for 45 min. A solution of HCl in dioxane (4 M; 10 mL, 40 mmol) was added and the mixture was heated at reflux for 1.5 h and then allowed to cool to room temperature. Dichloromethane (75 mL) and 1:1 water/brine (20 mL) were added. The mixture was shaken and the layers separated. The aqueous layer was back-extracted with dichloromethane (30 mL). The combined organic layers were dried (magnesium sulfate), filtered, evaporated, and purified using an ISCO40 g column, eluting with 40-100% ethyl acetate/hexanes. Fractions homogeneous for the product were evaporated, co-evaporated successively with methanol and ether, and then dried under high vacuum at 95° C. to give (4S,7R)-2-(2,5-bis-trifluoromethyl-phenyl)-1,7,8,8-tetramethyl-1,2,4,5,6,7-hexahydro-4,7-methano-indazol-3-one (256 mg, 46%) as an off-white solid. ES(+)-MS (M+H) 419.

Example 140

(4S,7R)-1,7,8,8-Tetramethyl-2-naphthalen-1-yl-1,2,4,5,6,7-hexahydro-4,7-methano-indazol-3-one

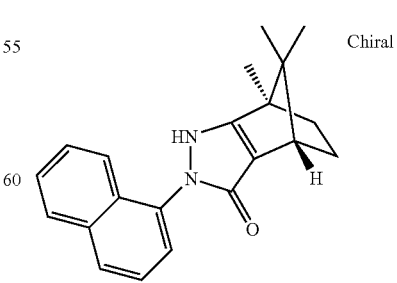

-continued

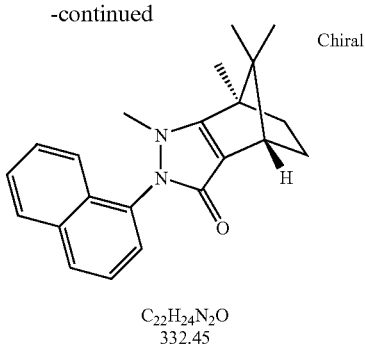

C₂₂H₂₄N₂O
332.45

A mixture of (4S,7R)-7,8,8-trimethyl-2-naphthalen-1-yl-1,2,4,5,6,7-hexahydro-4,7-methano-indazol-3-one (Intermediate 46; 150 mg, 0.47 mmol) and iodomethane (118 μL, 1.88 mmol) in dimethylformamide (5 mL) was heated in an oil-bath at 100° C. for 8 h. The solvent was evaporated and the residue was partitioned between dichloromethane and water. The aqueous layer was extracted with dichloromethane (2×100 mL) and the combined organic layers were washed with water (5×100 mL) and aqueous sodium thiosulfate (100 mL). The solvent was evaporated and the residue was purified using an ISCO 40 g column, eluting with 70-90% ethyl acetate/hexanes to give (4S,7R)-1,7,8,8-tetramethyl-2-naphthalen-1-yl-1,2,4,5,6,7-hexahydro-4,7-methano-indazol-3-one (54 mg, 35%) as a white solid. ES(+)-MS (M+H) 333.

Example 141

(4S,7R)-1-Ethyl-7,8,8-trimethyl-2-naphthalen-1-yl-1,2,4,5,6,7-hexahydro-4,7-methano-indazol-3-one

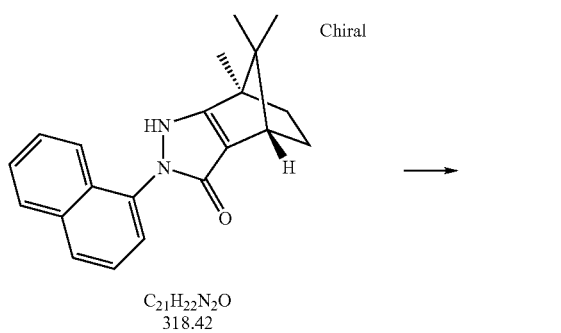

C₂₁H₂₂N₂O
318.42

C₂₃H₂₆N₂O
346.48

A mixture of (4S,7R)-7,8,8-trimethyl-2-naphthalen-1-yl-1,2,4,5,6,7-hexahydro-4,7-methano-indazol-3-one (Intermediate 46; 150 mg, 0.47 mmol) and iodoethane (151 μL, 1.88 mmol) in dimethylformamide (5 mL) was heated in an oil-bath at 100° C. for 8 h. The solvent was evaporated and the residue was partitioned between dichloromethane and water. The aqueous layer was extracted with dichloromethane (2×100 mL) and the combined organic layers were washed with water (5×100 mL) and aqueous sodium thiosulfate (100 mL). The solvent was evaporated and the residue was purified using an ISCO 12 g column, eluting with 90-100% ethyl acetate/hexanes to give (4S,7R)-1-ethyl-7,8,8-trimethyl-2-naphthalen-1-yl-1,2,4,5,6,7-hexahydro-4,7-methano-indazol-3-one (72 mg, 44%) as a light yellow foam. ES(+)-MS (M+H) 347.

Example 142

(4S,7R)-1-Allyl-7,8,8-trimethyl-2-naphthalen-1-yl-1,2,4,5,6,7-hexahydro-4,7-methano-indazol-3-one

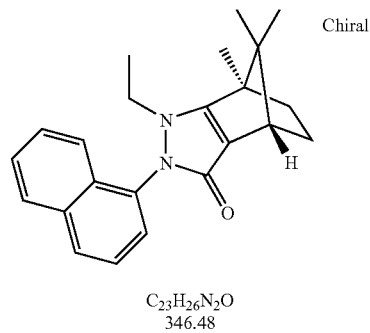

C₂₁H₂₂N₂O
318.42

C₂₄H₂₆N₂O
358.49

A mixture of (4S,7R)-7,8,8-trimethyl-2-naphthalen-1-yl-1,2,4,5,6,7-hexahydro-4,7-methano-indazol-3-one (Intermediate 46; 150 mg, 0.47 mmol) and allyl iodide (204 μL, 1.88 mmol) in dimethylformamide (5 mL) was heated in an oil-bath at 100° C. for 8 h. The solvent was evaporated and the residue was partitioned between dichloromethane and water. The aqueous layer was extracted with dichloromethane (2×100 mL) and the combined organic layers were washed with water (5×100 mL) and aqueous sodium thiosulfate (100 mL). The solvent was evaporated and the residue was purified using an ISCO 12 g column, eluting with 90-100% ethyl acetate/hexanes to give (4S,7R)-1-allyl-7,8,8-trimethyl-2-naphthalen-1-yl-1,2,4,5,6,7-hexahydro-4,7-methano-indazol-3-one (78 mg, 46%) as a white foam. ES(+)-MS (M+H) 359.

Example 143

(4R,7S)-1,7,8,8-Tetramethyl-2-naphthalen-2-yl-1,2,4,5,6,7-hexahydro-4,7-methano-indazol-3-one

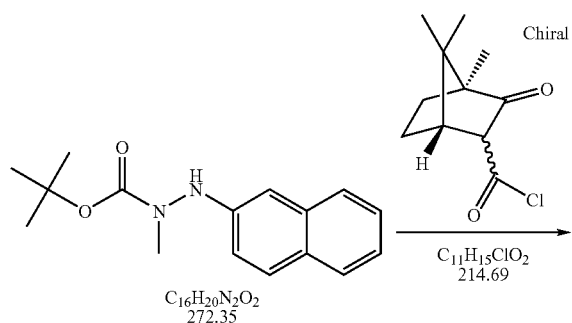

Example 144

(4S,7R)-1,7,8,8-Tetramethyl-2-naphthalen-2-yl-1,2,4,5,6,7-hexahydro-4,7-methano-indazol-3-one

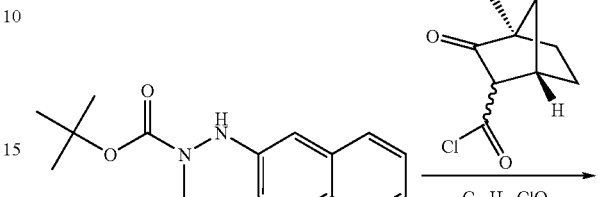

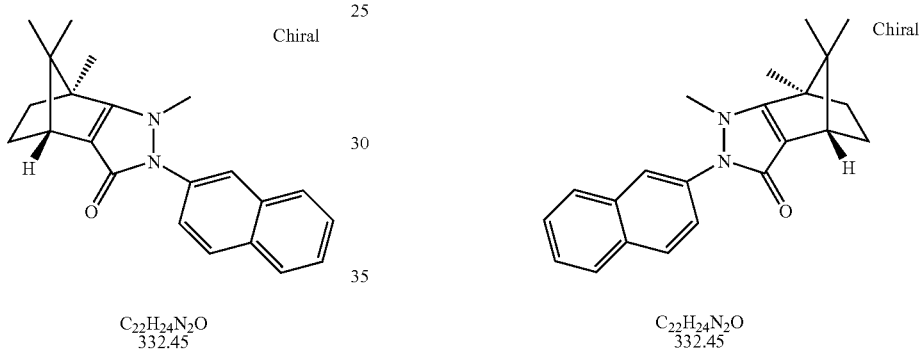

A solution of (1S,4S)-4,7,7-trimethyl-3-oxo-bicyclo[2.2.1]heptane-2-carbonyl chloride (Intermediate 25; 530 mg, 2.47 mmol) in 1,2-dichloroethane (12 mL) was added to a cooled (0° C.) solution of triethylamine (470 µL, 3.37 mmol) and N-methyl-N'-naphthalen-2-yl-hydrazinecarboxylic acid tert-butyl ester (Intermediate 36; 450 mg, 1.65 mmol) in 1,2-dichloroethane (6 mL) over 1 min. The reaction mixture was stirred at room temperature for 90 min. A solution of HCl in dioxane (4 M; 10 mL, 40 mmol) was added and the reaction mixture was heated at reflux for 90 min, and allowed to cool. The solvent was evaporated. The residue was purified twice using ISCO 40 g columns. The first column was eluted with 50-100% ethyl acetate and then with 10% methanol/ethyl acetate. The second column was eluted with 60-100% ethyl acetate/hexanes. Fractions homogeneous for the product were evaporated and the residue was co-evaporated with methanol and then with diethyl ether, and dried under high vacuum at room temperature to give (4R,7S)-1,7,8,8-tetramethyl-2-naphthalen-2-yl-1,2,4,5,6,7-hexahydro-4,7-methano-indazol-3-one (170 mg, 31%) as an off-white foam. ES(+)-MS (M+H) 333.

A solution of (1R,4R)-4,7,7-trimethyl-3-oxo-bicyclo[2.2.1]heptane-2-carbonyl chloride (Intermediate 20; 460 mg, 2.14 mmol) in 1,2-dichloroethane (12 mL) was added to a cooled (0° C.) solution of triethylamine (410 µL, 2.94 mmol) and N-methyl-N'-naphthalen-2-yl-hydrazinecarboxylic acid tert-butyl ester (Intermediate 36; 430 mg, 1.58 mmol) in 1,2-dichloroethane (6 mL) over 1 min. The reaction mixture was stirred at room temperature for 30 min. A solution of HCl in dioxane (4 M; 10 mL, 40 mmol) was added and the reaction mixture was heated in an oil-bath at 100° C. for 30 min, and allowed to cool. The solvent was evaporated and dichloromethane (100 mL) was added. The solution was washed with 1:1 water/brine (30 mL) and the aqueous wash was back-extracted with dichloromethane (30 mL). The combined organic layers were dried (magnesium sulfate), filtered, evaporated, and purified using an ISCO 40 g column, eluting with 60-100% ethyl acetate/hexanes. Fractions homogeneous for the product were evaporated and the residue was co-evaporated with methanol and then with diethyl ether, and dried under high vacuum at 40° C. to give (4S,7R)-1,7,8,8-tetramethyl-2-naphthalen-2-yl-1,2,4,5,6,7-hexahydro-4,7-methano-indazol-3-one (337 mg, 64%) as an off-white foam. ES(+)-MS (M+H) 333.

Example 145

(4R,7S)-1-Benzyl-7,8,8-trimethyl-2-naphthalen-2-yl-1,2,4,5,6,7-hexahydro-4,7-methano-indazol-3-one

Example 146

(4S,7R)-1-Benzyl-7,8,8-trimethyl-2-naphthalen-2-yl-1,2,4,5,6,7-hexahydro-4,7-methano-indazol-3-one

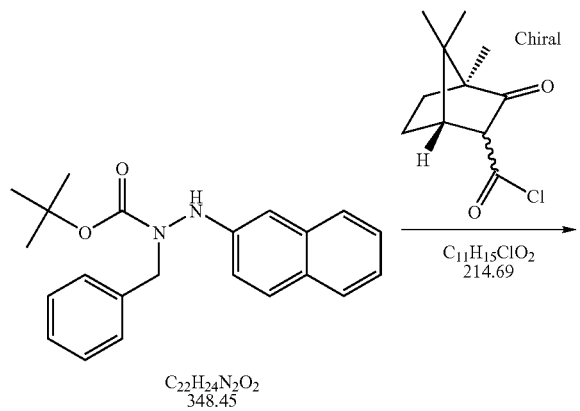
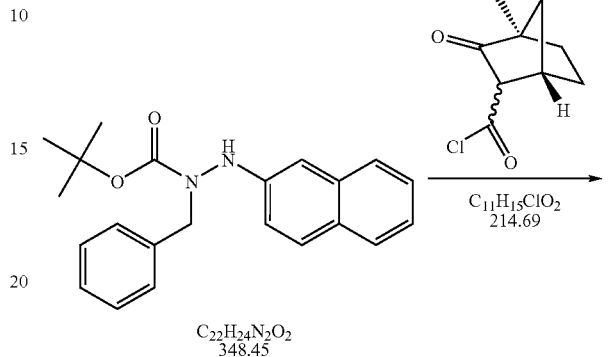
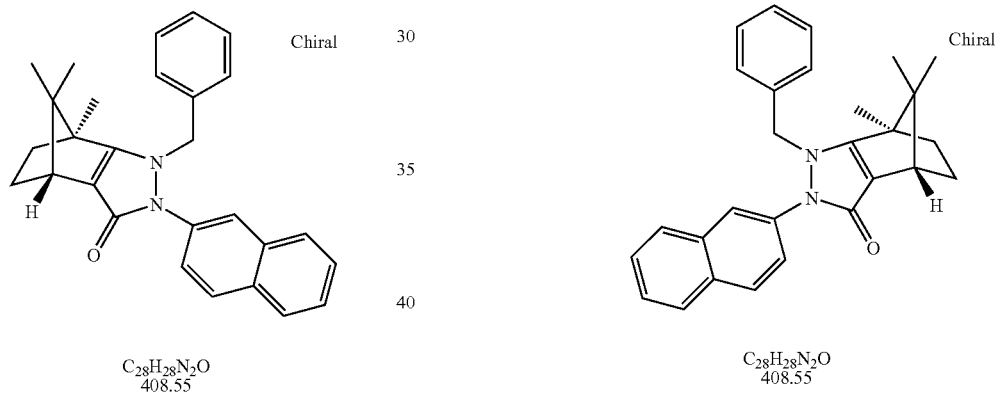

A solution of (1S,4S)-4,7,7-trimethyl-3-oxo-bicyclo[2.2.1]heptane-2-carbonyl chloride (Intermediate 25; 240 mg, 1.12 mmol) in 1,2-dichloroethane (8 mL) was added to a cooled (0° C.) solution of triethylamine (210 µL, 1.5 mmol) and N-benzyl-N'-naphthalen-2-yl-hydrazinecarboxylic acid tert-butyl ester (Intermediate 37; 260 mg, 0.75 mmol) in 1,2-dichloroethane (4 mL) over 1 min. The reaction mixture was stirred at room temperature for 15 min, and then in an oil bath at 50° C. for 30 min. A solution of HCl in dioxane (4 M; 4 mL, 16 mmol) was added and the reaction mixture was heated at reflux for 1 h, and allowed to cool. Silica gel was added and the solvent was evaporated. The residue was purified using an ISCO 40 g column, eluting with 50-100% ethyl acetate/hexanes. Fractions homogeneous for the product were evaporated and the residue was co-evaporated with diethyl ether and dried under high vacuum to give (4R,7S)-1-benzyl-7,8,8-trimethyl-2-naphthalen-2-yl-1,2,4,5,6,7-hexahydro-4,7-methano-indazol-3-one (93 mg, 30%) as an off-white solid. ES(+)-MS (M+H) 409.

A solution of (1R,4R)-4,7,7-trimethyl-3-oxo-bicyclo[2.2.1]heptane-2-carbonyl chloride (Intermediate 20; 240 mg, 1.12 mmol) in 1,2-dichloroethane (8 mL) was added to a cooled (0° C.) solution of triethylamine (210 µL, 1.5 mmol) and N-benzyl-N'-naphthalen-2-yl-hydrazinecarboxylic acid tert-butyl ester (Intermediate 37; 285 mg, 0.82 mmol) in 1,2-dichloroethane (4 mL) over 1 min. The reaction mixture was stirred at room temperature for 75 min. A solution of HCl in dioxane (4 M; 4 mL, 16 mmol) was added and the reaction mixture was heated at reflux for 1 h, allowed to cool, and concentrated. The residue was purified using an ISCO 40 g column, eluting with 50-100% ethyl acetate/hexanes. Fractions containing the product were evaporated and purified again using an ISCO 40 g column, eluting with 60-100% ethyl acetate/hexanes. Fractions containing the product were evaporated, then co-evaporated with methanol and then with diethyl ether and dried under high vacuum at room temperature overnight to give (4S,7R)-1-benzyl-7,8,8-trimethyl-2-naphthalen-2-yl-1,2,4,5,6,7-hexahydro-4,7-methano-indazol-3-one (53 mg, 16%) as a white foam. ES(+)-MS (M+H) 409.

Example 147

(4S,7R)-1,7,8,8-Tetramethyl-2-(4-methyl-naphthalen-1-yl)-1,2,4,5,6,7-hexahydro-4,7-methano-indazol-3-one

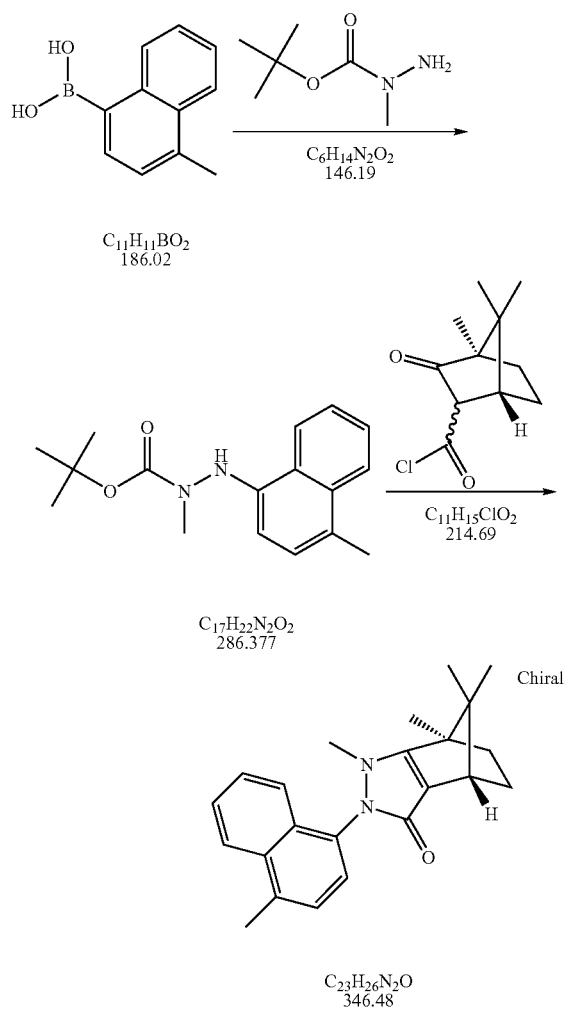

Step 1: N-Methyl-N'-(4-methyl-naphthalen-1-yl)-hydrazinecarboxylic acid tert-butyl ester A mixture of N-methyl-hydrazinecarboxylic acid tert-butyl ester (Intermediate 1; 450 mg, 3.1 mmol), (4-methyl-1-naphthalene)boronic acid (Aldrich; 561 mg, 3.0 mmol), copper(II) acetate (559 mg, 3.1 mmol) and triethylamine (430 μL, 3.1 mmol) in 1,2-dichloroethane (4 mL) was heated in an oil bath at 50° C. for 3 h. The mixture was allowed to cool, and it was then adsorbed onto silica gel and purified by chromatography using an ISCO 40 g column, eluting with 5% ethyl acetate/hexanes, to give N-methyl-N'-(4-methyl-naphthalen-1-yl)-hydrazinecarboxylic acid tert-butyl ester (79 mg, 9%) as a yellow solid.

Step 2: (4S,7R)-1,7,8,8-Tetramethyl-2-(4-methyl-naphthalen-1-yl)-1,2,4,5,6,7-hexahydro-4,7-methano-indazol-3-one Triethylamine (0.18 mL, 1.29 mmol) was added dropwise to a cooled (0° C.) solution of (1R,4R)-4,7,7-trimethyl-3-oxo-bicyclo[2.2.1]heptane-2-carbonyl chloride (Intermediate 20; 160 mg, 0.75 mmol) in 1,2-dichloroethane (2 mL) over 1 min. A solution of N-methyl-N'-(4-methyl-naphthalen-1-yl)-hydrazinecarboxylic acid tert-butyl ester (74 mg, 0.26 mmol) in 1,2-dichloroethane (4 mL) was added. The reaction mixture was stirred at 0° C. for 15 min, at room temperature for 15 min, and then in an oil bath at 50° C. for 30 min. The reaction mixture was cooled. A solution of HCl in dioxane (4 M; 4 mL, 16 mmol) was added and the mixture was heated in an oil bath at 100° C. for 1 h and allowed to cool. Dichloromethane (100 mL) was added and the mixture was washed with 1:1 water/brine (20 mL), dried (magnesium sulfate), filtered, evaporated, and purified by flash chromatography, eluting with 40-100% ethyl acetate/hexanes. Fractions homogeneous for the product were evaporated, and then co-evaporated with methanol and then diethyl ether. The residue was dried under high vacuum at 70° C. overnight to give (4S,7R)-1,7,8,8-tetramethyl-2-(4-methyl-naphthalen-1-yl)-1,2,4,5,6,7-hexahydro-4,7-methano-indazol-3-one (33 mg, 37%) as a light brown solid. ES(+)-MS (M+H) 347.

Example 148

(4S,7R)-2-Biphenyl-2-yl-1,7,8,8-tetramethyl-1,2,4,5,6,7-hexahydro-4,7-methano-indazol-3-one

221

-continued

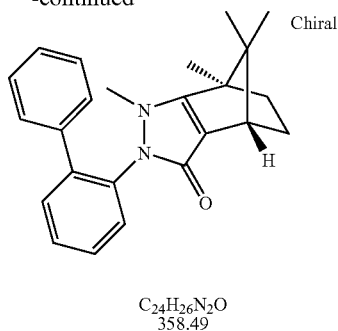

C₂₄H₂₆N₂O
358.49

Step 1: N'-Biphenyl-2-yl-N-methyl-hydrazinecarboxylic acid tert-butyl ester

A mixture of N-methyl-hydrazinecarboxylic acid tert-butyl ester (Intermediate 1; 1.46 g, 10.0 mmol), 2-biphenylboronic acid (Aldrich; 1.94 g, 10.0 mmol), copper(II) acetate (1.81 g, 10.0 mmol) and triethylamine (1.4 mL, 10.0 mmol) in 1,2-dichloroethane (10 mL) was heated in an oil bath at 50° C. for 2 h. The mixture was allowed to cool, and it was then adsorbed onto silica gel and purified by chromatography using an ISCO 40 g column, eluting with 5-40% ethyl acetate/hexanes, to give N'-biphenyl-2-yl-N-methyl-hydrazinecarboxylic acid tert-butyl ester (1.02 g, 34%) as an off-white solid.

Step 2: (4S,7R)-2-Biphenyl-2-yl-1,7,8,8-tetramethyl-1,2,4,5,6,7-hexahydro-4,7-methano-indazol-3-one Triethylamine (1.7 mL, 12.2 mmol) was added dropwise to a cooled (0° C.) solution of (1R,4R)-4,7,7-trimethyl-3-oxo-bicyclo[2.2.1]heptane-2-carbonyl chloride (Intermediate 20; 1.25 g, 5.82 mmol) in 1,2-dichloroethane (10 mL) over 1 min. A solution of N'-biphenyl-2-yl-N-methyl-hydrazinecarboxylic acid tert-butyl ester (1.09 g, 3.65 mmol) in 1,2-dichloroethane (15 mL) was added over 2 min. The reaction mixture was stirred at 0° C. for 15 min, at room temperature for 15 min, and then in an oil bath at 50° C. for 1 h. The reaction mixture was cooled. A solution of HCl in dioxane (4 M; 20 mL, 80 mmol) was added and the mixture was heated in an oil bath at 100° C. for 1.5 h. The reaction mixture was allowed to cool. Dichloromethane (200 mL) was added and the mixture was washed with 1:1 water/brine (50 mL), dried (magnesium sulfate), filtered, evaporated, and purified using an ISCO 120 g column, eluting with 5-10% methanol/dichloromethane. Fractions homogeneous for the product were evaporated, and then co-evaporated successively with methanol, diethyl ether and then petroleum ether. The residue was treated with petroleum ether and the mixture was stirred for 20 min. The solid was filtered off and dried under high vacuum at 90° C. for 1 h to give (4S,7R)-2-biphenyl-2-yl-1,7,8,8-tetramethyl-1,2,4,5,6,7-hexahydro-4,7-methano-indazol-3-one (612 mg, 47%) as a light yellow solid. APCI(+)-MS (M+H) 359.

222

Example 149

(4R,7S)-1,7,8,8-Tetramethyl-2-(3-trifluoromethyl-1H-pyrazol-4-ylmethyl)-1,2,4,5,6,7-hexahydro-4,7-methano-indazol-3-one

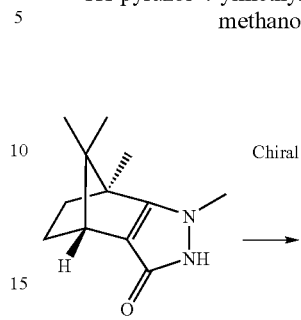

C₁₂H₁₈N₂O
206.29

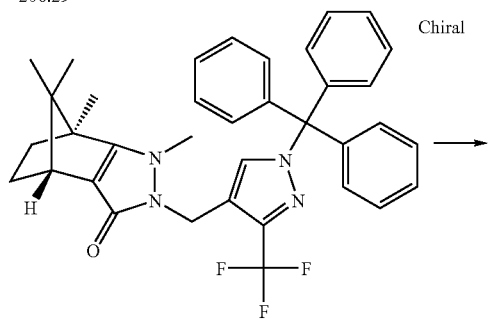

C₃₆H₃₅F₃N₄O
596.70

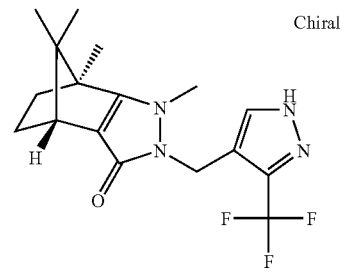

C₁₇H₂₁F₃N₄O
354.38

Step 1: (4R,7S)-1,7,8,8-Tetramethyl-2-(3-trifluoromethyl-1-trityl-1H-pyrazol-4-ylmethyl)-1,2,4,5,6,7-hexahydro-4,7-methano-indazol-3-one A solution of (4R,7S)-1,7,8,8-tetramethyl-1,2,4,5,6,7-hexahydro-4,7-methano-indazol-3-one (Intermediate 48; 250 mg, 1.2 mmol) and 4-bromomethyl-3-trifluoromethyl-1-trityl-1H-pyrazole (Intermediate 2; 580 mg, 1.2 mmol) in dimethylformamide (12 mL) was heated at 100° C. for 4.5 h. The solvent was evaporated and the residue was purified on a Biotage 40S chromatography system, eluting with 0-3% methanol/dichloromethane. Fractions homogeneous for the product were concentrated and the residue held under high vacuum to give (4R,7S)-1,7,8,8-tetramethyl-2-(3-trifluoromethyl-1-trityl-1H-pyrazol-4-ylmethyl)-1,2,4,5,6,7-hexahydro-4,7-methano-indazol-3-one (420 mg, 58%) as a viscous golden orange oil.

Step 2: (4R,7S)-1,7,8,8-Tetramethyl-2-(3-trifluoromethyl-1H-pyrazol-4-ylmethyl)-1,2,4,5,6,7-hexahydro-4,7-methano-indazol-3-one Trifluoroacetic acid (4 mL) was added to a solution of (4R,7S)-1,7,8,8-tetramethyl-2-(3-trifluoromethyl-1-trityl-1H-pyrazol-4-ylmethyl)-1,2,4,5,6,7-hexahydro-4,7-methano-indazol-3-one (410 mg, 0.69 mmol) in dichloromethane (4 mL) and the yellow solution was stirred at room temperature for 4 h. Triethylsilane (110 µL, 0.69 mmol) was added and the solution was stirred at room temperature for 10 min. The solvent was evaporated using a rotary evaporator and the residue was held under high vacuum overnight. The residue was taken up in dichloromethane (50 mL), the solution was transferred to a separatory funnel and water (50 mL) was added. Aqueous saturated sodium hydrogen carbonate (1 Pasteur pipette) was added and the layers were separated. The organic layer was washed with brine (50 mL), dried (magnesium sulfate), filtered, evaporated, and purified using a Biotage 40S system, eluting with 1-3% methanol/ethyl acetate, to give (4R,7S)-1,7,8,8-tetramethyl-2-(3-trifluoromethyl-1H-pyrazol-4-ylmethyl)-1,2,4,5,6,7-hexahydro-4,7-methano-indazol-3-one (118 mg, 48%) as an off-white solid. APCI(+)-MS (M+H) 355.

Example 150

(4R,7S)-1-Benzyl-7,8,8-trimethyl-2-(2-methyl-thiazol-4-ylmethyl)-1,2,4,5,6,7-hexahydro-4,7-methano-indazol-3-one

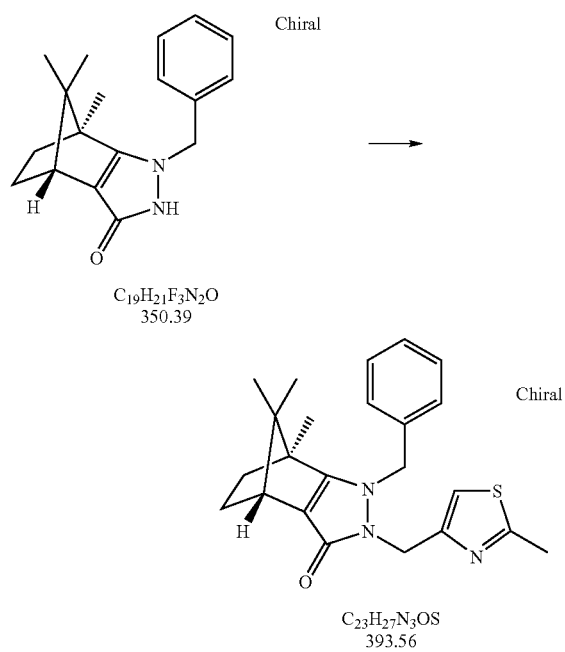

A solution of (4R,7S)-1-benzyl-7,8,8-trimethyl-1,2,4,5,6,7-hexahydro-4,7-methano-indazol-3-one (Intermediate 49; 109 mg, 0.38 mmol), tetrabutylammonium iodide (147 mg, 0.39 mmol) and 4-(chloromethyl)-2-methylthiazole (Maybridge plc, Tintagel, Cornwall, UK; 60 mg, 0.40 mmol) in dimethylformamide (3.9 mL) was heated at 100° C. for 24 h. A second portion of 4-(chloromethyl)-2-methylthiazole (120 mg, 0.81 mmol) was added and the mixture was heated at 110° C. overnight. The solvent was evaporated and dichloromethane (100 mL) was added. The solution was washed with saturated aqueous sodium thiosulfate (150 mL), saturated aqueous sodium hydrogen carbonate (150 mL) and brine (150 mL), dried (sodium sulfate), filtered, evaporated and purified using a Biotage 40S system, eluting with 2% methanol/dichloromethane, to give (4R,7S)-1-benzyl-7,8,8-trimethyl-2-(2-methyl-thiazol-4-ylmethyl)-1,2,4,5,6,7-hexahydro-4,7-methano-indazol-3-one (92 mg, 61%) as a reddish-brown semi-solid. APCI(+)-MS (M+H) 394.

Example 151

(4R,7S)-1,7,8,8-Tetramethyl-2-(2-trifluoromethyl-benzyl)-1,2,4,5,6,7-hexahydro-4,7-methano-indazol-3-one

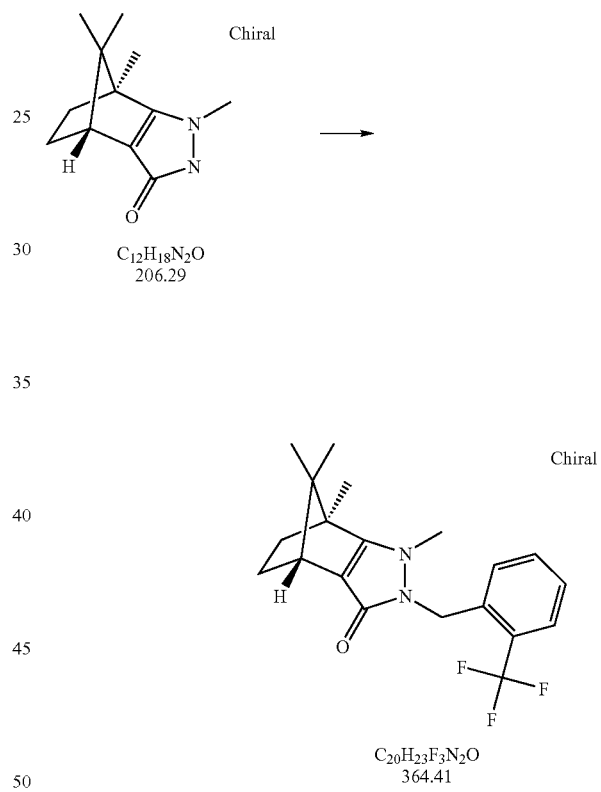

A solution of (4R,7S)-1,7,8,8-tetramethyl-1,2,4,5,6,7-hexahydro-4,7-methano-indazol-3-one (Intermediate 48; 115 mg, 0.55 mmol) and 2-(trifluoromethyl)benzyl bromide (133 mg, 0.55 mmol) in dimethylformamide (5.6 mL) was heated at 100° C. overnight. The solvent was evaporated and the residue was purified on a Biotage chromatography system, eluting with 0-5% methanol/dichloromethane. The resulting clear oil was taken up in dichloromethane, washed with saturated aqueous sodium hydrogen carbonate and water, dried (sodium sulfate), filtered, evaporated, and triturated with ether to give (4R,7S)-1,7,8,8-tetramethyl-2-(2-trifluoromethyl-benzyl)-1,2,4,5,6,7-hexahydro-4,7-methano-indazol-3-one (32 mg, 16%) as a white solid. APCI(+)-MS (M+H) 365.

Example 152

(4R,7S)-1-Benzyl-7,8,8-trimethyl-2-(2-trifluoromethyl-benzyl)-1,2,4,5,6,7-hexahydro-4,7-methano-indazol-3-one

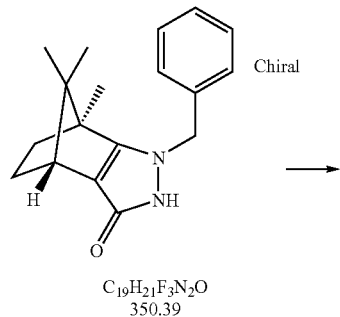

C$_{19}$H$_{21}$F$_3$N$_2$O
350.39

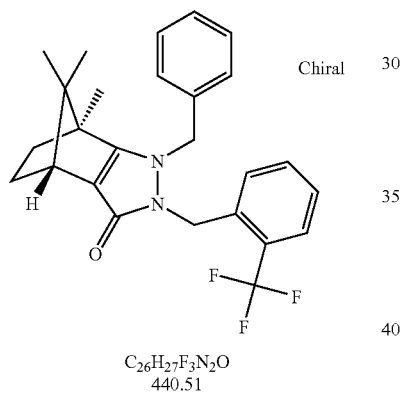

C$_{26}$H$_{27}$F$_3$N$_2$O
440.51

A solution of (4R,7S)-1-benzyl-7,8,8-trimethyl-1,2,4,5,6,7-hexahydro-4,7-methano-indazol-3-one (Intermediate 49; 96 mg, 0.33 mmol) and 2-(trifluoromethyl)benzyl bromide (85 mg, 0.35 mmol) in dimethylformamide (3.4 mL) was heated at 100° C. for 24 h. A second portion of 2-(trifluoromethyl)benzyl bromide (85 mg, 0.35 mmol) was added and the mixture was heated at 110° C. overnight. The solvent was evaporated and dichloromethane (100 mL) was added. The solution was washed with saturated aqueous sodium thiosulfate (150 mL), saturated aqueous sodium hydrogen carbonate (150 mL) and brine (150 mL), dried (sodium sulfate), filtered, evaporated and purified using a Biotage 40S system, eluting with 2% methanol/dichloromethane, to give (4R,7S)-1-benzyl-7,8,8-trimethyl-2-(2-trifluoromethyl-benzyl)-1,2,4,5,6,7-hexahydro-4,7-methano-indazol-3-one (82 mg, 55%) as an off-white solid. APCI(+)-MS (M+H) 441.

Example 153

2-((4S,7R)-1,7,8,8-Tetramethyl-3-oxo-1,3,4,5,6,7-hexahydro-4,7-methano-indazol-2-ylmethyl)-benzamide

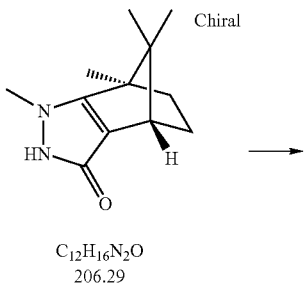

C$_{12}$H$_{16}$N$_2$O
206.29

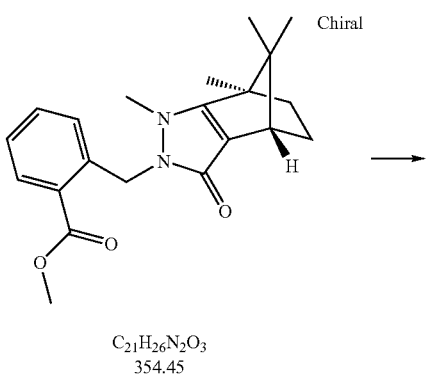

C$_{21}$H$_{26}$N$_2$O$_3$
354.45

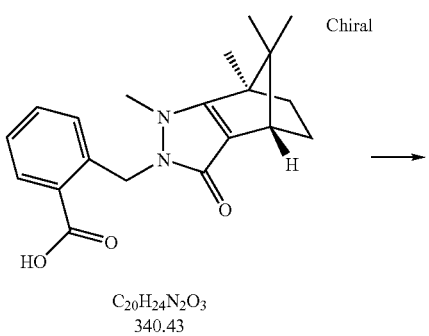

C$_{20}$H$_{24}$N$_2$O$_3$
340.43

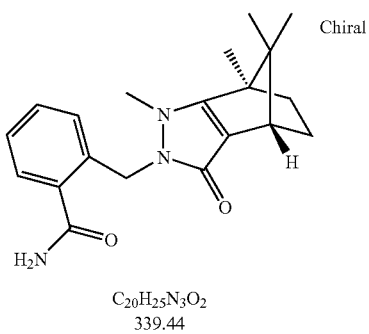

C$_{20}$H$_{25}$N$_3$O$_2$
339.44

Step 1: 2-((4S,7R)-1,7,8,8-Tetramethyl-3-oxo-1,3,4,5,6,7-hexahydro-4,7-methano-indazol-2-ylmethyl)-benzoic acid methyl ester A solution of (4S,7R)-1,7,8,8-tetramethyl-1,2,4,5,6,7-hexahydro-4,7-methano-indazol-3-one (Intermediate 19; 300 mg, 1.5 mmol) and methyl 2-bromomethyl-benzoate (370 mg, 1.6 mmol) in dimethylformamide (15 mL) was heated at ~100° C. for 2 days. The reaction mixture was allowed to cool and the solvent was evaporated. The residue was taken up in dichloromethane and purified on a Biotage 40S system, eluting with 0-2% methanol/dichloromethane to give 2-((4S,7R)-1,7,8,8-tetramethyl-3-oxo-1,3,4,5,6,7-hexahydro-4,7-methano-indazol-2-ylmethyl)-benzoic acid methyl ester (304 mg, 59%) as an orange oil. 1H NMR indicated that it contained minor impurities. It was used in the next step without further purification.

Step 2: 2-((4S,7R)-1,7,8,8-Tetramethyl-3-oxo-1,3,4,5,6,7-hexahydro-4,7-methano-indazol-2-ylmethyl)-benzoic acid A mixture of 2-((4S,7R)-1,7,8,8-tetramethyl-3-oxo-1,3,4,5,6,7-hexahydro-4,7-methano-indazol-2-ylmethyl)-benzoic acid methyl ester (304 mg, 0.86 mmol) and 1 M NaOH (1.5 mL, 1.5 mmol) in tetrahydrofuran (2.4 mL) and methanol (1.2 mL) was stirred overnight at room temperature. The reaction mixture was partitioned between water (100 mL) and ether (100 mL). The aqueous layer was acidified to pH<3 with 1 M HCl and the resulting mixture was extracted with chloroform (100 mL) and then chloroform containing a small amount of methanol (100 mL). The combined organic extracts were dried (magnesium sulfate), filtered, evaporated, and dried under vacuum to give 2-((4S,7R)-1,7,8,8-tetramethyl-3-oxo-1,3,4,5,6,7-hexahydro-4,7-methano-indazol-2-ylmethyl)-benzoic acid (188 mg, 64%) as an off-white solid).

Step 3: 2-((4S,7R)-1,7,8,8-Tetramethyl-3-oxo-1,3,4,5,6,7-hexahydro-4,7-methano-indazol-2-ylmethyl)-benzamide A mixture of 2-((4S,7R)-1,7,8,8-tetramethyl-3-oxo-1,3,4,5,6,7-hexahydro-4,7-methano-indazol-2-ylmethyl)-benzoic acid (100 mg, 0.29 mmol), oxalyl chloride (51 μL, 0.58 mmol) and catalytic dimethylformamide (1 drop) in dichloromethane (3 mL) was stirred at ~0° C. for 15 min and then at room temperature for 2.5 h. The solvent was evaporated and the residue was co-evaporated four times with dichloromethane to remove residual oxalyl chloride. The residue was taken up in dichloromethane (3 mL) and the solution was cooled to ~0° C. and placed behind a blast shield. Anhydrous ammonia gas was passed through a calcium carbonate drying tube and bubbled into the solution for 10-15 min. The reaction mixture was stirred at 0° C. for 5 min, and then at room temperature overnight. The solvent evaporated overnight and the residue was partitioned between chloroform (50 mL) and water (50 mL). The organic layer was washed with saturated aqueous sodium hydrogen carbonate (50 mL) and brine (50 mL), dried (magnesium sulfate), filtered, evaporated and purified on a Biotage 40S chromatography system, eluting with 3-5% methanol/dichloromethane, to give 2-((4S,7R)-1,7,8,8-tetramethyl-3-oxo-1,3,4,5,6,7-hexahydro-4,7-methano-indazol-2-ylmethyl)-benzamide (12.5 mg, 13%) as a light yellow solid. APCI(+)-MS (M+H) 340.

Example 154

(4S,7R)-2-[2-(4-Chloro-phenyl)-thiazol-4-ylmethyl]-1,7,8,8-tetramethyl-1,2,4,5,6,7-hexahydro-4,7-methano-indazol-3-one

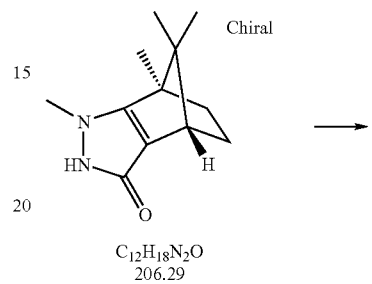

$C_{12}H_{18}N_2O$
206.29

$C_{22}H_{24}ClN_3OS$
413.97

A mixture of (4S,7R)-1,7,8,8-tetramethyl-1,2,4,5,6,7-hexahydro-4,7-methano-indazol-3-one (Intermediate 19; 100 mg, 0.49 mmol) and 4-chloromethyl-2-(4-chlorophenyl)-thiazole (Maybridge plc, Tintagel, Cornwall, UK; 153 mg, 0.63 mmol) in dimethylformamide (5 mL) was heated at 100° C. for 2 days. The solvent was evaporated and ethyl acetate (50 mL) was added. The solution was washed with water (twice) and brine, dried (magnesium sulfate), filtered, evaporated and purified by chromatography, eluting with 2-3% methanol/dichloromethane to give (4S,7R)-2-[2-(4-Chloro-phenyl)-thiazol-4-ylmethyl]-1,7,8,8-tetramethyl-1,2,4,5,6,7-hexahydro-4,7-methano-indazol-3-one (89 mg, 44%) as an off-white foam. APCI(+)-MS (M+H) 414.

Example 155

(4S,7R)-2-(5-Chloro-benzo[b]thiophen-3-ylmethyl)-1,7,8,8-tetramethyl-1,2,4,5,6,7-hexahydro-4,7-methano-indazol-3-one

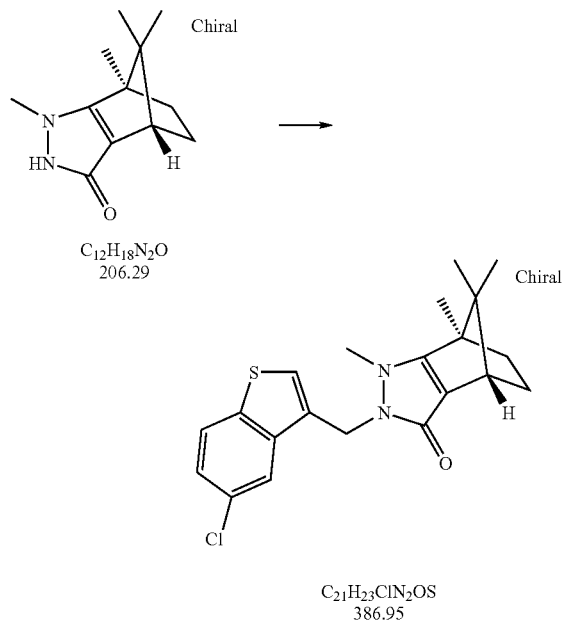

A mixture of (4S,7R)-1,7,8,8-tetramethyl-1,2,4,5,6,7-hexahydro-4,7-methano-indazol-3-one (Intermediate 19; 100 mg, 0.49 mmol) and 3-(bromomethyl)-5-chlorobenzo[b]thiophene (Maybridge plc, Tintagel, Cornwall, UK; 164 mg, 0.63 mmol) in dimethylformamide (5 mL) was heated at 100° C. for 2 days. The solvent was evaporated and ethyl acetate (50 mL) was added. The solution was washed with water (twice) and brine, dried (magnesium sulfate), filtered, evaporated and purified by chromatography, eluting with 1-3% methanol/dichloromethane to give (4S,7R)-2-(5-chloro-benzo[b]thiophen-3-ylmethyl)-1,7,8,8-tetramethyl-1,2,4,5,6,7-hexahydro-4,7-methano-indazol-3-one (140 mg, 74%) as an off-white foam. APCI(+)-MS (M+H) 387.

Example 156

(4S,7R)-1-Benzyl-7,8,8-trimethyl-2-(2,2,2-trifluoro-ethyl)-1,2,4,5,6,7-hexahydro-4,7-methano-indazol-3-one

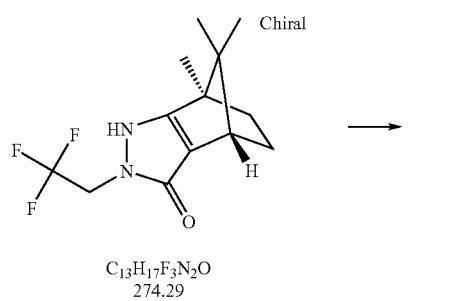

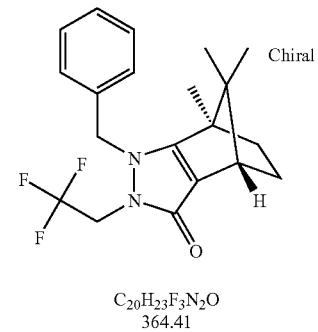

A mixture of (4S,7R)-7,8,8-trimethyl-2-(2,2,2-trifluoro-ethyl)-1,2,4,5,6,7-hexahydro-4,7-methano-indazol-3-one (Intermediate 47; 150 mg, 0.55 mmol), tetrabutylammonium iodide (220 mg, 0.60 mmol) and benzyl bromide (580 μL, 4.9 mmol) in dimethylformamide (2 mL) was heated in a pressure tube in an oil-bath at 100° C. for 20 h. Dichloromethane (75 mL) was added and the solution was washed with water (5×25 mL) and aqueous sodium thiosulfate (25 mL), dried (magnesium sulfate), filtered, evaporated and purified using an ISCO 40 g column, eluting with 20-100% ethyl acetate/hexanes. Fractions homogeneous for the product were evaporated, co-evaporated with petroleum ether, triturated with petroleum ether, evaporated, and dried under high vacuum at 70° C. overnight to give (4S,7R)-1-benzyl-7,8,8-trimethyl-2-(2,2,2-trifluoro-ethyl)-1,2,4,5,6,7-hexahydro-4,7-methano-indazol-3-one (139 mg, 70%) as a white solid. ES(+)-MS (M+H) 365.

Example 157

(4S,7R)-7,8,8-Trimethyl-1-phenethyl-2-(2,2,2-trifluoro-ethyl)-1,2,4,5,6,7-hexahydro-4,7-methano-indazol-3-one -continued

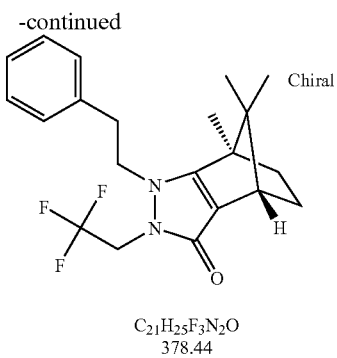

C₂₁H₂₅F₃N₂O
378.44

A mixture of (4S,7R)-7,8,8-trimethyl-2-(2,2,2-trifluoro-ethyl)-1,2,4,5,6,7-hexahydro-4,7-methano-indazol-3-one (Intermediate 47; 150 mg, 0.55 mmol), tetrabutylammonium iodide (220 mg, 0.60 mmol) and (2-bromoethyl)benzene (660 µL, 4.8 mmol) in dimethylformamide (2 mL) was heated in a pressure tube in an oil-bath at 100° C. for 24 h. Dichloromethane (75 mL) was added and the solution was washed with water (5×25 mL) and aqueous sodium thiosulfate (25 mL), dried (magnesium sulfate), filtered, evaporated and purified using an ISCO 40 g column, eluting with 20-100% ethyl acetate/hexanes. Fractions homogeneous for the product were evaporated, co-evaporated with methanol, and dried under high vacuum at 90° C. for 3 h to give (4S,7R)-7,8,8-trimethyl-1-phenethyl-2-(2,2,2-trifluoro-ethyl)-1,2,4,5,6,7-hexahydro-4,7-methano-indazol-3-one (24 mg, 12%) as a yellow gum. ES(+)-MS (M+H) 379.

Example 158

Testing of Compounds of the Invention In Vitro

The in vitro inhibition of 11β-HSD1 by compounds of the present invention was demonstrated by means of the following test:

Purified human HSD1 was diluted in 50 mM Tris-HCl, 100 mM NaCl, 0.1 mg/ml BSA, 0.02% Lubrol, 20 mM $MgCl_2$, 10 mM glucose 6-phosphate, 0.4 mM NADPH, 60 U/ml glucose 6-phosphate dehydrogenase to a concentration of 1.5 µg/ml (Enzyme Solution). Cortisone (100 µM) in DMSO was diluted to 1 µM with 50 mM Tris-HCl, 100 mM NaCl (Substrate Solution). Testing compounds (40 µM) in DMSO was diluted 3 fold in series in DMSO and further diluted 20 fold in Substrate Solution. Enzyme Solution (10 µl/well) was added into 384 well microtiter plates followed by diluted compound solutions (10 µl/well) and mixed well. Samples were then incubated at 370 C for 30 min. EDTA/biotin-cortisol solution (10 µl/well) in 28 mM EDTA, 100 mM biotin-cortisol, 50 mM Tris-HCl, 100 mM NaCl was then added followed by 5 ul/well of anti-cortisol antibody (3.2 µg/ml) in 50 mM Tris-HCl, 100 mM NaCl, 0.1 mg/ml BSA and the solution was incubated at 37 degrees for 30 min. Five ul per well of Eu-conjugated anti-mouse IgG (16 nM) and APC-conjugated streptavidin (160 nM) in 50 mM Tris-HCl, 100 mM NaCl, 0.1 mg/ml BSA was added and the solution was incubated at room temperature for 2 hours. Signals were quantitated by reading time-resolved fluorescence on a Victor 5 reader (Wallac).

Percent inhibition of HSD1 activity by an agent at various concentrations was calculated by the following formula:

% Inhibition=100*[1−(Fs−Fb)/(Ft−Fb)], where
Fs is the fluorescence signal of the sample which included the agent,
Fb is the fluorescence signal in the absence of HSD1 and agent,
Ft is the fluorescence signal in the presence of HSD1, but no agent.

The inhibitory activities of test compounds were determined by the $IC_{50}$s, or the concentration of compound that gave 50% inhibition.

The results obtained in the foregoing tests using representative compounds of the formula 1 as the test compound are compiled in the following Table:

| Compound | hHSD1 IC50 (µM) |
| --- | --- |
| Example 1 | 0.063 |
| Example 4 | 0.036 |
| Example 8 | 0.014 |
| Example 12 | 0.291 |
| Example 17 | 1.715 |
| Example 21 | 0.01 |
| Example 32 | 0.023 |
| Example 34 | 0.472 |
| Example 39 | 0.101 |
| Example 43 | 0.059 |
| Example 49 | 0.39 |

Example 159

Testing of Compounds of the Invention In Vivo

The in vivo inhibition of 11β-HSD1 by compounds of the present invention can be demonstrated by means of the following test:

The compound of the invention is formulated in 7.5% Modified Gelatin in water and is administered IP at 100 mg/kg to mice (male C57B1/6J, age ~97 Days). After 30 minutes, cortisone formulated in gelatin is administered by s.c. injection at 1 mg/kg. After a further 40 minutes, blood samples are taken from the mice and are analyzed using LC-MS for the concentrations of cortisone, cortisol, and drug.

Percent inhibition of HSD1 activity by the inhibitor is calculated by the following formula:

% Inhibition=100*[1−(Cinh/Cveh)]

wherein:
Cveh is the conversion of cortisone to cortisol when the animal is dosed with vehicle, and Cinh is the conversion of cortisone to cortisol when the animal is dosed with inhibitor, where the conversion C is represented by:

C=[Cortisol]/([Cortisol]+[Cortisone]).

Example 160

Testing of Compounds of the Invention In Vitro

Cell-Based Assay

The in vitro inhibition of 11β-HSD1 in a cell-based assay by compounds of the present invention was demonstrated by means of the following test:

HEK-293 cells stably transfected with full-length human 11betaHSD1 cDNA were propagated and expanded in DMEM high glucose media (Invitrogen Cat# 11995-065), supplemented with 10% FCS (Invitrogen Cat# 10082-147), pen/strep (10 μg/mL), and geneticin (10 μg/mL). One day prior to assay, cells were released from flasks using trypsin/EDTA, centrifuged, and washed with plating media (DMEM high glucose, without phenol red; Invitrogen Cat# 21063-029, supplemented with 2% charcoal stripped FCS; Gemini Cat# A22311P). From a 250,000 cells/ml suspension in plating media, 200 ul of cells were seeded into each well of a 96-well coated plate (BioCoat Cat#356461) and cultured overnight at 37° C. The following day, serially diluted 11bHSD1 inhibitor compounds dissolved in DMSO were added to plating media supplemented with BSA (2 mg/ml final). The final DMSO concentration was 1%. Media was aspirated from plates, and compounds in media were added to each well. The plates were incubated at 37° C. for 1 hour to allow for cellular uptake of compounds. 10 μL of substrate (cortisone) was then added to each well (100 nM final concentration) and incubated for 1 hour at 37° C. Plates were then transferred to ice and 80 μL of media transferred to a 96-well plate and stored at −30° C.

Quantitation of cortisol in cell media was performed by competitive ELISA using ELISA-Light (Tropix Cat# T10206/EL100S4), anti-cortisol EIA antibody (Assay Designs, Inc. Cat#80-1148), and cortisol-enzyme conjugate (Assay Designs, Inc. Cat# 80-1147). 384-well plates (Falcon Cat#3988) were precoated with anti-mouse IgG (Sigma Cat# M-1397) suspended in 0.9% NaCl (5 mg/mL), 50 μL per well, overnight at 4° C. Plates were washed with PBS, 0.1% Tween-20, then washed with PBS alone. Plates were blocked with Blocking Buffer (Tropix Cat# AI075) for 2 hours at room temperature. The plates were then washed as previously described. Assay samples were thawed, diluted 1:4 in DMEM, 2 mg/mL BSA, 1% DMSO, and 24 μL was transferred to wells of a pre-coated 384-well plate, as well as varying amounts of cortisol standard. To each well, 12 μL of cortisol-conjugate and 12 μL of anti-cortisol EIA antibody were added and incubated 2 hrs at room temperature on a orbital plate shaker. The wells were then emptied by inversion, then washed three times with 100 μL of Wash Buffer (Tropix), and then 2 times with 100 μL of Assay Buffer (Tropix). 60 μL of CDP-STAR (Tropix) was added to each well and incubated 10 minutes at room temperature. Chemiluminescence was measured using a Victor V Reader (Perkin Elmer). Cortisol in each sample was interpolated from a standard curve generated with known amounts of cortisol. IC50 values were calculated using the curve fitting software XLFit3 (IDBS).

The results obtained in the foregoing tests using representative compounds of the formula 1 as the test compound are compiled in the following Table:

| Compound | Cell-Based IC50 (μM) |
|---|---|
| Example 1 | 0.043 |
| Example 4 | 0.011 |
| Example 8 | 0.02 |
| Example 12 | 0.019 |
| Example 17 | 0.11 |
| Example 21 | 0.019 |
| Example 32 | 0.06 |
| Example 34 | 0.134 |
| Example 37 | 0.027 |
| Example 39 | 0.243 |

-continued

| Compound | Cell-Based IC50 (μM) |
|---|---|
| Example 43 | 0.025 |
| Example 49 | 0.025 |
| Example 66 | 0.019 |
| Example 67 | 0.001 |
| Example 69 | 0.019 |
| Example 75 | 0.017 |
| Example 76 | 0.02 |
| Example 87 | 0.014 |
| Example 98 | 0.028 |
| Example 99 | 0.014 |
| Example 103 | 0.011 |
| Example 113 | 0.036 |
| Example 120 | 0.018 |
| Example 122 | 0.021 |
| Example 123 | 0.009 |
| Example 126 | 0.006 |
| Example 132 | 0.21 |
| Example 133 | 0.021 |
| Example 137 | 0.004 |
| Example 144 | 0.024 |
| Example 145 | 0.021 |
| Example 150 | 0.208 |

It is to be understood that the invention is not limited to the particular embodiments of the invention described above, as variations of the particular embodiments may be made and still fall within the scope of the appended claims.

What is claimed is:

1. A compound of the formula (I):

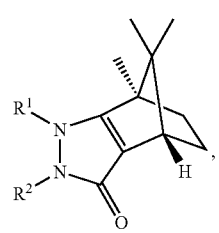

wherein:

$R^1$ is aryl, heteroaryl, aralkyl, heteroaralkyl, lower alkyl, lower-alkoxy-benzyl, lower-alkoxy-carbonyl-lower-alkyl, halo-lower-alkyl, hydroxy-lower-alkyl, lower-alkoxy-lower-alkyl, $(CH_2)$s-aryl, (CH2)s-heteroaryl or $(CH_2)$s-cycloalkyl, wherein said aryl, heteroaryl, aralkyl, heteroaralkyl $(CH_2)$s-aryl, (CH2)s-heteroaryl or $(CH_2)$s-cycloalkyl is unsubstituted or substituted with one or more substituents selected from the group consisting of halogen, lower alkyl, lower alkoxy, cyano, lower-alkoxy-carbonyl, halo-lower-alkyl, phenyl-(oxo-lower-alkyl) and hydroxy-lower-alkyl;

p is 0 or 1;

s is 0, 1 or 2; and $R^2$ is phenyl, which may be unsubstituted or substituted with one or more substituents selected from the group consisting of halogen, hydroxy, halo-lower-alkyl, lower alkoxy, trifluoromethoxy, aminocarbonyl, lower-alkyl, nitro, cyano, sulfonamido, lower-alkyl-sulfonyl, lower acyl and lower-alkoxy-carbonyl, halo-lower-alkyl, unsubstituted or substituted naphthyl, biphenyl, which may be unsubstituted or substituted with one or more substituents selected from the group consisting of acetyl, halogen, lower-alkoxy and lower-alkyl, a 5- or 6-membered monocyclic heterocycle with 1-3 atoms selected from N, O and S, which may be unsubstituted or substituted with halogen, lower-alkyl, unsubstituted or substituted phenyl, or halo-lower-alkyl, or unsubstituted or substituted benzothiophene, with the proviso that the following compounds are excluded:

1,7,8,8-Tetramethyl-2-phenyl-1,2,4,5,6,7-hexahydro-4,7-methano-indazol-3-one, 2,7,8,8-Tetramethyl-1-phenyl-1,2,4,5,6,7-hexahydro-4,7-methano-indazol-3-one, 1,7,8,8-Tetramethyl-2-naphthalen-2-yl-1,2,4,5,6,7-hexahydro-4,7-methano-indazol-3-one, 1,7,8,8-Tetramethyl-2-p-tolyl-1,2,4,5,6,7-hexahydro-4,7-methano-indazol-3-one, 2-(4-Methoxy-phenyl)-1,7,8,8-tetramethyl-1,2,4,5,6,7-hexahydro-4,7-methano-indazol-3-one and 1,7,8,8-Tetramethyl-2-o-tolyl-1,2,4,5,6,7-hexahydro-4,7-methano-indazol-3-one.

2. The compound according to claim 1, wherein $R^1$ is lower alkyl.

3. The compound according to claim 1, wherein R2 is phenyl, substituted at the ortho position by halogen.

4. The compound according to claim 1, wherein:
$R^1$ is phenyl; and
$R^2$ is phenyl, which may be unsubstituted or substituted with one or more substituents selected from the group consisting of halogen, trifluoromethyl, lower alkoxy, trifluoromethoxy, aminocarbonyl, lower-alkyl and lower-alkoxy-carbonyl.

5. The compound according to claim 1, wherein:
$R^1$ is phenyl; and
$R^2$ is biphenyl, which may be unsubstituted or substituted with a group selected from the group consisting of acetyl, halogen, lower-alkoxy and lower-alkyl.

6. The compound according to claim 1, wherein:
$R^1$ is phenyl; and
$R^2$ is a 5- or 6-membered monocyclic heterocycle with 1-3 atoms selected from N, S and O, which may be unsubstituted or substituted with lower-alkyl or trifluoromethyl.

7. The compound according to claim 1, wherein:
$R^1$ is benzyl, unsubstituted or substituted; and
$R^2$ is phenyl, which may be unsubstituted or substituted with one or more substituents selected from the group consisting of halogen, hydroxy, haloloweralkyl, lower alkoxy, trifluoromethoxy, aminocarbonyl, lower-alkyl, nitro, cyano, sulfonamido, lower-alkyl-sulfonyl, lower acyl and lower-alkoxy-carbonyl.

8. The compound according to claim 1, wherein:
$R^1$ is benzyl; and
$R^2$ is biphenyl, which may be unsubstituted or substituted with a group selected from the group consisting of acetyl, halogen, lower-alkoxy and lower-alkyl.

9. The compound according to claim 1, wherein:
$R^1$ is benzyl; and
$R^2$ is a 5- or 6-membered monocyclic heterocycle with 1-3 atoms selected from N, S and O, which may be unsubstituted or substituted with lower-alkyl or trifluoromethyl.

10. The compound according to claim 1, wherein:
$R^1$ is lower alkyl; and
$R^2$ is phenyl, which may be unsubstituted or substituted with one or more substituents selected from the group consisting of halogen, hydroxy, haloloweralkyl, lower alkoxy, trifluoromethoxy, aminocarbonyl, lower-alkyl, nitro, cyano, sulfonamido, lower-alkyl-sulfonyl, lower acyl and lower-alkoxy-carbonyl.

11. The compound according to claim 1, wherein:
$R^1$ is lower alkyl; and
$R^2$ is biphenyl, which may be unsubstituted or substituted with a group selected from the group consisting of acetyl, halogen, lower-alkoxy and lower-alkyl.

12. The compound according to claim 1, wherein:
$R^1$ is lower alkyl; and
$R^2$ is a 5- or 6-membered monocyclic heterocycle with 1-3 atoms selected from N, S and O, which may be unsubstituted or substituted with lower-alkyl or trifluoromethyl.

13. The compound according to claim 1, wherein:
$R^1$ is $(CH_2)$-cycloalkyl; and
$R^2$ is phenyl, which may be unsubstituted or substituted with one or more substituents selected from the group consisting of halogen, hydroxy, haloloweralkyl, lower alkoxy, trifluoromethoxy, aminocarbonyl, lower-alkyl, nitro, cyano, sulfonamido, lower-alkyl-sulfonyl, lower acyl and lower-alkoxy-carbonyl.

14. The compound according to claim 1, wherein:
$R^1$ is $(CH_2)$-cycloalkyl; and
$R^2$ is biphenyl, which may be unsubstituted or substituted with a group selected from the group consisting of acetyl, halogen, lower-alkoxy and lower-alkyl.

15. The compound according to claim 1, wherein:
$R^1$ is $(CH_2)$-cycloalkyl; and
$R^2$ is a 5- or 6-membered monocyclic heterocycle with 1-3 atoms selected from N, S and O, which may be unsubstituted or substituted with lower-alkyl or trifluoromethyl.

16. The compound according to claim 1, wherein said compound is selected from the group consisting of:
(4S,7R)-1-Benzyl-7,8,8-trimethyl-2-phenyl-1,2,4,5,6,7-hexahydro-4,7-methano-indazol-3-one;
(4S,7R)-2-(2-Chloro-phenyl)-1,7,8,8-tetramethyl-1,2,4,5,6,7-hexahydro-4,7-methano-indazol-3-one;
(4S,7R)-2-(2-Fluoro-phenyl)-1-isopropyl-7,8,8-trimethyl-1,2,4,5,6,7-hexahydro-4,7-methano-indazol-3-one;
(4S,7R)-1-Benzyl-2-(2-fluoro-phenyl)-7,8,8-trimethyl-1,2,4,5,6,7-hexahydro-4,7-methano-indazol-3-one;
(4S,7R)-1-Benzyl-2-(2,4-difluoro-phenyl)-7,8,8-trimethyl-1,2,4,5,6,7-hexahydro-4,7-methano-indazol-3-one;
(4S,7R)-1,7,8,8-Tetramethyl-2-(2-trifluoromethyl-benzyl)-1,2,4,5,6,7-hexahydro-4,7-methano-indazol-3-one;
(4S,7R)-2-(2-Fluoro-benzyl)-1,7,8,8-tetramethyl-1,2,4,5,6,7-hexahydro-4,7-methano-indazol-3-one;
(4S,7R)-1,7,8,8-Tetramethyl-2-(2'-methyl-biphenyl-3-yl)-1,2,4,5,6,7-hexahydro-4,7-methano-indazol-3-one;
(4S,7R)-1-Cyclopropylmethyl-7,8,8-trimethyl-2-phenyl-1,2,4,5,6,7-hexahydro-4,7-methano-indazol-3-one; and
(4S,7R)-1-Cyclopentylmethyl-7,8,8-trimethyl-2-phenyl-1,2,4,5,6,7-hexahydro-4,7-methano-indazol-3-one.

17. The compound according to claim 1, wherein said haloloweralkyl is trifluoromethyl or trifluoroethyl.

18. The compound according to claim 1, wherein said compound is selected from the group consisting of:
(4R,7S)-1-Benzyl-2-(2-fluoro-phenyl)-7,8,8-trimethyl-1,2,4,5,6,7-hexahydro-4,7-methano-indazol-3-one;

(4R,7S)-2-(2-Chloro-phenyl)-1,7,8,8-tetramethyl-1,2,4,5,6,7-hexahydro-4,7-methano-indazol-3-one;

(4R,7S)-1-Benzyl-2-(2,4-difluoro-phenyl)-7,8,8-trimethyl-1,2,4,5,6,7-hexahydro-4,7-methano-indazol-3-one;

(4R,7S)-1-(2,4-Difluoro-benzyl)-2-(2,4-difluoro-phenyl)-7,8,8-trimethyl-1,2,4,5,6,7-hexahydro-4,7-methano-indazol-3-one;

(4S,7R)-1-(2,4-Difluoro-benzyl)-2-(2,4-difluoro-phenyl)-7,8,8-trimethyl-1,2,4,5,6,7-hexahydro-4,7-methano-indazol-3-one;

(4S,7R)-2-(2-Chloro-5-fluoro-phenyl)-1,7,8,8-tetramethyl-1,2,4,5,6,7-hexahydro-4,7-methano-indazol-3-one;

(4S,7R)-2-(3-Chloro-2-fluoro-phenyl)-1,7,8,8-tetramethyl-1,2,4,5,6,7-hexahydro-4,7-methano-indazol-3-one;

(4S,7R)-2-(2,3-Dichloro-phenyl)-1,7,8,8-tetramethyl-1,2,4,5,6,7-hexahydro-4,7-methano-indazol-3-one;

(4R,7S)-2-(2,5-Dichloro-phenyl)-1,7,8,8-tetramethyl-1,2,4,5,6,7-hexahydro-4,7-methano-indazol-3-one;

(4S,7R)-2-(2,5-Dichloro-phenyl)-1,7,8,8-tetramethyl-1,2,4,5,6,7-hexahydro-4,7-methano-indazol-3-one;

(4R,7S)-1-Benzyl-2-(2,5-dichloro-phenyl)-7,8,8-trimethyl-1,2,4,5,6,7-hexahydro-4,7-methano-indazol-3-one; and (4R,7S)-1-Benzyl-2-(2,3-dimethyl-phenyl)-7,8,8-trimethyl-1,2,4,5,6,7-hexahydro-4,7-methano-indazol-3-one.

19. A pharmaceutical composition comprising a therapeutically effective amount of a compound according to formula (I),

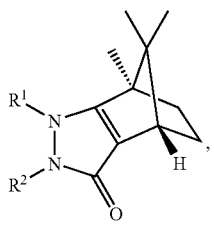

(I)

wherein:

$R^1$ is aryl, heteroaryl, aralkyl, heteroaralkyl, lower alkyl, lower-alkoxy-benzyl, lower-alkoxy-carbonyl-lower-alkyl, halo-lower-alkyl, hydroxy-lower-alkyl, lower-alkoxy-lower-alkyl, $(CH_2)$s-aryl, (CH2)s-heteroaryl or $(CH_2)$s-cycloalkyl, where said aryl, heteroaryl, aralkyl, heteroaralkyl $(CH_2)$s-aryl, (CH2)s-heteroaryl or $(CH_2)$s-cycloalkyl is unsubstituted or substituted with one or more substituents selected from the group consisting of halogen, lower alkyl, lower alkoxy, cyano, lower-alkoxy-carbonyl, halo-lower-alkyl, phenyl-(oxo-lower-alkyl) and hydroxy-lower-alkyl;

p is 0 or 1;

s is 0, 1 or 2; and $R^2$ is phenyl, which may be unsubstituted or substituted with one or more substituents selected from the group consisting of halogen, hydroxy, halo-lower-alkyl, lower alkoxy, trifluoromethoxy, aminocarbonyl, lower-alkyl, nitro, cyano, sulfonamido, lower-alkyl-sulfonyl, lower acyl and lower-alkoxy-carbonyl, halo-lower-alkyl, unsubstituted or substituted naphthyl, biphenyl, which may be unsubstituted or substituted with one or more substituents selected from the group consisting of acetyl, halogen, lower-alkoxy and lower-alkyl, a 5- or 6-membered monocyclic heterocycle with 1-3 atoms selected from N, O and S, which may be unsubstituted or substituted with halogen, lower-alkyl, unsubstituted or substituted phenyl, or halo-lower-alkyl, or unsubstituted or substituted benzothiophene, or pharmaceutically acceptable salts thereof, and a pharmaceutically acceptable carrier.

20. A method of treating a metabolic disorder, comprising the step of administering to a patient in need thereof a therapeutically effective amount of a compound according to formula (I),

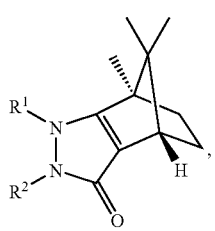

(I)

wherein:

$R^1$ is aryl, heteroaryl, aralkyl, heteroaralkyl, lower alkyl, lower-alkoxy-benzyl, lower-alkoxy-carbonyl-lower-alkyl, halo-lower-alkyl, hydroxy-lower-alkyl, lower-alkoxy-lower-alkyl, $(CH_2)$s-aryl, (CH2)s-heteroaryl or $(CH_2)$s-cycloalkyl, where said aryl, heteroaryl, aralkyl, heteroaralkyl $(CH_2)$s-aryl, (CH2)s-heteroaryl or $(CH_2)$s-cycloalkyl is unsubstituted or substituted with one or more substituents selected from the group consisting of halogen, lower alkyl, lower alkoxy, cyano, lower-alkoxy-carbonyl, halo-lower-alkyl, phenyl-(oxo-lower-alkyl) and hydroxy-lower-alkyl;

p is 0 or 1;

s is 0, 1 or 2; and $R^2$ is phenyl, which may be unsubstituted or substituted with one or more substituents selected from the group consisting of halogen, hydroxy, halo-lower-alkyl, lower alkoxy, trifluoromethoxy, aminocarbonyl, lower-alkyl, nitro, cyano, sulfonamido, lower-alkyl-sulfonyl, lower acyl and lower-alkoxy-carbonyl, halo-lower-alkyl, unsubstituted or substituted naphthyl, biphenyl, which may be unsubstituted or substituted with one or more substituents selected from the group consisting of acetyl, halogen, lower-alkoxy and lower-alkyl, a 5- or 6-membered monocyclic heterocycle with 1-3 atoms selected from N, O and S, which may be unsubstituted or substituted with halogen, lower-alkyl, unsubstituted or substituted phenyl, or halo-lower-alkyl, or unsubstituted or substituted benzothiophene, or a pharmaceutically acceptable salt thereof, and a pharmaceutically acceptable carrier.

21. The method according to claim 18, wherein said therapeutically effective amount is about 0.01 mg/kg to about 50 mg/kg.

22. The method according to claim 18, wherein said metabolic disorder comprises diabetes, obesity or metabolic syndrome.

* * * * *